US010961289B2

(12) United States Patent
Groth et al.

(10) Patent No.: US 10,961,289 B2
(45) Date of Patent: Mar. 30, 2021

(54) SMALL MOLECULES BLOCKING HISTONE READER DOMAINS

(71) Applicants: The University of Copenhagen, Copenhagen K (DK); Memorial Sloan-Kettering Cancer Center, New York, NY (US)

(72) Inventors: Anja Groth, Copenhagen N (DK); Giulia Saredi, Copenhagen N (DK); Hongda Huang, New York, NY (US); Colin Hammond, Copenhagen N (DK); Dinshaw Patel, New York, NY (US)

(73) Assignees: The University of Copenhagen, Copenhagen K (DK); Memorial Sloan-Kettering Cancer Center, New York, NY (US)

( * ) Notice: Subject to any disclaimer, the term of this patent is extended or adjusted under 35 U.S.C. 154(b) by 0 days.

(21) Appl. No.: 16/699,435

(22) Filed: Nov. 29, 2019

(65) Prior Publication Data

US 2020/0148732 A1 May 14, 2020

Related U.S. Application Data

(62) Division of application No. 15/765,344, filed as application No. PCT/DK2016/050317 on Sep. 30, 2016, now abandoned.

(60) Provisional application No. 62/324,257, filed on Apr. 18, 2016.

(30) Foreign Application Priority Data

Oct. 2, 2015 (DK) ............................ PA201500605

(51) Int. Cl.

| | |
|---|---|
| ***C07K 14/47*** | (2006.01) |
| ***A61K 38/00*** | (2006.01) |
| ***C07K 14/00*** | (2006.01) |
| *G16B 15/30* | (2019.01) |
| *G16C 20/50* | (2019.01) |

(52) U.S. Cl.

CPC .......... *C07K 14/4702* (2013.01); *A61K 38/00* (2013.01); *C07K 14/00* (2013.01); *C07K 14/47* (2013.01); *G01N 2500/02* (2013.01); *G01N 2500/04* (2013.01); *G01N 2500/10* (2013.01); *G16B 15/30* (2019.02); *G16C 20/50* (2019.02)

(58) Field of Classification Search

CPC ........................... C07K 14/4702; A61K 38/00

See application file for complete search history.

(56) References Cited

U.S. PATENT DOCUMENTS

| | | | | |
|---|---|---|---|---|
| 5,618,790 A | 4/1997 | Kennedy et al. | | |
| 2003/0021797 A1 | 1/2003 | Datta et al. | | |
| 2003/0072794 A1* | 4/2003 | Boulikas | C12N 15/88 | 424/450 |
| 2004/0031072 A1 | 2/2004 | La Rosa et al. | | |
| 2005/0214331 A1 | 9/2005 | Levy | | |
| 2007/0003543 A1 | 1/2007 | Datta et al. | | |
| 2007/0110756 A1 | 5/2007 | Reinberg | | |
| 2007/0224655 A1* | 9/2007 | Trievel | C12Q 1/34 | 435/15 |
| 2009/0183270 A1 | 7/2009 | Adams et al. | | |
| 2011/0152122 A1 | 6/2011 | Berger et al. | | |
| 2011/0166063 A1 | 7/2011 | Bossard et al. | | |
| 2011/0214206 A1 | 9/2011 | La Rosa et al. | | |
| 2012/0183596 A1 | 7/2012 | Boulikas | | |
| 2013/0196867 A1 | 8/2013 | Strahl et al. | | |
| 2013/0274182 A1 | 10/2013 | Erickson et al. | | |
| 2013/0274295 A1 | 10/2013 | Pujol Onofre | | |
| 2014/0134232 A1* | 5/2014 | Boulikas | C12N 15/88 | 424/450 |
| 2015/0297680 A1 | 10/2015 | Kwon et al. | | |
| 2015/0344589 A1* | 12/2015 | Muir | C07K 16/44 | 530/387.3 |

FOREIGN PATENT DOCUMENTS

| | | |
|---|---|---|
| WO | 2004/050828 A2 | 6/2004 |
| WO | WO-2005/012524 A1 | 2/2005 |
| WO | WO-2005/024380 A2 | 3/2005 |
| WO | WO-2007/132177 A1 | 11/2007 |
| WO | WO-2008/129239 A2 | 10/2008 |
| WO | WO-2011/010715 A1 | 1/2011 |
| WO | WO-2011/098400 A1 | 8/2011 |
| WO | WO-2012/040523 A2 | 3/2012 |
| WO | WO-2012/040523 A3 | 3/2012 |
| WO | WO-2012/050963 A2 | 4/2012 |
| WO | WO-2012/082752 A2 | 6/2012 |

(Continued)

OTHER PUBLICATIONS

Hill et al., 2014, Systemic screening reveals a role for BRAC1 in the response to transcription-associated DNA damage, Genes & Development, 28: 1957-1975.*

Campos et al., 2015, Analysis of the Histone H3.1 Interactome: A Suitable Chaperone for the Right Event, Mol Cell, 60(4): 697-709.*

Kurdistani, 2007, Histone modifications as markers of cancer prognosis: a cellular view, British Journal of Cancer, 97: 1-5.*

(Continued)

*Primary Examiner* — Amber D Steele

(74) *Attorney, Agent, or Firm* — Julie K. Staple; Dinsmore & Shohl LLP

(57) ABSTRACT

The present invention relates to small molecules interfering with the conformational space of the TONSL ARD occupied by the histone H4 tail. These small molecules targets the binding pocket of TONSL encompassing the H4 residues K12-R23 and act by preventing or disrupting the binding of the H4 tail K12-R23 with the TONSL ARD via direct competition or via allosteric disruption of the binding pocket.

18 Claims, 25 Drawing Sheets

Specification includes a Sequence Listing.

(56) References Cited

FOREIGN PATENT DOCUMENTS

| | | | |
|---|---|---|---|
| WO | WO-2012/123119 | A1 | 9/2012 |
| WO | WO-2012/158122 | A1 | 11/2012 |
| WO | WO-2013/040142 | A2 | 3/2013 |
| WO | WO-2013/148178 | A1 | 10/2013 |
| WO | WO-2015/001383 | A1 | 1/2015 |
| WO | WO-2015/023796 | A2 | 2/2015 |

OTHER PUBLICATIONS

Ropero et al., 2007, The role of histone deacetylases (HDACs) in human cancer, Molecular Oncology, 1: 19-25.*

Campbell et al., 2013, Altered Histone Modifications in Cancer, Adv Exp Med Biol, 754: 81-107.*

Waldmann et al., 2013, Targeting histone modifications—epigenetics in cancer, Current Opinion in Cell Biology, 25: 184-189.*

Riedel et al., 2015, Histone profiles in cancer, Pharmacology & Therapeutics, 154: 87-109.*

Vardabasso et al., 2014, Histone variants: emerging players in cancer biology, Cell Mol Life Sci, 71(3): 379-404.*

Sawan et al., 2010, Histone Modifications and Cancer, Advances in Genetics, 70: 57-85.*

Yuen et al., 2013, Histone H3.3 mutations: a variant path to cancer, Cancer Cell, 24(5): 15 pages.*

Adams-Cioaba et al., Structural basis for the recognition and cleavage of histone H3 by cathepsin L. Nature Communications, vol. 2, 2011.

Adams-Cioaba et al., Suppl info., Structural basis for the recognition and cleavage of histone H3 by cathepsin L Nature Communications; vol. 2, 2011.

Campos et al., Analysis of the Histone H3.1 Interactome: A Suitable Chaperone for the Right Event, Molecular Cell; 60(4): 697-709, Nov. 19, 2015.

Chernikova et al., Inhibiting homologous recombination for cancer therapy, Cancer Biology & Therapy; 13(2): 61-68, Jan. 15, 2012.

Collins et al., The ankyrin repeats of G9a and GLP histone methyltransferases are mono- and imethyliysine binding modules, Nat Struct Mol Biol. 15(3): 245-250, 2008.

Database UniProt (Online) Nov. 1, 1996 "SubName: Full= Histone H4-1" UniProt:Q27821, Database acc No. Q27821.

Database UniProt Apr. 8, 2008 "RecName: Full=Tonsoku-like protein; AltName: Full=Inhibitor of kappa B-related protein;" UniProt: Q96HA7, Database acc No. Q96HA7.

Dizdaroglu et al., Identification and Quantification of DNA Repair Proten by Liquid Chromatography/Isotope-Dilution Tandem Mass Spectrometry Using Their Fully 15 N-Labeled Analogues as Internal Standards, J Proteome Res, 10(5): 3802-3813, May 30, 2011.

Duro et al., Identification of the MMS22L-TONSL Complex that Promotes Homologous Recombination, Mol. Cell. 40(4): 632-644, Nov. 24, 2010.

Filippakopoulos et al., Histone Recognition and Large-Scale Structural Analysis of the Human Bromodomain Family, Cell, 149(1): 214-231, Mar. 30, 2012.

Livraghi et al., PARP inhibitors in the management of breast cancer: current data and future prospects, BMC Medicine, 13:188, pp. 1-16, Aug. 13, 2015.

Sequence UPI000290A5B1, UniParc (Online) May 26, 2015, URL:http:77www.uniprot.org/uniparc/UPI000290A5B1 (retrieved on Jan. 10, 2017).

Westermark et al., BARD1 Participates with BRCA1 in Homology-Directed Repair of Chromosome Breaks, Mol Cell Biol, 23(21): 7926-7936, Nov. 2003.

Yuan et al., MYST protein acetyltransferase requires active site lysine autoacetylation, EMBO Journal; 31(1): 58-70, 2012.

Bailon et al., PEG-modified biopharmaceuticals, Expert Opinion on Drug Delivery, 6(1 ): 1-16, 2009.

Lauta et al., Pharmacological elements in clinical application of synthetic peptides, Fundam Clin Pharmcol, 14: 425-442, 2000.

Li, F., et al., A Direct Method for Site-Specific Protein Acetylation, Angewandte Chemie International Edition, 50(41): 9611-9614, 2011.

Seeliger, D. et al., Quantitative Assessment of Protein Interaction with Methyl-Lysine Analogues by Hybrid Computational and Experimental Approached, ACS Chemical Biology, 7(1): 150-154, Oct. 12, 2011.

Southall, S. et al., A novel route to product specificity in the Suv4-20 family of histone H4K0 methyltransferases, Nucleic Acids Research, 42(1): 661-667, Sep. 18, 2013.

Chapman, S. et al., Common NFKBIL2 polymorphisms and susceptibility to pneumococcal disease: a genetic association study, Critical Care, 14: R227 (10 pages), 2010.

O'Donnell, L. et al., The MMS22L-TONSL Complex Mediates Recovery from Replication Stress and Homologous Recombination, Mol. Cell, 40(4): 619-631, Nov. 4, 2010.

Cosmic, Catalogue of somatic mutations in cancer, http://grch37-cancer.sanger.ac.uk/cosmic/search?q=TONSL May 23, 2018.

Database UniProt (Online) Nov. 1, 1996 "SubName: Full= Histone H4-1" UNIPROT:Q2781, Database acc No. Q27821.

Database UniProt (Online) Jul. 21, 1986 "RecName: Full=Histone H4," UNIPROT :P62805, Database acc No. P62805.

Database UniProt (Online) Nov. 26, 2014 "RecName: Full=Histone H¤, Flags: Fragment" UNIPROT: A0A09VRC9, Database acc No. A0A091VRC9.

Database UniProt (Online) Jan. 9, 2013 "Subname: Full=Tonsoku-like, DNA repair protein" , UNIPROT: K7B3J4, Database acc No. K7B3J4.

Database UniProt Apr. 8, 2008 "RecName: Full=Tonsoku-like protein; AltName: Full=Inhibitor of kappa B-related protein; " UNIPROT: Q96HA7, Database acc No. Q9SHA7.

Dizdaroglu et al., Identification and Quantification of DNA Repair by Liquid Chromatography/Isotope-Dilution Tandem Mass Spectrometry Using Their Fully 15 N-Labeled Analogues as Internal Standards, J Proteome Res, 10(5): 3802-3813, May 30, 2011.

Duro et al., Identification of the MMS22L-TONSL Complex that Promotes Homologous Recombination. Mol. Cell, 40(64): 632-644, Nov. 24, 2010.

Filippakopoulos et al., Historic Recognition and Large-Scale Structural Analysis of the Human Bromodomain Family, Cell, 149(1): 214-231, Mar. 30 2012.

Fox et al, Crystal Structure of the BARD1 Ankyrin Repeat Domain and Its Functional Consequences, J Biol Chem, 283(30): 21179-21186, Jul. 25, 2008.

Fuchs et al., Influence of Combinatorial Histone on Antibody and Effector Protein Recognition, Current Biology, Current Science, 21(1): 53-58, Jan. 11, 2010.

Fuchs et al., Suppl Info, Influence of Combinatorial Histone on Antibody and Effector Protein Recognition, Current Biology, Current Science, 21(1), Jan. 11, 2010.

Kimura et al., Kinetics of Core Histones in Living Human Cells: Little Exchange of H3 and H4 and Some Rapid Exchange of H2B, The Journal of Cell Biology, 153(7): 1341-1353, Jun. 25, 2001.

Livragh et al., PARP inhibitors in the management of breast cancer: current data and future prospects, BMC Medicine, 13:188, pp. 1-16, Aug. 13, 2015.

Saredi et al., H4K20me0 marks post-replicative chromatin and recruits the TONSL-MMS22L DNA repair complex, Nature, 534 (7609); 714-718, Jun. 22, 2016.

* cited by examiner

FIG. 21A
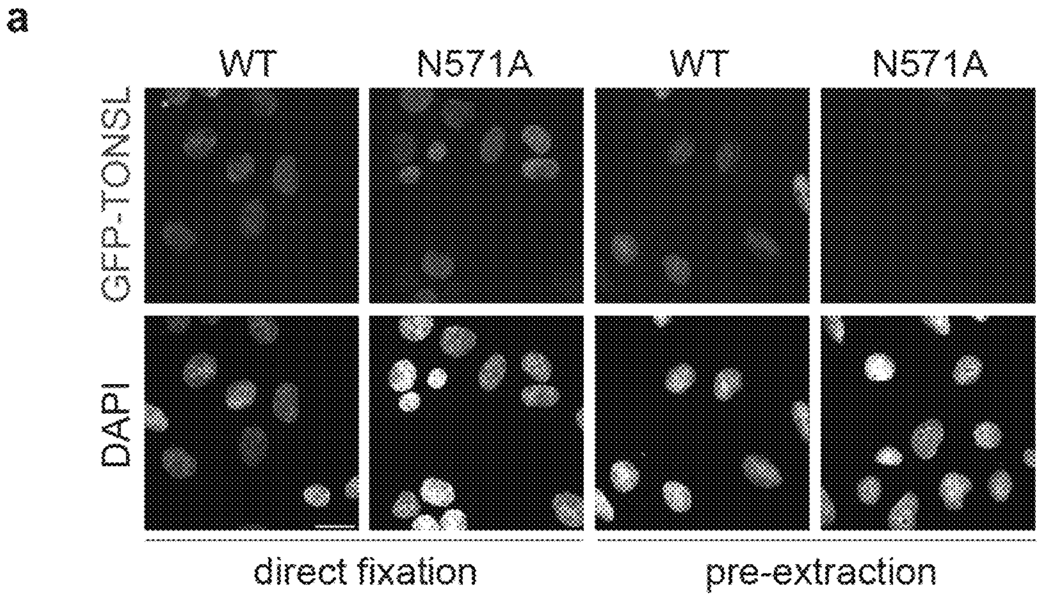
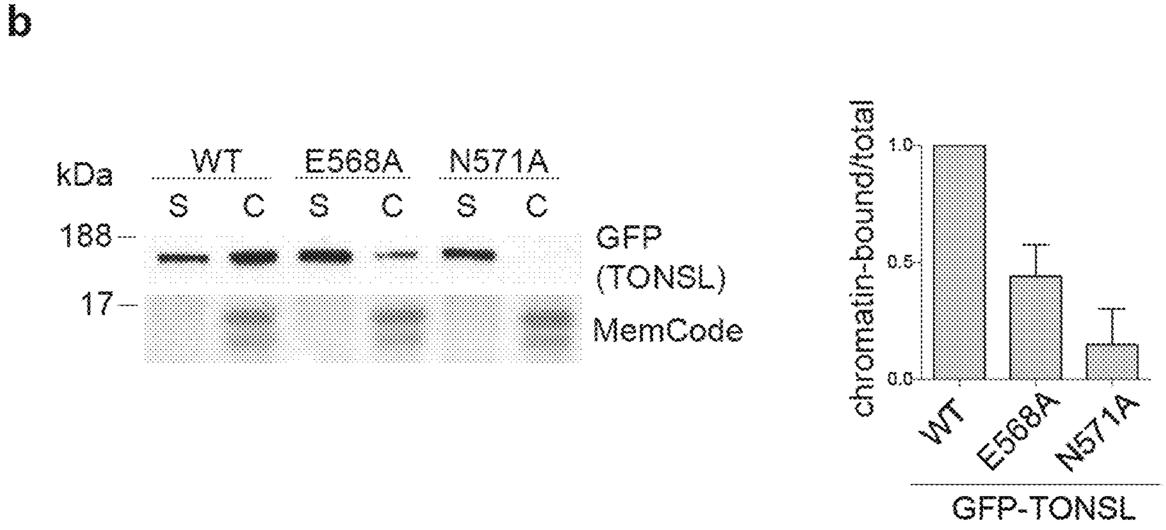
FIG. 21B

FIG. 30A
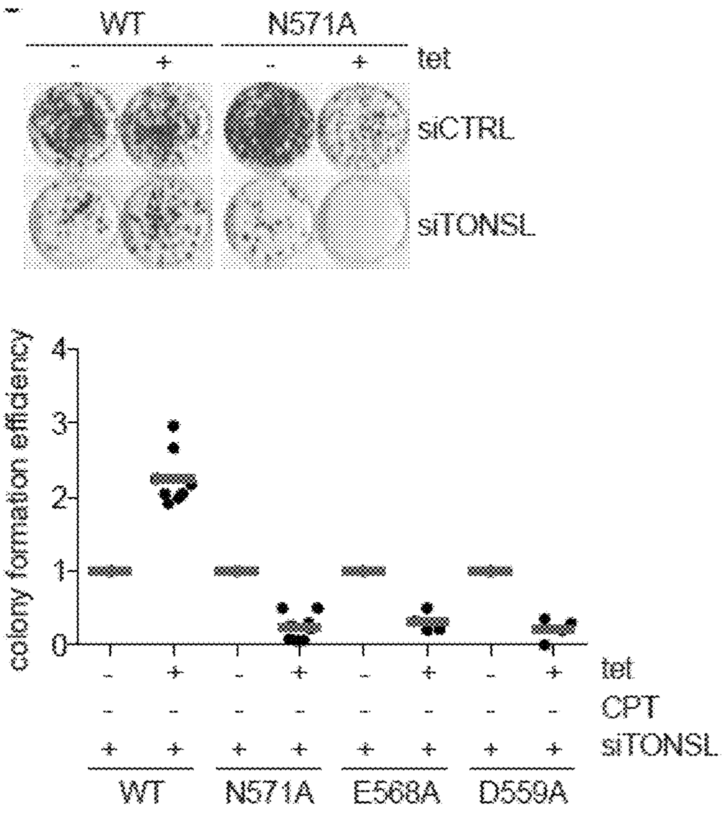
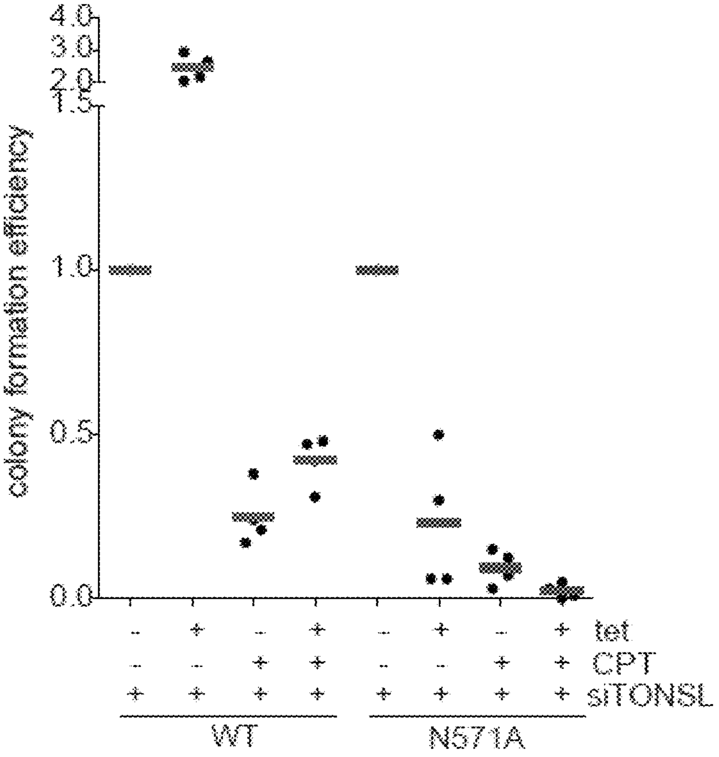
FIG. 30B

SEQUENCE LISTING

```
<160> NUMBER OF SEQ ID NOS: 34

<210> SEQ ID NO 1
<211> LENGTH: 4863
<212> TYPE: DNA
<213> ORGANISM: Artificial sequence
<220> FEATURE:
<223> OTHER INFORMATION: DNA encoding fusion protein

<400> SEQUENCE: 1

atggtgagca agggcgagga gctgttcacc ggggtggtgc ccatcctggt cgagctggac     60

ggcgacgtaa acggccacaa gttcagcgtg tccggcgagg gcgagggcga tgccacctac    120

ggcaagctga ccctgaagtt catctgcacc accggcaagc tgcccgtgcc ctggcccacc    180

ctcgtgacca ccctgaccta cggcgtgcag tgcttcagcc gctaccccga ccacatgaag    240

cagcacgact tcttcaagtc cgccatgccc gaaggctacg tccaggagcg caccatcttc    300

ttcaaggacg acggcaacta caagacccgc gccgaggtga agttcgaggg cgacaccctg    360

gtgaaccgca tcgagctgaa gggcatcgac ttcaaggagg acggcaacat cctggggcac    420

aagctggagt acaactacaa cagccacaac gtctatatca tggccgacaa gcagaagaac    480

ggcatcaagg tgaacttcaa gatccgccac aacatcgagg acggcagcgt gcagctcgcc    540

gaccactacc agcagaacac ccccatcggc gacggccccg tgctgctgcc cgacaaccac    600

tacctgagca cccagtccgc cctgagcaaa gaccccaacg agaagcgcga tcacatggtc    660

ctgctggagt tcgtgaccgc cgccgggatc actctcggca tggacgagct gtacaagggc    720

gcgccaatga gcctggagcg cgagcttcgc cagctgagca aggcgaaagc caaggcgcag    780

agggccgggc agcggcgcga agaggccgcg ctgtgccacc agctggggga gctcctggcc    840

ggccatggcc gctacgccga ggctctggag cagcactggc aggagctgca gcttcgggag    900

cgcgctgacg accctctggg ctgtgccgtg gcccaccgca agatcggaga gcgcctggcc    960

gagatggagg actacccggc tgccttgcag caccagcacc agtacctgga gctggcacat   1020

tccctgcgca accacacgga gctgcagagg gcctgggcca ccatcggccg cacccacctg   1080

gacatctatg accactgcca gtcgagggat gctttgctgc aggcacaggc tgcctttgag   1140

aagagcttgg ctattgtgga tgaggagctg gaggggacac tggcccaggg agagctgaat   1200
```

-continued

```
gagatgagga cccgcctcta tctcaacctg ggcctcacct ttgagagcct gcagcagaca   1260
gccctgtgca acgattactt caggaagagc atcttccttg cggagcagaa ccacctttac   1320
gaggacctat tccgcgcccg ctacaacctg ggcaccatcc actggcgcgc gggccagcac   1380
tcccaggcta tgcgctgctt ggagggtgcc cgggagtgtg cgcacaccat gaggaagcgg   1440
ttcatggaga gcgagtgctg cgtggttatt gcacaggtcc tccaagacct gggagacttt   1500
ttggctgcca agcgagccct gaagaaggcc tacaggctgg gctcccagaa gcctgtgcag   1560
agggcagcca tctgtcagaa cctccagcat gtgctggcag tggtccggct gcagcaacag   1620
ctggaagagg ctgagggcag agaccctcag ggtgccatgg tcatctgtga gcagctaggg   1680
gacctcttct ccaaggcagg agactttccc agggcagctg aggcttacca gaagcagctg   1740
cgttttgctg agctgctgga cagaccgggt gctgagcggg ccatcatcca cgtgtccctg   1800
gccaccacac tgggagacat gaaggaccac catggggccg tgcgccacta tgaggaggaa   1860
ctgaggctgc gcagcggcaa cgtgctggag gaggccaaga cctggctgaa cattgcactg   1920
tcccgcgagg aggccggcga tgcctacgag ctgctggccc cgtgcttcca gaaagcgctc   1980
agctgtgccc agcaggccca gcgtccccag ctgcagaggc aggtcttgca gcatctccat   2040
accgtgcagc tgaggctgca gccccaggag gcccctgaga ccgaaaccag actgcgggag   2100
ctcagtgtag ctgaagatga agatgaggag gaggaggcgg aggaggcggc agccacagcg   2160
gagagcgaag ccctggaggc cggcgaggtg gagctctcag agggcgagga cgacaccgat   2220
ggcctgaccc cgcagctgga ggaggacgag gagcttcagg gccacctggg ccggcggaag   2280
gggagcaagt ggaaccggcg aaacgacatg ggggcgaccc tgctgcaccg agcctgcatc   2340
gagggccagc tgcgccgcgt ccaggacctt gtgaggcagg gccacccccct taaccctcgg   2400
gactactgtg gctggacacc tctgcacgag gcctgcaact acgggcatct agaaattgtc   2460
cgcttcctgc tggaccacgg ggccgcagtg gacgacccag gtggccaggg ctgcgaaggc   2520
atcacccccc tccacgatgc cctcaactgt ggccacttcg aggtggctga gctgctgctt   2580
gaacgggggg cgtccgtcac cctccgcact cgaaagggcc tcagcccgct ggagacgctg   2640
cagcagtggg tgaagctgta ccgcagggac ctggacctgg agacgcggca gaaggccagg   2700
gccatggaga tgctgctcca ggcggctgcc tcgggccaag atccccacag ctcccaggcc   2760
ttccacaccc caagcagcct tctgtttgac cccgagacct ctcctccttt gagcccctgc   2820
ccagaacccc cctctaatag cactagactc ccagaggcct ctcaggtcca tgtcagggtc   2880
tccccagggc aggcggcacc agccatggcc aggcctcgga ggagcaggca tgggccagcc   2940
agcagcagca gcagctcaga aggcgaggac agcgcaggcc ccgcacggcc gtcccagaag   3000
aggcctcggt gctcggccac agcacaacgg gtggcagcct ggacgcctgg ccccgccagc   3060
aacagggaag cagccacagc cagcaccagc cgggcagcct accaggcagc catccggggt   3120
gtgggcagtg ctcagagccg gctggggcct ggcccaccgc ggggccacag caaagccctt   3180
gccccccagg cagcgctcat cccggaggag gagtgcctgg ctggggactg gctggagctg   3240
gacatgcccc tgacccgcag ccgccggccc cgcccccggg gcactggaga caaccgcagg   3300
cccagtagta cctctgggtc ggacagtgag gagagcaggc cccgtgcccg agccaagcag   3360
gtccgcctga cctgcatgca gagttgcagt gcgccagtta acgcagggcc cagcagcctg   3420
gcttcagaac ctccagggag ccccagcacc cccagggtct cagagcccag tggggacagc   3480
tctgcggcag gccagccctt gggtccggcc ccgccccctc ccatccgggt tcgagttcaa   3540
gttcaggatc atctcttcct catccctgtc ccacacagca gtgacaccca ctctgtggcc   3600
```

-continued tggctggccg agcaggcggc ccagcgctac taccagacct gcgggctgct gcccaggctc 3660
accctacgga aagagggggc cctgctggcc ccacaggacc tcatccctga tgtgctgcag 3720
agcaatgacg aggtgttggc tgaggtgact tcgtgggacc tgccccgtt gactgaccgc 3780 taccgcaggg cctgccagag cctggggcaa ggggagcacc aacaggtgct gcaggccgtg 3840
gagctccagg gcttgggcct ctcgttcagc gcctgctccc tggccctgga ccaggcccag 3900
cttacacccc tgctgcgggc cctcaagctg cacacagcac tccgggagct gcgcctggca 3960
gggaaccggc tgggggacaa gtgtgtggct gagctggtgg ctgccctggg caccatgccc 4020
agcctggccc tccttgacct ctcctccaat cacctgggtc ccgaaggcct gcgccagctt 4080
gccatggggc tcccaggcca agccaccttg cagagtttgg aggaattaga tctatcgatg 4140
aaccccctgg gggacggctg tggccagtcc ctggcctccc tcctgcacgc ctgcccctta 4200
ctcagcaccc tgcgcctgca ggcgtgtggc ttcggcccca gcttctttct gagccaccag 4260
acagcactgg gtagtgcttt ccaagatgct gagcacctga agaccctgtc cctgtcctac 4320
aacgccctgg gagcccctgc cctggccagg accctgcaga gcctgcccgc cggcaccctc 4380
ctgcacttag agctcagctc cgtggcagcc ggcaagggtg attcggacct catggagcct 4440
gtattccgat acctggccaa ggaaggctgt gctctagccc acctgaccct gtctgcaaac 4500
cacctggggg acaaggctgt tagagacctg tgcagatgtc tctctctgtg cccctcactc 4560
atctcactgg atctgtctgc caaccctgag atcagctgtg ccagcttgga agagctcctg 4620
tccaccctcc aaaagcggcc ccaaggcctt agcttccttg gcctgtcagg ctgcgccgtc 4680
cagggtcccc tgggcctggg cctgtgggac aagatagccg cgcagctccg ggaactgcag 4740
ctgtgcagca gacgcctctg cgctgaggac agggacgccc tgcgccagct gcagcccagt 4800
cggccgggcc ccggcgagtg cacgctggac cacggctcca agctcttctt tcggcgcctc 4860
tag 4863

<210> SEQ ID NO 2
<211> LENGTH: 4137
<212> TYPE: DNA
<213> ORGANISM: Homo sapiens

<400> SEQUENCE: 2
atgagcctgg agcgcgagct tcgccagctg agcaaggcga aagccaaggc gcagagggcc 60
gggcagcggc gcgaagaggc cgcgctgtgc caccagctgg gggagctcct ggccggccat 120
ggccgctacg ccgaggctct ggagcagcac tggcaggagc tgcagcttcg ggagcgcgct 180
gacgaccctc tgggctgtgc cgtggcccac cgcaagatcg gagagcgcct ggccgagatg 240
gaggactacc cggctgcctt gcagcaccag caccagtacc tggagctggc acattccctg 300
cgcaaccaca cggagctgca gagggcctgg gccaccatcg gccgcaccca cctggacatc 360
tatgaccact gccagtcgag ggatgctttg ctgcaggcac aggctgcctt tgagaagagc 420
ttggctattg tggatgagga gctggagggg acactggccc agggagagct gaatgagatg 480
aggacccgcc tctatctcaa cctgggcctc acctttgaga gcctgcagca gacagccctg 540
tgcaacgatt acttcaggaa gagcatcttc cttgcggagc agaaccacct ttacgaggac 600
ctattccgcg cccgctacaa cctgggcacc atccactggc gcgcgggcca gcactcccag 660
gctatgcgct gcttggaggg tgcccgggag tgtgcgcaca ccatgaggaa gcggttcatg 720
gagagcgagt gctgcgtggt tattgcacag gtcctccaag acctgggaga ctttttggct 780

-continued

```
gccaagcgag ccctgaagaa ggcctacagg ctgggctccc agaagcctgt gcagagggca    840
gccatctgtc agaacctcca gcatgtgctg gcagtggtcc ggctgcagca acagctggaa    900
gaggctgagg gcagagaccc tcagggtgcc atggtcatct gtgagcagct aggggacctc    960
ttctccaagg caggagactt tcccagggca gctgaggctt accagaagca gctgcgtttt   1020
gctgagctgc tggacagacc gggtgctgag cgggccatca tccacgtgtc cctggccacc   1080
acactgggag acatgaagga ccaccatggg gccgtgcgcc actatgagga ggaactgagg   1140
ctgcgcagcg gcaacgtgct ggaggaggcc aagacctggc tgaacattgc actgtcccgc   1200
gaggaggccg gcgatgccta cgagctgctg gccccgtgct tccagaaagc gctcagctgt   1260
gcccagcagg cccagcgtcc ccagctgcag aggcaggtct tgcagcatct ccataccgtg   1320
cagctgaggc tgcagcccca ggaggcccct gagaccgaaa ccagactgcg ggagctcagt   1380
gtagctgaag atgaagatga ggaggaggag gcggaggagg cggcagccac agcggagagc   1440
gaagccctgg aggccggcga ggtggagctc tcagagggcg aggacgacac cgatggcctg   1500
accccgcagc tggaggagga cgaggagctt cagggccacc tgggccggcg gaaggggagc   1560
aagtggaacc ggcgaaacga catgggggcg accctgctgc accgagcctg catcgagggc   1620
cagctgcgcc gcgtccagga ccttgtgagg cagggccacc cccttaaccc tcgggactac   1680
tgtggctgga cacctctgca cgaggcctgc aactacgggc atctagaaat tgtccgcttc   1740
ctgctggacc acggggccgc agtggacgac ccaggtggcc agggctgcga aggcatcacc   1800
cccctccacg atgccctcaa ctgtggccac ttcgaggtgg ctgagctgct gcttgaacgg   1860
ggggcgtccg tcaccctccg cactcgaaag ggcctcagcc cgctggagac gctgcagcag   1920
tgggtgaagc tgtaccgcag ggacctggac ctggagacgc ggcagaaggc cagggccatg   1980
gagatgctgc tccaggcggc tgcctcgggc caagatcccc acagctccca ggccttccac   2040
accccaagca gccttctgtt tgaccccgag acctctcctc ctttgagccc ctgcccagaa   2100
ccccctcta atagcactag actcccagag gcctctcagg tccatgtcag ggtctcccca    2160
gggcaggcgg caccagccat ggccaggcct cggaggagca ggcatgggcc agccagcagc   2220
agcagcagct cagaaggcga ggacagcgca ggccccgcac ggccgtccca gaagaggcct   2280
cggtgctcgg ccacagcaca acgggtggca gcctggacgc ctggccccgc cagcaacagg   2340
gaagcagcca cagccagcac cagccgggca gcctaccagg cagccatccg gggtgtgggc   2400
agtgctcaga gccggctggg gcctggccca ccgcggggcc acagcaaagc ccttgccccc   2460
caggcagcgc tcatcccgga ggaggagtgc ctggctgggg actggctgga gctggacatg   2520
cccctgaccc gcagccgccg gccccgcccc cggggcactg gagacaaccg caggcccagt   2580
agtacctctg ggtcggacag tgaggagagc aggccccgtg cccgagccaa gcaggtccgc   2640
ctgacctgca tgcagagttg cagtgcgcca gttaacgcag ggcccagcag cctggcttca   2700
gaacctccag ggagccccag cacccccagg gtctcagagc ccagtgggga cagctctgcg   2760
gcaggccagc ccttgggtcc ggccccgccc cctcccatcc gggttcgagt tcaagttcag   2820
gatcatctct tcctcatccc tgtcccacac agcagtgaca cccactctgt ggcctggctg   2880
gccgagcagg cggcccagcg ctactaccag acctgcgggc tgctgcccag gctcacccta   2940
cggaaagagg gggccctgct ggccccacag gacctcatcc ctgatgtgct gcagagcaat   3000
gacgaggtgt tggctgaggt gacttcgtgg gacctgcccc cgttgactga ccgctaccgc   3060
agggcctgcc agagcctggg gcaaggggag caccaacagg tgctgcaggc cgtggagctc   3120
cagggcttgg gcctctcgtt cagcgcctgc tccctggccc tggaccaggc ccagcttaca   3180
```

cccctgctgc gggccctcaa gctgcacaca gcactccggg agctgcgcct ggcagggaac 3240
cggctggggg acaagtgtgt ggctgagctg gtggctgccc tgggcaccat gcccagcctg 3300
gccctccttg acctctcctc caatcacctg ggtcccgaag gcctgcgcca gcttgccatg 3360
gggctcccag gccaagccac cttgcagagt ttggaggaat tagatctatc gatgaacccc 3420
ctgggggacg gctgtggcca gtccctggcc tccctcctgc acgcctgccc cttactcagc 3480
accctgcgcc tgcaggcgtg tggcttcggc cccagcttct ttctgagcca ccagacagca 3540
ctgggtagtg ctttccaaga tgctgagcac ctgaagaccc tgtccctgtc ctacaacgcc 3600
ctgggagccc ctgccctggc caggaccctg cagagcctgc ccgccggcac cctcctgcac 3660
ttagagctca gctccgtggc agccggcaag ggtgattcgg acctcatgga gcctgtattc 3720
cgatacctgg ccaaggaagg ctgtgctcta gcccacctga ccctgtctgc aaaccacctg 3780
ggggacaagg ctgttagaga cctgtgcaga tgtctctctc tgtgcccctc actcatctca 3840
ctggatctgt ctgccaaccc tgagatcagc tgtgccagct tggaagagct cctgtccacc 3900
ctccaaaagc ggccccaagg ccttagcttc cttggcctgt caggctgcgc cgtccagggt 3960
cccctgggcc tgggcctgtg ggacaagata gccgcgcagc tccgggaact gcagctgtgc 4020
agcagacgcc tctgcgctga ggacagggac gccctgcgcc agctgcagcc cagtcggccg 4080
ggccccggcg agtgcacgct ggaccacggc tccaagctct tctttcggcg cctctag 4137

<210> SEQ ID NO 3
<211> LENGTH: 4137
<212> TYPE: DNA
<213> ORGANISM: Artificial sequence
<220> FEATURE:
<223> OTHER INFORMATION: DNA encoding mutant protein

<400> SEQUENCE: 3
atgagcctgg agcgcgagct tcgccagctg agcaaggcga aagccaaggc gcagagggcc 60
gggcagcggc gcgaagaggc cgcgctgtgc caccagctgg gggagctcct ggccggccat 120
ggccgctacg ccgaggctct ggagcagcac tggcaggagc tgcagcttcg ggagcgcgct 180
gacgaccctc tgggctgtgc cgtggcccac cgcaagatcg gagagcgcct ggccgagatg 240
gaggactacc cggctgcctt gcagcaccag caccagtacc tggagctggc acattccctg 300
cgcaaccaca cggagctgca gagggcctgg gccaccatcg gccgcaccca cctggacatc 360
tatgaccact gccagtcgag ggatgctttg ctgcaggcac aggctgcctt tgagaagagc 420
ttggctattg tggatgagga gctggagggg acactggccc agggagagct gaatgagatg 480
aggacccgcc tctatctcaa cctgggcctc acctttgaga gcctgcagca gacagccctg 540
tgcaacgatt acttcaggaa gagcatcttc cttgcggagc agaaccacct ttacgaggac 600
ctattccgcg cccgctacaa cctgggcacc atccactggc gcgcgggcca gcactcccag 660
gctatgcgct gcttggaggg tgcccgggag tgtgcgcaca ccatgaggaa gcggttcatg 720
gagagcgagt gctgcgtggt tattgcacag gtcctccaag acctgggaga ctttttggct 780
gccaagcgag ccctgaagaa ggcctacagg ctgggctccc agaagcctgt gcagagggca 840
gccatctgtc agaacctcca gcatgtgctg gcagtggtcc ggctgcagca acagctggaa 900
gaggctgagg gcagagaccc tcagggtgcc atggtcatct gtgagcagct aggggacctc 960
ttctccaagg caggagactt tcccagggca gctgaggctt accagaagca gctgcgtttt 1020
gctgagctgc tggacagacc gggtgctgag cgggccatca tccacgtgtc cctggccacc 1080

-continued

```
acactgggag acatgaagga ccaccatggg gccgtgcgcc actatgagga ggaactgagg   1140
ctgcgcagcg gcaacgtgct ggaggaggcc aagacctggc tgaacattgc actgtcccgc   1200
gaggaggccg gcgatgccta cgagctgctg gccccgtgct tccagaaagc gctcagctgt   1260
gcccagcagg cccagcgtcc ccagctgcag aggcaggtct tgcagcatct ccataccgtg   1320
cagctgaggc tgcagcccca ggaggcccct gagaccgaaa ccagactgcg ggagctcagt   1380
gtagctgaag atgaagatga ggaggaggag gcggaggagg cggcagccac agcggagagc   1440
gaagccctgg aggccggcga ggtggagctc tcagagggcg aggacgacac cgatggcctg   1500
accccgcagc tggaggagga cgaggagctt cagggccacc tgggccggcg gaaggggagc   1560
aagtggaacc ggcgaaacga catgggggcg accctgctgc accgagcctg catcgagggc   1620
cagctgcgcc gcgtccagga ccttgtgagg cagggccacc cccttaaccc tcgggactac   1680
tgtggctgga cacctctgca cgaggcctgc aactacgggc atctagaaat tgtccgcttc   1740
ctgctggacc acggggccgc agtggacgac ccaggtggcc agggctgcga aggcatcacc   1800
cccctccacg atgccctcaa ctgtggccac ttcgaggtgg ctgagctgct gcttgaacgg   1860
ggggcgtccg tcaccctccg cactcgaaag ggcctcagcc cgctggagac gctgcagcag   1920
tgggtgaagc tgtaccgcag ggacctggac ctggagacgc ggcagaaggc cagggccatg   1980
gagatgctgc tccaggcggc tgcctcgggc caagatcccc acagctccca ggccttccac   2040
accccaagca gccttctgtt tgaccccgag acctctcctc ctttgagccc ctgcccagaa   2100
ccccccctcta atagcactag actcccagag gcctctcagg tccatgtcag ggtctcccca   2160
gggcaggcgg caccagccat ggccaggcct cggaggagca ggcatgggcc agccagcagc   2220
agcagcagct cagaaggcga ggacagcgca ggccccgcac ggccgtccca gaagaggcct   2280
cggtgctcgg ccacagcaca acgggtggca gcctggacgc ctggccccgc cagcaacagg   2340
gaagcagcca cagccagcac cagccgggca gcctaccagg cagccatccg gggtgtgggc   2400
agtgctcaga gccggctggg gcctggccca ccgcggggcc acagcaaagc ccttgccccc   2460
caggcagcgc tcatcccgga ggaggagtgc ctggctgggg actggctgga gctggacatg   2520
cccctgaccc gcagccgccg gccccgcccc cggggcactg gagacaaccg caggcccagt   2580
agtacctctg ggtcggacag tgaggagagc aggccccgtg cccgagccaa gcaggtccgc   2640
ctgacctgca tgcagagttg cagtgcgcca gttaacgcag ggcccagcag cctggcttca   2700
gaacctccag ggagccccag cacccccagg gtctcagagc ccagtgggga cagctctgcg   2760
gcaggccagc ccttgggtcc ggccccgccc cctcccatcc gggttcgagt tcaagttcag   2820
gatcatctct tcctcatccc tgtcccacac agcagtgaca cccactctgt ggcctggctg   2880
gccgagcagg cggcccagcg ctactaccag acctgcgggc tgctgcccag gctcacccta   2940
cggaaagagg gggccctgct ggccccacag gacctcatcc ctgatgtgct gcagagcaat   3000
gacgaggtgt tggctgaggt gacttcgtgg gacctgcccc cgttgactga ccgctaccgc   3060
agggcctgcc agagcctggg gcaaggggag caccaacagg tgctgcaggc cgtggagctc   3120
cagggcttgg gcctctcgtt cagcgcctgc tccctggccc tggaccaggc ccagcttaca   3180
cccctgctgc gggccctcaa gctgcacaca gcactccggg agctgcgcct ggcagggaac   3240
cggctggggg acaagtgtgt ggctgagctg gtggctgccc tgggcaccat gcccagcctg   3300
gccctccttg acctctcctc caatcacctg ggtcccgaag gcctgcgcca gcttgccatg   3360
gggctcccag gccaagccac cttgcagagt ttggaggaat tagatctatc gatgaacccc   3420
ctgggggacg gctgtggcca gtccctggcc tccctcctgc acgcctgccc cttactcagc   3480
```

```
accctgcgcc tgcaggcgtg tggcttcggc cccagcttct ttctgagcca ccagacagca   3540

ctgggtagtg ctttccaaga tgctgagcac ctgaagaccc tgtccctgtc ctacaacgcc   3600

ctgggagccc ctgccctggc caggaccctg cagagcctgc ccgccggcac cctcctgcac   3660

ttagagctca gctccgtggc agccggcaag ggtgattcgg acctcatgga gcctgtattc   3720

cgatacctgg ccaaggaagg ctgtgctcta gcccacctga ccctgtctgc aaaccacctg   3780

ggggacaagg ctgttagaga cctgtgcaga tgtctctctc tgtgcccctc actcatctca   3840

ctggatctgt ctgccaaccc tgagatcagc tgtgccagct tggaagagct cctgtccacc   3900

ctccaaaagc ggccccaagg ccttagcttc cttggcctgt caggctgcgc cgtccagggt   3960

cccctgggcc tgggcctgtg ggacaagata gccgcgcagc tccgggaact gcagctgtgc   4020

agcagacgcc tctgcgctga ggacagggac gccctgcgcc agctgcagcc cagtcggccg   4080

ggccccggcg agtgcacgct ggaccacggc tccaagctct tctttcggcg cctctag      4137
```

```
<210> SEQ ID NO 4
<211> LENGTH: 4863
<212> TYPE: DNA
<213> ORGANISM: Artificial sequence
<220> FEATURE:
<223> OTHER INFORMATION: DNA encoding fusion protein

<400> SEQUENCE: 4

atggtgagca agggcgagga gctgttcacc ggggtggtgc ccatcctggt cgagctggac     60

ggcgacgtaa acggccacaa gttcagcgtg tccggcgagg gcgagggcga tgccacctac    120

ggcaagctga ccctgaagtt catctgcacc accggcaagc tgcccgtgcc ctggcccacc    180

ctcgtgacca ccctgaccta cggcgtgcag tgcttcagcc gctaccccga ccacatgaag    240

cagcacgact tcttcaagtc cgccatgccc gaaggctacg tccaggagcg caccatcttc    300

ttcaaggacg acggcaacta caagacccgc gccgaggtga agttcgaggg cgacaccctg    360

gtgaaccgca tcgagctgaa gggcatcgac ttcaaggagg acggcaacat cctggggcac    420

aagctggagt acaactacaa cagccacaac gtctatatca tggccgacaa gcagaagaac    480

ggcatcaagg tgaacttcaa gatccgccac aacatcgagg acggcagcgt gcagctcgcc    540

gaccactacc agcagaacac ccccatcggc gacggccccg tgctgctgcc cgacaaccac    600

tacctgagca cccagtccgc cctgagcaaa gaccccaacg agaagcgcga tcacatggtc    660

ctgctggagt tcgtgaccgc cgccgggatc actctcggca tggacgagct gtacaagggc    720

gcgccaatga gcctggagcg cgagcttcgc cagctgagca aggcgaaagc caaggcgcag    780

agggccgggc agcggcgcga agaggccgcg ctgtgccacc agctggggga gctcctggcc    840

ggccatggcc gctacgccga ggctctggag cagcactggc aggagctgca gcttcgggag    900

cgcgctgacg accctctggg ctgtgccgtg gcccaccgca agatcggaga gcgcctggcc    960

gagatggagg actacccggc tgccttgcag caccagcacc agtacctgga gctggcacat   1020

tccctgcgca accacacgga gctgcagagg gcctgggcca ccatcggccg cacccacctg   1080

gacatctatg accactgcca gtcgagggat gctttgctgc aggcacaggc tgcctttgag   1140

aagagcttgg ctattgtgga tgaggagctg gaggggacac tggcccaggg agagctgaat   1200

gagatgagga cccgcctcta tctcaacctg ggcctcacct ttgagagcct gcagcagaca   1260

gccctgtgca acgattactt caggaagagc atcttccttg cggagcagaa ccacctttac   1320

gaggacctat tccgcgcccg ctacaacctg ggcaccatcc actggcgcgc gggccagcac   1380
```

-continued tcccaggcta tgcgctgctt ggagggtgcc cgggagtgtg cgcacaccat gaggaagcgg 1440
ttcatggaga gcgagtgctg cgtggttatt gcacaggtcc tccaagacct gggagacttt 1500
ttggctgcca agcgagccct gaagaaggcc tacaggctgg gctcccagaa gcctgtgcag 1560
agggcagcca tctgtcagaa cctccagcat gtgctggcag tggtccggct gcagcaacag 1620
ctggaagagg ctgagggcag agaccctcag ggtgccatgg tcatctgtga gcagctaggg 1680
gacctcttct ccaaggcagg agactttccc agggcagctg aggcttacca gaagcagctg 1740
cgttttgctg agctgctgga cagaccgggt gctgagcggg ccatcatcca cgtgtccctg 1800
gccaccacac tgggagacat gaaggaccac catggggccg tgcgccacta tgaggaggaa 1860
ctgaggctgc gcagcggcaa cgtgctggag gaggccaaga cctggctgaa cattgcactg 1920
tcccgcgagg aggccggcga tgcctacgag ctgctggccc cgtgcttcca gaaagcgctc 1980
agctgtgccc agcaggccca gcgtccccag ctgcagaggc aggtcttgca gcatctccat 2040
accgtgcagc tgaggctgca gccccaggag gcccctgaga ccgaaaccag actgcgggag 2100
ctcagtgtag ctgaagatga agatgaggag gaggaggcgg aggaggcggc agccacagcg 2160
gagagcgaag ccctggaggc cggcgaggtg gagctctcag agggcgagga cgacaccgat 2220
ggcctgaccc cgcagctgga ggaggacgag gagcttcagg gccacctggg ccggcggaag 2280
gggagcaagt ggaaccggcg aaacgacatg ggggcgaccc tgctgcaccg agcctgcatc 2340
gagggccagc tgcgccgcgt ccaggacctt gtgaggcagg gccacccccct taaccctcgg 2400
gactactgtg gctggacacc tctgcacgag gcctgcaact acgggcatct agaaattgtc 2460
cgcttcctgc tggaccacgg ggccgcagtg gacgacccag gtggccaggg ctgcgaaggc 2520
atcacccccc tccacgatgc cctcaactgt ggccacttcg aggtggctga gctgctgctt 2580
gaacgggggg cgtccgtcac cctccgcact cgaaagggcc tcagcccgct ggagacgctg 2640
cagcagtggg tgaagctgta ccgcagggac ctggacctgg agacgcggca gaaggccagg 2700
gccatggaga tgctgctcca ggcggctgcc tcgggccaag atccccacag ctcccaggcc 2760
ttccacaccc caagcagcct tctgtttgac cccgagacct ctcctccttt gagcccctgc 2820
ccagaacccc cctctaatag cactagactc ccagaggcct ctcaggtcca tgtcagggtc 2880
tccccagggc aggcggcacc agccatggcc aggcctcgga ggagcaggca tgggccagcc 2940
agcagcagca gcagctcaga aggcgaggac agcgcaggcc ccgcacggcc gtcccagaag 3000
aggcctcggt gctcggccac agcacaacgg gtggcagcct ggacgcctgg ccccgccagc 3060
aacagggaag cagccacagc cagcaccagc cgggcagcct accaggcagc catccggggt 3120
gtgggcagtg ctcagagccg gctggggcct ggcccaccgc ggggccacag caaagccctt 3180
gccccccagg cagcgctcat cccggaggag gagtgcctgg ctggggactg gctggagctg 3240
gacatgcccc tgacccgcag ccgccggccc cgcccccggg gcactggaga caaccgcagg 3300
cccagtagta cctctgggtc ggacagtgag gagagcaggc cccgtgcccg agccaagcag 3360
gtccgcctga cctgcatgca gagttgcagt gcgccagtta acgcagggcc cagcagcctg 3420
gcttcagaac ctccagggag ccccagcacc cccagggtct cagagcccag tggggacagc 3480
tctgcggcag gccagccctt gggtccggcc ccgccccctc ccatccgggt tcgagttcaa 3540
gttcaggatc atctcttcct catccctgtc ccacacagca gtgacaccca ctctgtggcc 3600
tggctggccg agcaggcggc ccagcgctac taccagacct gcgggctgct gcccaggctc 3660
accctacgga aagagggggc cctgctggcc ccacaggacc tcatccctga tgtgctgcag 3720
agcaatgacg aggtgttggc tgaggtgact tcgtgggacc tgcccccgtt gactgaccgc 3780

```
taccgcaggg cctgccagag cctggggcaa ggggagcacc aacaggtgct gcaggccgtg   3840

gagctccagg gcttgggcct ctcgttcagc gcctgctccc tggccctgga ccaggcccag   3900

cttacacccc tgctgcgggc cctcaagctg cacacagcac tccgggagct gcgcctggca   3960

gggaaccggc tgggggacaa gtgtgtggct gagctggtgg ctgccctggg caccatgccc   4020

agcctggccc tccttgacct ctcctccaat cacctgggtc ccgaaggcct gcgccagctt   4080

gccatggggc tcccaggcca agccaccttg cagagtttgg aggaattaga tctatcgatg   4140

aaccccctgg gggacggctg tggccagtcc ctggcctccc tcctgcacgc ctgcccctta   4200

ctcagcaccc tgcgcctgca ggcgtgtggc ttcggcccca gcttctttct gagccaccag   4260

acagcactgg gtagtgcttt ccaagatgct gagcacctga agaccctgtc cctgtcctac   4320

aacgccctgg gagcccctgc cctggccagg accctgcaga gcctgcccgc cggcaccctc   4380

ctgcacttag agctcagctc cgtggcagcc ggcaagggtg attcggacct catggagcct   4440

gtattccgat acctggccaa ggaaggctgt gctctagccc acctgaccct gtctgcaaac   4500

cacctggggg acaaggctgt tagagacctg tgcagatgtc tctctctgtg cccctcactc   4560

atctcactgg atctgtctgc caaccctgag atcagctgtg ccagcttgga agagctcctg   4620

tccaccctcc aaaagcggcc ccaaggcctt agcttccttg gcctgtcagg ctgcgccgtc   4680

cagggtcccc tgggcctggg cctgtgggac aagatagccg cgcagctccg ggaactgcag   4740

ctgtgcagca gacgcctctg cgctgaggac agggacgccc tgcgccagct gcagcccagt   4800

cggccgggcc ccggcgagtg cacgctggac cacggctcca agctcttctt tcggcgcctc   4860

tag                                                                 4863
```

```
<210> SEQ ID NO 5
<211> LENGTH: 4137
<212> TYPE: DNA
<213> ORGANISM: Artificial sequence
<220> FEATURE:
<223> OTHER INFORMATION: DNA encoding mutant protein

<400> SEQUENCE: 5

atgagcctgg agcgcgagct tcgccagctg agcaaggcga aagccaaggc gcagagggcc     60

gggcagcggc gcgaagaggc cgcgctgtgc caccagctgg gggagctcct ggccggccat    120

ggccgctacg ccgaggctct ggagcagcac tggcaggagc tgcagcttcg ggagcgcgct    180

gacgaccctc tgggctgtgc cgtggcccac cgcaagatcg gagagcgcct ggccgagatg    240

gaggactacc cggctgcctt gcagcaccag caccagtacc tggagctggc acattccctg    300

cgcaaccaca cggagctgca gagggcctgg gccaccatcg gccgcaccca cctggacatc    360

tatgaccact gccagtcgag ggatgctttg ctgcaggcac aggctgcctt tgagaagagc    420

ttggctattg tggatgagga gctggagggg acactggccc agggagagct gaatgagatg    480

aggacccgcc tctatctcaa cctgggcctc acctttgaga gcctgcagca gacagccctg    540

tgcaacgatt acttcaggaa gagcatcttc cttgcggagc agaaccacct ttacgaggac    600

ctattccgcg cccgctacaa cctgggcacc atccactggc gcgcgggcca gcactcccag    660

gctatgcgct gcttggaggg tgcccgggag tgtgcgcaca ccatgaggaa gcggttcatg    720

gagagcgagt gctgcgtggt tattgcacag gtcctccaag acctgggaga ctttttggct    780

gccaagcgag ccctgaagaa ggcctacagg ctgggctccc agaagcctgt gcagagggca    840

gccatctgtc agaacctcca gcatgtgctg gcagtggtcc ggctgcagca acagctggaa    900
```

-continued

```
gaggctgagg gcagagaccc tcagggtgcc atggtcatct gtgagcagct aggggacctc    960
ttctccaagg caggagactt tcccagggca gctgaggctt accagaagca gctgcgtttt   1020
gctgagctgc tggacagacc gggtgctgag cgggccatca tccacgtgtc cctggccacc   1080
acactgggag acatgaagga ccaccatggg gccgtgcgcc actatgagga ggaactgagg   1140
ctgcgcagcg gcaacgtgct ggaggaggcc aagacctggc tgaacattgc actgtcccgc   1200
gaggaggccg gcgatgccta cgagctgctg gccccgtgct tccagaaagc gctcagctgt   1260
gcccagcagg cccagcgtcc ccagctgcag aggcaggtct tgcagcatct ccataccgtg   1320
cagctgaggc tgcagcccca ggaggcccct gagaccgaaa ccagactgcg ggagctcagt   1380
gtagctgaag atgaagatga ggaggaggag gcggaggagg cggcagccac agcggagagc   1440
gaagccctgg aggccggcga ggtggagctc tcagagggcg aggacgacac cgatggcctg   1500
accccgcagc tggaggagga cgaggagctt cagggccacc tgggccggcg gaaggggagc   1560
aagtggaacc ggcgaaacga catgggggag accctgctgc accgagcctg catcgagggc   1620
cagctgcgcc gcgtccagga ccttgtgagg cagggccacc cccttaaccc tcgggcctac   1680
tgtggctgga cacctctgca cgaggcctgc aactacgggc atctagaaat tgtccgcttc   1740
ctgctggacc acggggccgc agtggacgac ccaggtggcc agggctgcga aggcatcacc   1800
cccctccacg atgccctcaa ctgtggccac ttcgaggtgg ctgagctgct gcttgaacgg   1860
ggggcgtccg tcaccctccg cactcgaaag ggcctcagcc cgctggagac gctgcagcag   1920
tgggtgaagc tgtaccgcag ggacctggac ctggagacgc ggcagaaggc cagggccatg   1980
gagatgctgc tccaggcggc tgcctcgggc caagatcccc acagctccca ggccttccac   2040
accccaagca gccttctgtt tgaccccgag acctctcctc ctttgagccc ctgcccagaa   2100
ccccccctcta atagcactag actcccagag gcctctcagg tccatgtcag ggtctcccca   2160
gggcaggcgg caccagccat ggccaggcct cggaggagca ggcatgggcc agccagcagc   2220
agcagcagct cagaaggcga ggacagcgca ggccccgcac ggccgtccca gaagaggcct   2280
cggtgctcgg ccacagcaca acgggtggca gcctggacgc ctggccccgc cagcaacagg   2340
gaagcagcca cagccagcac cagccgggca gcctaccagg cagccatccg gggtgtgggc   2400
agtgctcaga gccggctggg gcctggccca ccgcggggcc acagcaaagc ccttgccccc   2460
caggcagcgc tcatcccgga ggaggagtgc ctggctgggg actggctgga gctggacatg   2520
cccctgaccc gcagccgccg gccccgcccc cggggcactg gagacaaccg caggcccagt   2580
agtacctctg ggtcggacag tgaggagagc aggccccgtg cccgagccaa gcaggtccgc   2640
ctgacctgca tgcagagttg cagtgcgcca gttaacgcag ggcccagcag cctggcttca   2700
gaacctccag ggagccccag cacccccagg gtctcagagc ccagtgggga cagctctgcg   2760
gcaggccagc ccttgggtcc ggccccgccc cctcccatcc gggttcgagt tcaagttcag   2820
gatcatctct tcctcatccc tgtcccacac agcagtgaca cccactctgt ggcctggctg   2880
gccgagcagg cggcccagcg ctactaccag acctgcgggc tgctgcccag gctcacccta   2940
cggaaagagg gggccctgct ggccccacag gacctcatcc ctgatgtgct gcagagcaat   3000
gacgaggtgt tggctgaggt gacttcgtgg gacctgcccc cgttgactga ccgctaccgc   3060
agggcctgcc agagcctggg gcaaggggag caccaacagg tgctgcaggc cgtggagctc   3120
cagggcttgg gcctctcgtt cagcgcctgc tccctggccc tggaccaggc ccagcttaca   3180
cccctgctgc gggccctcaa gctgcacaca gcactccggg agctgcgcct ggcagggaac   3240
cggctggggg acaagtgtgt ggctgagctg gtggctgccc tgggcaccat gcccagcctg   3300
```

gccctccttg acctctcctc caatcacctg ggtcccgaag gcctgcgcca gcttgccatg 3360
gggctcccag gccaagccac cttgcagagt ttggaggaat tagatctatc gatgaacccc 3420
ctgggggacg gctgtggcca gtccctggcc tccctcctgc acgcctgccc cttactcagc 3480
accctgcgcc tgcaggcgtg tggcttcggc cccagcttct ttctgagcca ccagacagca 3540
ctgggtagtg ctttccaaga tgctgagcac ctgaagaccc tgtccctgtc ctacaacgcc 3600
ctgggagccc ctgccctggc caggaccctg cagagcctgc ccgccggcac cctcctgcac 3660
ttagagctca gctccgtggc agccggcaag ggtgattcgg acctcatgga gcctgtattc 3720
cgatacctgg ccaaggaagg ctgtgctcta gcccacctga ccctgtctgc aaaccacctg 3780
ggggacaagg ctgttagaga cctgtgcaga tgtctctctc tgtgcccctc actcatctca 3840
ctggatctgt ctgccaaccc tgagatcagc tgtgccagct tggaagagct cctgtccacc 3900
ctccaaaagc ggccccaagg ccttagcttc cttggcctgt caggctgcgc cgtccagggt 3960
cccctgggcc tgggcctgtg ggacaagata gccgcgcagc tccgggaact gcagctgtgc 4020
agcagacgcc tctgcgctga ggacagggac gccctgcgcc agctgcagcc cagtcggccg 4080
ggccccggcg agtgcacgct ggaccacggc tccaagctct tctttcggcg cctctag 4137

<210> SEQ ID NO 6
<211> LENGTH: 4863
<212> TYPE: DNA
<213> ORGANISM: Artificial sequence
<220> FEATURE:
<223> OTHER INFORMATION: DNA encoding fusion protein

<400> SEQUENCE: 6
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaagg tgaacttcaa gatccgccac aacatcgagg acggcagcgt gcagctcgcc 540
gaccactacc agcagaacac ccccatcggc gacggccccg tgctgctgcc cgacaaccac 600
tacctgagca cccagtccgc cctgagcaaa gaccccaacg agaagcgcga tcacatggtc 660
ctgctggagt tcgtgaccgc cgccgggatc actctcggca tggacgagct gtacaagggc 720
gcgccaatga gcctggagcg cgagcttcgc cagctgagca aggcgaaagc caaggcgcag 780
agggccgggc agcggcgcga agaggccgcg ctgtgccacc agctggggga gctcctggcc 840
ggccatggcc gctacgccga ggctctggag cagcactggc aggagctgca gcttcgggag 900
cgcgctgacg accctctggg ctgtgccgtg gcccaccgca agatcggaga gcgcctggcc 960
gagatggagg actacccggc tgccttgcag caccagcacc agtacctgga gctggcacat 1020
tccctgcgca accacacgga gctgcagagg gcctgggcca ccatcggccg cacccacctg 1080
gacatctatg accactgcca gtcgagggat gctttgctgc aggcacaggc tgcctttgag 1140
aagagcttgg ctattgtgga tgaggagctg gaggggacac tggcccaggg agagctgaat 1200

-continued

```
gagatgagga cccgcctcta tctcaacctg ggcctcacct ttgagagcct gcagcagaca   1260
gccctgtgca acgattactt caggaagagc atcttccttg cggagcagaa ccacctttac   1320
gaggacctat tccgcgcccg ctacaacctg ggcaccatcc actggcgcgc gggccagcac   1380
tcccaggcta tgcgctgctt ggagggtgcc cgggagtgtg cgcacaccat gaggaagcgg   1440
ttcatggaga gcgagtgctg cgtggttatt gcacaggtcc tccaagacct gggagacttt   1500
ttggctgcca agcgagccct gaagaaggcc tacaggctgg gctcccagaa gcctgtgcag   1560
agggcagcca tctgtcagaa cctccagcat gtgctggcag tggtccggct gcagcaacag   1620
ctggaagagg ctgagggcag agaccctcag ggtgccatgg tcatctgtga gcagctaggg   1680
gacctcttct ccaaggcagg agactttccc agggcagctg aggcttacca gaagcagctg   1740
cgttttgctg agctgctgga cagaccgggt gctgagcggg ccatcatcca cgtgtccctg   1800
gccaccacac tgggagacat gaaggaccac catggggccg tgcgccacta tgaggaggaa   1860
ctgaggctgc gcagcggcaa cgtgctggag gaggccaaga cctggctgaa cattgcactg   1920
tcccgcgagg aggccggcga tgcctacgag ctgctggccc cgtgcttcca gaaagcgctc   1980
agctgtgccc agcaggccca gcgtccccag ctgcagaggc aggtcttgca gcatctccat   2040
accgtgcagc tgaggctgca gccccaggag gcccctgaga ccgaaaccag actgcgggag   2100
ctcagtgtag ctgaagatga agatgaggag gaggaggcgg aggaggcggc agccacagcg   2160
gagagcgaag ccctggaggc cggcgaggtg gagctctcag agggcgagga cgacaccgat   2220
ggcctgaccc cgcagctgga ggaggacgag gagcttcagg gccacctggg ccggcggaag   2280
gggagcaagt ggaaccggcg aaacgacatg ggggagaccc tgctgcaccg agcctgcatc   2340
gagggccagc tgcgccgcgt ccaggacctt gtgaggcagg gccacccccct taaccctcgg   2400
gcctactgtg gctggacacc tctgcacgag gcctgcaact acgggcatct agaaattgtc   2460
cgcttcctgc tggaccacgg ggccgcagtg gacgacccag gtggccaggg ctgcgaaggc   2520
atcacccccc tccacgatgc cctcaactgt ggccacttcg aggtggctga gctgctgctt   2580
gaacgggggg cgtccgtcac cctccgcact cgaaagggcc tcagcccgct ggagacgctg   2640
cagcagtggg tgaagctgta ccgcagggac ctggacctgg agacgcggca gaaggccagg   2700
gccatggaga tgctgctcca ggcggctgcc tcgggccaag atccccacag ctcccaggcc   2760
ttccacaccc caagcagcct tctgtttgac cccgagacct ctcctccttt gagcccctgc   2820
ccagaacccc cctctaatag cactagactc ccagaggcct ctcaggtcca tgtcagggtc   2880
tccccagggc aggcggcacc agccatggcc aggcctcgga ggagcaggca tgggccagcc   2940
agcagcagca gcagctcaga aggcgaggac agcgcaggcc ccgcacggcc gtcccagaag   3000
aggcctcggt gctcggccac agcacaacgg gtggcagcct ggacgcctgg ccccgccagc   3060
aacagggaag cagccacagc cagcaccagc cgggcagcct accaggcagc catccggggt   3120
gtgggcagtg ctcagagccg gctggggcct ggcccaccgc ggggccacag caaagccctt   3180
gccccccagg cagcgctcat cccggaggag gagtgcctgg ctggggactg gctggagctg   3240
gacatgcccc tgacccgcag ccgccggccc cgcccccggg gcactggaga caaccgcagg   3300
cccagtagta cctctgggtc ggacagtgag gagagcaggc cccgtgcccg agccaagcag   3360
gtccgcctga cctgcatgca gagttgcagt gcgccagtta acgcagggcc cagcagcctg   3420
gcttcagaac ctccagggag ccccagcacc cccagggtct cagagcccag tggggacagc   3480
tctgcggcag gccagccctt gggtccggcc ccgccccctc ccatccgggt tcgagttcaa   3540
gttcaggatc atctcttcct catccctgtc ccacacagca gtgacaccca ctctgtggcc   3600
```

tggctggccg agcaggcggc ccagcgctac taccagacct gcgggctgct gcccaggctc 3660
accctacgga aagagggggc cctgctggcc ccacaggacc tcatccctga tgtgctgcag 3720
agcaatgacg aggtgttggc tgaggtgact tcgtgggacc tgcccccgtt gactgaccgc 3780
taccgcaggg cctgccagag cctggggcaa ggggagcacc aacaggtgct gcaggccgtg 3840
gagctccagg gcttgggcct ctcgttcagc gcctgctccc tggccctgga ccaggcccag 3900
cttacacccc tgctgcgggc cctcaagctg cacacagcac tccgggagct gcgcctggca 3960
gggaaccggc tgggggacaa gtgtgtggct gagctggtgg ctgccctggg caccatgccc 4020
agcctggccc tccttgacct ctcctccaat cacctgggtc ccgaaggcct gcgccagctt 4080
gccatggggc tcccaggcca agccaccttg cagagtttgg aggaattaga tctatcgatg 4140
aaccccctgg gggacggctg tggccagtcc ctggcctccc tcctgcacgc ctgcccctta 4200
ctcagcaccc tgcgcctgca ggcgtgtggc ttcggcccca gcttctttct gagccaccag 4260
acagcactgg gtagtgcttt ccaagatgct gagcacctga agaccctgtc cctgtcctac 4320
aacgccctgg gagcccctgc cctggccagg accctgcaga gcctgcccgc cggcaccctc 4380
ctgcacttag agctcagctc cgtggcagcc ggcaagggtg attcggacct catggagcct 4440
gtattccgat acctggccaa ggaaggctgt gctctagccc acctgaccct gtctgcaaac 4500
cacctggggg acaaggctgt tagagacctg tgcagatgtc tctctctgtg cccctcactc 4560
atctcactgg atctgtctgc caaccctgag atcagctgtg ccagcttgga agagctcctg 4620
tccaccctcc aaaagcggcc ccaaggcctt agcttccttg gcctgtcagg ctgcgccgtc 4680
cagggtcccc tgggcctggg cctgtgggac aagatagccg cgcagctccg ggaactgcag 4740
ctgtgcagca gacgcctctg cgctgaggac agggacgccc tgcgccagct gcagcccagt 4800
cggccgggcc ccggcgagtg cacgctggac cacggctcca agctcttctt tcggcgcctc 4860
tag 4863

<210> SEQ ID NO 7
<211> LENGTH: 4137
<212> TYPE: DNA
<213> ORGANISM: Artificial sequence
<220> FEATURE:
<223> OTHER INFORMATION: DNA encoding mutant protein

<400> SEQUENCE: 7
atgagcctgg agcgcgagct tcgccagctg agcaaggcga aagccaaggc gcagagggcc 60
gggcagcggc gcgaagaggc cgcgctgtgc caccagctgg gggagctcct ggccggccat 120
ggccgctacg ccgaggctct ggagcagcac tggcaggagc tgcagcttcg ggagcgcgct 180
gacgaccctc tgggctgtgc cgtggcccac cgcaagatcg gagagcgcct ggccgagatg 240
gaggactacc cggctgcctt gcagcaccag caccagtacc tggagctggc acattccctg 300
cgcaaccaca cggagctgca gagggcctgg gccaccatcg gccgcaccca cctggacatc 360
tatgaccact gccagtcgag ggatgctttg ctgcaggcac aggctgcctt tgagaagagc 420
ttggctattg tggatgagga gctggagggg acactggccc agggagagct gaatgagatg 480
aggacccgcc tctatctcaa cctgggcctc acctttgaga gcctgcagca gacagccctg 540
tgcaacgatt acttcaggaa gagcatcttc cttgcggagc agaaccacct ttacgaggac 600
ctattccgcg cccgctacaa cctgggcacc atccactggc gcgcgggcca gcactcccag 660
gctatgcgct gcttggaggg tgcccgggag tgtgcgcaca ccatgaggaa gcggttcatg 720

-continued

```
gagagcgagt gctgcgtggt tattgcacag gtcctccaag acctgggaga ctttttggct    780
gccaagcgag ccctgaagaa ggcctacagg ctgggctccc agaagcctgt gcagagggca    840
gccatctgtc agaacctcca gcatgtgctg gcagtggtcc ggctgcagca acagctggaa    900
gaggctgagg gcagagaccc tcagggtgcc atggtcatct gtgagcagct aggggacctc    960
ttctccaagg caggagactt tcccagggca gctgaggctt accagaagca gctgcgtttt   1020
gctgagctgc tggacagacc gggtgctgag cgggccatca tccacgtgtc cctggccacc   1080
acactgggag acatgaagga ccaccatggg gccgtgcgcc actatgagga ggaactgagg   1140
ctgcgcagcg gcaacgtgct ggaggaggcc aagacctggc tgaacattgc actgtcccgc   1200
gaggaggccg gcgatgccta cgagctgctg gccccgtgct tccagaaagc gctcagctgt   1260
gcccagcagg cccagcgtcc ccagctgcag aggcaggtct tgcagcatct ccataccgtg   1320
cagctgaggc tgcagcccca ggaggcccct gagaccgaaa ccagactgcg ggagctcagt   1380
gtagctgaag atgaagatga ggaggaggag gcggaggagg cggcagccac agcggagagc   1440
gaagccctgg aggccggcga ggtggagctc tcagagggcg aggacgacac cgatggcctg   1500
accccgcagc tggaggagga cgaggagctt cagggccacc tgggccggcg gaaggggagc   1560
aagtggaacc ggcgaaacga catgggggag accctgctgc accgagcctg catcgagggc   1620
cagctgcgcc gcgtccagga ccttgtgagg cagggccacc cccttaaccc tcgggactac   1680
tgtggcgcga cacctctgca cgaggcctgc aactacgggc atctagaaat tgtccgcttc   1740
ctgctggacc acggggccgc agtggacgac ccaggtggcc agggctgcga aggcatcacc   1800
cccctccacg atgccctcaa ctgtggccac ttcgaggtgg ctgagctgct gcttgaacgg   1860
ggggcgtccg tcaccctccg cactcgaaag ggcctcagcc cgctggagac gctgcagcag   1920
tgggtgaagc tgtaccgcag ggacctggac ctggagacgc ggcagaaggc cagggccatg   1980
gagatgctgc tccaggcggc tgcctcgggc caagatcccc acagctccca ggccttccac   2040
accccaagca gccttctgtt tgaccccgag acctctcctc ctttgagccc ctgcccagaa   2100
ccccctcta atagcactag actcccagag gcctctcagg tccatgtcag ggtctcccca   2160
gggcaggcgg caccagccat ggccaggcct cggaggagca ggcatgggcc agccagcagc   2220
agcagcagct cagaaggcga ggacagcgca ggccccgcac ggccgtccca gaagaggcct   2280
cggtgctcgg ccacagcaca acgggtggca gcctggacgc ctggccccgc cagcaacagg   2340
gaagcagcca cagccagcac cagccgggca gcctaccagg cagccatccg gggtgtgggc   2400
agtgctcaga gccggctggg gcctggccca ccgcggggcc acagcaaagc ccttgccccc   2460
caggcagcgc tcatcccgga ggaggagtgc ctggctgggg actggctgga gctggacatg   2520
cccctgaccc gcagccgccg gccccgcccc cggggcactg gagacaaccg caggcccagt   2580
agtacctctg ggtcggacag tgaggagagc aggccccgtg cccgagccaa gcaggtccgc   2640
ctgacctgca tgcagagttg cagtgcgcca gttaacgcag ggcccagcag cctggcttca   2700
gaacctccag ggagccccag cacccccagg gtctcagagc ccagtgggga cagctctgcg   2760
gcaggccagc ccttgggtcc ggccccgccc cctcccatcc gggttcgagt tcaagttcag   2820
gatcatctct tcctcatccc tgtcccacac agcagtgaca cccactctgt ggcctggctg   2880
gccgagcagg cggcccagcg ctactaccag acctgcgggc tgctgcccag gctcacccta   2940
cggaaagagg gggccctgct ggccccacag gacctcatcc ctgatgtgct gcagagcaat   3000
gacgaggtgt tggctgaggt gacttcgtgg gacctgcccc cgttgactga ccgctaccgc   3060
agggcctgcc agagcctggg gcaaggggag caccaacagg tgctgcaggc cgtggagctc   3120
```

cagggcttgg gcctctcgtt cagcgcctgc tccctggccc tggaccaggc ccagcttaca 3180
cccctgctgc gggccctcaa gctgcacaca gcactccggg agctgcgcct ggcagggaac 3240
cggctggggg acaagtgtgt ggctgagctg gtggctgccc tgggcaccat gcccagcctg 3300
gccctccttg acctctcctc caatcacctg ggtcccgaag gcctgcgcca gcttgccatg 3360
gggctcccag gccaagccac cttgcagagt ttggaggaat tagatctatc gatgaacccc 3420
ctgggggacg gctgtggcca gtccctggcc tccctcctgc acgcctgccc cttactcagc 3480
accctgcgcc tgcaggcgtg tggcttcggc cccagcttct ttctgagcca ccagacagca 3540
ctgggtagtg ctttccaaga tgctgagcac ctgaagaccc tgtccctgtc ctacaacgcc 3600
ctgggagccc ctgccctggc caggaccctg cagagcctgc ccgccggcac cctcctgcac 3660
ttagagctca gctccgtggc agccggcaag ggtgattcgg acctcatgga gcctgtattc 3720
cgatacctgg ccaaggaagg ctgtgctcta gcccacctga ccctgtctgc aaaccacctg 3780
ggggacaagg ctgttagaga cctgtgcaga tgtctctctc tgtgcccctc actcatctca 3840
ctggatctgt ctgccaaccc tgagatcagc tgtgccagct tggaagagct cctgtccacc 3900
ctccaaaagc ggccccaagg ccttagcttc cttggcctgt caggctgcgc cgtccagggt 3960
cccctgggcc tgggcctgtg ggacaagata gccgcgcagc tccgggaact gcagctgtgc 4020
agcagacgcc tctgcgctga ggacagggac gccctgcgcc agctgcagcc cagtcggccg 4080
ggccccggcg agtgcacgct ggaccacggc tccaagctct tctttcggcg cctctag 4137

<210> SEQ ID NO 8
<211> LENGTH: 4863
<212> TYPE: DNA
<213> ORGANISM: Artificial sequence
<220> FEATURE:
<223> OTHER INFORMATION: DNA encoding fusion protein

<400> SEQUENCE: 8
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaagg tgaacttcaa gatccgccac aacatcgagg acggcagcgt gcagctcgcc 540
gaccactacc agcagaacac ccccatcggc gacggccccg tgctgctgcc cgacaaccac 600
tacctgagca cccagtccgc cctgagcaaa gaccccaacg agaagcgcga tcacatggtc 660
ctgctggagt tcgtgaccgc cgccgggatc actctcggca tggacgagct gtacaagggc 720
gcgccaatga gcctggagcg cgagcttcgc cagctgagca aggcgaaagc caaggcgcag 780
agggccgggc agcggcgcga agaggccgcg ctgtgccacc agctggggga gctcctggcc 840
ggccatggcc gctacgccga ggctctggag cagcactggc aggagctgca gcttcgggag 900
cgcgctgacg accctctggg ctgtgccgtg gcccaccgca agatcggaga gcgcctggcc 960
gagatggagg actacccggc tgccttgcag caccagcacc agtacctgga gctggcacat 1020

-continued

```
tccctgcgca accacacgga gctgcagagg gcctgggcca ccatcggccg cacccacctg   1080

gacatctatg accactgcca gtcgagggat gctttgctgc aggcacaggc tgcctttgag   1140

aagagcttgg ctattgtgga tgaggagctg gaggggacac tggcccaggg agagctgaat   1200

gagatgagga cccgcctcta tctcaacctg ggcctcacct ttgagagcct gcagcagaca   1260

gccctgtgca acgattactt caggaagagc atcttccttg cggagcagaa ccacctttac   1320

gaggacctat tccgcgcccg ctacaacctg ggcaccatcc actggcgcgc gggccagcac   1380

tcccaggcta tgcgctgctt ggagggtgcc cgggagtgtg cgcacaccat gaggaagcgg   1440

ttcatggaga gcgagtgctg cgtggttatt gcacaggtcc tccaagacct gggagacttt   1500

ttggctgcca agcgagccct gaagaaggcc tacaggctgg gctcccagaa gcctgtgcag   1560

agggcagcca tctgtcagaa cctccagcat gtgctggcag tggtccggct gcagcaacag   1620

ctggaagagg ctgagggcag agaccctcag ggtgccatgg tcatctgtga gcagctaggg   1680

gacctcttct ccaaggcagg agactttccc agggcagctg aggcttacca gaagcagctg   1740

cgttttgctg agctgctgga cagaccgggt gctgagcggg ccatcatcca cgtgtccctg   1800

gccaccacac tgggagacat gaaggaccac catggggccg tgcgccacta tgaggaggaa   1860

ctgaggctgc gcagcggcaa cgtgctggag gaggccaaga cctggctgaa cattgcactg   1920

tcccgcgagg aggccggcga tgcctacgag ctgctggccc cgtgcttcca gaaagcgctc   1980

agctgtgccc agcaggccca gcgtccccag ctgcagaggc aggtcttgca gcatctccat   2040

accgtgcagc tgaggctgca gccccaggag gcccctgaga ccgaaaccag actgcgggag   2100

ctcagtgtag ctgaagatga agatgaggag gaggaggcgg aggaggcggc agccacagcg   2160

gagagcgaag ccctggaggc cggcgaggtg gagctctcag agggcgagga cgacaccgat   2220

ggcctgaccc cgcagctgga ggaggacgag gagcttcagg gccacctggg ccggcggaag   2280

gggagcaagt ggaaccggcg aaacgacatg ggggagaccc tgctgcaccg agcctgcatc   2340

gagggccagc tgcgccgcgt ccaggacctt gtgaggcagg gccacccccct taaccctcgg   2400

gactactgtg gcgcgacacc tctgcacgag gcctgcaact acgggcatct agaaattgtc   2460

cgcttcctgc tggaccacgg ggccgcagtg gacgacccag gtggccaggg ctgcgaaggc   2520

atcacccccc tccacgatgc cctcaactgt ggccacttcg aggtggctga gctgctgctt   2580

gaacgggggg cgtccgtcac cctccgcact cgaaagggcc tcagcccgct ggagacgctg   2640

cagcagtggg tgaagctgta ccgcagggac ctggacctgg agacgcggca gaaggccagg   2700

gccatggaga tgctgctcca ggcggctgcc tcgggccaag atccccacag ctcccaggcc   2760

ttccacaccc caagcagcct tctgtttgac cccgagacct ctcctccttt gagcccctgc   2820

ccagaacccc cctctaatag cactagactc ccagaggcct ctcaggtcca tgtcagggtc   2880

tccccagggc aggcggcacc agccatggcc aggcctcgga ggagcaggca tgggccagcc   2940

agcagcagca gcagctcaga aggcgaggac agcgcaggcc ccgcacggcc gtcccagaag   3000

aggcctcggt gctcggccac agcacaacgg gtggcagcct ggacgcctgg ccccgccagc   3060

aacagggaag cagccacagc cagcaccagc cgggcagcct accaggcagc catccggggt   3120

gtgggcagtg ctcagagccg gctggggcct ggcccaccgc ggggccacag caaagccctt   3180

gccccccagg cagcgctcat cccggaggag gagtgcctgg ctggggactg gctggagctg   3240

gacatgcccc tgacccgcag ccgccggccc cgcccccggg gcactggaga caaccgcagg   3300

cccagtagta cctctgggtc ggacagtgag gagagcaggc cccgtgcccg agccaagcag   3360

gtccgcctga cctgcatgca gagttgcagt gcgccagtta acgcagggcc cagcagcctg   3420
```

gcttcagaac ctccagggag ccccagcacc cccagggtct cagagcccag tggggacagc 3480
tctgcggcag gccagccctt gggtccggcc ccgccccctc ccatccgggt tcgagttcaa 3540
gttcaggatc atctcttcct catccctgtc ccacacagca gtgacaccca ctctgtggcc 3600
tggctggccg agcaggcggc ccagcgctac taccagacct gcgggctgct gcccaggctc 3660
accctacgga aagagggggc cctgctggcc ccacaggacc tcatccctga tgtgctgcag 3720
agcaatgacg aggtgttggc tgaggtgact tcgtgggacc tgccccccgtt gactgaccgc 3780 taccgcaggg cctgccagag cctggggcaa ggggagcacc aacaggtgct gcaggccgtg 3840
gagctccagg gcttgggcct ctcgttcagc gcctgctccc tggccctgga ccaggcccag 3900
cttacacccc tgctgcgggc cctcaagctg cacacagcac tccgggagct gcgcctggca 3960
gggaaccggc tgggggacaa gtgtgtggct gagctggtgg ctgccctggg caccatgccc 4020
agcctggccc tccttgacct ctcctccaat cacctgggtc ccgaaggcct gcgccagctt 4080
gccatggggc tcccaggcca agccaccttg cagagtttgg aggaattaga tctatcgatg 4140
aaccccctgg gggacggctg tggccagtcc ctggcctccc tcctgcacgc ctgcccctta 4200
ctcagcaccc tgcgcctgca ggcgtgtggc ttcggcccca gcttctttct gagccaccag 4260
acagcactgg gtagtgcttt ccaagatgct gagcacctga agaccctgtc cctgtcctac 4320
aacgccctgg gagcccctgc cctggccagg accctgcaga gcctgcccgc cggcaccctc 4380
ctgcacttag agctcagctc cgtggcagcc ggcaagggtg attcggacct catggagcct 4440
gtattccgat acctggccaa ggaaggctgt gctctagccc acctgaccct gtctgcaaac 4500
cacctggggg acaaggctgt tagagacctg tgcagatgtc tctctctgtg cccctcactc 4560
atctcactgg atctgtctgc caaccctgag atcagctgtg ccagcttgga agagctcctg 4620
tccaccctcc aaaagcggcc ccaaggcctt agcttccttg gcctgtcagg ctgcgccgtc 4680
cagggtcccc tgggcctggg cctgtgggac aagatagccg cgcagctccg ggaactgcag 4740
ctgtgcagca gacgcctctg cgctgaggac agggacgccc tgcgccagct gcagcccagt 4800
cggccgggcc ccggcgagtg cacgctggac cacggctcca agctcttctt tcggcgcctc 4860
tag 4863

<210> SEQ ID NO 9
<211> LENGTH: 4137
<212> TYPE: DNA
<213> ORGANISM: Artificial sequence
<220> FEATURE:
<223> OTHER INFORMATION: DNA encoding mutant protein

<400> SEQUENCE: 9
atgagcctgg agcgcgagct tcgccagctg agcaaggcga aagccaaggc gcagagggcc 60
gggcagcggc gcgaagaggc cgcgctgtgc caccagctgg gggagctcct ggccggccat 120
ggccgctacg ccgaggctct ggagcagcac tggcaggagc tgcagcttcg ggagcgcgct 180
gacgaccctc tgggctgtgc cgtggcccac cgcaagatcg gagagcgcct ggccgagatg 240
gaggactacc cggctgcctt gcagcaccag caccagtacc tggagctggc acattccctg 300
cgcaaccaca cggagctgca gagggcctgg gccaccatcg gccgcaccca cctggacatc 360
tatgaccact gccagtcgag ggatgctttg ctgcaggcac aggctgcctt tgagaagagc 420
ttggctattg tggatgagga gctggagggg acactggccc agggagagct gaatgagatg 480
aggacccgcc tctatctcaa cctgggcctc acctttgaga gcctgcagca gacagccctg 540

-continued

```
tgcaacgatt acttcaggaa gagcatcttc cttgcggagc agaaccacct ttacgaggac    600
ctattccgcg cccgctacaa cctgggcacc atccactggc gcgcgggcca gcactcccag    660
gctatgcgct gcttggaggg tgcccgggag tgtgcgcaca ccatgaggaa gcggttcatg    720
gagagcgagt gctgcgtggt tattgcacag gtcctccaag acctgggaga ctttttggct    780
gccaagcgag ccctgaagaa ggcctacagg ctgggctccc agaagcctgt gcagagggca    840
gccatctgtc agaacctcca gcatgtgctg gcagtggtcc ggctgcagca acagctggaa    900
gaggctgagg gcagagaccc tcagggtgcc atggtcatct gtgagcagct aggggacctc    960
ttctccaagg caggagactt tcccagggca gctgaggctt accagaagca gctgcgtttt   1020
gctgagctgc tggacagacc gggtgctgag cgggccatca tccacgtgtc cctggccacc   1080
acactgggag acatgaagga ccaccatggg gccgtgcgcc actatgagga ggaactgagg   1140
ctgcgcagcg gcaacgtgct ggaggaggcc aagacctggc tgaacattgc actgtcccgc   1200
gaggaggccg gcgatgccta cgagctgctg gccccgtgct tccagaaagc gctcagctgt   1260
gcccagcagg cccagcgtcc ccagctgcag aggcaggtct tgcagcatct ccataccgtg   1320
cagctgaggc tgcagcccca ggaggcccct gagaccgaaa ccagactgcg ggagctcagt   1380
gtagctgaag atgaagatga ggaggaggag gcggaggagg cggcagccac agcggagagc   1440
gaagccctgg aggccggcga ggtggagctc tcagagggcg aggacgacac cgatggcctg   1500
accccgcagc tggaggagga cgaggagctt cagggccacc tgggccggcg gaaggggagc   1560
aagtggaacc ggcgaaacga catgggggag accctgctgc accgagcctg catcgagggc   1620
cagctgcgcc gcgtccagga ccttgtgagg cagggccacc cccttaaccc tcgggactac   1680
tgtggctgga cacctctgca cgcggcctgc aactacgggc atctagaaat tgtccgcttc   1740
ctgctggacc acggggccgc agtggacgac ccaggtggcc agggctgcga aggcatcacc   1800
cccctccacg atgccctcaa ctgtggccac ttcgaggtgg ctgagctgct gcttgaacgg   1860
ggggcgtccg tcaccctccg cactcgaaag ggcctcagcc cgctggagac gctgcagcag   1920
tgggtgaagc tgtaccgcag ggacctggac ctggagacgc ggcagaaggc cagggccatg   1980
gagatgctgc tccaggcggc tgcctcgggc caagatcccc acagctccca ggccttccac   2040
accccaagca gccttctgtt tgaccccgag acctctcctc ctttgagccc ctgcccagaa   2100
cccccctcta atagcactag actcccagag gcctctcagg tccatgtcag ggtctcccca   2160
gggcaggcgg caccagccat ggccaggcct cggaggagca ggcatgggcc agccagcagc   2220
agcagcagct cagaaggcga ggacagcgca ggccccgcac ggccgtccca gaagaggcct   2280
cggtgctcgg ccacagcaca acgggtggca gcctggacgc ctggccccgc cagcaacagg   2340
gaagcagcca cagccagcac cagccgggca gcctaccagg cagccatccg gggtgtgggc   2400
agtgctcaga gccggctggg gcctggccca ccgcggggcc acagcaaagc ccttgccccc   2460
caggcagcgc tcatcccgga ggaggagtgc ctggctgggg actggctgga gctggacatg   2520
cccctgaccc gcagccgccg gccccgcccc cggggcactg gagacaaccg caggcccagt   2580
agtacctctg ggtcggacag tgaggagagc aggccccgtg cccgagccaa gcaggtccgc   2640
ctgacctgca tgcagagttg cagtgcgcca gttaacgcag ggcccagcag cctggcttca   2700
gaacctccag ggagccccag cacccccagg gtctcagagc ccagtgggga cagctctgcg   2760
gcaggccagc ccttgggtcc ggccccgccc cctcccatcc gggttcgagt tcaagttcag   2820
gatcatctct tcctcatccc tgtcccacac agcagtgaca cccactctgt ggcctggctg   2880
gccgagcagg cggcccagcg ctactaccag acctgcgggc tgctgcccag gctcacccta   2940
```

cggaaagagg gggccctgct ggccccacag gacctcatcc ctgatgtgct gcagagcaat 3000
gacgaggtgt tggctgaggt gacttcgtgg gacctgcccc cgttgactga ccgctaccgc 3060
agggcctgcc agagcctggg gcaaggggag caccaacagg tgctgcaggc cgtggagctc 3120
cagggcttgg gcctctcgtt cagcgcctgc tccctggccc tggaccaggc ccagcttaca 3180
cccctgctgc gggccctcaa gctgcacaca gcactccggg agctgcgcct ggcagggaac 3240
cggctggggg acaagtgtgt ggctgagctg gtggctgccc tgggcaccat gcccagcctg 3300
gccctccttg acctctcctc caatcacctg ggtcccgaag gcctgcgcca gcttgccatg 3360
gggctcccag gccaagccac cttgcagagt ttggaggaat tagatctatc gatgaacccc 3420
ctgggggacg gctgtggcca gtccctggcc tccctcctgc acgcctgccc cttactcagc 3480
accctgcgcc tgcaggcgtg tggcttcggc cccagcttct ttctgagcca ccagacagca 3540
ctgggtagtg ctttccaaga tgctgagcac ctgaagaccc tgtccctgtc ctacaacgcc 3600
ctgggagccc ctgccctggc caggaccctg cagagcctgc ccgccggcac cctcctgcac 3660
ttagagctca gctccgtggc agccggcaag ggtgattcgg acctcatgga gcctgtattc 3720
cgatacctgg ccaaggaagg ctgtgctcta gcccacctga ccctgtctgc aaaccacctg 3780
ggggacaagg ctgttagaga cctgtgcaga tgtctctctc tgtgcccctc actcatctca 3840
ctggatctgt ctgccaaccc tgagatcagc tgtgccagct tggaagagct cctgtccacc 3900
ctccaaaagc ggccccaagg ccttagcttc cttggcctgt caggctgcgc cgtccagggt 3960
cccctgggcc tgggcctgtg ggacaagata gccgcgcagc tccgggaact gcagctgtgc 4020
agcagacgcc tctgcgctga ggacagggac gccctgcgcc agctgcagcc cagtcggccg 4080
ggccccggcg agtgcacgct ggaccacggc tccaagctct tctttcggcg cctctag 4137

<210> SEQ ID NO 10
<211> LENGTH: 4863
<212> TYPE: DNA
<213> ORGANISM: Artificial sequence
<220> FEATURE:
<223> OTHER INFORMATION: DNA encoding fusion protein

<400> SEQUENCE: 10
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaagg tgaacttcaa gatccgccac aacatcgagg acggcagcgt gcagctcgcc 540
gaccactacc agcagaacac ccccatcggc gacggccccg tgctgctgcc cgacaaccac 600
tacctgagca cccagtccgc cctgagcaaa gaccccaacg agaagcgcga tcacatggtc 660
ctgctggagt tcgtgaccgc cgccgggatc actctcggca tggacgagct gtacaagggc 720
gcgccaatga gcctggagcg cgagcttcgc cagctgagca aggcgaaagc caaggcgcag 780
agggccgggc agcggcgcga agaggccgcg ctgtgccacc agctggggga gctcctggcc 840

-continued

```
ggccatggcc gctacgccga ggctctggag cagcactggc aggagctgca gcttcgggag    900
cgcgctgacg accctctggg ctgtgccgtg gcccaccgca agatcggaga gcgcctggcc    960
gagatggagg actacccggc tgccttgcag caccagcacc agtacctgga gctggcacat   1020
tccctgcgca accacacgga gctgcagagg gcctgggcca ccatcggccg cacccacctg   1080
gacatctatg accactgcca gtcgagggat gctttgctgc aggcacaggc tgcctttgag   1140
aagagcttgg ctattgtgga tgaggagctg gaggggacac tggcccaggg agagctgaat   1200
gagatgagga cccgcctcta tctcaacctg ggcctcacct ttgagagcct gcagcagaca   1260
gccctgtgca acgattactt caggaagagc atcttccttg cggagcagaa ccacctttac   1320
gaggacctat tccgcgcccg ctacaacctg ggcaccatcc actggcgcgc gggccagcac   1380
tcccaggcta tgcgctgctt ggagggtgcc cgggagtgtg cgcacaccat gaggaagcgg   1440
ttcatggaga gcgagtgctg cgtggttatt gcacaggtcc tccaagacct gggagacttt   1500
ttggctgcca agcgagccct gaagaaggcc tacaggctgg gctcccagaa gcctgtgcag   1560
agggcagcca tctgtcagaa cctccagcat gtgctggcag tggtccggct gcagcaacag   1620
ctggaagagg ctgagggcag agaccctcag ggtgccatgg tcatctgtga gcagctaggg   1680
gacctcttct ccaaggcagg agactttccc agggcagctg aggcttacca gaagcagctg   1740
cgttttgctg agctgctgga cagaccgggt gctgagcggg ccatcatcca cgtgtccctg   1800
gccaccacac tgggagacat gaaggaccac catggggccg tgcgccacta tgaggaggaa   1860
ctgaggctgc gcagcggcaa cgtgctggag gaggccaaga cctggctgaa cattgcactg   1920
tcccgcgagg aggccggcga tgcctacgag ctgctggccc cgtgcttcca gaaagcgctc   1980
agctgtgccc agcaggccca gcgtccccag ctgcagaggc aggtcttgca gcatctccat   2040
accgtgcagc tgaggctgca gccccaggag gcccctgaga ccgaaaccag actgcgggag   2100
ctcagtgtag ctgaagatga agatgaggag gaggaggcgg aggaggcggc agccacagcg   2160
gagagcgaag ccctggaggc cggcgaggtg gagctctcag agggcgagga cgacaccgat   2220
ggcctgaccc cgcagctgga ggaggacgag gagcttcagg gccacctggg ccggcggaag   2280
gggagcaagt ggaaccggcg aaacgacatg ggggagaccc tgctgcaccg agcctgcatc   2340
gagggccagc tgcgccgcgt ccaggacctt gtgaggcagg gccacccccct taaccctcgg   2400
gactactgtg gctggacacc tctgcacgcg gcctgcaact acgggcatct agaaattgtc   2460
cgcttcctgc tggaccacgg ggccgcagtg gacgacccag gtggccaggg ctgcgaaggc   2520
atcacccccc tccacgatgc cctcaactgt ggccacttcg aggtggctga gctgctgctt   2580
gaacgggggg cgtccgtcac cctccgcact cgaaagggcc tcagcccgct ggagacgctg   2640
cagcagtggg tgaagctgta ccgcagggac ctggacctgg agacgcggca gaaggccagg   2700
gccatggaga tgctgctcca ggcggctgcc tcgggccaag atccccacag ctcccaggcc   2760
ttccacaccc caagcagcct tctgtttgac cccgagacct ctcctccttt gagcccctgc   2820
ccagaacccc cctctaatag cactagactc ccagaggcct ctcaggtcca tgtcagggtc   2880
tccccagggc aggcggcacc agccatggcc aggcctcgga ggagcaggca tgggccagcc   2940
agcagcagca gcagctcaga aggcgaggac agcgcaggcc ccgcacggcc gtcccagaag   3000
aggcctcggt gctcggccac agcacaacgg gtggcagcct ggacgcctgg ccccgccagc   3060
aacagggaag cagccacagc cagcaccagc cgggcagcct accaggcagc catccggggt   3120
gtgggcagtg ctcagagccg gctggggcct ggcccaccgc ggggccacag caaagccctt   3180
gccccccagg cagcgctcat cccggaggag gagtgcctgg ctggggactg gctggagctg   3240
```

gacatgcccc tgacccgcag ccgccggccc cgcccccggg gcactggaga caaccgcagg 3300
cccagtagta cctctgggtc ggacagtgag gagagcaggc cccgtgcccg agccaagcag 3360
gtccgcctga cctgcatgca gagttgcagt gcgccagtta acgcagggcc cagcagcctg 3420
gcttcagaac ctccagggag ccccagcacc cccagggtct cagagcccag tggggacagc 3480
tctgcggcag gccagccctt gggtccggcc ccgcccccctc ccatccgggt tcgagttcaa 3540
gttcaggatc atctcttcct catccctgtc ccacacagca gtgacaccca ctctgtggcc 3600
tggctggccg agcaggcggc ccagcgctac taccagacct gcgggctgct gcccaggctc 3660
accctacgga aagagggggc cctgctggcc ccacaggacc tcatccctga tgtgctgcag 3720
agcaatgacg aggtgttggc tgaggtgact tcgtgggacc tgcccccgtt gactgaccgc 3780
taccgcaggg cctgccagag cctggggcaa ggggagcacc aacaggtgct gcaggccgtg 3840
gagctccagg gcttgggcct ctcgttcagc gcctgctccc tggccctgga ccaggcccag 3900
cttacacccc tgctgcgggc cctcaagctg cacacagcac tccgggagct gcgcctggca 3960
gggaaccggc tgggggacaa gtgtgtggct gagctggtgg ctgccctggg caccatgccc 4020
agcctggccc tccttgacct ctcctccaat cacctgggtc ccgaaggcct gcgccagctt 4080
gccatggggc tcccaggcca agccaccttg cagagtttgg aggaattaga tctatcgatg 4140
aaccccctgg gggacggctg tggccagtcc ctggcctccc tcctgcacgc ctgcccctta 4200
ctcagcaccc tgcgcctgca ggcgtgtggc ttcggcccca gcttctttct gagccaccag 4260
acagcactgg gtagtgcttt ccaagatgct gagcacctga agaccctgtc cctgtcctac 4320
aacgccctgg gagcccctgc cctggccagg accctgcaga gcctgcccgc cggcaccctc 4380
ctgcacttag agctcagctc cgtggcagcc ggcaagggtg attcggacct catggagcct 4440
gtattccgat acctggccaa ggaaggctgt gctctagccc acctgaccct gtctgcaaac 4500
cacctggggg acaaggctgt tagagacctg tgcagatgtc tctctctgtg cccctcactc 4560
atctcactgg atctgtctgc caaccctgag atcagctgtg ccagcttgga agagctcctg 4620
tccaccctcc aaaagcggcc ccaaggcctt agcttccttg gcctgtcagg ctgcgccgtc 4680
cagggtcccc tgggcctggg cctgtgggac aagatagccg cgcagctccg ggaactgcag 4740
ctgtgcagca gacgcctctg cgctgaggac agggacgccc tgcgccagct gcagcccagt 4800
cggccgggcc ccggcgagtg cacgctggac cacggctcca agctcttctt tcggcgcctc 4860
tag 4863

<210> SEQ ID NO 11
<211> LENGTH: 4137
<212> TYPE: DNA
<213> ORGANISM: Artificial sequence
<220> FEATURE:
<223> OTHER INFORMATION: DNA encoding mutant protein

<400> SEQUENCE: 11
atgagcctgg agcgcgagct tcgccagctg agcaaggcga aagccaaggc gcagagggcc 60
gggcagcggc gcgaagaggc cgcgctgtgc caccagctgg gggagctcct ggccggccat 120
ggccgctacg ccgaggctct ggagcagcac tggcaggagc tgcagcttcg ggagcgcgct 180
gacgaccctc tgggctgtgc cgtggcccac cgcaagatcg gagagcgcct ggccgagatg 240
gaggactacc cggctgcctt gcagcaccag caccagtacc tggagctggc acattccctg 300
cgcaaccaca cggagctgca gagggcctgg gccaccatcg gccgcaccca cctggacatc 360

-continued

```
tatgaccact gccagtcgag ggatgctttg ctgcaggcac aggctgcctt tgagaagagc    420
ttggctattg tggatgagga gctggagggg acactggccc agggagagct gaatgagatg    480
aggacccgcc tctatctcaa cctgggcctc acctttgaga gcctgcagca gacagccctg    540
tgcaacgatt acttcaggaa gagcatcttc cttgcggagc agaaccacct ttacgaggac    600
ctattccgcg cccgctacaa cctgggcacc atccactggc gcgcgggcca gcactcccag    660
gctatgcgct gcttggaggg tgcccgggag tgtgcgcaca ccatgaggaa gcggttcatg    720
gagagcgagt gctgcgtggt tattgcacag gtcctccaag acctgggaga ctttttggct    780
gccaagcgag ccctgaagaa ggcctacagg ctgggctccc agaagcctgt gcagagggca    840
gccatctgtc agaacctcca gcatgtgctg gcagtggtcc ggctgcagca acagctggaa    900
gaggctgagg gcagagaccc tcagggtgcc atggtcatct gtgagcagct aggggacctc    960
ttctccaagg caggagactt tcccagggca gctgaggctt accagaagca gctgcgtttt   1020
gctgagctgc tggacagacc gggtgctgag cgggccatca tccacgtgtc cctggccacc   1080
acactgggag acatgaagga ccaccatggg gccgtgcgcc actatgagga ggaactgagg   1140
ctgcgcagcg gcaacgtgct ggaggaggcc aagacctggc tgaacattgc actgtcccgc   1200
gaggaggccg gcgatgccta cgagctgctg gccccgtgct tccagaaagc gctcagctgt   1260
gcccagcagg cccagcgtcc ccagctgcag aggcaggtct tgcagcatct ccataccgtg   1320
cagctgaggc tgcagcccca ggaggcccct gagaccgaaa ccagactgcg ggagctcagt   1380
gtagctgaag atgaagatga ggaggaggag gcggaggagg cggcagccac agcggagagc   1440
gaagccctgg aggccggcga ggtggagctc tcagagggcg aggacgacac cgatggcctg   1500
accccgcagc tggaggagga cgaggagctt cagggccacc tgggccggcg gaaggggagc   1560
aagtggaacc ggcgaaacga catgggggag accctgctgc accgagcctg catcgagggc   1620
cagctgcgcc gcgtccagga ccttgtgagg cagggccacc cccttaaccc tcgggactac   1680
tgtggctgga cacctctgca cgaggcctgc gcctacgggc atctagaaat tgtccgcttc   1740
ctgctggacc acggggccgc agtggacgac ccaggtggcc agggctgcga aggcatcacc   1800
cccctccacg atgccctcaa ctgtggccac ttcgaggtgg ctgagctgct gcttgaacgg   1860
ggggcgtccg tcaccctccg cactcgaaag ggcctcagcc cgctggagac gctgcagcag   1920
tgggtgaagc tgtaccgcag ggacctggac ctggagacgc ggcagaaggc cagggccatg   1980
gagatgctgc tccaggcggc tgcctcgggc caagatcccc acagctccca ggccttccac   2040
accccaagca gccttctgtt tgaccccgag acctctcctc ctttgagccc ctgcccagaa   2100
ccccccctcta atagcactag actcccagag gcctctcagg tccatgtcag ggtctcccca   2160
gggcaggcgg caccagccat ggccaggcct cggaggagca ggcatgggcc agccagcagc   2220
agcagcagct cagaaggcga ggacagcgca ggccccgcac ggccgtccca gaagaggcct   2280
cggtgctcgg ccacagcaca acgggtggca gcctggacgc ctggccccgc cagcaacagg   2340
gaagcagcca cagccagcac cagccgggca gcctaccagg cagccatccg gggtgtgggc   2400
agtgctcaga gccggctggg gcctggccca ccgcggggcc acagcaaagc ccttgccccc   2460
caggcagcgc tcatcccgga ggaggagtgc ctggctgggg actggctgga gctggacatg   2520
cccctgaccc gcagccgccg gccccgcccc cggggcactg gagacaaccg caggcccagt   2580
agtacctctg ggtcggacag tgaggagagc aggccccgtg cccgagccaa gcaggtccgc   2640
ctgacctgca tgcagagttg cagtgcgcca gttaacgcag ggcccagcag cctggcttca   2700
gaacctccag ggagccccag cacccccagg gtctcagagc ccagtgggga cagctctgcg   2760
```

gcaggccagc ccttgggtcc ggccccgccc cctcccatcc gggttcgagt tcaagttcag 2820
gatcatctct tcctcatccc tgtcccacac agcagtgaca cccactctgt ggcctggctg 2880
gccgagcagg cggcccagcg ctactaccag acctgcgggc tgctgcccag gctcacccta 2940
cggaaagagg gggccctgct ggccccacag gacctcatcc ctgatgtgct gcagagcaat 3000
gacgaggtgt tggctgaggt gacttcgtgg gacctgcccc cgttgactga ccgctaccgc 3060
agggcctgcc agagcctggg gcaaggggag caccaacagg tgctgcaggc cgtggagctc 3120
cagggcttgg gcctctcgtt cagcgcctgc tccctggccc tggaccaggc ccagcttaca 3180
cccctgctgc gggccctcaa gctgcacaca gcactccggg agctgcgcct ggcagggaac 3240
cggctggggg acaagtgtgt ggctgagctg gtggctgccc tgggcaccat gcccagcctg 3300
gccctccttg acctctcctc caatcacctg ggtcccgaag gcctgcgcca gcttgccatg 3360
gggctcccag gccaagccac cttgcagagt ttggaggaat tagatctatc gatgaacccc 3420
ctgggggacg gctgtggcca gtccctggcc tccctcctgc acgcctgccc cttactcagc 3480
accctgcgcc tgcaggcgtg tggcttcggc cccagcttct ttctgagcca ccagacagca 3540
ctgggtagtg ctttccaaga tgctgagcac ctgaagaccc tgtccctgtc ctacaacgcc 3600
ctgggagccc ctgccctggc caggaccctg cagagcctgc ccgccggcac cctcctgcac 3660
ttagagctca gctccgtggc agccggcaag ggtgattcgg acctcatgga gcctgtattc 3720
cgatacctgg ccaaggaagg ctgtgctcta gcccacctga ccctgtctgc aaaccacctg 3780
ggggacaagg ctgttagaga cctgtgcaga tgtctctctc tgtgcccctc actcatctca 3840
ctggatctgt ctgccaaccc tgagatcagc tgtgccagct tggaagagct cctgtccacc 3900
ctccaaaagc ggccccaagg ccttagcttc cttggcctgt caggctgcgc cgtccagggt 3960
cccctgggcc tgggcctgtg ggacaagata gccgcgcagc tccgggaact gcagctgtgc 4020
agcagacgcc tctgcgctga ggacagggac gccctgcgcc agctgcagcc cagtcggccg 4080
ggccccggcg agtgcacgct ggaccacggc tccaagctct tctttcggcg cctctag 4137

<210> SEQ ID NO 12
<211> LENGTH: 4863
<212> TYPE: DNA
<213> ORGANISM: Artificial sequence
<220> FEATURE:
<223> OTHER INFORMATION: DNA encoding fusion protein

<400> SEQUENCE: 12
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaagg tgaacttcaa gatccgccac aacatcgagg acggcagcgt gcagctcgcc 540
gaccactacc agcagaacac ccccatcggc gacggccccg tgctgctgcc cgacaaccac 600
tacctgagca cccagtccgc cctgagcaaa gaccccaacg agaagcgcga tcacatggtc 660

-continued

```
ctgctggagt tcgtgaccgc cgccgggatc actctcggca tggacgagct gtacaagggc    720
gcgccaatga gcctggagcg cgagcttcgc cagctgagca aggcgaaagc caaggcgcag    780
agggccgggc agcggcgcga agaggccgcg ctgtgccacc agctggggga gctcctggcc    840
ggccatggcc gctacgccga ggctctggag cagcactggc aggagctgca gcttcgggag    900
cgcgctgacg accctctggg ctgtgccgtg gcccaccgca agatcggaga gcgcctggcc    960
gagatggagg actacccggc tgccttgcag caccagcacc agtacctgga gctggcacat   1020
tccctgcgca accacacgga gctgcagagg gcctgggcca ccatcggccg cacccacctg   1080
gacatctatg accactgcca gtcgagggat gctttgctgc aggcacaggc tgcctttgag   1140
aagagcttgg ctattgtgga tgaggagctg gaggggacac tggcccaggg agagctgaat   1200
gagatgagga cccgcctcta tctcaacctg ggcctcacct ttgagagcct gcagcagaca   1260
gccctgtgca acgattactt caggaagagc atcttccttg cggagcagaa ccacctttac   1320
gaggacctat tccgcgcccg ctacaacctg ggcaccatcc actggcgcgc gggccagcac   1380
tcccaggcta tgcgctgctt ggagggtgcc cgggagtgtg cgcacaccat gaggaagcgg   1440
ttcatggaga gcgagtgctg cgtggttatt gcacaggtcc tccaagacct gggagacttt   1500
ttggctgcca agcgagccct gaagaaggcc tacaggctgg gctcccagaa gcctgtgcag   1560
agggcagcca tctgtcagaa cctccagcat gtgctggcag tggtccggct gcagcaacag   1620
ctggaagagg ctgagggcag agaccctcag ggtgccatgg tcatctgtga gcagctaggg   1680
gacctcttct ccaaggcagg agactttccc agggcagctg aggcttacca gaagcagctg   1740
cgttttgctg agctgctgga cagaccgggt gctgagcggg ccatcatcca cgtgtccctg   1800
gccaccacac tgggagacat gaaggaccac catggggccg tgcgccacta tgaggaggaa   1860
ctgaggctgc gcagcggcaa cgtgctggag gaggccaaga cctggctgaa cattgcactg   1920
tcccgcgagg aggccggcga tgcctacgag ctgctggccc cgtgcttcca gaaagcgctc   1980
agctgtgccc agcaggccca gcgtccccag ctgcagaggc aggtcttgca gcatctccat   2040
accgtgcagc tgaggctgca gccccaggag gcccctgaga ccgaaaccag actgcgggag   2100
ctcagtgtag ctgaagatga agatgaggag gaggaggcgg aggaggcggc agccacagcg   2160
gagagcgaag ccctggaggc cggcgaggtg gagctctcag agggcgagga cgacaccgat   2220
ggcctgaccc cgcagctgga ggaggacgag gagcttcagg gccacctggg ccggcggaag   2280
gggagcaagt ggaaccggcg aaacgacatg ggggagaccc tgctgcaccg agcctgcatc   2340
gagggccagc tgcgccgcgt ccaggacctt gtgaggcagg gccacccccct taaccctcgg   2400
gactactgtg gctggacacc tctgcacgag gcctgcgcct acgggcatct agaaattgtc   2460
cgcttcctgc tggaccacgg ggccgcagtg gacgacccag gtggccaggg ctgcgaaggc   2520
atcacccccc tccacgatgc cctcaactgt ggccacttcg aggtggctga gctgctgctt   2580
gaacgggggg cgtccgtcac cctccgcact cgaaagggcc tcagcccgct ggagacgctg   2640
cagcagtggg tgaagctgta ccgcagggac ctggacctgg agacgcggca gaaggccagg   2700
gccatggaga tgctgctcca ggcggctgcc tcgggccaag atccccacag ctcccaggcc   2760
ttccacaccc caagcagcct tctgtttgac cccgagacct ctcctccttt gagcccctgc   2820
ccagaacccc cctctaatag cactagactc ccagaggcct ctcaggtcca tgtcagggtc   2880
tccccagggc aggcggcacc agccatggcc aggcctcgga ggagcaggca tgggccagcc   2940
agcagcagca gcagctcaga aggcgaggac agcgcaggcc ccgcacggcc gtcccagaag   3000
aggcctcggt gctcggccac agcacaacgg gtggcagcct ggacgcctgg ccccgccagc   3060
```

-continued aacagggaag cagccacagc cagcaccagc cgggcagcct accaggcagc catccggggt 3120
gtgggcagtg ctcagagccg gctggggcct ggcccaccgc ggggccacag caaagccctt 3180
gccccccagg cagcgctcat cccggaggag gagtgcctgg ctggggactg gctggagctg 3240
gacatgcccc tgacccgcag ccgccggccc cgcccccggg gcactggaga caaccgcagg 3300
cccagtagta cctctgggtc ggacagtgag gagagcaggc cccgtgcccg agccaagcag 3360
gtccgcctga cctgcatgca gagttgcagt gcgccagtta acgcagggcc cagcagcctg 3420
gcttcagaac ctccagggag ccccagcacc cccagggtct cagagcccag tggggacagc 3480
tctgcggcag gccagccctt gggtccggcc ccgccccctc ccatccgggt tcgagttcaa 3540
gttcaggatc atctcttcct catccctgtc ccacacagca gtgacaccca ctctgtggcc 3600
tggctggccg agcaggcggc ccagcgctac taccagacct gcgggctgct gcccaggctc 3660
accctacgga aagagggggc cctgctggcc ccacaggacc tcatccctga tgtgctgcag 3720
agcaatgacg aggtgttggc tgaggtgact tcgtgggacc tgcccccgtt gactgaccgc 3780
taccgcaggg cctgccagag cctggggcaa ggggagcacc aacaggtgct gcaggccgtg 3840
gagctccagg gcttgggcct ctcgttcagc gcctgctccc tggccctgga ccaggcccag 3900
cttacacccc tgctgcgggc cctcaagctg cacacagcac tccgggagct gcgcctggca 3960
gggaaccggc tgggggacaa gtgtgtggct gagctggtgg ctgccctggg caccatgccc 4020
agcctggccc tccttgacct ctcctccaat cacctgggtc ccgaaggcct gcgccagctt 4080
gccatggggc tcccaggcca agccaccttg cagagtttgg aggaattaga tctatcgatg 4140
aaccccctgg gggacggctg tggccagtcc ctggcctccc tcctgcacgc ctgcccctta 4200
ctcagcaccc tgcgcctgca ggcgtgtggc ttcggcccca gcttctttct gagccaccag 4260
acagcactgg gtagtgcttt ccaagatgct gagcacctga agaccctgtc cctgtcctac 4320
aacgccctgg gagcccctgc cctggccagg accctgcaga gcctgcccgc cggcaccctc 4380
ctgcacttag agctcagctc cgtggcagcc ggcaagggtg attcggacct catggagcct 4440
gtattccgat acctggccaa ggaaggctgt gctctagccc acctgaccct gtctgcaaac 4500
cacctggggg acaaggctgt tagagacctg tgcagatgtc tctctctgtg cccctcactc 4560
atctcactgg atctgtctgc caaccctgag atcagctgtg ccagcttgga agagctcctg 4620
tccaccctcc aaaagcggcc ccaaggcctt agcttccttg gcctgtcagg ctgcgccgtc 4680
cagggtcccc tgggcctggg cctgtgggac aagatagccg cgcagctccg ggaactgcag 4740
ctgtgcagca gacgcctctg cgctgaggac agggacgccc tgcgccagct gcagcccagt 4800
cggccgggcc ccggcgagtg cacgctggac cacggctcca agctcttctt tcggcgcctc 4860
tag 4863

<210> SEQ ID NO 13
<211> LENGTH: 4137
<212> TYPE: DNA
<213> ORGANISM: Artificial sequence
<220> FEATURE:
<223> OTHER INFORMATION: DNA encoding mutant protein
<400> SEQUENCE: 13
atgagcctgg agcgcgagct tcgccagctg agcaaggcga aagccaaggc gcagagggcc 60
gggcagcggc gcgaagaggc cgcgctgtgc caccagctgg gggagctcct ggccggccat 120
ggccgctacg ccgaggctct ggagcagcac tggcaggagc tgcagcttcg ggagcgcgct 180

-continued

```
gacgaccctc tgggctgtgc cgtggcccac cgcaagatcg gagagcgcct ggccgagatg    240
gaggactacc cggctgcctt gcagcaccag caccagtacc tggagctggc acattccctg    300
cgcaaccaca cggagctgca gagggcctgg gccaccatcg gccgcaccca cctggacatc    360
tatgaccact gccagtcgag ggatgctttg ctgcaggcac aggctgcctt tgagaagagc    420
ttggctattg tggatgagga gctggagggg acactggccc agggagagct gaatgagatg    480
aggacccgcc tctatctcaa cctgggcctc acctttgaga gcctgcagca gacagccctg    540
tgcaacgatt acttcaggaa gagcatcttc cttgcggagc agaaccacct ttacgaggac    600
ctattccgcg cccgctacaa cctgggcacc atccactggc gcgcgggcca gcactcccag    660
gctatgcgct gcttggaggg tgcccgggag tgtgcgcaca ccatgaggaa gcggttcatg    720
gagagcgagt gctgcgtggt tattgcacag gtcctccaag acctgggaga ctttttggct    780
gccaagcgag ccctgaagaa ggcctacagg ctgggctccc agaagcctgt gcagagggca    840
gccatctgtc agaacctcca gcatgtgctg gcagtggtcc ggctgcagca acagctggaa    900
gaggctgagg gcagagaccc tcagggtgcc atggtcatct gtgagcagct aggggacctc    960
ttctccaagg caggagactt tcccagggca gctgaggctt accagaagca gctgcgtttt   1020
gctgagctgc tggacagacc gggtgctgag cgggccatca tccacgtgtc cctggccacc   1080
acactgggag acatgaagga ccaccatggg gccgtgcgcc actatgagga ggaactgagg   1140
ctgcgcagcg gcaacgtgct ggaggaggcc aagacctggc tgaacattgc actgtcccgc   1200
gaggaggccg gcgatgccta cgagctgctg gccccgtgct tccagaaagc gctcagctgt   1260
gcccagcagg cccagcgtcc ccagctgcag aggcaggtct tgcagcatct ccataccgtg   1320
cagctgaggc tgcagcccca ggaggcccct gagaccgaaa ccagactgcg ggagctcagt   1380
gtagctgaag atgaagatga ggaggaggag gcggaggagg cggcagccac agcggagagc   1440
gaagccctgg aggccggcga ggtggagctc tcagagggcg aggacgacac cgatggcctg   1500
accccgcagc tggaggagga cgaggagctt cagggccacc tgggccggcg gaaggggagc   1560
aagtggaacc ggcgaaacga catgggggag accctgctgc accgagcctg catcgagggc   1620
cagctgcgcc gcgtccagga ccttgtgagg cagggccacc cccttaaccc tcgggactac   1680
tgtggctgga cacctctgca cgaggcctgc aactacgggc atctagaaat tgtccgcttc   1740
ctgctggacc acggggccgc agtggacgac ccaggtggcc agggctgcga aggcatcacc   1800
cccctccacg ctgccctcaa ctgtggccac ttcgaggtgg ctgagctgct gcttgaacgg   1860
ggggcgtccg tcaccctccg cactcgaaag ggcctcagcc cgctggagac gctgcagcag   1920
tgggtgaagc tgtaccgcag ggacctggac ctggagacgc ggcagaaggc cagggccatg   1980
gagatgctgc tccaggcggc tgcctcgggc caagatcccc acagctccca ggccttccac   2040
accccaagca gccttctgtt tgaccccgag acctctcctc ctttgagccc ctgcccagaa   2100
ccccccctcta atagcactag actcccagag gcctctcagg tccatgtcag ggtctcccca   2160
gggcaggcgg caccagccat ggccaggcct cggaggagca ggcatgggcc agccagcagc   2220
agcagcagct cagaaggcga ggacagcgca ggccccgcac ggccgtccca gaagaggcct   2280
cggtgctcgg ccacagcaca acgggtggca gcctggacgc ctggccccgc cagcaacagg   2340
gaagcagcca cagccagcac cagccgggca gcctaccagg cagccatccg gggtgtgggc   2400
agtgctcaga gccggctggg gcctggccca ccgcggggcc acagcaaagc ccttgccccc   2460
caggcagcgc tcatcccgga ggaggagtgc ctggctgggg actggctgga gctggacatg   2520
cccctgaccc gcagccgccg gccccgcccc cggggcactg gagacaaccg caggcccagt   2580
```

agtacctctg ggtcggacag tgaggagagc aggccccgtg cccgagccaa gcaggtccgc 2640
ctgacctgca tgcagagttg cagtgcgcca gttaacgcag ggcccagcag cctggcttca 2700
gaacctccag ggagccccag cacccccagg gtctcagagc ccagtgggga cagctctgcg 2760
gcaggccagc ccttgggtcc ggccccgccc cctcccatcc gggttcgagt tcaagttcag 2820
gatcatctct tcctcatccc tgtcccacac agcagtgaca cccactctgt ggcctggctg 2880
gccgagcagg cggcccagcg ctactaccag acctgcgggc tgctgcccag gctcacccta 2940
cggaaagagg gggccctgct ggccccacag gacctcatcc ctgatgtgct gcagagcaat 3000
gacgaggtgt tggctgaggt gacttcgtgg gacctgcccc cgttgactga ccgctaccgc 3060
agggcctgcc agagcctggg gcaaggggag caccaacagg tgctgcaggc cgtggagctc 3120
cagggcttgg gcctctcgtt cagcgcctgc tccctggccc tggaccaggc ccagcttaca 3180
cccctgctgc gggccctcaa gctgcacaca gcactccggg agctgcgcct ggcagggaac 3240
cggctggggg acaagtgtgt ggctgagctg gtggctgccc tgggcaccat gcccagcctg 3300
gccctccttg acctctcctc caatcacctg ggtcccgaag gcctgcgcca gcttgccatg 3360
gggctcccag gccaagccac cttgcagagt ttggaggaat tagatctatc gatgaacccc 3420
ctgggggacg gctgtggcca gtccctggcc tccctcctgc acgcctgccc cttactcagc 3480
accctgcgcc tgcaggcgtg tggcttcggc cccagcttct ttctgagcca ccagacagca 3540
ctgggtagtg ctttccaaga tgctgagcac ctgaagaccc tgtccctgtc ctacaacgcc 3600
ctgggagccc ctgccctggc caggaccctg cagagcctgc ccgccggcac cctcctgcac 3660
ttagagctca gctccgtggc agccggcaag ggtgattcgg acctcatgga gcctgtattc 3720
cgatacctgg ccaaggaagg ctgtgctcta gcccacctga ccctgtctgc aaaccacctg 3780
ggggacaagg ctgttagaga cctgtgcaga tgtctctctc tgtgcccctc actcatctca 3840
ctggatctgt ctgccaaccc tgagatcagc tgtgccagct tggaagagct cctgtccacc 3900
ctccaaaagc ggccccaagg ccttagcttc cttggcctgt caggctgcgc cgtccagggt 3960
cccctgggcc tgggcctgtg ggacaagata gccgcgcagc tccgggaact gcagctgtgc 4020
agcagacgcc tctgcgctga ggacagggac gccctgcgcc agctgcagcc cagtcggccg 4080
ggccccggcg agtgcacgct ggaccacggc tccaagctct tctttcggcg cctctag 4137

<210> SEQ ID NO 14
<211> LENGTH: 4863
<212> TYPE: DNA
<213> ORGANISM: Artificial sequence
<220> FEATURE:
<223> OTHER INFORMATION: DNA encoding fusion protein

<400> SEQUENCE: 14
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480

-continued

```
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagggc    720
gcgccaatga gcctggagcg cgagcttcgc cagctgagca aggcgaaagc caaggcgcag    780
agggccgggc agcggcgcga agaggccgcg ctgtgccacc agctggggga gctcctggcc    840
ggccatggcc gctacgccga ggctctggag cagcactggc aggagctgca gcttcgggag    900
cgcgctgacg accctctggg ctgtgccgtg gcccaccgca agatcggaga gcgcctggcc    960
gagatggagg actacccggc tgccttgcag caccagcacc agtacctgga gctggcacat   1020
tccctgcgca accacacgga gctgcagagg gcctgggcca ccatcggccg cacccacctg   1080
gacatctatg accactgcca gtcgagggat gctttgctgc aggcacaggc tgcctttgag   1140
aagagcttgg ctattgtgga tgaggagctg gaggggacac tggcccaggg agagctgaat   1200
gagatgagga cccgcctcta tctcaacctg ggcctcacct ttgagagcct gcagcagaca   1260
gccctgtgca acgattactt caggaagagc atcttccttg cggagcagaa ccacctttac   1320
gaggacctat tccgcgcccg ctacaacctg ggcaccatcc actggcgcgc gggccagcac   1380
tcccaggcta tgcgctgctt ggagggtgcc cgggagtgtg cgcacaccat gaggaagcgg   1440
ttcatggaga gcgagtgctg cgtggttatt gcacaggtcc tccaagacct gggagacttt   1500
ttggctgcca agcgagccct gaagaaggcc tacaggctgg gctcccagaa gcctgtgcag   1560
agggcagcca tctgtcagaa cctccagcat gtgctggcag tggtccggct gcagcaacag   1620
ctggaagagg ctgagggcag agaccctcag ggtgccatgg tcatctgtga gcagctaggg   1680
gacctcttct ccaaggcagg agactttccc agggcagctg aggcttacca gaagcagctg   1740
cgttttgctg agctgctgga cagaccgggt gctgagcggg ccatcatcca cgtgtccctg   1800
gccaccacac tgggagacat gaaggaccac catggggccg tgcgccacta tgaggaggaa   1860
ctgaggctgc gcagcggcaa cgtgctggag gaggccaaga cctggctgaa cattgcactg   1920
tcccgcgagg aggccggcga tgcctacgag ctgctggccc cgtgcttcca gaaagcgctc   1980
agctgtgccc agcaggccca gcgtccccag ctgcagaggc aggtcttgca gcatctccat   2040
accgtgcagc tgaggctgca gccccaggag gcccctgaga ccgaaaccag actgcgggag   2100
ctcagtgtag ctgaagatga agatgaggag gaggaggcgg aggaggcggc agccacagcg   2160
gagagcgaag ccctggaggc cggcgaggtg gagctctcag agggcgagga cgacaccgat   2220
ggcctgaccc cgcagctgga ggaggacgag gagcttcagg gccacctggg ccggcggaag   2280
gggagcaagt ggaaccggcg aaacgacatg ggggagaccc tgctgcaccg agcctgcatc   2340
gagggccagc tgcgccgcgt ccaggacctt gtgaggcagg gccaccccct taaccctcgg   2400
gactactgtg gctggacacc tctgcacgag gcctgcaact acgggcatct agaaattgtc   2460
cgcttcctgc tggaccacgg ggccgcagtg gacgacccag gtggccaggg ctgcgaaggc   2520
atcacccccc tccacgctgc cctcaactgt ggccacttcg aggtggctga gctgctgctt   2580
gaacgggggg cgtccgtcac cctccgcact cgaaagggcc tcagcccgct ggagacgctg   2640
cagcagtggg tgaagctgta ccgcagggac ctggacctgg agacgcggca gaaggccagg   2700
gccatggaga tgctgctcca ggcggctgcc tcgggccaag atccccacag ctcccaggcc   2760
ttccacaccc caagcagcct tctgtttgac cccgagacct ctcctccttt gagcccctgc   2820
ccagaacccc cctctaatag cactagactc ccagaggcct ctcaggtcca tgtcagggtc   2880
```

-continued

```
tccccagggc aggcggcacc agccatggcc aggcctcgga ggagcaggca tgggccagcc   2940

agcagcagca gcagctcaga aggcgaggac agcgcaggcc ccgcacggcc gtcccagaag   3000

aggcctcggt gctcggccac agcacaacgg gtggcagcct ggacgcctgg ccccgccagc   3060

aacagggaag cagccacagc cagcaccagc cgggcagcct accaggcagc catccggggt   3120

gtgggcagtg ctcagagccg gctggggcct ggcccaccgc ggggccacag caaagccctt   3180

gccccccagg cagcgctcat cccggaggag gagtgcctgg ctggggactg gctggagctg   3240

gacatgcccc tgacccgcag ccgccggccc cgcccccggg gcactggaga caaccgcagg   3300

cccagtagta cctctgggtc ggacagtgag gagagcaggc cccgtgcccg agccaagcag   3360

gtccgcctga cctgcatgca gagttgcagt gcgccagtta acgcagggcc cagcagcctg   3420

gcttcagaac ctccagggag ccccagcacc cccagggtct cagagcccag tggggacagc   3480

tctgcggcag gccagccctt gggtccggcc ccgccccctc ccatccgggt tcgagttcaa   3540

gttcaggatc atctcttcct catccctgtc ccacacagca gtgacaccca ctctgtggcc   3600

tggctggccg agcaggcggc ccagcgctac taccagacct gcgggctgct gcccaggctc   3660

accctacgga aagaggggc cctgctggcc ccacaggacc tcatccctga tgtgctgcag   3720

agcaatgacg aggtgttggc tgaggtgact tcgtgggacc tgccccgtt gactgaccgc   3780

taccgcaggg cctgccagag cctggggcaa ggggagcacc aacaggtgct gcaggccgtg   3840

gagctccagg gcttgggcct ctcgttcagc gcctgctccc tggccctgga ccaggcccag   3900

cttacacccc tgctgcgggc cctcaagctg cacacagcac tccgggagct gcgcctggca   3960

gggaaccggc tgggggacaa gtgtgtggct gagctggtgg ctgccctggg caccatgccc   4020

agcctggccc tccttgacct ctcctccaat cacctgggtc ccgaaggcct gcgccagctt   4080

gccatggggc tcccaggcca agccaccttg cagagtttgg aggaattaga tctatcgatg   4140

aaccccctgg gggacggctg tggccagtcc ctggcctccc tcctgcacgc ctgcccctta   4200

ctcagcaccc tgcgcctgca ggcgtgtggc ttcggcccca gcttctttct gagccaccag   4260

acagcactgg gtagtgcttt ccaagatgct gagcacctga agaccctgtc cctgtcctac   4320

aacgccctgg gagcccctgc cctggccagg accctgcaga gcctgcccgc cggcaccctc   4380

ctgcacttag agctcagctc cgtggcagcc ggcaagggtg attcggacct catggagcct   4440

gtattccgat acctggccaa ggaaggctgt gctctagccc acctgaccct gtctgcaaac   4500

cacctggggg acaaggctgt tagagacctg tgcagatgtc tctctctgtg cccctcactc   4560

atctcactgg atctgtctgc caaccctgag atcagctgtg ccagcttgga agagctcctg   4620

tccaccctcc aaaagcggcc ccaaggcctt agcttccttg gcctgtcagg ctgcgccgtc   4680

cagggtcccc tgggcctggg cctgtgggac aagatagccg cgcagctccg ggaactgcag   4740

ctgtgcagca gacgcctctg cgctgaggac agggacgccc tgcgccagct gcagcccagt   4800

cggccgggcc ccggcgagtg cacgctggac cacggctcca agctcttctt tcggcgcctc   4860

tag                                                                 4863
```

<210> SEQ ID NO 15
<211> LENGTH: 780
<212> TYPE: DNA
<213> ORGANISM: Artificial sequence
<220> FEATURE:
<223> OTHER INFORMATION: DNA encoding fusion protein

<400> SEQUENCE: 15

-continued

```
ggatccgggc ccctggagga agaagaggat ggagaggagc tcattggaga tggcatggaa     60

agggactacc gcgccatccc agagctggac gcctatgagg ccgagggact ggctctggat    120

gatgaggacg tagaggagct gacggccagt cagagggagg cagcagagcg ggccatgcgg    180

cagcgtgacc gggaggctgg ccggggcctg ggccgaggag gtggaggtgg ccacctgggc    240

cggcggaagg ggagcaagtg gaaccggcga aacgacatgg gggagaccct gctgcaccga    300

gcctgcatcg agggccagct gcgccgcgtc caggaccttg tgaggcaggg ccacccccctt    360

aaccctcggg actactgtgg ctggacacct ctgcacgagg cctgcaacta cgggcatcta    420

gaaattgtcc gcttcctgct ggaccacggg gccgcagtgg acgacccagg tggccagggc    480

tgcgaaggca tcacccccct ccacgatgcc ctcaactgtg gccacttcga ggtggctgag    540

ctgctgcttg aacgggggggc gtccgtcacc ctccgcactc gaaagggcct cagcccgctg    600

gagacgctgc agcagtgggt gaagctgtac cgcagggacc tggacctgga gacgcggcag    660

aaggccaggg ccatggagat gctgctccag gcggctgcct cgggccaaga tccccacagc    720

tcccaggcct tccacacccc aagcagcctt ctgtttgacc ccgagacctc ttaactcgag    780
```

```
<210> SEQ ID NO 16
<211> LENGTH: 1378
<212> TYPE: PRT
<213> ORGANISM: Homo sapiens

<400> SEQUENCE: 16

Met Ser Leu Glu Arg Glu Leu Arg Gln Leu Ser Lys Ala Lys Ala Lys
1               5                   10                  15

Ala Gln Arg Ala Gly Gln Arg Arg Glu Glu Ala Ala Leu Cys His Gln
            20                  25                  30

Leu Gly Glu Leu Leu Ala Gly His Gly Arg Tyr Ala Glu Ala Leu Glu
        35                  40                  45

Gln His Trp Gln Glu Leu Gln Leu Arg Glu Arg Ala Asp Asp Pro Leu
    50                  55                  60

Gly Cys Ala Val Ala His Arg Lys Ile Gly Glu Arg Leu Ala Glu Met
65                  70                  75                  80

Glu Asp Tyr Pro Ala Ala Leu Gln His Gln His Gln Tyr Leu Glu Leu
                85                  90                  95

Ala His Ser Leu Arg Asn His Thr Glu Leu Gln Arg Ala Trp Ala Thr
            100                 105                 110

Ile Gly Arg Thr His Leu Asp Ile Tyr Asp His Cys Gln Ser Arg Asp
        115                 120                 125

Ala Leu Leu Gln Ala Gln Ala Ala Phe Glu Lys Ser Leu Ala Ile Val
    130                 135                 140

Asp Glu Glu Leu Glu Gly Thr Leu Ala Gln Gly Glu Leu Asn Glu Met
145                 150                 155                 160

Arg Thr Arg Leu Tyr Leu Asn Leu Gly Leu Thr Phe Glu Ser Leu Gln
                165                 170                 175

Gln Thr Ala Leu Cys Asn Asp Tyr Phe Arg Lys Ser Ile Phe Leu Ala
            180                 185                 190

Glu Gln Asn His Leu Tyr Glu Asp Leu Phe Arg Ala Arg Tyr Asn Leu
        195                 200                 205

Gly Thr Ile His Trp Arg Ala Gly Gln His Ser Gln Ala Met Arg Cys
    210                 215                 220

Leu Glu Gly Ala Arg Glu Cys Ala His Thr Met Arg Lys Arg Phe Met
225                 230                 235                 240
```

-continued

```
Glu Ser Glu Cys Cys Val Val Ile Ala Gln Val Leu Gln Asp Leu Gly
            245                 250                 255

Asp Phe Leu Ala Ala Lys Arg Ala Leu Lys Lys Ala Tyr Arg Leu Gly
            260                 265                 270

Ser Gln Lys Pro Val Gln Arg Ala Ala Ile Cys Gln Asn Leu Gln His
        275                 280                 285

Val Leu Ala Val Val Arg Leu Gln Gln Gln Leu Glu Glu Ala Glu Gly
    290                 295                 300

Arg Asp Pro Gln Gly Ala Met Val Ile Cys Glu Gln Leu Gly Asp Leu
305                 310                 315                 320

Phe Ser Lys Ala Gly Asp Phe Pro Arg Ala Ala Glu Ala Tyr Gln Lys
            325                 330                 335

Gln Leu Arg Phe Ala Glu Leu Leu Asp Arg Pro Gly Ala Glu Arg Ala
            340                 345                 350

Ile Ile His Val Ser Leu Ala Thr Thr Leu Gly Asp Met Lys Asp His
        355                 360                 365

His Gly Ala Val Arg His Tyr Glu Glu Glu Leu Arg Leu Arg Ser Gly
    370                 375                 380

Asn Val Leu Glu Glu Ala Lys Thr Trp Leu Asn Ile Ala Leu Ser Arg
385                 390                 395                 400

Glu Glu Ala Gly Asp Ala Tyr Glu Leu Leu Ala Pro Cys Phe Gln Lys
            405                 410                 415

Ala Leu Ser Cys Ala Gln Gln Ala Gln Arg Pro Gln Leu Gln Arg Gln
            420                 425                 430

Val Leu Gln His Leu His Thr Val Gln Leu Arg Leu Gln Pro Gln Glu
        435                 440                 445

Ala Pro Glu Thr Glu Thr Arg Leu Arg Glu Leu Ser Val Ala Glu Asp
    450                 455                 460

Glu Asp Glu Glu Glu Glu Ala Glu Glu Ala Ala Ala Thr Ala Glu Ser
465                 470                 475                 480

Glu Ala Leu Glu Ala Gly Glu Val Glu Leu Ser Glu Gly Glu Asp Asp
            485                 490                 495

Thr Asp Gly Leu Thr Pro Gln Leu Glu Glu Asp Glu Glu Leu Gln Gly
            500                 505                 510

His Leu Gly Arg Arg Lys Gly Ser Lys Trp Asn Arg Arg Asn Asp Met
        515                 520                 525

Gly Glu Thr Leu Leu His Arg Ala Cys Ile Glu Gly Gln Leu Arg Arg
    530                 535                 540

Val Gln Asp Leu Val Arg Gln Gly His Pro Leu Asn Pro Arg Asp Tyr
545                 550                 555                 560

Cys Gly Trp Thr Pro Leu His Glu Ala Cys Asn Tyr Gly His Leu Glu
            565                 570                 575

Ile Val Arg Phe Leu Leu Asp His Gly Ala Ala Val Asp Asp Pro Gly
            580                 585                 590

Gly Gln Gly Cys Glu Gly Ile Thr Pro Leu His Asp Ala Leu Asn Cys
        595                 600                 605

Gly His Phe Glu Val Ala Glu Leu Leu Leu Glu Arg Gly Ala Ser Val
    610                 615                 620

Thr Leu Arg Thr Arg Lys Gly Leu Ser Pro Leu Glu Thr Leu Gln Gln
625                 630                 635                 640

Trp Val Lys Leu Tyr Arg Arg Asp Leu Asp Leu Glu Thr Arg Gln Lys
            645                 650                 655

Ala Arg Ala Met Glu Met Leu Leu Gln Ala Ala Ala Ser Gly Gln Asp
```

-continued

```
            660                 665                 670

Pro His Ser Ser Gln Ala Phe His Thr Pro Ser Ser Leu Leu Phe Asp
        675                 680                 685

Pro Glu Thr Ser Pro Pro Leu Ser Pro Cys Pro Glu Pro Pro Ser Asn
    690                 695                 700

Ser Thr Arg Leu Pro Glu Ala Ser Gln Ala His Val Arg Val Ser Pro
705                 710                 715                 720

Gly Gln Ala Ala Pro Ala Met Ala Arg Pro Arg Arg Ser Arg His Gly
                725                 730                 735

Pro Ala Ser Ser Ser Ser Ser Ser Glu Gly Glu Asp Ser Ala Gly Pro
            740                 745                 750

Ala Arg Pro Ser Gln Lys Arg Pro Arg Cys Ser Ala Thr Ala Gln Arg
        755                 760                 765

Val Ala Ala Trp Thr Pro Gly Pro Ala Ser Asn Arg Glu Ala Ala Thr
    770                 775                 780

Ala Ser Thr Ser Arg Ala Ala Tyr Gln Ala Ala Ile Arg Gly Val Gly
785                 790                 795                 800

Ser Ala Gln Ser Arg Leu Gly Pro Gly Pro Pro Arg Gly His Ser Lys
                805                 810                 815

Ala Leu Ala Pro Gln Ala Ala Leu Ile Pro Glu Glu Glu Cys Leu Ala
            820                 825                 830

Gly Asp Trp Leu Glu Leu Asp Met Pro Leu Thr Arg Ser Arg Arg Pro
        835                 840                 845

Arg Pro Arg Gly Thr Gly Asp Asn Arg Arg Pro Ser Ser Thr Ser Gly
    850                 855                 860

Ser Asp Ser Glu Glu Ser Arg Pro Arg Ala Arg Ala Lys Gln Val Arg
865                 870                 875                 880

Leu Thr Cys Met Gln Ser Cys Ser Ala Pro Val Asn Ala Gly Pro Ser
                885                 890                 895

Ser Leu Ala Ser Glu Pro Pro Gly Ser Pro Ser Thr Pro Arg Val Ser
            900                 905                 910

Glu Pro Ser Gly Asp Ser Ser Ala Ala Gly Gln Pro Leu Gly Pro Ala
        915                 920                 925

Pro Pro Pro Pro Ile Arg Val Arg Val Gln Val Gln Asp His Leu Phe
    930                 935                 940

Leu Ile Pro Val Pro His Ser Ser Asp Thr His Ser Val Ala Trp Leu
945                 950                 955                 960

Ala Glu Gln Ala Ala Gln Arg Tyr Tyr Gln Thr Cys Gly Leu Leu Pro
                965                 970                 975

Arg Leu Thr Leu Arg Lys Glu Gly Ala Leu Leu Ala Pro Gln Asp Leu
            980                 985                 990

Ile Pro Asp Val Leu Gln Ser Asn  Asp Glu Val Leu Ala  Glu Val Thr
        995                 1000                1005

Ser Trp  Asp Leu Pro Pro Leu  Thr Asp Arg Tyr Arg  Arg Ala Cys
    1010                1015                1020

Gln Ser  Leu Gly Gln Gly Glu  His Gln Gln Val Leu  Gln Ala Val
    1025                1030                1035

Glu Leu  Gln Gly Leu Gly Leu  Ser Phe Ser Ala Cys  Ser Leu Ala
    1040                1045                1050

Leu Asp  Gln Ala Gln Leu Thr  Pro Leu Leu Arg Ala  Leu Lys Leu
    1055                1060                1065

His Thr  Ala Leu Arg Glu Leu  Arg Leu Ala Gly Asn  Arg Leu Gly
    1070                1075                1080
```

Asp Lys Cys Val Ala Glu Leu Val Ala Ala Leu Gly Thr Met Pro
    1085                1090                1095

Ser Leu Ala Leu Leu Asp Leu Ser Ser Asn His Leu Gly Pro Glu
    1100                1105                1110

Gly Leu Arg Gln Leu Ala Met Gly Leu Pro Gly Gln Ala Thr Leu
    1115                1120                1125

Gln Ser Leu Glu Glu Leu Asp Leu Ser Met Asn Pro Leu Gly Asp
    1130                1135                1140

Gly Cys Gly Gln Ser Leu Ala Ser Leu Leu His Ala Cys Pro Leu
    1145                1150                1155

Leu Ser Thr Leu Arg Leu Gln Ala Cys Gly Phe Gly Pro Ser Phe
    1160                1165                1170

Phe Leu Ser His Gln Thr Ala Leu Gly Ser Ala Phe Gln Asp Ala
    1175                1180                1185

Glu His Leu Lys Thr Leu Ser Leu Ser Tyr Asn Ala Leu Gly Ala
    1190                1195                1200

Pro Ala Leu Ala Arg Thr Leu Gln Ser Leu Pro Ala Gly Thr Leu
    1205                1210                1215

Leu His Leu Glu Leu Ser Ser Val Ala Ala Gly Lys Gly Asp Ser
    1220                1225                1230

Asp Leu Met Glu Pro Val Phe Arg Tyr Leu Ala Lys Glu Gly Cys
    1235                1240                1245

Ala Leu Ala His Leu Thr Leu Ser Ala Asn His Leu Gly Asp Lys
    1250                1255                1260

Ala Val Arg Asp Leu Cys Arg Cys Leu Ser Leu Cys Pro Ser Leu
    1265                1270                1275

Ile Ser Leu Asp Leu Ser Ala Asn Pro Glu Ile Ser Cys Ala Ser
    1280                1285                1290

Leu Glu Glu Leu Leu Ser Thr Leu Gln Lys Arg Pro Gln Gly Leu
    1295                1300                1305

Ser Phe Leu Gly Leu Ser Gly Cys Ala Val Gln Gly Pro Leu Gly
    1310                1315                1320

Leu Gly Leu Trp Asp Lys Ile Ala Ala Gln Leu Arg Glu Leu Gln
    1325                1330                1335

Leu Cys Ser Arg Arg Leu Cys Ala Glu Asp Arg Asp Ala Leu Arg
    1340                1345                1350

Gln Leu Gln Pro Ser Arg Pro Gly Pro Gly Glu Cys Thr Leu Asp
    1355                1360                1365

His Gly Ser Lys Leu Phe Phe Arg Arg Leu
    1370                1375

<210> SEQ ID NO 17
<211> LENGTH: 1378
<212> TYPE: PRT
<213> ORGANISM: Artificial sequence
<220> FEATURE:
<223> OTHER INFORMATION: Mutant protein

<400> SEQUENCE: 17

Met Ser Leu Glu Arg Glu Leu Arg Gln Leu Ser Lys Ala Lys Ala Lys
1               5                   10                  15

Ala Gln Arg Ala Gly Gln Arg Arg Glu Glu Ala Ala Leu Cys His Gln
            20                  25                  30

Leu Gly Glu Leu Leu Ala Gly His Gly Arg Tyr Ala Glu Ala Leu Glu
        35                  40                  45

-continued

```
Gln His Trp Gln Glu Leu Gln Leu Arg Glu Arg Ala Asp Asp Pro Leu
    50                  55                  60

Gly Cys Ala Val Ala His Arg Lys Ile Gly Glu Arg Leu Ala Glu Met
65                  70                  75                  80

Glu Asp Tyr Pro Ala Ala Leu Gln His Gln His Gln Tyr Leu Glu Leu
                85                  90                  95

Ala His Ser Leu Arg Asn His Thr Glu Leu Gln Arg Ala Trp Ala Thr
            100                 105                 110

Ile Gly Arg Thr His Leu Asp Ile Tyr Asp His Cys Gln Ser Arg Asp
        115                 120                 125

Ala Leu Leu Gln Ala Gln Ala Ala Phe Glu Lys Ser Leu Ala Ile Val
    130                 135                 140

Asp Glu Glu Leu Glu Gly Thr Leu Ala Gln Gly Glu Leu Asn Glu Met
145                 150                 155                 160

Arg Thr Arg Leu Tyr Leu Asn Leu Gly Leu Thr Phe Glu Ser Leu Gln
                165                 170                 175

Gln Thr Ala Leu Cys Asn Asp Tyr Phe Arg Lys Ser Ile Phe Leu Ala
            180                 185                 190

Glu Gln Asn His Leu Tyr Glu Asp Leu Phe Arg Ala Arg Tyr Asn Leu
        195                 200                 205

Gly Thr Ile His Trp Arg Ala Gly Gln His Ser Gln Ala Met Arg Cys
    210                 215                 220

Leu Glu Gly Ala Arg Glu Cys Ala His Thr Met Arg Lys Arg Phe Met
225                 230                 235                 240

Glu Ser Glu Cys Cys Val Val Ile Ala Gln Val Leu Gln Asp Leu Gly
                245                 250                 255

Asp Phe Leu Ala Ala Lys Arg Ala Leu Lys Lys Ala Tyr Arg Leu Gly
            260                 265                 270

Ser Gln Lys Pro Val Gln Arg Ala Ala Ile Cys Gln Asn Leu Gln His
        275                 280                 285

Val Leu Ala Val Val Arg Leu Gln Gln Gln Leu Glu Glu Ala Glu Gly
    290                 295                 300

Arg Asp Pro Gln Gly Ala Met Val Ile Cys Glu Gln Leu Gly Asp Leu
305                 310                 315                 320

Phe Ser Lys Ala Gly Asp Phe Pro Arg Ala Ala Glu Ala Tyr Gln Lys
                325                 330                 335

Gln Leu Arg Phe Ala Glu Leu Leu Asp Arg Pro Gly Ala Glu Arg Ala
            340                 345                 350

Ile Ile His Val Ser Leu Ala Thr Thr Leu Gly Asp Met Lys Asp His
        355                 360                 365

His Gly Ala Val Arg His Tyr Glu Glu Glu Leu Arg Leu Arg Ser Gly
    370                 375                 380

Asn Val Leu Glu Glu Ala Lys Thr Trp Leu Asn Ile Ala Leu Ser Arg
385                 390                 395                 400

Glu Glu Ala Gly Asp Ala Tyr Glu Leu Leu Ala Pro Cys Phe Gln Lys
                405                 410                 415

Ala Leu Ser Cys Ala Gln Gln Ala Gln Arg Pro Gln Leu Gln Arg Gln
            420                 425                 430

Val Leu Gln His Leu His Thr Val Gln Leu Arg Leu Gln Pro Gln Glu
        435                 440                 445

Ala Pro Glu Thr Glu Thr Arg Leu Arg Glu Leu Ser Val Ala Glu Asp
    450                 455                 460
```

-continued

Glu Asp Glu Glu Glu Glu Ala Glu Glu Ala Ala Ala Thr Ala Glu Ser
465 470 475 480

Glu Ala Leu Glu Ala Gly Glu Val Glu Leu Ser Glu Gly Glu Asp Asp
485 490 495

Thr Asp Gly Leu Thr Pro Gln Leu Glu Glu Asp Glu Glu Leu Gln Gly
500 505 510

His Leu Gly Arg Arg Lys Gly Ser Lys Trp Asn Arg Arg Asn Asp Met
515 520 525

Gly Ala Thr Leu Leu His Arg Ala Cys Ile Glu Gly Gln Leu Arg Arg
530 535 540

Val Gln Asp Leu Val Arg Gln Gly His Pro Leu Asn Pro Arg Asp Tyr
545 550 555 560

Cys Gly Trp Thr Pro Leu His Glu Ala Cys Asn Tyr Gly His Leu Glu
565 570 575

Ile Val Arg Phe Leu Leu Asp His Gly Ala Ala Val Asp Asp Pro Gly
580 585 590

Gly Gln Gly Cys Glu Gly Ile Thr Pro Leu His Asp Ala Leu Asn Cys
595 600 605

Gly His Phe Glu Val Ala Glu Leu Leu Leu Glu Arg Gly Ala Ser Val
610 615 620

Thr Leu Arg Thr Arg Lys Gly Leu Ser Pro Leu Glu Thr Leu Gln Gln
625 630 635 640

Trp Val Lys Leu Tyr Arg Arg Asp Leu Asp Leu Glu Thr Arg Gln Lys
645 650 655

Ala Arg Ala Met Glu Met Leu Leu Gln Ala Ala Ala Ser Gly Gln Asp
660 665 670

Pro His Ser Ser Gln Ala Phe His Thr Pro Ser Ser Leu Leu Phe Asp
675 680 685

Pro Glu Thr Ser Pro Pro Leu Ser Pro Cys Pro Glu Pro Pro Ser Asn
690 695 700

Ser Thr Arg Leu Pro Glu Ala Ser Gln Ala His Val Arg Val Ser Pro
705 710 715 720

Gly Gln Ala Ala Pro Ala Met Ala Arg Pro Arg Arg Ser Arg His Gly
725 730 735

Pro Ala Ser Ser Ser Ser Ser Ser Glu Gly Glu Asp Ser Ala Gly Pro
740 745 750

Ala Arg Pro Ser Gln Lys Arg Pro Arg Cys Ser Ala Thr Ala Gln Arg
755 760 765

Val Ala Ala Trp Thr Pro Gly Pro Ala Ser Asn Arg Glu Ala Ala Thr
770 775 780

Ala Ser Thr Ser Arg Ala Ala Tyr Gln Ala Ala Ile Arg Gly Val Gly
785 790 795 800

Ser Ala Gln Ser Arg Leu Gly Pro Gly Pro Pro Arg Gly His Ser Lys
805 810 815

Ala Leu Ala Pro Gln Ala Ala Leu Ile Pro Glu Glu Glu Cys Leu Ala
820 825 830

Gly Asp Trp Leu Glu Leu Asp Met Pro Leu Thr Arg Ser Arg Arg Pro
835 840 845

Arg Pro Arg Gly Thr Gly Asp Asn Arg Arg Pro Ser Ser Thr Ser Gly
850 855 860

Ser Asp Ser Glu Glu Ser Arg Pro Arg Ala Arg Ala Lys Gln Val Arg
865 870 875 880

Leu Thr Cys Met Gln Ser Cys Ser Ala Pro Val Asn Ala Gly Pro Ser

-continued

```
                885                 890                 895

Ser Leu Ala Ser Glu Pro Pro Gly Ser Pro Ser Thr Pro Arg Val Ser
            900                 905                 910

Glu Pro Ser Gly Asp Ser Ser Ala Ala Gly Gln Pro Leu Gly Pro Ala
        915                 920                 925

Pro Pro Pro Pro Ile Arg Val Arg Val Gln Val Gln Asp His Leu Phe
    930                 935                 940

Leu Ile Pro Val Pro His Ser Ser Asp Thr His Ser Val Ala Trp Leu
945                 950                 955                 960

Ala Glu Gln Ala Ala Gln Arg Tyr Tyr Gln Thr Cys Gly Leu Leu Pro
                965                 970                 975

Arg Leu Thr Leu Arg Lys Glu Gly Ala Leu Leu Ala Pro Gln Asp Leu
            980                 985                 990

Ile Pro Asp Val Leu Gln Ser Asn  Asp Glu Val Leu Ala  Glu Val Thr
        995                 1000                1005

Ser Trp  Asp Leu Pro Pro Leu  Thr Asp Arg Tyr Arg  Arg Ala Cys
    1010                1015                1020

Gln Ser  Leu Gly Gln Gly Glu  His Gln Gln Val Leu  Gln Ala Val
    1025                1030                1035

Glu Leu  Gln Gly Leu Gly Leu  Ser Phe Ser Ala Cys  Ser Leu Ala
    1040                1045                1050

Leu Asp  Gln Ala Gln Leu Thr  Pro Leu Leu Arg Ala  Leu Lys Leu
    1055                1060                1065

His Thr  Ala Leu Arg Glu Leu  Arg Leu Ala Gly Asn  Arg Leu Gly
    1070                1075                1080

Asp Lys  Cys Val Ala Glu Leu  Val Ala Ala Leu Gly  Thr Met Pro
    1085                1090                1095

Ser Leu  Ala Leu Leu Asp Leu  Ser Ser Asn His Leu  Gly Pro Glu
    1100                1105                1110

Gly Leu  Arg Gln Leu Ala Met  Gly Leu Pro Gly Gln  Ala Thr Leu
    1115                1120                1125

Gln Ser  Leu Glu Glu Leu Asp  Leu Ser Met Asn Pro  Leu Gly Asp
    1130                1135                1140

Gly Cys  Gly Gln Ser Leu Ala  Ser Leu Leu His Ala  Cys Pro Leu
    1145                1150                1155

Leu Ser  Thr Leu Arg Leu Gln  Ala Cys Gly Phe Gly  Pro Ser Phe
    1160                1165                1170

Phe Leu  Ser His Gln Thr Ala  Leu Gly Ser Ala Phe  Gln Asp Ala
    1175                1180                1185

Glu His  Leu Lys Thr Leu Ser  Leu Ser Tyr Asn Ala  Leu Gly Ala
    1190                1195                1200

Pro Ala  Leu Ala Arg Thr Leu  Gln Ser Leu Pro Ala  Gly Thr Leu
    1205                1210                1215

Leu His  Leu Glu Leu Ser Ser  Val Ala Ala Gly Lys  Gly Asp Ser
    1220                1225                1230

Asp Leu  Met Glu Pro Val Phe  Arg Tyr Leu Ala Lys  Glu Gly Cys
    1235                1240                1245

Ala Leu  Ala His Leu Thr Leu  Ser Ala Asn His Leu  Gly Asp Lys
    1250                1255                1260

Ala Val  Arg Asp Leu Cys Arg  Cys Leu Ser Leu Cys  Pro Ser Leu
    1265                1270                1275

Ile Ser  Leu Asp Leu Ser Ala  Asn Pro Glu Ile Ser  Cys Ala Ser
    1280                1285                1290
```

```
Leu Glu  Glu Leu Leu Ser Thr  Leu Gln Lys Arg Pro  Gln Gly Leu
    1295                 1300                 1305

Ser Phe  Leu Gly Leu Ser Gly  Cys Ala Val Gln Gly  Pro Leu Gly
    1310                 1315                 1320

Leu Gly  Leu Trp Asp Lys Ile  Ala Ala Gln Leu Arg  Glu Leu Gln
    1325                 1330                 1335

Leu Cys  Ser Arg Arg Leu Cys  Ala Glu Asp Arg Asp  Ala Leu Arg
    1340                 1345                 1350

Gln Leu  Gln Pro Ser Arg Pro  Gly Pro Gly Glu Cys  Thr Leu Asp
    1355                 1360                 1365

His Gly  Ser Lys Leu Phe Phe  Arg Arg Leu
    1370                 1375


<210> SEQ ID NO 18
<211> LENGTH: 1378
<212> TYPE: PRT
<213> ORGANISM: Artificial sequence
<220> FEATURE:
<223> OTHER INFORMATION: Mutant protein

<400> SEQUENCE: 18

Met Ser Leu Glu Arg Glu Leu Arg Gln Leu Ser Lys Ala Lys Ala Lys
1               5                   10                  15

Ala Gln Arg Ala Gly Gln Arg Arg Glu Glu Ala Ala Leu Cys His Gln
            20                  25                  30

Leu Gly Glu Leu Leu Ala Gly His Gly Arg Tyr Ala Glu Ala Leu Glu
        35                  40                  45

Gln His Trp Gln Glu Leu Gln Leu Arg Glu Arg Ala Asp Asp Pro Leu
    50                  55                  60

Gly Cys Ala Val Ala His Arg Lys Ile Gly Glu Arg Leu Ala Glu Met
65                  70                  75                  80

Glu Asp Tyr Pro Ala Ala Leu Gln His Gln His Gln Tyr Leu Glu Leu
                85                  90                  95

Ala His Ser Leu Arg Asn His Thr Glu Leu Gln Arg Ala Trp Ala Thr
            100                 105                 110

Ile Gly Arg Thr His Leu Asp Ile Tyr Asp His Cys Gln Ser Arg Asp
        115                 120                 125

Ala Leu Leu Gln Ala Gln Ala Ala Phe Glu Lys Ser Leu Ala Ile Val
    130                 135                 140

Asp Glu Glu Leu Glu Gly Thr Leu Ala Gln Gly Glu Leu Asn Glu Met
145                 150                 155                 160

Arg Thr Arg Leu Tyr Leu Asn Leu Gly Leu Thr Phe Glu Ser Leu Gln
                165                 170                 175

Gln Thr Ala Leu Cys Asn Asp Tyr Phe Arg Lys Ser Ile Phe Leu Ala
            180                 185                 190

Glu Gln Asn His Leu Tyr Glu Asp Leu Phe Arg Ala Arg Tyr Asn Leu
        195                 200                 205

Gly Thr Ile His Trp Arg Ala Gly Gln His Ser Gln Ala Met Arg Cys
    210                 215                 220

Leu Glu Gly Ala Arg Glu Cys Ala His Thr Met Arg Lys Arg Phe Met
225                 230                 235                 240

Glu Ser Glu Cys Cys Val Val Ile Ala Gln Val Leu Gln Asp Leu Gly
                245                 250                 255

Asp Phe Leu Ala Ala Lys Arg Ala Leu Lys Lys Ala Tyr Arg Leu Gly
            260                 265                 270
```

```
Ser Gln Lys Pro Val Gln Arg Ala Ala Ile Cys Gln Asn Leu Gln His
        275                 280                 285

Val Leu Ala Val Val Arg Leu Gln Gln Gln Leu Glu Glu Ala Glu Gly
    290                 295                 300

Arg Asp Pro Gln Gly Ala Met Val Ile Cys Glu Gln Leu Gly Asp Leu
305                 310                 315                 320

Phe Ser Lys Ala Gly Asp Phe Pro Arg Ala Ala Glu Ala Tyr Gln Lys
                325                 330                 335

Gln Leu Arg Phe Ala Glu Leu Leu Asp Arg Pro Gly Ala Glu Arg Ala
            340                 345                 350

Ile Ile His Val Ser Leu Ala Thr Thr Leu Gly Asp Met Lys Asp His
        355                 360                 365

His Gly Ala Val Arg His Tyr Glu Glu Glu Leu Arg Leu Arg Ser Gly
    370                 375                 380

Asn Val Leu Glu Glu Ala Lys Thr Trp Leu Asn Ile Ala Leu Ser Arg
385                 390                 395                 400

Glu Glu Ala Gly Asp Ala Tyr Glu Leu Leu Ala Pro Cys Phe Gln Lys
                405                 410                 415

Ala Leu Ser Cys Ala Gln Gln Ala Gln Arg Pro Gln Leu Gln Arg Gln
            420                 425                 430

Val Leu Gln His Leu His Thr Val Gln Leu Arg Leu Gln Pro Gln Glu
        435                 440                 445

Ala Pro Glu Thr Glu Thr Arg Leu Arg Glu Leu Ser Val Ala Glu Asp
    450                 455                 460

Glu Asp Glu Glu Glu Glu Ala Glu Glu Ala Ala Ala Thr Ala Glu Ser
465                 470                 475                 480

Glu Ala Leu Glu Ala Gly Glu Val Glu Leu Ser Glu Gly Glu Asp Asp
                485                 490                 495

Thr Asp Gly Leu Thr Pro Gln Leu Glu Glu Asp Glu Glu Leu Gln Gly
            500                 505                 510

His Leu Gly Arg Arg Lys Gly Ser Lys Trp Asn Arg Arg Asn Asp Met
        515                 520                 525

Gly Glu Thr Leu Leu His Arg Ala Cys Ile Glu Gly Gln Leu Arg Arg
    530                 535                 540

Val Gln Asp Leu Val Arg Gln Gly His Pro Leu Asn Pro Arg Ala Tyr
545                 550                 555                 560

Cys Gly Trp Thr Pro Leu His Glu Ala Cys Asn Tyr Gly His Leu Glu
                565                 570                 575

Ile Val Arg Phe Leu Leu Asp His Gly Ala Ala Val Asp Asp Pro Gly
            580                 585                 590

Gly Gln Gly Cys Glu Gly Ile Thr Pro Leu His Asp Ala Leu Asn Cys
        595                 600                 605

Gly His Phe Glu Val Ala Glu Leu Leu Leu Glu Arg Gly Ala Ser Val
    610                 615                 620

Thr Leu Arg Thr Arg Lys Gly Leu Ser Pro Leu Glu Thr Leu Gln Gln
625                 630                 635                 640

Trp Val Lys Leu Tyr Arg Arg Asp Leu Asp Leu Glu Thr Arg Gln Lys
                645                 650                 655

Ala Arg Ala Met Glu Met Leu Leu Gln Ala Ala Ala Ser Gly Gln Asp
            660                 665                 670

Pro His Ser Ser Gln Ala Phe His Thr Pro Ser Ser Leu Leu Phe Asp
        675                 680                 685
```

-continued

```
Pro Glu Thr Ser Pro Pro Leu Ser Pro Cys Pro Glu Pro Pro Ser Asn
    690                 695                 700

Ser Thr Arg Leu Pro Glu Ala Ser Gln Ala His Val Arg Val Ser Pro
705                 710                 715                 720

Gly Gln Ala Ala Pro Ala Met Ala Arg Pro Arg Arg Ser Arg His Gly
                725                 730                 735

Pro Ala Ser Ser Ser Ser Ser Ser Glu Gly Glu Asp Ser Ala Gly Pro
            740                 745                 750

Ala Arg Pro Ser Gln Lys Arg Pro Arg Cys Ser Ala Thr Ala Gln Arg
        755                 760                 765

Val Ala Ala Trp Thr Pro Gly Pro Ala Ser Asn Arg Glu Ala Ala Thr
    770                 775                 780

Ala Ser Thr Ser Arg Ala Ala Tyr Gln Ala Ala Ile Arg Gly Val Gly
785                 790                 795                 800

Ser Ala Gln Ser Arg Leu Gly Pro Gly Pro Pro Arg Gly His Ser Lys
                805                 810                 815

Ala Leu Ala Pro Gln Ala Ala Leu Ile Pro Glu Glu Glu Cys Leu Ala
            820                 825                 830

Gly Asp Trp Leu Glu Leu Asp Met Pro Leu Thr Arg Ser Arg Arg Pro
        835                 840                 845

Arg Pro Arg Gly Thr Gly Asp Asn Arg Arg Pro Ser Ser Thr Ser Gly
    850                 855                 860

Ser Asp Ser Glu Glu Ser Arg Pro Arg Ala Arg Ala Lys Gln Val Arg
865                 870                 875                 880

Leu Thr Cys Met Gln Ser Cys Ser Ala Pro Val Asn Ala Gly Pro Ser
                885                 890                 895

Ser Leu Ala Ser Glu Pro Pro Gly Ser Pro Ser Thr Pro Arg Val Ser
            900                 905                 910

Glu Pro Ser Gly Asp Ser Ser Ala Ala Gly Gln Pro Leu Gly Pro Ala
        915                 920                 925

Pro Pro Pro Pro Ile Arg Val Arg Val Gln Val Gln Asp His Leu Phe
    930                 935                 940

Leu Ile Pro Val Pro His Ser Ser Asp Thr His Ser Val Ala Trp Leu
945                 950                 955                 960

Ala Glu Gln Ala Ala Gln Arg Tyr Tyr Gln Thr Cys Gly Leu Leu Pro
                965                 970                 975

Arg Leu Thr Leu Arg Lys Glu Gly Ala Leu Leu Ala Pro Gln Asp Leu
            980                 985                 990

Ile Pro Asp Val Leu Gln Ser Asn  Asp Glu Val Leu Ala  Glu Val Thr
        995                 1000                1005

Ser Trp  Asp Leu Pro Pro Leu  Thr Asp Arg Tyr Arg  Arg Ala Cys
    1010                1015                1020

Gln Ser  Leu Gly Gln Gly Glu  His Gln Gln Val Leu  Gln Ala Val
    1025                1030                1035

Glu Leu  Gln Gly Leu Gly Leu  Ser Phe Ser Ala Cys  Ser Leu Ala
    1040                1045                1050

Leu Asp  Gln Ala Gln Leu Thr  Pro Leu Leu Arg Ala  Leu Lys Leu
    1055                1060                1065

His Thr  Ala Leu Arg Glu Leu  Arg Leu Ala Gly Asn  Arg Leu Gly
    1070                1075                1080

Asp Lys  Cys Val Ala Glu Leu  Val Ala Ala Leu Gly  Thr Met Pro
    1085                1090                1095

Ser Leu  Ala Leu Leu Asp Leu  Ser Ser Asn His Leu  Gly Pro Glu
```

1100 1105 1110

Gly Leu Arg Gln Leu Ala Met Gly Leu Pro Gly Gln Ala Thr Leu
1115 1120 1125

Gln Ser Leu Glu Glu Leu Asp Leu Ser Met Asn Pro Leu Gly Asp
1130 1135 1140

Gly Cys Gly Gln Ser Leu Ala Ser Leu Leu His Ala Cys Pro Leu
1145 1150 1155

Leu Ser Thr Leu Arg Leu Gln Ala Cys Gly Phe Gly Pro Ser Phe
1160 1165 1170

Phe Leu Ser His Gln Thr Ala Leu Gly Ser Ala Phe Gln Asp Ala
1175 1180 1185

Glu His Leu Lys Thr Leu Ser Leu Ser Tyr Asn Ala Leu Gly Ala
1190 1195 1200

Pro Ala Leu Ala Arg Thr Leu Gln Ser Leu Pro Ala Gly Thr Leu
1205 1210 1215

Leu His Leu Glu Leu Ser Ser Val Ala Ala Gly Lys Gly Asp Ser
1220 1225 1230

Asp Leu Met Glu Pro Val Phe Arg Tyr Leu Ala Lys Glu Gly Cys
1235 1240 1245

Ala Leu Ala His Leu Thr Leu Ser Ala Asn His Leu Gly Asp Lys
1250 1255 1260

Ala Val Arg Asp Leu Cys Arg Cys Leu Ser Leu Cys Pro Ser Leu
1265 1270 1275

Ile Ser Leu Asp Leu Ser Ala Asn Pro Glu Ile Ser Cys Ala Ser
1280 1285 1290

Leu Glu Glu Leu Leu Ser Thr Leu Gln Lys Arg Pro Gln Gly Leu
1295 1300 1305

Ser Phe Leu Gly Leu Ser Gly Cys Ala Val Gln Gly Pro Leu Gly
1310 1315 1320

Leu Gly Leu Trp Asp Lys Ile Ala Ala Gln Leu Arg Glu Leu Gln
1325 1330 1335

Leu Cys Ser Arg Arg Leu Cys Ala Glu Asp Arg Asp Ala Leu Arg
1340 1345 1350

Gln Leu Gln Pro Ser Arg Pro Gly Pro Gly Glu Cys Thr Leu Asp
1355 1360 1365

His Gly Ser Lys Leu Phe Phe Arg Arg Leu
1370 1375

<210> SEQ ID NO 19
<211> LENGTH: 1378
<212> TYPE: PRT
<213> ORGANISM: Artificial sequence
<220> FEATURE:
<223> OTHER INFORMATION: Mutant protein

<400> SEQUENCE: 19

Met Ser Leu Glu Arg Glu Leu Arg Gln Leu Ser Lys Ala Lys Ala Lys
1 5 10 15

Ala Gln Arg Ala Gly Gln Arg Arg Glu Glu Ala Ala Leu Cys His Gln
20 25 30

Leu Gly Glu Leu Leu Ala Gly His Gly Arg Tyr Ala Glu Ala Leu Glu
35 40 45

Gln His Trp Gln Glu Leu Gln Leu Arg Glu Arg Ala Asp Asp Pro Leu
50 55 60

Gly Cys Ala Val Ala His Arg Lys Ile Gly Glu Arg Leu Ala Glu Met

-continued

```
65                  70                  75                  80

Glu Asp Tyr Pro Ala Ala Leu Gln His Gln His Gln Tyr Leu Glu Leu
                85                  90                  95

Ala His Ser Leu Arg Asn His Thr Glu Leu Gln Arg Ala Trp Ala Thr
            100                 105                 110

Ile Gly Arg Thr His Leu Asp Ile Tyr Asp His Cys Gln Ser Arg Asp
        115                 120                 125

Ala Leu Leu Gln Ala Gln Ala Ala Phe Glu Lys Ser Leu Ala Ile Val
    130                 135                 140

Asp Glu Glu Leu Glu Gly Thr Leu Ala Gln Gly Glu Leu Asn Glu Met
145                 150                 155                 160

Arg Thr Arg Leu Tyr Leu Asn Leu Gly Leu Thr Phe Glu Ser Leu Gln
                165                 170                 175

Gln Thr Ala Leu Cys Asn Asp Tyr Phe Arg Lys Ser Ile Phe Leu Ala
            180                 185                 190

Glu Gln Asn His Leu Tyr Glu Asp Leu Phe Arg Ala Arg Tyr Asn Leu
        195                 200                 205

Gly Thr Ile His Trp Arg Ala Gly Gln His Ser Gln Ala Met Arg Cys
    210                 215                 220

Leu Glu Gly Ala Arg Glu Cys Ala His Thr Met Arg Lys Arg Phe Met
225                 230                 235                 240

Glu Ser Glu Cys Cys Val Val Ile Ala Gln Val Leu Gln Asp Leu Gly
                245                 250                 255

Asp Phe Leu Ala Ala Lys Arg Ala Leu Lys Lys Ala Tyr Arg Leu Gly
            260                 265                 270

Ser Gln Lys Pro Val Gln Arg Ala Ala Ile Cys Gln Asn Leu Gln His
        275                 280                 285

Val Leu Ala Val Val Arg Leu Gln Gln Gln Leu Glu Glu Ala Glu Gly
    290                 295                 300

Arg Asp Pro Gln Gly Ala Met Val Ile Cys Glu Gln Leu Gly Asp Leu
305                 310                 315                 320

Phe Ser Lys Ala Gly Asp Phe Pro Arg Ala Ala Glu Ala Tyr Gln Lys
                325                 330                 335

Gln Leu Arg Phe Ala Glu Leu Leu Asp Arg Pro Gly Ala Glu Arg Ala
            340                 345                 350

Ile Ile His Val Ser Leu Ala Thr Thr Leu Gly Asp Met Lys Asp His
        355                 360                 365

His Gly Ala Val Arg His Tyr Glu Glu Glu Leu Arg Leu Arg Ser Gly
    370                 375                 380

Asn Val Leu Glu Glu Ala Lys Thr Trp Leu Asn Ile Ala Leu Ser Arg
385                 390                 395                 400

Glu Glu Ala Gly Asp Ala Tyr Glu Leu Leu Ala Pro Cys Phe Gln Lys
                405                 410                 415

Ala Leu Ser Cys Ala Gln Gln Ala Gln Arg Pro Gln Leu Gln Arg Gln
            420                 425                 430

Val Leu Gln His Leu His Thr Val Gln Leu Arg Leu Gln Pro Gln Glu
        435                 440                 445

Ala Pro Glu Thr Glu Thr Arg Leu Arg Glu Leu Ser Val Ala Glu Asp
    450                 455                 460

Glu Asp Glu Glu Glu Glu Ala Glu Glu Ala Ala Ala Thr Ala Glu Ser
465                 470                 475                 480

Glu Ala Leu Glu Ala Gly Glu Val Glu Leu Ser Glu Gly Glu Asp Asp
                485                 490                 495
```

-continued

```
Thr Asp Gly Leu Thr Pro Gln Leu Glu Glu Asp Glu Glu Leu Gln Gly
            500                 505                 510

His Leu Gly Arg Arg Lys Gly Ser Lys Trp Asn Arg Arg Asn Asp Met
        515                 520                 525

Gly Glu Thr Leu Leu His Arg Ala Cys Ile Glu Gly Gln Leu Arg Arg
    530                 535                 540

Val Gln Asp Leu Val Arg Gln Gly His Pro Leu Asn Pro Arg Asp Tyr
545                 550                 555                 560

Cys Gly Ala Thr Pro Leu His Glu Ala Cys Asn Tyr Gly His Leu Glu
                565                 570                 575

Ile Val Arg Phe Leu Leu Asp His Gly Ala Ala Val Asp Asp Pro Gly
            580                 585                 590

Gly Gln Gly Cys Glu Gly Ile Thr Pro Leu His Asp Ala Leu Asn Cys
        595                 600                 605

Gly His Phe Glu Val Ala Glu Leu Leu Leu Glu Arg Gly Ala Ser Val
    610                 615                 620

Thr Leu Arg Thr Arg Lys Gly Leu Ser Pro Leu Glu Thr Leu Gln Gln
625                 630                 635                 640

Trp Val Lys Leu Tyr Arg Arg Asp Leu Asp Leu Glu Thr Arg Gln Lys
                645                 650                 655

Ala Arg Ala Met Glu Met Leu Leu Gln Ala Ala Ala Ser Gly Gln Asp
            660                 665                 670

Pro His Ser Ser Gln Ala Phe His Thr Pro Ser Ser Leu Leu Phe Asp
        675                 680                 685

Pro Glu Thr Ser Pro Pro Leu Ser Pro Cys Pro Glu Pro Pro Ser Asn
    690                 695                 700

Ser Thr Arg Leu Pro Glu Ala Ser Gln Ala His Val Arg Val Ser Pro
705                 710                 715                 720

Gly Gln Ala Ala Pro Ala Met Ala Arg Pro Arg Arg Ser Arg His Gly
                725                 730                 735

Pro Ala Ser Ser Ser Ser Ser Ser Glu Gly Glu Asp Ser Ala Gly Pro
            740                 745                 750

Ala Arg Pro Ser Gln Lys Arg Pro Arg Cys Ser Ala Thr Ala Gln Arg
        755                 760                 765

Val Ala Ala Trp Thr Pro Gly Pro Ala Ser Asn Arg Glu Ala Ala Thr
    770                 775                 780

Ala Ser Thr Ser Arg Ala Ala Tyr Gln Ala Ala Ile Arg Gly Val Gly
785                 790                 795                 800

Ser Ala Gln Ser Arg Leu Gly Pro Gly Pro Pro Arg Gly His Ser Lys
                805                 810                 815

Ala Leu Ala Pro Gln Ala Ala Leu Ile Pro Glu Glu Glu Cys Leu Ala
            820                 825                 830

Gly Asp Trp Leu Glu Leu Asp Met Pro Leu Thr Arg Ser Arg Arg Pro
        835                 840                 845

Arg Pro Arg Gly Thr Gly Asp Asn Arg Arg Pro Ser Ser Thr Ser Gly
    850                 855                 860

Ser Asp Ser Glu Glu Ser Arg Pro Arg Ala Arg Ala Lys Gln Val Arg
865                 870                 875                 880

Leu Thr Cys Met Gln Ser Cys Ser Ala Pro Val Asn Ala Gly Pro Ser
                885                 890                 895

Ser Leu Ala Ser Glu Pro Pro Gly Ser Pro Ser Thr Pro Arg Val Ser
            900                 905                 910
```

-continued

```
Glu Pro Ser Gly Asp Ser Ser Ala Ala Gly Gln Pro Leu Gly Pro Ala
        915                 920                 925

Pro Pro Pro Pro Ile Arg Val Arg Val Gln Val Gln Asp His Leu Phe
    930                 935                 940

Leu Ile Pro Val Pro His Ser Ser Asp Thr His Ser Val Ala Trp Leu
945                 950                 955                 960

Ala Glu Gln Ala Ala Gln Arg Tyr Tyr Gln Thr Cys Gly Leu Leu Pro
                965                 970                 975

Arg Leu Thr Leu Arg Lys Glu Gly Ala Leu Leu Ala Pro Gln Asp Leu
            980                 985                 990

Ile Pro Asp Val Leu Gln Ser Asn  Asp Glu Val Leu Ala  Glu Val Thr
        995                 1000                 1005

Ser Trp  Asp Leu Pro Pro Leu  Thr Asp Arg Tyr Arg  Arg Ala Cys
    1010                 1015                 1020

Gln Ser  Leu Gly Gln Gly Glu  His Gln Gln Val Leu  Gln Ala Val
    1025                 1030                 1035

Glu Leu  Gln Gly Leu Gly Leu  Ser Phe Ser Ala Cys  Ser Leu Ala
    1040                 1045                 1050

Leu Asp  Gln Ala Gln Leu Thr  Pro Leu Leu Arg Ala  Leu Lys Leu
    1055                 1060                 1065

His Thr  Ala Leu Arg Glu Leu  Arg Leu Ala Gly Asn  Arg Leu Gly
    1070                 1075                 1080

Asp Lys  Cys Val Ala Glu Leu  Val Ala Ala Leu Gly  Thr Met Pro
    1085                 1090                 1095

Ser Leu  Ala Leu Leu Asp Leu  Ser Ser Asn His Leu  Gly Pro Glu
    1100                 1105                 1110

Gly Leu  Arg Gln Leu Ala Met  Gly Leu Pro Gly Gln  Ala Thr Leu
    1115                 1120                 1125

Gln Ser  Leu Glu Glu Leu Asp  Leu Ser Met Asn Pro  Leu Gly Asp
    1130                 1135                 1140

Gly Cys  Gly Gln Ser Leu Ala  Ser Leu Leu His Ala  Cys Pro Leu
    1145                 1150                 1155

Leu Ser  Thr Leu Arg Leu Gln  Ala Cys Gly Phe Gly  Pro Ser Phe
    1160                 1165                 1170

Phe Leu  Ser His Gln Thr Ala  Leu Gly Ser Ala Phe  Gln Asp Ala
    1175                 1180                 1185

Glu His  Leu Lys Thr Leu Ser  Leu Ser Tyr Asn Ala  Leu Gly Ala
    1190                 1195                 1200

Pro Ala  Leu Ala Arg Thr Leu  Gln Ser Leu Pro Ala  Gly Thr Leu
    1205                 1210                 1215

Leu His  Leu Glu Leu Ser Ser  Val Ala Ala Gly Lys  Gly Asp Ser
    1220                 1225                 1230

Asp Leu  Met Glu Pro Val Phe  Arg Tyr Leu Ala Lys  Glu Gly Cys
    1235                 1240                 1245

Ala Leu  Ala His Leu Thr Leu  Ser Ala Asn His Leu  Gly Asp Lys
    1250                 1255                 1260

Ala Val  Arg Asp Leu Cys Arg  Cys Leu Ser Leu Cys  Pro Ser Leu
    1265                 1270                 1275

Ile Ser  Leu Asp Leu Ser Ala  Asn Pro Glu Ile Ser  Cys Ala Ser
    1280                 1285                 1290

Leu Glu  Glu Leu Leu Ser Thr  Leu Gln Lys Arg Pro  Gln Gly Leu
    1295                 1300                 1305

Ser Phe  Leu Gly Leu Ser Gly  Cys Ala Val Gln Gly  Pro Leu Gly
```

```
    1310                1315                1320

Leu Gly  Leu Trp Asp Lys Ile  Ala Ala Gln Leu Arg  Glu Leu Gln
    1325                1330                1335

Leu Cys  Ser Arg Arg Leu Cys  Ala Glu Asp Arg Asp  Ala Leu Arg
    1340                1345                1350

Gln Leu  Gln Pro Ser Arg Pro  Gly Pro Gly Glu Cys  Thr Leu Asp
    1355                1360                1365

His Gly  Ser Lys Leu Phe Phe  Arg Arg Leu
    1370                1375


<210> SEQ ID NO 20
<211> LENGTH: 1378
<212> TYPE: PRT
<213> ORGANISM: Artificial sequence
<220> FEATURE:
<223> OTHER INFORMATION: Mutant protein

<400> SEQUENCE: 20

Met Ser Leu Glu Arg Glu Leu Arg Gln Leu Ser Lys Ala Lys Ala Lys
1               5                   10                  15

Ala Gln Arg Ala Gly Gln Arg Arg Glu Glu Ala Ala Leu Cys His Gln
            20                  25                  30

Leu Gly Glu Leu Leu Ala Gly His Gly Arg Tyr Ala Glu Ala Leu Glu
        35                  40                  45

Gln His Trp Gln Glu Leu Gln Leu Arg Glu Arg Ala Asp Asp Pro Leu
    50                  55                  60

Gly Cys Ala Val Ala His Arg Lys Ile Gly Glu Arg Leu Ala Glu Met
65                  70                  75                  80

Glu Asp Tyr Pro Ala Ala Leu Gln His Gln His Gln Tyr Leu Glu Leu
                85                  90                  95

Ala His Ser Leu Arg Asn His Thr Glu Leu Gln Arg Ala Trp Ala Thr
            100                 105                 110

Ile Gly Arg Thr His Leu Asp Ile Tyr Asp His Cys Gln Ser Arg Asp
        115                 120                 125

Ala Leu Leu Gln Ala Gln Ala Ala Phe Glu Lys Ser Leu Ala Ile Val
    130                 135                 140

Asp Glu Glu Leu Glu Gly Thr Leu Ala Gln Gly Glu Leu Asn Glu Met
145                 150                 155                 160

Arg Thr Arg Leu Tyr Leu Asn Leu Gly Leu Thr Phe Glu Ser Leu Gln
                165                 170                 175

Gln Thr Ala Leu Cys Asn Asp Tyr Phe Arg Lys Ser Ile Phe Leu Ala
            180                 185                 190

Glu Gln Asn His Leu Tyr Glu Asp Leu Phe Arg Ala Arg Tyr Asn Leu
        195                 200                 205

Gly Thr Ile His Trp Arg Ala Gly Gln His Ser Gln Ala Met Arg Cys
    210                 215                 220

Leu Glu Gly Ala Arg Glu Cys Ala His Thr Met Arg Lys Arg Phe Met
225                 230                 235                 240

Glu Ser Glu Cys Cys Val Val Ile Ala Gln Val Leu Gln Asp Leu Gly
                245                 250                 255

Asp Phe Leu Ala Ala Lys Arg Ala Leu Lys Lys Ala Tyr Arg Leu Gly
            260                 265                 270

Ser Gln Lys Pro Val Gln Arg Ala Ala Ile Cys Gln Asn Leu Gln His
        275                 280                 285

Val Leu Ala Val Val Arg Leu Gln Gln Gln Leu Glu Glu Ala Glu Gly
```

```
    290                 295                 300

Arg Asp Pro Gln Gly Ala Met Val Ile Cys Glu Gln Leu Gly Asp Leu
305                 310                 315                 320

Phe Ser Lys Ala Gly Asp Phe Pro Arg Ala Ala Glu Ala Tyr Gln Lys
                325                 330                 335

Gln Leu Arg Phe Ala Glu Leu Leu Asp Arg Pro Gly Ala Glu Arg Ala
            340                 345                 350

Ile Ile His Val Ser Leu Ala Thr Thr Leu Gly Asp Met Lys Asp His
        355                 360                 365

His Gly Ala Val Arg His Tyr Glu Glu Glu Leu Arg Leu Arg Ser Gly
    370                 375                 380

Asn Val Leu Glu Glu Ala Lys Thr Trp Leu Asn Ile Ala Leu Ser Arg
385                 390                 395                 400

Glu Glu Ala Gly Asp Ala Tyr Glu Leu Leu Ala Pro Cys Phe Gln Lys
                405                 410                 415

Ala Leu Ser Cys Ala Gln Gln Ala Gln Arg Pro Gln Leu Gln Arg Gln
            420                 425                 430

Val Leu Gln His Leu His Thr Val Gln Leu Arg Leu Gln Pro Gln Glu
        435                 440                 445

Ala Pro Glu Thr Glu Thr Arg Leu Arg Glu Leu Ser Val Ala Glu Asp
    450                 455                 460

Glu Asp Glu Glu Glu Glu Ala Glu Glu Ala Ala Ala Thr Ala Glu Ser
465                 470                 475                 480

Glu Ala Leu Glu Ala Gly Glu Val Glu Leu Ser Glu Gly Glu Asp Asp
                485                 490                 495

Thr Asp Gly Leu Thr Pro Gln Leu Glu Glu Asp Glu Glu Leu Gln Gly
            500                 505                 510

His Leu Gly Arg Arg Lys Gly Ser Lys Trp Asn Arg Arg Asn Asp Met
        515                 520                 525

Gly Glu Thr Leu Leu His Arg Ala Cys Ile Glu Gly Gln Leu Arg Arg
    530                 535                 540

Val Gln Asp Leu Val Arg Gln Gly His Pro Leu Asn Pro Arg Asp Tyr
545                 550                 555                 560

Cys Gly Trp Thr Pro Leu His Ala Ala Cys Asn Tyr Gly His Leu Glu
                565                 570                 575

Ile Val Arg Phe Leu Leu Asp His Gly Ala Ala Val Asp Asp Pro Gly
            580                 585                 590

Gly Gln Gly Cys Glu Gly Ile Thr Pro Leu His Asp Ala Leu Asn Cys
        595                 600                 605

Gly His Phe Glu Val Ala Glu Leu Leu Leu Glu Arg Gly Ala Ser Val
    610                 615                 620

Thr Leu Arg Thr Arg Lys Gly Leu Ser Pro Leu Glu Thr Leu Gln Gln
625                 630                 635                 640

Trp Val Lys Leu Tyr Arg Arg Asp Leu Asp Leu Glu Thr Arg Gln Lys
                645                 650                 655

Ala Arg Ala Met Glu Met Leu Leu Gln Ala Ala Ala Ser Gly Gln Asp
            660                 665                 670

Pro His Ser Ser Gln Ala Phe His Thr Pro Ser Ser Leu Leu Phe Asp
        675                 680                 685

Pro Glu Thr Ser Pro Pro Leu Ser Pro Cys Pro Glu Pro Pro Ser Asn
    690                 695                 700

Ser Thr Arg Leu Pro Glu Ala Ser Gln Ala His Val Arg Val Ser Pro
705                 710                 715                 720
```

-continued

```
Gly Gln Ala Ala Pro Ala Met Ala Arg Pro Arg Arg Ser Arg His Gly
                725                 730                 735

Pro Ala Ser Ser Ser Ser Ser Ser Glu Gly Glu Asp Ser Ala Gly Pro
            740                 745                 750

Ala Arg Pro Ser Gln Lys Arg Pro Arg Cys Ser Ala Thr Ala Gln Arg
        755                 760                 765

Val Ala Ala Trp Thr Pro Gly Pro Ala Ser Asn Arg Glu Ala Ala Thr
    770                 775                 780

Ala Ser Thr Ser Arg Ala Ala Tyr Gln Ala Ala Ile Arg Gly Val Gly
785                 790                 795                 800

Ser Ala Gln Ser Arg Leu Gly Pro Gly Pro Pro Arg Gly His Ser Lys
                805                 810                 815

Ala Leu Ala Pro Gln Ala Ala Leu Ile Pro Glu Glu Glu Cys Leu Ala
            820                 825                 830

Gly Asp Trp Leu Glu Leu Asp Met Pro Leu Thr Arg Ser Arg Arg Pro
        835                 840                 845

Arg Pro Arg Gly Thr Gly Asp Asn Arg Arg Pro Ser Ser Thr Ser Gly
    850                 855                 860

Ser Asp Ser Glu Glu Ser Arg Pro Arg Ala Arg Ala Lys Gln Val Arg
865                 870                 875                 880

Leu Thr Cys Met Gln Ser Cys Ser Ala Pro Val Asn Ala Gly Pro Ser
                885                 890                 895

Ser Leu Ala Ser Glu Pro Pro Gly Ser Pro Ser Thr Pro Arg Val Ser
            900                 905                 910

Glu Pro Ser Gly Asp Ser Ser Ala Ala Gly Gln Pro Leu Gly Pro Ala
        915                 920                 925

Pro Pro Pro Pro Ile Arg Val Arg Val Gln Val Gln Asp His Leu Phe
    930                 935                 940

Leu Ile Pro Val Pro His Ser Ser Asp Thr His Ser Val Ala Trp Leu
945                 950                 955                 960

Ala Glu Gln Ala Ala Gln Arg Tyr Tyr Gln Thr Cys Gly Leu Leu Pro
                965                 970                 975

Arg Leu Thr Leu Arg Lys Glu Gly Ala Leu Leu Ala Pro Gln Asp Leu
            980                 985                 990

Ile Pro Asp Val Leu Gln Ser Asn  Asp Glu Val Leu Ala  Glu Val Thr
        995                 1000                 1005

Ser Trp  Asp Leu Pro Pro Leu  Thr Asp Arg Tyr Arg  Arg Ala Cys
    1010                 1015                 1020

Gln Ser  Leu Gly Gln Gly Glu  His Gln Gln Val Leu  Gln Ala Val
    1025                 1030                 1035

Glu Leu  Gln Gly Leu Gly Leu  Ser Phe Ser Ala Cys  Ser Leu Ala
    1040                 1045                 1050

Leu Asp  Gln Ala Gln Leu Thr  Pro Leu Leu Arg Ala  Leu Lys Leu
    1055                 1060                 1065

His Thr  Ala Leu Arg Glu Leu  Arg Leu Ala Gly Asn  Arg Leu Gly
    1070                 1075                 1080

Asp Lys  Cys Val Ala Glu Leu  Val Ala Ala Leu Gly  Thr Met Pro
    1085                 1090                 1095

Ser Leu  Ala Leu Leu Asp Leu  Ser Ser Asn His Leu  Gly Pro Glu
    1100                 1105                 1110

Gly Leu  Arg Gln Leu Ala Met  Gly Leu Pro Gly Gln  Ala Thr Leu
    1115                 1120                 1125
```

Gln Ser Leu Glu Glu Leu Asp Leu Ser Met Asn Pro Leu Gly Asp
1130 1135 1140

Gly Cys Gly Gln Ser Leu Ala Ser Leu Leu His Ala Cys Pro Leu
1145 1150 1155

Leu Ser Thr Leu Arg Leu Gln Ala Cys Gly Phe Gly Pro Ser Phe
1160 1165 1170

Phe Leu Ser His Gln Thr Ala Leu Gly Ser Ala Phe Gln Asp Ala
1175 1180 1185

Glu His Leu Lys Thr Leu Ser Leu Ser Tyr Asn Ala Leu Gly Ala
1190 1195 1200

Pro Ala Leu Ala Arg Thr Leu Gln Ser Leu Pro Ala Gly Thr Leu
1205 1210 1215

Leu His Leu Glu Leu Ser Ser Val Ala Ala Gly Lys Gly Asp Ser
1220 1225 1230

Asp Leu Met Glu Pro Val Phe Arg Tyr Leu Ala Lys Glu Gly Cys
1235 1240 1245

Ala Leu Ala His Leu Thr Leu Ser Ala Asn His Leu Gly Asp Lys
1250 1255 1260

Ala Val Arg Asp Leu Cys Arg Cys Leu Ser Leu Cys Pro Ser Leu
1265 1270 1275

Ile Ser Leu Asp Leu Ser Ala Asn Pro Glu Ile Ser Cys Ala Ser
1280 1285 1290

Leu Glu Glu Leu Leu Ser Thr Leu Gln Lys Arg Pro Gln Gly Leu
1295 1300 1305

Ser Phe Leu Gly Leu Ser Gly Cys Ala Val Gln Gly Pro Leu Gly
1310 1315 1320

Leu Gly Leu Trp Asp Lys Ile Ala Ala Gln Leu Arg Glu Leu Gln
1325 1330 1335

Leu Cys Ser Arg Arg Leu Cys Ala Glu Asp Arg Asp Ala Leu Arg
1340 1345 1350

Gln Leu Gln Pro Ser Arg Pro Gly Pro Gly Glu Cys Thr Leu Asp
1355 1360 1365

His Gly Ser Lys Leu Phe Phe Arg Arg Leu
1370 1375

<210> SEQ ID NO 21
<211> LENGTH: 1378
<212> TYPE: PRT
<213> ORGANISM: Artificial sequence
<220> FEATURE:
<223> OTHER INFORMATION: Mutant protein

<400> SEQUENCE: 21

Met Ser Leu Glu Arg Glu Leu Arg Gln Leu Ser Lys Ala Lys Ala Lys
1 5 10 15

Ala Gln Arg Ala Gly Gln Arg Arg Glu Glu Ala Ala Leu Cys His Gln
20 25 30

Leu Gly Glu Leu Leu Ala Gly His Gly Arg Tyr Ala Glu Ala Leu Glu
35 40 45

Gln His Trp Gln Glu Leu Gln Leu Arg Glu Arg Ala Asp Asp Pro Leu
50 55 60

Gly Cys Ala Val Ala His Arg Lys Ile Gly Glu Arg Leu Ala Glu Met
65 70 75 80

Glu Asp Tyr Pro Ala Ala Leu Gln His Gln His Gln Tyr Leu Glu Leu
85 90 95

-continued

```
Ala His Ser Leu Arg Asn His Thr Glu Leu Gln Arg Ala Trp Ala Thr
            100                 105                 110

Ile Gly Arg Thr His Leu Asp Ile Tyr Asp His Cys Gln Ser Arg Asp
        115                 120                 125

Ala Leu Leu Gln Ala Gln Ala Ala Phe Glu Lys Ser Leu Ala Ile Val
    130                 135                 140

Asp Glu Glu Leu Glu Gly Thr Leu Ala Gln Gly Glu Leu Asn Glu Met
145                 150                 155                 160

Arg Thr Arg Leu Tyr Leu Asn Leu Gly Leu Thr Phe Glu Ser Leu Gln
                165                 170                 175

Gln Thr Ala Leu Cys Asn Asp Tyr Phe Arg Lys Ser Ile Phe Leu Ala
            180                 185                 190

Glu Gln Asn His Leu Tyr Glu Asp Leu Phe Arg Ala Arg Tyr Asn Leu
        195                 200                 205

Gly Thr Ile His Trp Arg Ala Gly Gln His Ser Gln Ala Met Arg Cys
    210                 215                 220

Leu Glu Gly Ala Arg Glu Cys Ala His Thr Met Arg Lys Arg Phe Met
225                 230                 235                 240

Glu Ser Glu Cys Cys Val Val Ile Ala Gln Val Leu Gln Asp Leu Gly
                245                 250                 255

Asp Phe Leu Ala Ala Lys Arg Ala Leu Lys Lys Ala Tyr Arg Leu Gly
            260                 265                 270

Ser Gln Lys Pro Val Gln Arg Ala Ala Ile Cys Gln Asn Leu Gln His
        275                 280                 285

Val Leu Ala Val Val Arg Leu Gln Gln Gln Leu Glu Glu Ala Glu Gly
    290                 295                 300

Arg Asp Pro Gln Gly Ala Met Val Ile Cys Glu Gln Leu Gly Asp Leu
305                 310                 315                 320

Phe Ser Lys Ala Gly Asp Phe Pro Arg Ala Ala Glu Ala Tyr Gln Lys
                325                 330                 335

Gln Leu Arg Phe Ala Glu Leu Leu Asp Arg Pro Gly Ala Glu Arg Ala
            340                 345                 350

Ile Ile His Val Ser Leu Ala Thr Thr Leu Gly Asp Met Lys Asp His
        355                 360                 365

His Gly Ala Val Arg His Tyr Glu Glu Glu Leu Arg Leu Arg Ser Gly
    370                 375                 380

Asn Val Leu Glu Glu Ala Lys Thr Trp Leu Asn Ile Ala Leu Ser Arg
385                 390                 395                 400

Glu Glu Ala Gly Asp Ala Tyr Glu Leu Leu Ala Pro Cys Phe Gln Lys
                405                 410                 415

Ala Leu Ser Cys Ala Gln Gln Ala Gln Arg Pro Gln Leu Gln Arg Gln
            420                 425                 430

Val Leu Gln His Leu His Thr Val Gln Leu Arg Leu Gln Pro Gln Glu
        435                 440                 445

Ala Pro Glu Thr Glu Thr Arg Leu Arg Glu Leu Ser Val Ala Glu Asp
    450                 455                 460

Glu Asp Glu Glu Glu Glu Ala Glu Glu Ala Ala Ala Thr Ala Glu Ser
465                 470                 475                 480

Glu Ala Leu Glu Ala Gly Glu Val Glu Leu Ser Glu Gly Glu Asp Asp
                485                 490                 495

Thr Asp Gly Leu Thr Pro Gln Leu Glu Glu Asp Glu Glu Leu Gln Gly
            500                 505                 510

His Leu Gly Arg Arg Lys Gly Ser Lys Trp Asn Arg Arg Asn Asp Met
```

```
        515                 520                 525

Gly Glu Thr Leu Leu His Arg Ala Cys Ile Glu Gly Gln Leu Arg Arg
    530                 535                 540

Val Gln Asp Leu Val Arg Gln Gly His Pro Leu Asn Pro Arg Asp Tyr
545                 550                 555                 560

Cys Gly Trp Thr Pro Leu His Glu Ala Cys Ala Tyr Gly His Leu Glu
                565                 570                 575

Ile Val Arg Phe Leu Leu Asp His Gly Ala Ala Val Asp Asp Pro Gly
            580                 585                 590

Gly Gln Gly Cys Glu Gly Ile Thr Pro Leu His Asp Ala Leu Asn Cys
        595                 600                 605

Gly His Phe Glu Val Ala Glu Leu Leu Leu Glu Arg Gly Ala Ser Val
    610                 615                 620

Thr Leu Arg Thr Arg Lys Gly Leu Ser Pro Leu Glu Thr Leu Gln Gln
625                 630                 635                 640

Trp Val Lys Leu Tyr Arg Arg Asp Leu Asp Leu Glu Thr Arg Gln Lys
                645                 650                 655

Ala Arg Ala Met Glu Met Leu Leu Gln Ala Ala Ala Ser Gly Gln Asp
            660                 665                 670

Pro His Ser Ser Gln Ala Phe His Thr Pro Ser Ser Leu Leu Phe Asp
        675                 680                 685

Pro Glu Thr Ser Pro Pro Leu Ser Pro Cys Pro Glu Pro Pro Ser Asn
    690                 695                 700

Ser Thr Arg Leu Pro Glu Ala Ser Gln Ala His Val Arg Val Ser Pro
705                 710                 715                 720

Gly Gln Ala Ala Pro Ala Met Ala Arg Pro Arg Arg Ser Arg His Gly
                725                 730                 735

Pro Ala Ser Ser Ser Ser Ser Ser Glu Gly Glu Asp Ser Ala Gly Pro
            740                 745                 750

Ala Arg Pro Ser Gln Lys Arg Pro Arg Cys Ser Ala Thr Ala Gln Arg
        755                 760                 765

Val Ala Ala Trp Thr Pro Gly Pro Ala Ser Asn Arg Glu Ala Ala Thr
    770                 775                 780

Ala Ser Thr Ser Arg Ala Ala Tyr Gln Ala Ala Ile Arg Gly Val Gly
785                 790                 795                 800

Ser Ala Gln Ser Arg Leu Gly Pro Gly Pro Pro Arg Gly His Ser Lys
                805                 810                 815

Ala Leu Ala Pro Gln Ala Ala Leu Ile Pro Glu Glu Glu Cys Leu Ala
            820                 825                 830

Gly Asp Trp Leu Glu Leu Asp Met Pro Leu Thr Arg Ser Arg Arg Pro
        835                 840                 845

Arg Pro Arg Gly Thr Gly Asp Asn Arg Arg Pro Ser Ser Thr Ser Gly
    850                 855                 860

Ser Asp Ser Glu Glu Ser Arg Pro Arg Ala Arg Ala Lys Gln Val Arg
865                 870                 875                 880

Leu Thr Cys Met Gln Ser Cys Ser Ala Pro Val Asn Ala Gly Pro Ser
                885                 890                 895

Ser Leu Ala Ser Glu Pro Pro Gly Ser Pro Ser Thr Pro Arg Val Ser
            900                 905                 910

Glu Pro Ser Gly Asp Ser Ser Ala Ala Gly Gln Pro Leu Gly Pro Ala
        915                 920                 925

Pro Pro Pro Pro Ile Arg Val Arg Val Gln Val Gln Asp His Leu Phe
    930                 935                 940
```

-continued

```
Leu Ile Pro Val Pro His Ser Ser Asp Thr His Ser Val Ala Trp Leu
945                 950                 955                 960

Ala Glu Gln Ala Ala Gln Arg Tyr Tyr Gln Thr Cys Gly Leu Leu Pro
                965                 970                 975

Arg Leu Thr Leu Arg Lys Glu Gly Ala Leu Leu Ala Pro Gln Asp Leu
            980                 985                 990

Ile Pro Asp Val Leu Gln Ser Asn  Asp Glu Val Leu Ala  Glu Val Thr
        995                 1000                1005

Ser Trp  Asp Leu Pro Pro Leu  Thr Asp Arg Tyr Arg  Arg Ala Cys
    1010                1015                1020

Gln Ser  Leu Gly Gln Gly Glu  His Gln Gln Val Leu  Gln Ala Val
    1025                1030                1035

Glu Leu  Gln Gly Leu Gly Leu  Ser Phe Ser Ala Cys  Ser Leu Ala
    1040                1045                1050

Leu Asp  Gln Ala Gln Leu Thr  Pro Leu Leu Arg Ala  Leu Lys Leu
    1055                1060                1065

His Thr  Ala Leu Arg Glu Leu  Arg Leu Ala Gly Asn  Arg Leu Gly
    1070                1075                1080

Asp Lys  Cys Val Ala Glu Leu  Val Ala Ala Leu Gly  Thr Met Pro
    1085                1090                1095

Ser Leu  Ala Leu Leu Asp Leu  Ser Ser Asn His Leu  Gly Pro Glu
    1100                1105                1110

Gly Leu  Arg Gln Leu Ala Met  Gly Leu Pro Gly Gln  Ala Thr Leu
    1115                1120                1125

Gln Ser  Leu Glu Glu Leu Asp  Leu Ser Met Asn Pro  Leu Gly Asp
    1130                1135                1140

Gly Cys  Gly Gln Ser Leu Ala  Ser Leu Leu His Ala  Cys Pro Leu
    1145                1150                1155

Leu Ser  Thr Leu Arg Leu Gln  Ala Cys Gly Phe Gly  Pro Ser Phe
    1160                1165                1170

Phe Leu  Ser His Gln Thr Ala  Leu Gly Ser Ala Phe  Gln Asp Ala
    1175                1180                1185

Glu His  Leu Lys Thr Leu Ser  Leu Ser Tyr Asn Ala  Leu Gly Ala
    1190                1195                1200

Pro Ala  Leu Ala Arg Thr Leu  Gln Ser Leu Pro Ala  Gly Thr Leu
    1205                1210                1215

Leu His  Leu Glu Leu Ser Ser  Val Ala Ala Gly Lys  Gly Asp Ser
    1220                1225                1230

Asp Leu  Met Glu Pro Val Phe  Arg Tyr Leu Ala Lys  Glu Gly Cys
    1235                1240                1245

Ala Leu  Ala His Leu Thr Leu  Ser Ala Asn His Leu  Gly Asp Lys
    1250                1255                1260

Ala Val  Arg Asp Leu Cys Arg  Cys Leu Ser Leu Cys  Pro Ser Leu
    1265                1270                1275

Ile Ser  Leu Asp Leu Ser Ala  Asn Pro Glu Ile Ser  Cys Ala Ser
    1280                1285                1290

Leu Glu  Glu Leu Leu Ser Thr  Leu Gln Lys Arg Pro  Gln Gly Leu
    1295                1300                1305

Ser Phe  Leu Gly Leu Ser Gly  Cys Ala Val Gln Gly  Pro Leu Gly
    1310                1315                1320

Leu Gly  Leu Trp Asp Lys Ile  Ala Ala Gln Leu Arg  Glu Leu Gln
    1325                1330                1335
```

-continued

Leu Cys Ser Arg Arg Leu Cys Ala Glu Asp Arg Asp Ala Leu Arg
    1340                1345                1350

Gln Leu Gln Pro Ser Arg Pro Gly Pro Gly Glu Cys Thr Leu Asp
    1355                1360                1365

His Gly Ser Lys Leu Phe Phe Arg Arg Leu
    1370                1375

<210> SEQ ID NO 22
<211> LENGTH: 1378
<212> TYPE: PRT
<213> ORGANISM: Artificial sequence
<220> FEATURE:
<223> OTHER INFORMATION: Mutant protein

<400> SEQUENCE: 22

Met Ser Leu Glu Arg Glu Leu Arg Gln Leu Ser Lys Ala Lys Ala Lys
1               5                   10                  15

Ala Gln Arg Ala Gly Gln Arg Arg Glu Glu Ala Ala Leu Cys His Gln
            20                  25                  30

Leu Gly Glu Leu Leu Ala Gly His Gly Arg Tyr Ala Glu Ala Leu Glu
        35                  40                  45

Gln His Trp Gln Glu Leu Gln Leu Arg Glu Arg Ala Asp Asp Pro Leu
    50                  55                  60

Gly Cys Ala Val Ala His Arg Lys Ile Gly Glu Arg Leu Ala Glu Met
65                  70                  75                  80

Glu Asp Tyr Pro Ala Ala Leu Gln His Gln His Gln Tyr Leu Glu Leu
                85                  90                  95

Ala His Ser Leu Arg Asn His Thr Glu Leu Gln Arg Ala Trp Ala Thr
            100                 105                 110

Ile Gly Arg Thr His Leu Asp Ile Tyr Asp His Cys Gln Ser Arg Asp
        115                 120                 125

Ala Leu Leu Gln Ala Gln Ala Ala Phe Glu Lys Ser Leu Ala Ile Val
    130                 135                 140

Asp Glu Glu Leu Glu Gly Thr Leu Ala Gln Gly Glu Leu Asn Glu Met
145                 150                 155                 160

Arg Thr Arg Leu Tyr Leu Asn Leu Gly Leu Thr Phe Glu Ser Leu Gln
                165                 170                 175

Gln Thr Ala Leu Cys Asn Asp Tyr Phe Arg Lys Ser Ile Phe Leu Ala
            180                 185                 190

Glu Gln Asn His Leu Tyr Glu Asp Leu Phe Arg Ala Arg Tyr Asn Leu
        195                 200                 205

Gly Thr Ile His Trp Arg Ala Gly Gln His Ser Gln Ala Met Arg Cys
    210                 215                 220

Leu Glu Gly Ala Arg Glu Cys Ala His Thr Met Arg Lys Arg Phe Met
225                 230                 235                 240

Glu Ser Glu Cys Cys Val Val Ile Ala Gln Val Leu Gln Asp Leu Gly
                245                 250                 255

Asp Phe Leu Ala Ala Lys Arg Ala Leu Lys Lys Ala Tyr Arg Leu Gly
            260                 265                 270

Ser Gln Lys Pro Val Gln Arg Ala Ala Ile Cys Gln Asn Leu Gln His
        275                 280                 285

Val Leu Ala Val Val Arg Leu Gln Gln Gln Leu Glu Glu Ala Glu Gly
    290                 295                 300

Arg Asp Pro Gln Gly Ala Met Val Ile Cys Glu Gln Leu Gly Asp Leu
305                 310                 315                 320

-continued

```
Phe Ser Lys Ala Gly Asp Phe Pro Arg Ala Ala Glu Ala Tyr Gln Lys
                325                 330                 335

Gln Leu Arg Phe Ala Glu Leu Leu Asp Arg Pro Gly Ala Glu Arg Ala
            340                 345                 350

Ile Ile His Val Ser Leu Ala Thr Thr Leu Gly Asp Met Lys Asp His
        355                 360                 365

His Gly Ala Val Arg His Tyr Glu Glu Glu Leu Arg Leu Arg Ser Gly
    370                 375                 380

Asn Val Leu Glu Glu Ala Lys Thr Trp Leu Asn Ile Ala Leu Ser Arg
385                 390                 395                 400

Glu Glu Ala Gly Asp Ala Tyr Glu Leu Leu Ala Pro Cys Phe Gln Lys
                405                 410                 415

Ala Leu Ser Cys Ala Gln Gln Ala Gln Arg Pro Gln Leu Gln Arg Gln
            420                 425                 430

Val Leu Gln His Leu His Thr Val Gln Leu Arg Leu Gln Pro Gln Glu
        435                 440                 445

Ala Pro Glu Thr Glu Thr Arg Leu Arg Glu Leu Ser Val Ala Glu Asp
    450                 455                 460

Glu Asp Glu Glu Glu Glu Ala Glu Glu Ala Ala Ala Thr Ala Glu Ser
465                 470                 475                 480

Glu Ala Leu Glu Ala Gly Glu Val Glu Leu Ser Glu Gly Glu Asp Asp
                485                 490                 495

Thr Asp Gly Leu Thr Pro Gln Leu Glu Glu Asp Glu Glu Leu Gln Gly
            500                 505                 510

His Leu Gly Arg Arg Lys Gly Ser Lys Trp Asn Arg Arg Asn Asp Met
        515                 520                 525

Gly Glu Thr Leu Leu His Arg Ala Cys Ile Glu Gly Gln Leu Arg Arg
    530                 535                 540

Val Gln Asp Leu Val Arg Gln Gly His Pro Leu Asn Pro Arg Asp Tyr
545                 550                 555                 560

Cys Gly Trp Thr Pro Leu His Glu Ala Cys Asn Tyr Gly His Leu Glu
                565                 570                 575

Ile Val Arg Phe Leu Leu Asp His Gly Ala Ala Val Asp Asp Pro Gly
            580                 585                 590

Gly Gln Gly Cys Glu Gly Ile Thr Pro Leu His Ala Ala Leu Asn Cys
        595                 600                 605

Gly His Phe Glu Val Ala Glu Leu Leu Leu Glu Arg Gly Ala Ser Val
    610                 615                 620

Thr Leu Arg Thr Arg Lys Gly Leu Ser Pro Leu Glu Thr Leu Gln Gln
625                 630                 635                 640

Trp Val Lys Leu Tyr Arg Arg Asp Leu Asp Leu Glu Thr Arg Gln Lys
                645                 650                 655

Ala Arg Ala Met Glu Met Leu Leu Gln Ala Ala Ala Ser Gly Gln Asp
            660                 665                 670

Pro His Ser Ser Gln Ala Phe His Thr Pro Ser Ser Leu Leu Phe Asp
        675                 680                 685

Pro Glu Thr Ser Pro Pro Leu Ser Pro Cys Pro Glu Pro Pro Ser Asn
    690                 695                 700

Ser Thr Arg Leu Pro Glu Ala Ser Gln Ala His Val Arg Val Ser Pro
705                 710                 715                 720

Gly Gln Ala Ala Pro Ala Met Ala Arg Pro Arg Arg Ser Arg His Gly
                725                 730                 735

Pro Ala Ser Ser Ser Ser Ser Ser Glu Gly Glu Asp Ser Ala Gly Pro
```

-continued

```
            740                 745                 750

Ala Arg Pro Ser Gln Lys Arg Pro Arg Cys Ser Ala Thr Ala Gln Arg
        755                 760                 765

Val Ala Ala Trp Thr Pro Gly Pro Ala Ser Asn Arg Glu Ala Ala Thr
    770                 775                 780

Ala Ser Thr Ser Arg Ala Ala Tyr Gln Ala Ala Ile Arg Gly Val Gly
785                 790                 795                 800

Ser Ala Gln Ser Arg Leu Gly Pro Gly Pro Pro Arg Gly His Ser Lys
                805                 810                 815

Ala Leu Ala Pro Gln Ala Ala Leu Ile Pro Glu Glu Glu Cys Leu Ala
            820                 825                 830

Gly Asp Trp Leu Glu Leu Asp Met Pro Leu Thr Arg Ser Arg Arg Pro
        835                 840                 845

Arg Pro Arg Gly Thr Gly Asp Asn Arg Arg Pro Ser Ser Thr Ser Gly
    850                 855                 860

Ser Asp Ser Glu Glu Ser Arg Pro Arg Ala Arg Ala Lys Gln Val Arg
865                 870                 875                 880

Leu Thr Cys Met Gln Ser Cys Ser Ala Pro Val Asn Ala Gly Pro Ser
                885                 890                 895

Ser Leu Ala Ser Glu Pro Pro Gly Ser Pro Ser Thr Pro Arg Val Ser
            900                 905                 910

Glu Pro Ser Gly Asp Ser Ser Ala Ala Gly Gln Pro Leu Gly Pro Ala
        915                 920                 925

Pro Pro Pro Pro Ile Arg Val Arg Val Gln Val Gln Asp His Leu Phe
    930                 935                 940

Leu Ile Pro Val Pro His Ser Ser Asp Thr His Ser Val Ala Trp Leu
945                 950                 955                 960

Ala Glu Gln Ala Ala Gln Arg Tyr Tyr Gln Thr Cys Gly Leu Leu Pro
                965                 970                 975

Arg Leu Thr Leu Arg Lys Glu Gly Ala Leu Leu Ala Pro Gln Asp Leu
            980                 985                 990

Ile Pro Asp Val Leu Gln Ser Asn  Asp Glu Val Leu Ala  Glu Val Thr
        995                 1000                1005

Ser Trp  Asp Leu Pro Pro Leu  Thr Asp Arg Tyr Arg  Arg Ala Cys
    1010                1015                1020

Gln Ser  Leu Gly Gln Gly Glu  His Gln Gln Val Leu  Gln Ala Val
    1025                1030                1035

Glu Leu  Gln Gly Leu Gly Leu  Ser Phe Ser Ala Cys  Ser Leu Ala
    1040                1045                1050

Leu Asp  Gln Ala Gln Leu Thr  Pro Leu Leu Arg Ala  Leu Lys Leu
    1055                1060                1065

His Thr  Ala Leu Arg Glu Leu  Arg Leu Ala Gly Asn  Arg Leu Gly
    1070                1075                1080

Asp Lys  Cys Val Ala Glu Leu  Val Ala Ala Leu Gly  Thr Met Pro
    1085                1090                1095

Ser Leu  Ala Leu Leu Asp Leu  Ser Ser Asn His Leu  Gly Pro Glu
    1100                1105                1110

Gly Leu  Arg Gln Leu Ala Met  Gly Leu Pro Gly Gln  Ala Thr Leu
    1115                1120                1125

Gln Ser  Leu Glu Glu Leu Asp  Leu Ser Met Asn Pro  Leu Gly Asp
    1130                1135                1140

Gly Cys  Gly Gln Ser Leu Ala  Ser Leu Leu His Ala  Cys Pro Leu
    1145                1150                1155
```

Leu Ser Thr Leu Arg Leu Gln Ala Cys Gly Phe Gly Pro Ser Phe
1160 1165 1170

Phe Leu Ser His Gln Thr Ala Leu Gly Ser Ala Phe Gln Asp Ala
1175 1180 1185

Glu His Leu Lys Thr Leu Ser Leu Ser Tyr Asn Ala Leu Gly Ala
1190 1195 1200

Pro Ala Leu Ala Arg Thr Leu Gln Ser Leu Pro Ala Gly Thr Leu
1205 1210 1215

Leu His Leu Glu Leu Ser Ser Val Ala Ala Gly Lys Gly Asp Ser
1220 1225 1230

Asp Leu Met Glu Pro Val Phe Arg Tyr Leu Ala Lys Glu Gly Cys
1235 1240 1245

Ala Leu Ala His Leu Thr Leu Ser Ala Asn His Leu Gly Asp Lys
1250 1255 1260

Ala Val Arg Asp Leu Cys Arg Cys Leu Ser Leu Cys Pro Ser Leu
1265 1270 1275

Ile Ser Leu Asp Leu Ser Ala Asn Pro Glu Ile Ser Cys Ala Ser
1280 1285 1290

Leu Glu Glu Leu Leu Ser Thr Leu Gln Lys Arg Pro Gln Gly Leu
1295 1300 1305

Ser Phe Leu Gly Leu Ser Gly Cys Ala Val Gln Gly Pro Leu Gly
1310 1315 1320

Leu Gly Leu Trp Asp Lys Ile Ala Ala Gln Leu Arg Glu Leu Gln
1325 1330 1335

Leu Cys Ser Arg Arg Leu Cys Ala Glu Asp Arg Asp Ala Leu Arg
1340 1345 1350

Gln Leu Gln Pro Ser Arg Pro Gly Pro Gly Glu Cys Thr Leu Asp
1355 1360 1365

His Gly Ser Lys Leu Phe Phe Arg Arg Leu
1370 1375

<210> SEQ ID NO 23
<211> LENGTH: 103
<212> TYPE: PRT
<213> ORGANISM: Homo sapiens

<400> SEQUENCE: 23

Met Ser Gly Arg Gly Lys Gly Gly Lys Gly Leu Gly Lys Gly Gly Ala
1 5 10 15

Lys Arg His Arg Lys Val Leu Arg Asp Asn Ile Gln Gly Ile Thr Lys
20 25 30

Pro Ala Ile Arg Arg Leu Ala Arg Arg Gly Gly Val Lys Arg Ile Ser
35 40 45

Gly Leu Ile Tyr Glu Glu Thr Arg Gly Val Leu Lys Val Phe Leu Glu
50 55 60

Asn Val Ile Arg Asp Ala Val Thr Tyr Thr Glu His Ala Lys Arg Lys
65 70 75 80

Thr Val Thr Ala Met Asp Val Val Tyr Ala Leu Lys Arg Gln Gly Arg
85 90 95

Thr Leu Tyr Gly Phe Gly Gly
100

<210> SEQ ID NO 24
<211> LENGTH: 904
<212> TYPE: PRT

-continued

<213> ORGANISM: Homo sapiens

<400> SEQUENCE: 24

Met Ala Glu Ser Ser Glu Ser Phe Thr Met Ala Ser Ser Pro Ala Gln
1 5 10 15

Arg Arg Arg Gly Asn Asp Pro Leu Thr Ser Ser Pro Gly Arg Ser Ser
20 25 30

Arg Arg Thr Asp Ala Leu Thr Ser Ser Pro Gly Arg Asp Leu Pro Pro
35 40 45

Phe Glu Asp Glu Ser Glu Gly Leu Leu Gly Thr Glu Gly Pro Leu Glu
50 55 60

Glu Glu Glu Asp Gly Glu Glu Leu Ile Gly Asp Gly Met Glu Arg Asp
65 70 75 80

Tyr Arg Ala Ile Pro Glu Leu Asp Ala Tyr Glu Ala Glu Gly Leu Ala
85 90 95

Leu Asp Asp Glu Asp Val Glu Glu Leu Thr Ala Ser Gln Arg Glu Ala
100 105 110

Ala Glu Arg Ala Met Arg Gln Arg Asp Arg Glu Ala Gly Arg Gly Leu
115 120 125

Gly Arg Met Arg Arg Gly Leu Leu Tyr Asp Ser Asp Glu Glu Asp Glu
130 135 140

Glu Arg Pro Ala Arg Lys Arg Arg Gln Val Glu Arg Ala Thr Glu Asp
145 150 155 160

Gly Glu Glu Asp Glu Glu Met Ile Glu Ser Ile Glu Asn Leu Glu Asp
165 170 175

Leu Lys Gly His Ser Val Arg Glu Trp Val Ser Met Ala Gly Pro Arg
180 185 190

Leu Glu Ile His His Arg Phe Lys Asn Phe Leu Arg Thr His Val Asp
195 200 205

Ser His Gly His Asn Val Phe Lys Glu Arg Ile Ser Asp Met Cys Lys
210 215 220

Glu Asn Arg Glu Ser Leu Val Val Asn Tyr Glu Asp Leu Ala Ala Arg
225 230 235 240

Glu His Val Leu Ala Tyr Phe Leu Pro Glu Ala Pro Ala Glu Leu Leu
245 250 255

Gln Ile Phe Asp Glu Ala Ala Leu Glu Val Val Leu Ala Met Tyr Pro
260 265 270

Lys Tyr Asp Arg Ile Thr Asn His Ile His Val Arg Ile Ser His Leu
275 280 285

Pro Leu Val Glu Glu Leu Arg Ser Leu Arg Gln Leu His Leu Asn Gln
290 295 300

Leu Ile Arg Thr Ser Gly Val Val Thr Ser Cys Thr Gly Val Leu Pro
305 310 315 320

Gln Leu Ser Met Val Lys Tyr Asn Cys Asn Lys Cys Asn Phe Val Leu
325 330 335

Gly Pro Phe Cys Gln Ser Gln Asn Gln Glu Val Lys Pro Gly Ser Cys
340 345 350

Pro Glu Cys Gln Ser Ala Gly Pro Phe Glu Val Asn Met Glu Glu Thr
355 360 365

Ile Tyr Gln Asn Tyr Gln Arg Ile Arg Ile Gln Glu Ser Pro Gly Lys
370 375 380

Val Ala Ala Gly Arg Leu Pro Arg Ser Lys Asp Ala Ile Leu Leu Ala
385 390 395 400

-continued

```
Asp Leu Val Asp Ser Cys Lys Pro Gly Asp Glu Ile Glu Leu Thr Gly
                405                 410                 415

Ile Tyr His Asn Asn Tyr Asp Gly Ser Leu Asn Thr Ala Asn Gly Phe
            420                 425                 430

Pro Val Phe Ala Thr Val Ile Leu Ala Asn His Val Ala Lys Lys Asp
        435                 440                 445

Asn Lys Val Ala Val Gly Glu Leu Thr Asp Glu Asp Val Lys Met Ile
    450                 455                 460

Thr Ser Leu Ser Lys Asp Gln Gln Ile Gly Glu Lys Ile Phe Ala Ser
465                 470                 475                 480

Ile Ala Pro Ser Ile Tyr Gly His Glu Asp Ile Lys Arg Gly Leu Ala
                485                 490                 495

Leu Ala Leu Phe Gly Gly Glu Pro Lys Asn Pro Gly Gly Lys His Lys
            500                 505                 510

Val Arg Gly Asp Ile Asn Val Leu Leu Cys Gly Asp Pro Gly Thr Ala
        515                 520                 525

Lys Ser Gln Phe Leu Lys Tyr Ile Glu Lys Val Ser Ser Arg Ala Ile
    530                 535                 540

Phe Thr Thr Gly Gln Gly Ala Ser Ala Val Gly Leu Thr Ala Tyr Val
545                 550                 555                 560

Gln Arg His Pro Val Ser Arg Glu Trp Thr Leu Glu Ala Gly Ala Leu
                565                 570                 575

Val Leu Ala Asp Arg Gly Val Cys Leu Ile Asp Glu Phe Asp Lys Met
            580                 585                 590

Asn Asp Gln Asp Arg Thr Ser Ile His Glu Ala Met Glu Gln Gln Ser
        595                 600                 605

Ile Ser Ile Ser Lys Ala Gly Ile Val Thr Ser Leu Gln Ala Arg Cys
    610                 615                 620

Thr Val Ile Ala Ala Ala Asn Pro Ile Gly Gly Arg Tyr Asp Pro Ser
625                 630                 635                 640

Leu Thr Phe Ser Glu Asn Val Asp Leu Thr Glu Pro Ile Ile Ser Arg
                645                 650                 655

Phe Asp Ile Leu Cys Val Val Arg Asp Thr Val Asp Pro Val Gln Asp
            660                 665                 670

Glu Met Leu Ala Arg Phe Val Val Gly Ser His Val Arg His His Pro
        675                 680                 685

Ser Asn Lys Glu Glu Glu Gly Leu Ala Asn Gly Ser Ala Ala Glu Pro
    690                 695                 700

Ala Met Pro Asn Thr Tyr Gly Val Glu Pro Leu Pro Gln Glu Val Leu
705                 710                 715                 720

Lys Lys Tyr Ile Ile Tyr Ala Lys Glu Arg Val His Pro Lys Leu Asn
                725                 730                 735

Gln Met Asp Gln Asp Lys Val Ala Lys Met Tyr Ser Asp Leu Arg Lys
            740                 745                 750

Glu Ser Met Ala Thr Gly Ser Ile Pro Ile Thr Val Arg His Ile Glu
        755                 760                 765

Ser Met Ile Arg Met Ala Glu Ala His Ala Arg Ile His Leu Arg Asp
    770                 775                 780

Tyr Val Ile Glu Asp Asp Val Asn Met Ala Ile Arg Val Met Leu Glu
785                 790                 795                 800

Ser Phe Ile Asp Thr Gln Lys Phe Ser Val Met Arg Ser Met Arg Lys
                805                 810                 815

Thr Phe Ala Arg Tyr Leu Ser Phe Arg Arg Asp Asn Asn Glu Leu Leu
```

```
            820                 825                 830

Leu Phe Ile Leu Lys Gln Leu Val Ala Glu Gln Val Thr Tyr Gln Arg
        835                 840                 845

Asn Arg Phe Gly Ala Gln Gln Asp Thr Ile Glu Val Pro Glu Lys Asp
    850                 855                 860

Leu Val Asp Lys Ala Arg Gln Ile Asn Ile His Asn Leu Ser Ala Phe
865                 870                 875                 880

Tyr Asp Ser Glu Leu Phe Arg Met Asn Lys Phe Ser His Asp Leu Lys
                885                 890                 895

Arg Lys Met Ile Leu Gln Gln Phe
            900


<210> SEQ ID NO 25
<211> LENGTH: 136
<212> TYPE: PRT
<213> ORGANISM: Homo sapiens

<400> SEQUENCE: 25

Met Ala Arg Thr Lys Gln Thr Ala Arg Lys Ser Thr Gly Gly Lys Ala
1               5                   10                  15

Pro Arg Lys Gln Leu Ala Thr Lys Ala Ala Arg Lys Ser Ala Pro Ser
            20                  25                  30

Thr Gly Gly Val Lys Lys Pro His Arg Tyr Arg Pro Gly Thr Val Ala
        35                  40                  45

Leu Arg Glu Ile Arg Arg Tyr Gln Lys Ser Thr Glu Leu Leu Ile Arg
    50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ala Ala Ile Gly Ala Leu Gln Glu Ala
                85                  90                  95

Ser Glu Ala Tyr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
    130                 135


<210> SEQ ID NO 26
<211> LENGTH: 4
<212> TYPE: PRT
<213> ORGANISM: Artificial sequence
<220> FEATURE:
<223> OTHER INFORMATION: Peptide motif
<220> FEATURE:
<221> NAME/KEY: MISC_FEATURE
<222> LOCATION: (3)..(3)
<223> OTHER INFORMATION: Xaa may be any amino acid

<400> SEQUENCE: 26

Arg His Xaa Lys
1


<210> SEQ ID NO 27
<211> LENGTH: 6
<212> TYPE: PRT
<213> ORGANISM: Artificial sequence
<220> FEATURE:
<223> OTHER INFORMATION: Peptide motif
<220> FEATURE:
<221> NAME/KEY: MISC_FEATURE
<222> LOCATION: (3)..(3)
```

<223> OTHER INFORMATION: Xaa may be any amino acid

<400> SEQUENCE: 27

Arg His Xaa Lys Val Leu
1 5

<210> SEQ ID NO 28
<211> LENGTH: 7
<212> TYPE: PRT
<213> ORGANISM: Artificial sequence
<220> FEATURE:
<223> OTHER INFORMATION: Peptide motif
<220> FEATURE:
<221> NAME/KEY: MISC_FEATURE
<222> LOCATION: (3)..(3)
<223> OTHER INFORMATION: Xaa may be any amino acid

<400> SEQUENCE: 28

Arg His Xaa Lys Val Leu Arg
1 5

<210> SEQ ID NO 29
<211> LENGTH: 9
<212> TYPE: PRT
<213> ORGANISM: Artificial sequence
<220> FEATURE:
<223> OTHER INFORMATION: Peptide

<400> SEQUENCE: 29

Ala Lys Arg His Arg Lys Val Leu Arg
1 5

<210> SEQ ID NO 30
<211> LENGTH: 12
<212> TYPE: PRT
<213> ORGANISM: Artificial sequence
<220> FEATURE:
<223> OTHER INFORMATION: Peptide

<400> SEQUENCE: 30

Lys Gly Gly Ala Lys Arg His Arg Lys Val Leu Arg
1 5 10

<210> SEQ ID NO 31
<211> LENGTH: 12
<212> TYPE: PRT
<213> ORGANISM: Artificial sequence
<220> FEATURE:
<223> OTHER INFORMATION: Peptide

<400> SEQUENCE: 31

Lys Gly Gly Ala Lys Arg His Ala Lys Val Leu Arg
1 5 10

<210> SEQ ID NO 32
<211> LENGTH: 12
<212> TYPE: PRT
<213> ORGANISM: Artificial sequence
<220> FEATURE:
<223> OTHER INFORMATION: Peptide

<400> SEQUENCE: 32

Lys Gly Gly Ala Ala Arg His Arg Lys Val Leu Arg
1 5 10

<210> SEQ ID NO 33
<211> LENGTH: 17

-continued

```
<212> TYPE: PRT
<213> ORGANISM: Artificial sequence
<220> FEATURE:
<223> OTHER INFORMATION: Peptide

<400> SEQUENCE: 33

Leu Gly Lys Gly Gly Ala Lys Arg His Arg Lys Val Leu Arg Asp Asn
1               5                   10                  15

Ile


<210> SEQ ID NO 34
<211> LENGTH: 102
<212> TYPE: PRT
<213> ORGANISM: Homo sapiens

<400> SEQUENCE: 34

Ser Gly Arg Gly Lys Gly Gly Lys Gly Leu Gly Lys Gly Gly Ala Lys
1               5                   10                  15

Arg His Arg Lys Val Leu Arg Asp Asn Ile Gln Gly Ile Thr Lys Pro
            20                  25                  30

Ala Ile Arg Arg Leu Ala Arg Arg Gly Gly Val Lys Arg Ile Ser Gly
        35                  40                  45

Leu Ile Tyr Glu Glu Thr Arg Gly Val Leu Lys Val Phe Leu Glu Asn
    50                  55                  60

Val Ile Arg Asp Ala Val Thr Tyr Thr Glu His Ala Lys Arg Lys Thr
65                  70                  75                  80

Val Thr Ala Met Asp Val Val Tyr Ala Leu Lys Arg Gln Gly Arg Thr
                85                  90                  95

Leu Tyr Gly Phe Gly Gly
            100
```

SMALL MOLECULES BLOCKING HISTONE READER DOMAINS

REFERENCE TO RELATED APPLICATIONS

This application is a divisional application of U.S. patent application Ser. No. 15/765,344, filed Apr. 2, 2018, which is a U.S. national stage application of PCT/DK2016/050317, filed Sep. 30, 2016, which claims priority from U.S. Provisional Patent Application Ser. No. 62/324,257, filed Apr. 18, 2016 and Danish Application No. PA201500605, filed Oct. 2, 2015. The entire content of each application is incorporated herein by reference.

FIELD OF THE INVENTION

The present invention relates to novel inhibitors of the TONSL protein required for genome stability. TONSL functions as an obligate heterodimer with MMS22L in DNA repair of double strand breaks (DSBs) and stabilization of replicating DNA intermediates via error-free homologous recombination (HR).

The present inventors have solved the structure of the TONSL ARD in complex with its histone substrate, histone H4 tails, providing grounds for structure-based rational drug design of small molecules, peptides or polypeptides capable of preventing or disrupting the binding of the H4 tail with the TONSL ARD via direct competition or via allosteric disruption of the binding pocket.

BACKGROUND OF THE INVENTION

Cells are continuously exposed to diverse sources of DNA damage, and to face this challenge they have devised an array of DNA repair strategies. One of the key repair pathways for DNA double strand breaks, damaged replication forks and key for survival of proliferating cells is homologous recombination (HR).

Many cancer cells experience high load of replication stress, making them vulnerable to HR inhibition.

Cancer cells often also depend on this pathway to repair DNA damage generated by conventional chemotherapy; therefore, HR targeting drugs are clinically attractive due to synthetic lethality of affected cells.

Development of HR inhibitors is also of great clinical interest because PARP inhibitors kill HR defective cells. Therefore blocking two alternative pathways will deliver a much bigger impact than targeting either pathway alone. Additionally, some tumours cells are defective in other DNA repair pathways and therefore dependent on HR, making them sensitive to inhibition of HR repair.

TONSL (Tonsoku-like, NFKBIL2) is a crucial HR regulator that functions in a heterodimeric complex with MMS22L to promote repair of DSBs and damaged replication forks by HR. In HR, TONSL-MMS22L is proposed to regulate Rad51 loading onto ssDNA. Depletion of MMS22L or TONSL results in a pronounced decrease of cell proliferation and marked hypersensitivity to the topoisomerase I poison camptothecin (CPT), which is most likely caused by an inability to promote RAD51-mediated repair of broken replication forks. However, the molecular mechanisms regulating TONSL-MMS22L function in DNA repair are not known.

TONSL-MMS22L forms a complex with histones H3-H4, the histone chaperone ASF1 and MCM2, 4, 6, 7 that depend on the TONSL Ankyrin Repeat Domain (ARD), suggesting that the ARD could be important for TONSL function.

ARD is a common protein-protein interaction motif consisting of tandemly repeated modules of about 33 amino acids, occurring in a large number of functionally diverse proteins including transcriptional initiators, cell cycle regulators, cytoskeletal proteins, ion transporters and signal transducers.

Crystal structures of several ARD proteins are solved, including G9a/GLP ARD that binds specifically histone H3 methylated at lysine 9 (Collins et al., Nat Struct Mol Cell Biol 15:245, 2008). Yet the specificity of most ARDs remain unknown.

By sequence similarity, TONSL ARD is highly similar to the BARD1 ARD. BARD1 is a well-characterized HR factor, obligate partner of BRCA1, and is required for most cellular and tumour-suppressor functions of BRCA1 (Westermark et al., Mol Cell Biol 23:7926, 2003).

The crystal structure of BARD1 ARD is available (Fox et al., J Biol Chem 283:21179, 2008) but the binding specificity of the BARD1 ARD is unknown, and thus does not provide grounds for inhibitor design.

Therefore, it is desirable to identify target molecules bound by TONSL ARD and obtain crystals of these protein complexes in order to solve their structures at atomic resolution. This provides basis to determine whether the binding is important for TONSL-MMS22L function, thus making it an attractive drug target. Further, high-resolution structures of binding pockets with their substrates can enable the skilled addressee in designing small molecules interfering with the binding of TONSL ARD to its target molecule and subsequently verifying the effect in biological assays in a rapid and reproducible manner.

SUMMARY OF THE INVENTION

The present inventors have discovered a molecular mechanism for recruitment of TONSL and its partner MMS22L to post-replicative chromatin that opens an avenue to target the HR repair pathway in cancer treatment. This mechanism relies on recognition of histone H4 unmodified at K20 (H4K20me0) by the TONSL Ankyrin Repeat Domain (ARD) domain that functions as a novel histone reader domain.

The highlights of this the discovery work include

1. Structural and biochemical data identifying the TONSL ARD as the first histone reader specific for H4 tails unmethylated at K20 (H4K20me0). H4K20me0 is specific to newly synthesized histones incorporated during DNA replication, marking post-replicative chromatin until late G2/M when K20me1 is established.
2. Functional and structural data revealing that TONSL via ARD recognition of H4K20me0 binds soluble new histones in complex with MCM2 and ASF1, proving a means to deliver TONSL-MMS22L to replicating chromatin.
3. Functional data that TONSL binds nucleosomal histones in post-replicative chromatin via ARD recognition of H4K20me0 and demonstration that this is required for TONSL-MMS22L accumulation at damaged replication forks and DNA lesions.
4. Functional data that TONLS ARD mutant protein titrates MMS22L away from chromatin and is toxic to cells.
5. The TONSL ARD mutant proteins induce G2/M arrest, replication-associated DNA damage (53BP1 foci) and reduce viability in the presence and absence of camptothecin (CPT).

6. By removing TONSL from chromatin, the function of TONSL-MMS22L complex in DNA repair is disabled.
7. Inhibitors of TONSL, e.g inhibitors of TONSL capable of associating with the TONSL ARD.
7. Histone H4 peptides or functional homologues thereof could act as inhibitors of TONSL Taken together, this shows that DNA replication leaves a mark, in the form of deposited new histones unmodified at H4K20, which are recognized by the TONSL-MMS22L HR repair complex to differentiate pre- and post-replicative chromatin.

Furthermore, this work provides a breakthrough in understanding how the post-replicative chromatin state is read by a key HR factor TONSL, which mediates loading of Rad51 at damaged replication forks and DSBs. Small molecule inhibitors targeting TONSL ARD are thus capable to disable efficient HR repair of DSBs and damaged replication forks.

The present invention thus relates to small molecules interfering with the conformational space of the TONSL ARD occupied by the histone H4 tail. These small molecules targets the binding pocket of TONSL encompassing the H4 residues K12-R23 and act by preventing or disrupting the binding of the H4 tail K12-R23 with the TONSL ARD via direct competition or via allosteric disruption of the binding pocket.

Therefore, in one aspect the present invention relates to small molecules that prevent or disrupt the binding of a substrate in the binding pocket of the BARD1 ARD (defined by its high structural similarity to the H4 tail K12-R23 binding pocket in TONSL ARD) via direct competition or via allosteric disruption of the binding pocket.

BRIEF DESCRIPTION OF THE DRAWINGS

FIGS. 21A and 21B show TONSL recruitment to chromatin requires recognition of H4K20me0. FIG. 21A shows U-2-OS cells conditional for GFP-TONSL WT or N571A were directly fixed or pre-extracted to remove soluble proteins. Scale bar, 20 μm. FIG. 21B (left) Analysis of GFP-TONSL WT and mutants by cellular fractionation; (right) the chromatin-bound fraction (C) was quantified by western blotting relative to total GFP-TONSL (error bar, SD; $n\geq3$). S—soluble fraction, C—chromatin bound fraction. Staining with MemCode (ThermoFisher) was used to control the protein loading;

FIG. 30A shows Colony formation upon GFP-TONSL expression induced by tetracycline in TONSL depleted and control cells as shown in FIG. 28 but including additional ARD mutants. Two cell concentrations in technical triplicate from two (E568A, D559A) or four (WT, N571A) biological replicates are shown;

FIG. 30B Representation of the complementation analysis from FIG. 28 in a single panel including both CPT treated and untreated cells. This illustrates that the toxicity of the TONSL ARD mutant is comparable to CPT treatment of cells expressing WT TONSL;

DETAILED DESCRIPTION OF THE INVENTION

Figure 1:
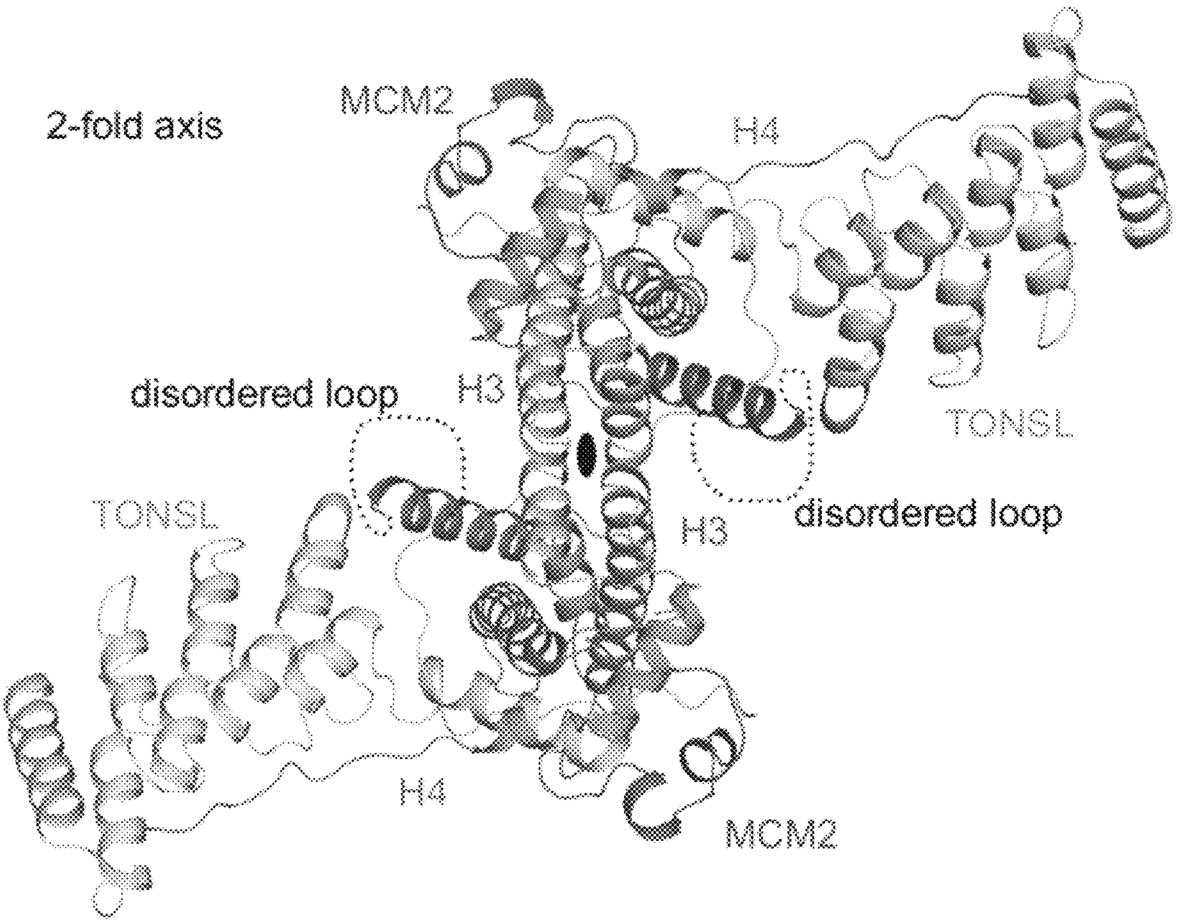
FIG. 1 is a view of the overall structure of the TONSL-ARD-MCM2 HBD-H3-H4 tetramer complex showing the relative positions of two TONSL ARDs, two MCM2 HBDs and an H3-H4 tetramer.

The present inventors have identified and solved the structure of a histone reader domain of TONSL termed the ARD (ankyrin repeat domain). Importantly, the present inventors have solved the structure of the TONSL ARD in complex with its histone substrate, histone H4 tails, providing grounds for structure-based rational drug design of TONSL inhibitors. Given the requirement of TONSL for HR of DSBs and repair of damaged replication forks, TONSL inhibitors can be efficient in compromising HR and be used either alone or in combination with conventional chemotherapy in killing cancer cells. Thus, any of the TONSL inhibitors described herein may be useful in the treatment of cancer.

The crystal structure of the complex, recombinant TONSL ARD, cell lines expressing GFP-TONSL (wild type and histone H4 binding mutants) of the present invention are all instrumental to design and identify specific small molecule inhibitors that interfere with TONSL ARD recognition of H4K20me0.

Below the present inventors, also disclose the development of a pipeline of biochemical and cell-based assays useful for TONSL inhibitor development.

These data and information are indispensable for the design of novel inhibitors suitable as anti-cancer therapeutics. The invention thus provides the means for designing in silico and subsequently synthesizing and testing in assays also provided by the invention, small molecule inhibitors that are capable of inhibiting the binding between TONSL and its histone substrate, thereby interfering with HR, in turn resulting in direct anti-tumour effects and/or increased efficacy of available cytostatic compounds.

The present inventors have identified the key determinant for binding of H4 tails to TONSL using interfacial mutants. Furthermore, the present inventors have demonstrated that TONSL ARD mutants that disrupt the H4 tail binding sites are no longer recruited to post-replicative chromatin, damaged replication forks, or DNA lesions (e.g., DNA double strand breaks). The TONSL ARD mutant proteins induce G2M arrest, replication-associated DNA damage (53BP1 foci) and reduce viability in the presence and absence of camptothecin (CPT).

As described in more detail below, said TONSL ARD mutants may phenocopy the effect of inhibitors of TONSL, in particular the effect of inhibitors which inhibit binding of TONSL ARD to histone H4. Thus, the invention provides that such inhibitors are useful for inducing G2/M arrest, replication-associated DNA damage (53BP1 foci) and/or reduce cell viability in the presence and/or absence of camptothecin (CPT). This render the inhibitors useful in the treatment of cancer. The inhibitor may be any of the inhibitors described herein.

The present inventors also note that several TONSL mutants in the ARD domain (residues 512-692) have been identified in cancer tissues of multiple organs including lung, skin, stomach, large intestine, biliary tract, prostate, endometrium, ovary, pancreas, oesophagus, urinary tract and central nervous system (COSMIC, Catalogue of somatic mutations in cancer, http://grch37-cancer.sanger.ac.ukicosmicsearch?q=TONSL). The term TONSL ARD refers to amino acids 512 to 692 of SEQ ID NO:16.

The present inventors have determined that the TONSL ARD is highly similar to the ARD of BARD1 for which a structure has been published, but since the binding specificity of BARD ARD is unknown, this again does not provide grounds for inhibitor design.

However, the details of TONSL ARD binding to H4 tails predict that inhibitors that disrupt TONSL binding to histones may also bind the BARD1 ARD and disrupt interaction with its substrate (e.g. histones). This would be desirable and probably increase drug efficacy as BARD1 and TONSL operate in separate steps within the same DNA repair pathway (HR). The present inventors also note that an established tumour suppressor mutation in BARD1 found in breast cancer targets a key residue predicted to be required for histone binding on the basis of the TONSL ARD-H4 structure.

In one aspect, the present invention relates to designing and developing drugs, small molecule inhibitors that would prevent recruitment of TONSL, a HR protein, to sites of DNA damage. Because TONSL together with its partner protein MMS22L is required for HR, interfering with TONSL recruitment to DNA lesion will impair HR repair and kill cancer cells or cells dependent on HR repair pathway either alone or in combination treatment with conventional chemotherapy.

The Crystal Structure

The present invention relates to the use of structure-based drug design methods to identify compounds that interfere with TONSL and TONSL-MMS22L complex recruitment to DNA lesions and DNA replication forks.

The invention discloses the crystal structure of the TONSL ARD in complex with its histone substrate, histone H4 tails. The TONSL ARD targets the H4 tail spanning residues Lys12 to Arg23, primarily through intermolecular hydrogen-bonding, electrostatic and van der Waals interactions (FIGS. 1-9).

The invention relates to the atomic details of the TONSL ARD binding pocket architecture and the intermolecular interactions with the H4 tail peptide that account for recognition specificity between the H4 tail (K4-R23) and residues lining the TONSL binding pocket.

In a preferred embodiment, the present invention relates to a crystal structure having the atomic coordinates available in the PDB Protein Databank under the PDB ID 5JA4 as deposited 11 Apr. 2016, DOI: 10.2210/pdb5ja4/pdb or having a structure in which the atomic coordinates vary by less than 3 Å in any direction from those set out in the PDB Protein Databank under the PDB ID 5JA4, DOI: 10.2210/pdb5ja4/pdb.

The variation of the atomic coordinates of the present invention should preferably be less than 3 Å, such as less than 2.75 Å, such as less than 2.5 Å, such as less than 2.25 Å, such as less than 2.0 Å, such as less than 1.75 Å, such as less than 1.5 Å, such as less than 1.25 Å, such as less than 1.0 Å, such as less than 0.75 Å, such as less than 0.5 Å or such as less than 0.25 Å.

In one embodiment, the invention relates to at least part of the atomic co-ordinate data available in the PDB Protein Databank under the PDB ID 5JA4, DOI: 10.2210/pdb5ja4/pdb or data derivable therefrom.

In one embodiment, the present invention relates to a crystal comprising at least part of the crystal structure of the TONSL ARD in complex with its histone substrate, histone H4 tails.

In another embodiment, the invention relates to the distances between the atomic co-ordinates in the crystal structure available in the PDB Protein Databank under the PDB ID 5JA4, DOI: 10.2210/pdb5ja4/pdb or any variation thereof that defines the binding surface of TONSL interacting with the histone H4 tail residues Lys12-Arg23 (FIGS. 1-9).

The histone H4(K12 to R23) peptide is positioned within a channel on the surface of the ankyrin repeat domains of TONSL. This surface constitutes an acidic patch and contains shallow binding pockets for the His18 and Lys20 side chains of H4. Further, the side chain of H4 R17 is aligned by being sandwiched between the side chains of Tyr572 and Cys608. Hence, any inhibitor must target the two shallow pockets and be compatible with the electrostatic nature of the binding surface.

Methods of Forming a Crystal Structure

In one embodiment, the invention relates to a three dimensional crystal of a complex between

- a polypeptide comprising:
  - TONSL ARD consisting of amino acids 512 to 692 of SEQ ID NO:16 or a functional homologue thereof sharing at least 90% sequence identity therewith; and
  - optionally MCM2 HBD consisting of amino acids 61 to 130 of SEQ ID NO:24 or a functional homologue thereof sharing at least 90% sequence identity therewith;
- Histone H4 of SEQ ID NO:23 or a functional homologue thereof sharing at least 90% sequence identity therewith; and
- optionally Histone H3 or a fragment thereof, e.g. histone H3.3 Δ56 consisting of amino acids 57-135 of SEQ ID NO:25 or a functional homologue thereof sharing at least 90% sequence identity therewith.

In particular, the polypeptide may comprise said TONSL ARD or a functional homologue thereof linked to said MCM2 HBD or a functional homologue thereof by way of a peptide linker. Such a peptide linker typically consists of in the range 4 to 20 amino acids, e.g. 4 to 12 amino acids. Said amino acids may be Gly, and thus the linker may consist of in the range of 4 to 20 Gly residues, such as in the range of 4 to 12 Gly-residues. In general, the complex comprises one polypeptide comprising TONSL ARD, whereas histone H4 and optionally histone H3 typically are present as separate peptides. Preferably, the polypeptide comprising TONSL ARD also comprise MCM2 HBD, wherein TONSL ARD may be linked to MCM2 HBD by way of a linker, e.g. a peptide linker. Said fragment of Histone H3 may be a fragment of histone H3.3, e.g. amino acids 57-135 of SEQ ID NO:25. This fragment may also be a fragment of Histone H3.1 or Histone H3.2, which contains an identical fragment.

The present invention may in particular be based on the use of a unique fusion protein, MCM2 HBD-G4-TONSL ARD (SEQ ID NO: 15), allowing crystallization of the TONSL ARD-MCM2 HBD-H3-H4 tetramer complex. The fusion protein consists of the human TONSL Ankyrin Repeat Domain (ARD, residues 512-692 of SEQ ID NO: 16) and MCM2 Histone-binding Domain (HBD, fragments 61-130 of SEQ ID NO:24) covalently linked through a four-Glycine linker (G4 linker) into one expression cassette.

Useful isolated polynucleotide or amino acid sequences of the present invention is disclosed in the SEQUENCE DATA listing below having at least 90% sequence identity, such as 91% sequence identity, 92% sequence identity, 93% sequence identity, 94% sequence identity, 95% sequence identity, 96% sequence identity, 97% sequence identity, 98% sequence identity, 99% sequence identity or 100% sequence identity. All sequence listed are embodiments of the present invention. There are many ways to define the sequence identity of genes, nucleotides, or protein sequences. One way is through a direct comparison of two aligned sequences. Such a comparison is technically straightforward.

In particular, the term "sequence identity" as used herein may refer to the % of identical amino acids or nucleotides between a candidate sequence and a reference sequence following alignment. Thus, a candidate sequence sharing 80% amino acid identity with a reference sequence requires that, following alignment, 80% of the amino acids in the candidate sequence are identical to the corresponding amino acids in the reference sequence. Identity according to the present invention is preferably determined by aid of computer analysis, such as, without limitations, the ClustalW computer alignment program (Higgins D., Thompson J., Gibson T., Thompson J. D., Higgins D. G., Gibson T. J., 1994. CLUSTAL W: improving the sensitivity of progressive multiple sequence alignment through sequence weighting, position-specific gap penalties and weight matrix choice. Nucleic Acids Res. 22:4673-4680), and the default parameters suggested therein. The ClustalW software is available from as a ClustalW WWW Service at the European Bioinformatics Institute http://www.ebi.ac.uk/clustalw. Using this program with its default settings, the candidate amino acid sequence and the reference amino acid sequence are aligned. The number of fully conserved residues are counted and divided by the length of the reference sequence. Thus, sequence identity is preferably determined over the entire length of the reference sequence. The ClustalW algorithm may similarly be used to align nucleotide sequences. Sequence identities may be calculated in a similar way as indicated for amino acid sequences. Sequence identity as provided herein is calculated over the entire length of the reference sequence.

Functional homologues of a reference peptide or polypeptide according to the invention may be peptides or polypeptides sharing at least 70%, such as at least 80%, for example at least 90% sequence identity, such as at least 95% sequence identity, for example at least 98% sequence identity sequence identity with said reference peptide or polypeptide.

In another embodiment sequences that hybridize to any of the isolated polynucleotide of the present invention is disclosed in the SEQUENCE DATA listing below under conditions of low stringency, are embodiments of the present invention.

In the present context, sequence that hybridize under low stringency is defined as a sequence which specifically hybridizes to said e.g. DNA or said complementary sequence in a hybridization solution containing 0.5M sodium phosphate buffer, pH 7.2, containing 7% SDS, 1 mM EDTA at 650° C. for 16 hours and washing twice at 65° C. for twenty minutes in a washing solution containing 0.5× SSC and 0.1% SDS.

Crystallization of TONSL ARD in complex with a H4 tail or H3-H4 tetramer failed even with extensive screening. Because an additional binding protein may help to stabilize the whole complex and help crystallization, crystallization of TONSL ARD in complex with the MCM2 HBD and H3-H4 tetramer was tested.

Very tiny crystals were obtained for this complex, but failed to give big and well-diffracted crystals. The whole complex of TONSL ARD with MCM2 HBD and H3-H4 tetramer might be destabilized by the harsh crystallization conditions and form sub complexes thus hindering the optimization of the crystals.

Covalently linkage of TONSL ARD and MCM2 HBD into one cassette was thus tested through different length of Glycine linker ($G_x$ linker). The $G_{12}$, $G_{11}$, $G_{10}$, $G_9$, $G_8$, $G_7$, $G_6$, $G_5$ and $G_4$ linkers had been tried and all these cassettes could be crystallized.

One of the constructs with a G4 linker (MCM2 HBD-G4-TONSL ARD cassette) gave well diffracted crystals in complex with H3.3(Δ56)-H4 (see Example 1), herein denoted as TONSL ARD-MCM2 HBD-H3-H4 tetramer complex (FIG. 1).

Thus, the present invention relates to a composition comprising a protein assembly of TONSL ARD-MCM2 HBD-H3-H4 in its crystalline form and/or the details of the structure of the complex deduced from structural analysis of this crystal.

Specific data defining this crystal are detailed in Table 1, Example 1. Specifically, this aspect of the invention relates to the TONSL ARD binding pocket architecture and the intermolecular interactions with the H4 tail peptide deduced from the atomic co-ordinates that define the binding surface of TONSL ARD with the histone H4 tail residues Lys12-Arg23 (e.g. in the crystal structure available in the PDB Protein Databank under the PDB ID 5JA4, DOI: 10.2210/pdb5ja4/pdb or variation thereof).

The Binding Pocket Data

Figure 2:
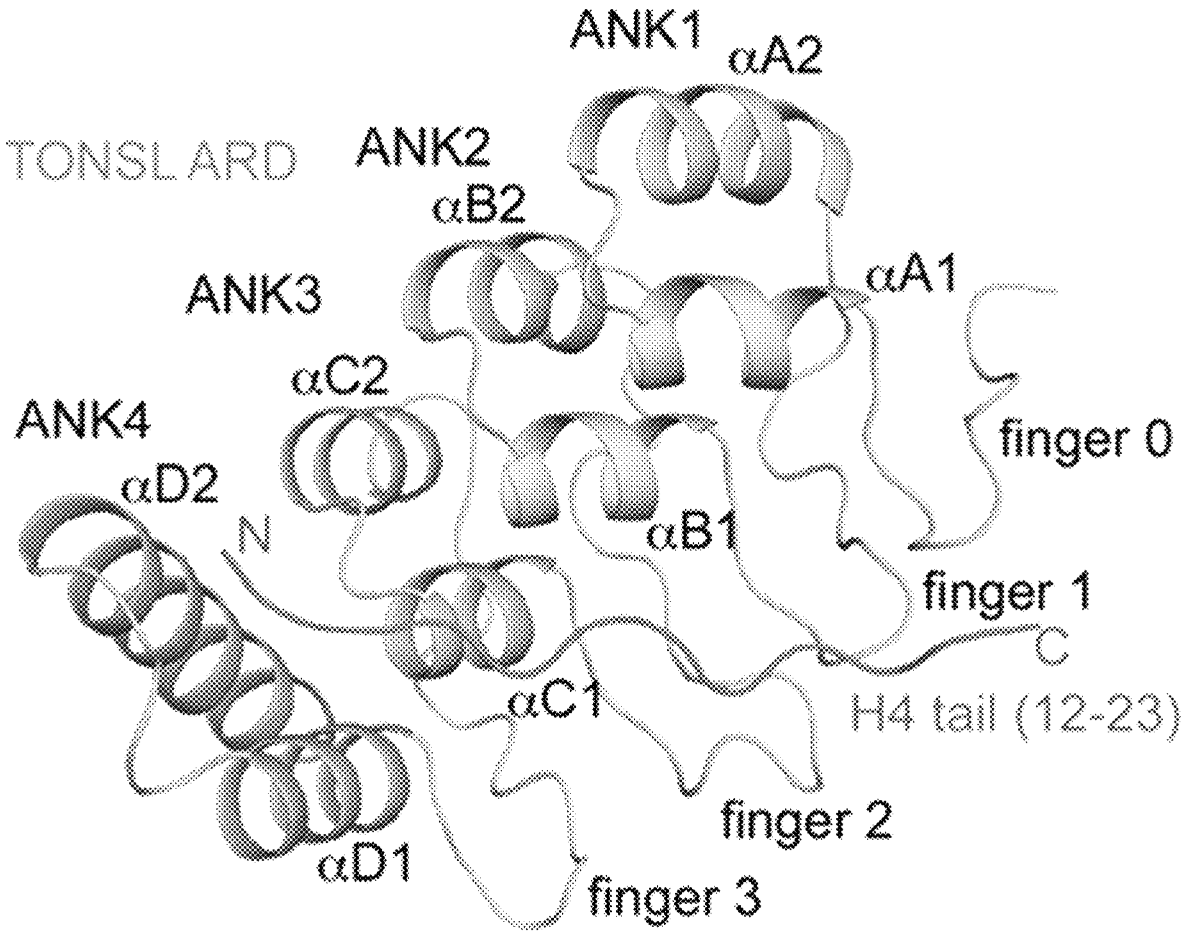
FIG. 2 shows TONSL ARD which consists of four ANK repeats and uses its elongated concave surface to target the H4 tail spanning residues 12 to 23.
Figure 3:
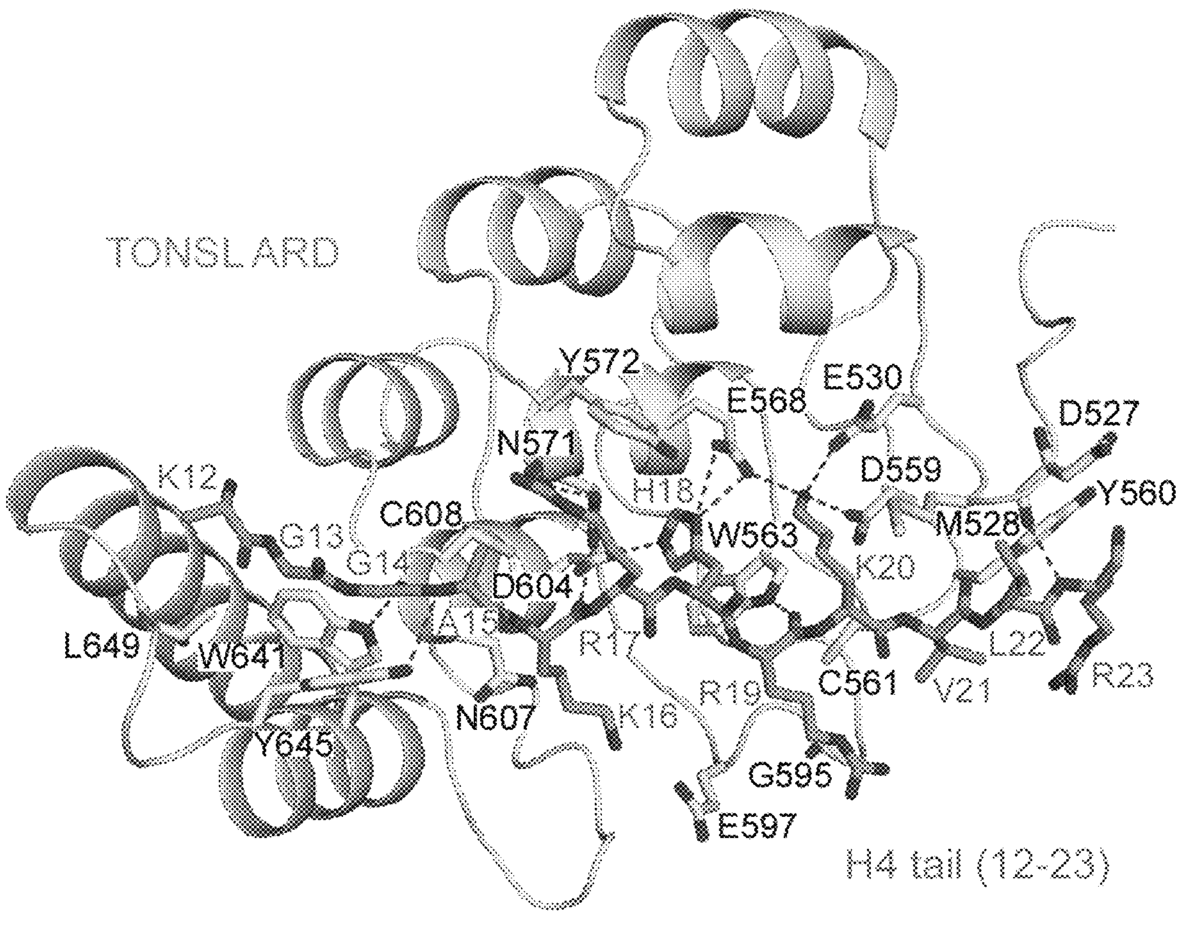
FIG. 3 shows an intermolecular interactions between TONSL ARD and the H4 tail (12-23)
Figure 4:
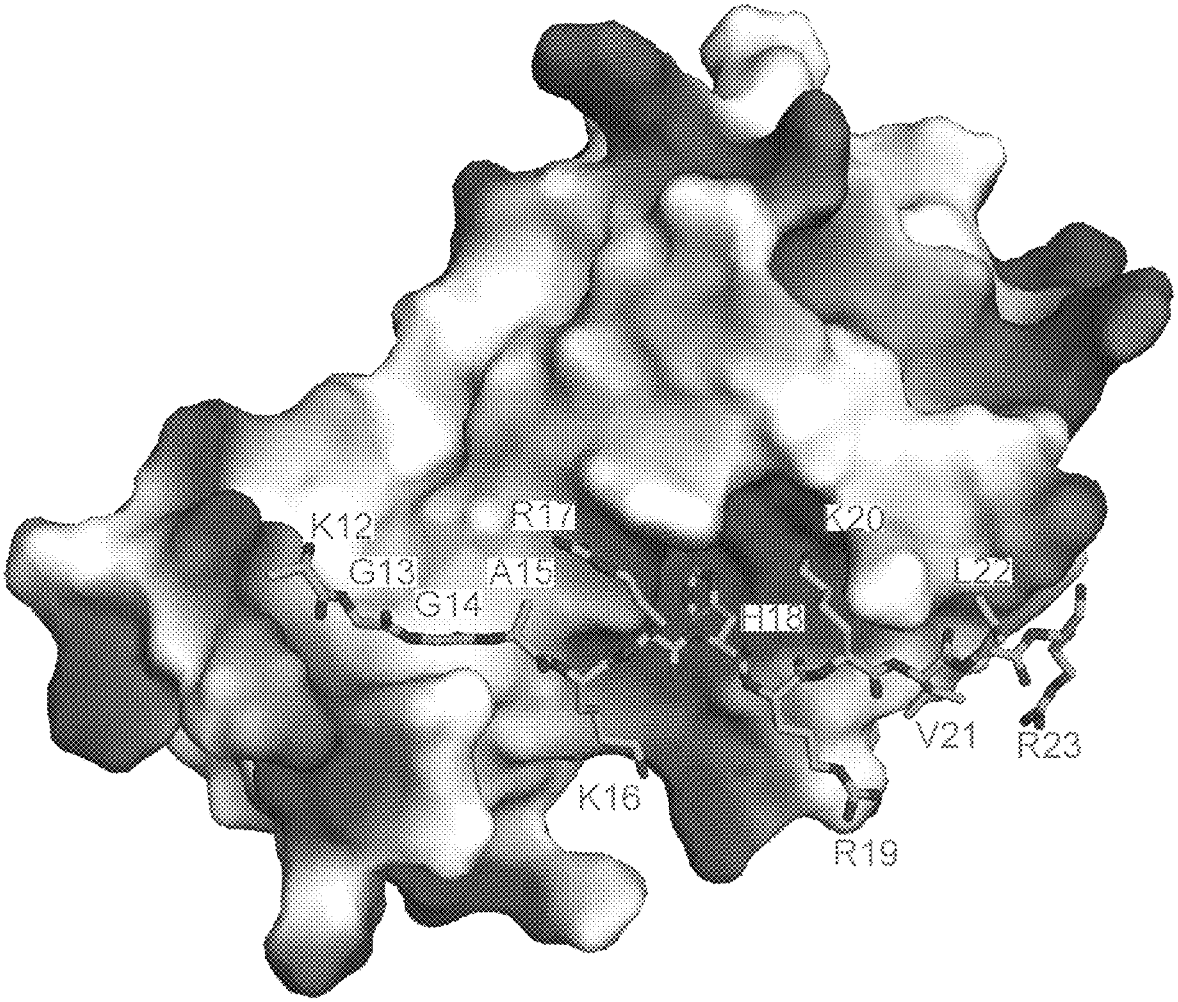
FIG. 4 shows the electrostatic potential surface of ARD showing the acidic concave surface-binding site for the H4 tail.

The Lys12-Gly13-Gly14-Ala15 segment of H4 is positioned within a narrow surface channel of the TONSL ARD scaffold (FIGS. 2-4). The amino acid number provided in relation to histone H4 are general provided in relation to histone H4 of SEQ ID NO:34.

The intermolecular contacts spanning the Lys12-Gly13-Gly14-Ala15 segment of H4 include hydrophobic interactions between residues Gly13, Gly14 and Ala15 of H4 and residues Asn507, Cys508, Trp641, Tyr645 and Leu649 of ARD, as well as hydrogen bonds between the main-chain O of H4 Gly14 and Nε1 of ARD Trp641, and between the main-chain N of H4 Ala15 and Oη of ARD Tyr645 (FIG. 3, 8).

The main-chain O of H4 Lys16 hydrogen bonds with the Nδ2 of ARD Asn571, while the side-chain of H4 Lys16 forms contacts with ARD Asn607 and electrostatic interactions with the side-chain of ARD Glu597 (FIG. 3).

Figure 5:
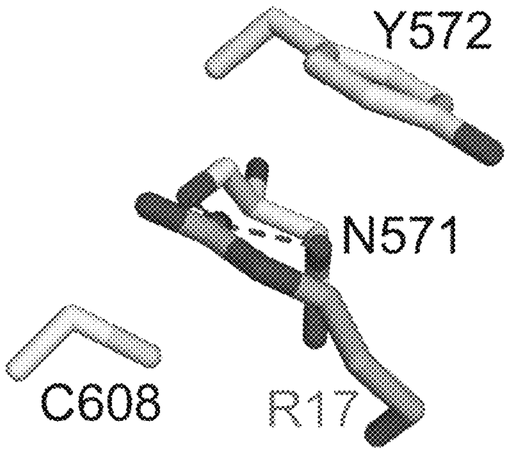
FIG. 5 shows the highlight of the inter-molecular interactions of H4 Arg17 with TONSL ARD.

The side-chain of H4 Arg17 stacks over the side-chains of ARD Tyr572 and Cys608, while its Nη1 atom forms two hydrogen bonds with main-chain O and 081 of ARD Asn571 (FIGS. 3, 5).

Figure 6:
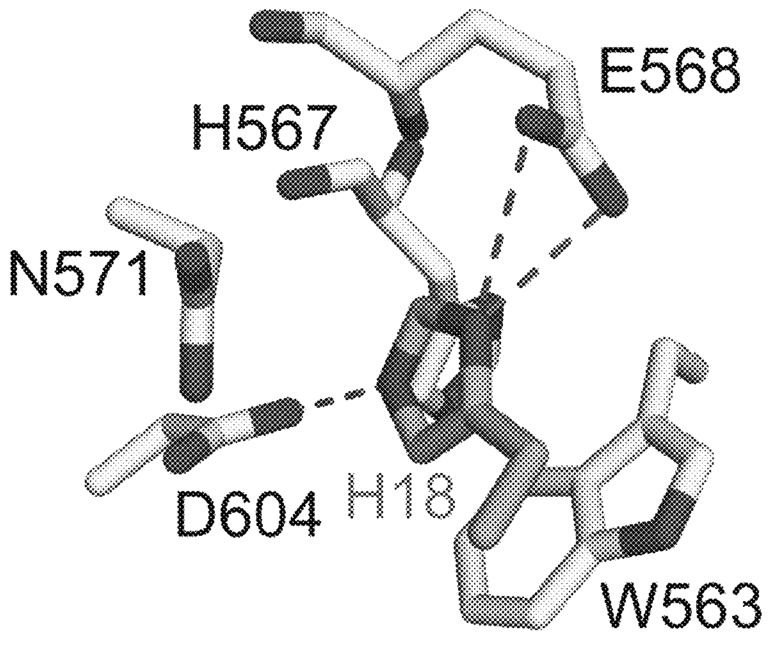
FIG. 6 shows a highlight of the inter-molecular interactions of H4 His18 with TONSL ARD.

The side-chain of H4 H18 penetrates into a pocket lined by four strictly conserved residues (Trp563, Glu568, Asn571 and Asp604) and is positioned over His567 of ARD. The side chain of H4 His18 is stacked between Trp563 and Asn571 and forms hydrogen bonds to Glu568 and Asp604 of ARD (FIGS. 3, 6).

The main-chain O of H4 Arg19 forms a hydrogen bond with Nε1 of Trp563 and its side-chain forms contacts with Cys561 and Gly595 of ARD (FIG. 3).

Figure 7:
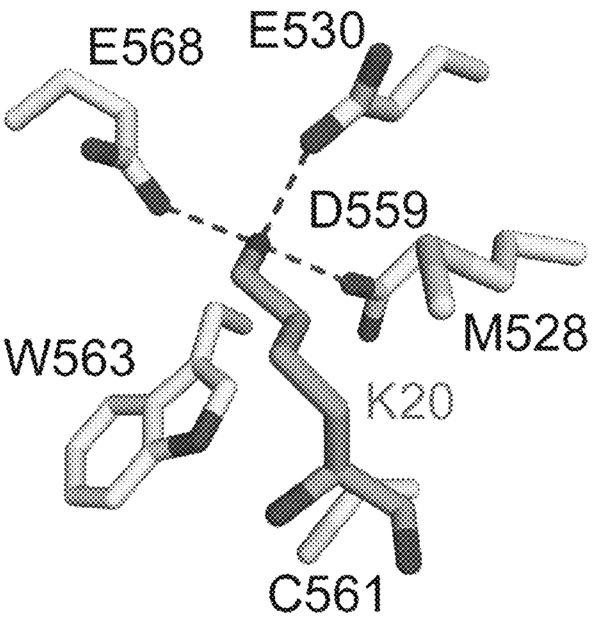
FIG. 7 shows a highlight of the inter-molecular interactions of H4 Lys20 with TONSL ARD.
Figure 8:
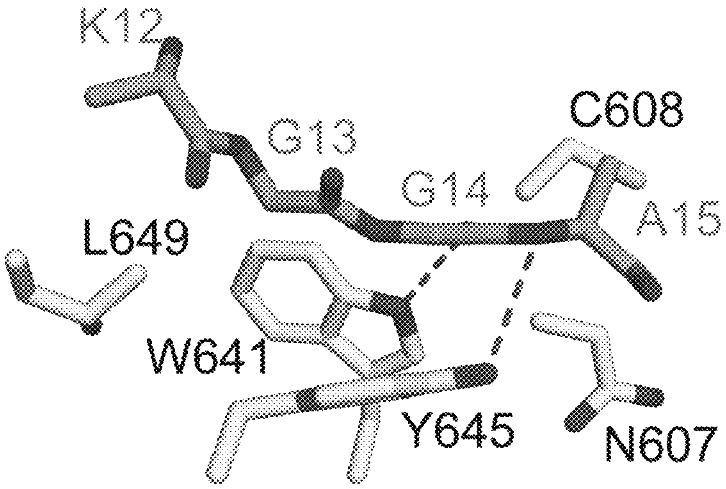
FIG. 8 shows the molecular details of the interactions of TONSL ARD with H4 tail region residues 12-15.

The H4 Lys20 residue is bound within an acidic surface pocket on ARD adjacent to the H4 His18 binding pocket. The side-chain of H4 Lys20 interacts with the side-chain of Met528 and contacts the edge of Trp563 of ARD, while the main-chain atoms of H4 Lys20 packs against Cys561 of ARD. The Nζ atom of H4 Lys20 forms three strong hydrogen bonds (distance <3 Å) with the side-chains of strictly conserved residues Glu530, Asp559 and Glu568 of ARD, which surround H4 Lys20 within a regular triangle-like alignment (FIGS. 3, 7).

Figure 9:
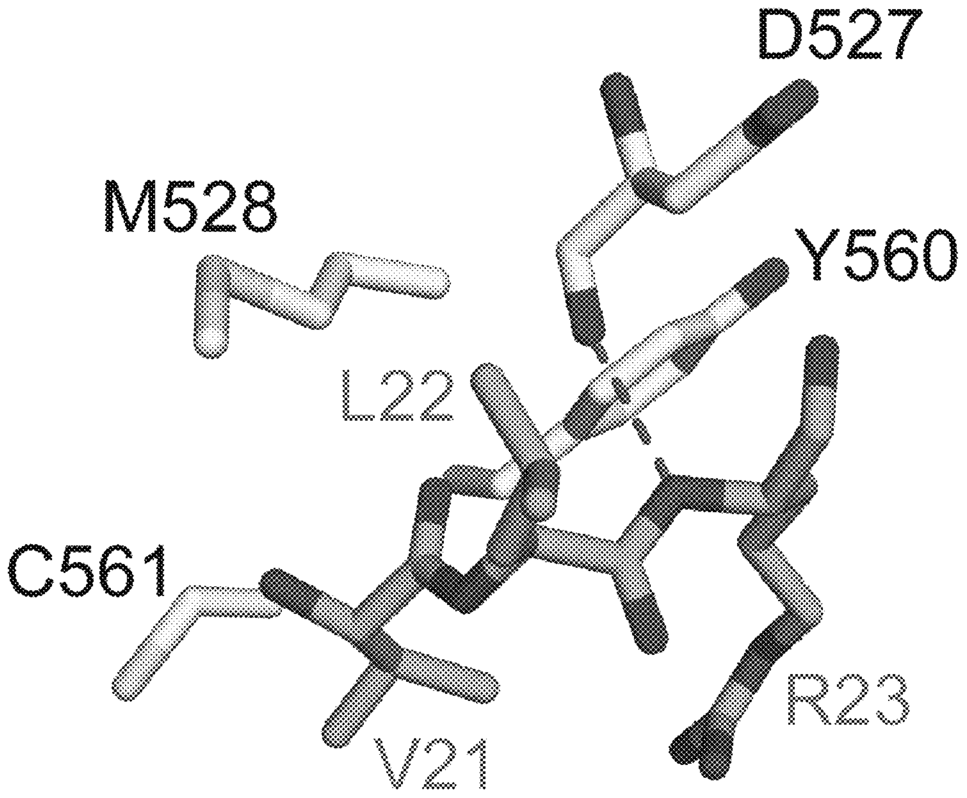
FIG. 9 shows the molecular details of the interactions of TONSL ARD with H4 tail region residues 21-23.

The intermolecular contacts spanning the Val21-Leu22-Arg23 segment of H4 include contacts between side-chains of H4 Val21 with Tyr560 and Cys561 of ARD, while H4 Leu22 interacts with Asp527 and Met528 of ARD. The main-chain N of H4 Arg23 forms a hydrogen bond with the main-chain O of Asp527 of ARD, while the side-chain packs against the side-chain of Tyr560 of ARD (FIGS. 3, 9).

From the structure descriptions above, it is apparent that the H4 tail (residues 12-23) with an extended β-strand like conformation lies in an elongated channel on the concave surface of the TONSL ARD. This channel is primary acidic, which provides an electrostatic complementary fit with the positively charged H4 tail. Most importantly, the side chains of H4 His18 and Lys20 are accommodated within two adjacent pockets (FIG. 4).

Substitution of H4 His18 with the larger Trp residue totally disrupts binding with TONSL ARD (FIG. 13), underscoring the importance of fitting His18 in the pocket. As the Nζ atom of H4 Lys20 forms three strong hydrogen bonds within its binding pocket, it can be predicted that methylation on H4K20 should break these critical interactions.

Both isothermal titration calorimetry (ITC) and H4 tail peptide pull-downs of recombinant ARD and full length TONSL from cell extracts confirmed that H4K20me1/2 is incompatible with TONSL binding (FIGS. 13, 14, 15, 17, 18, 19).

Figure 16:
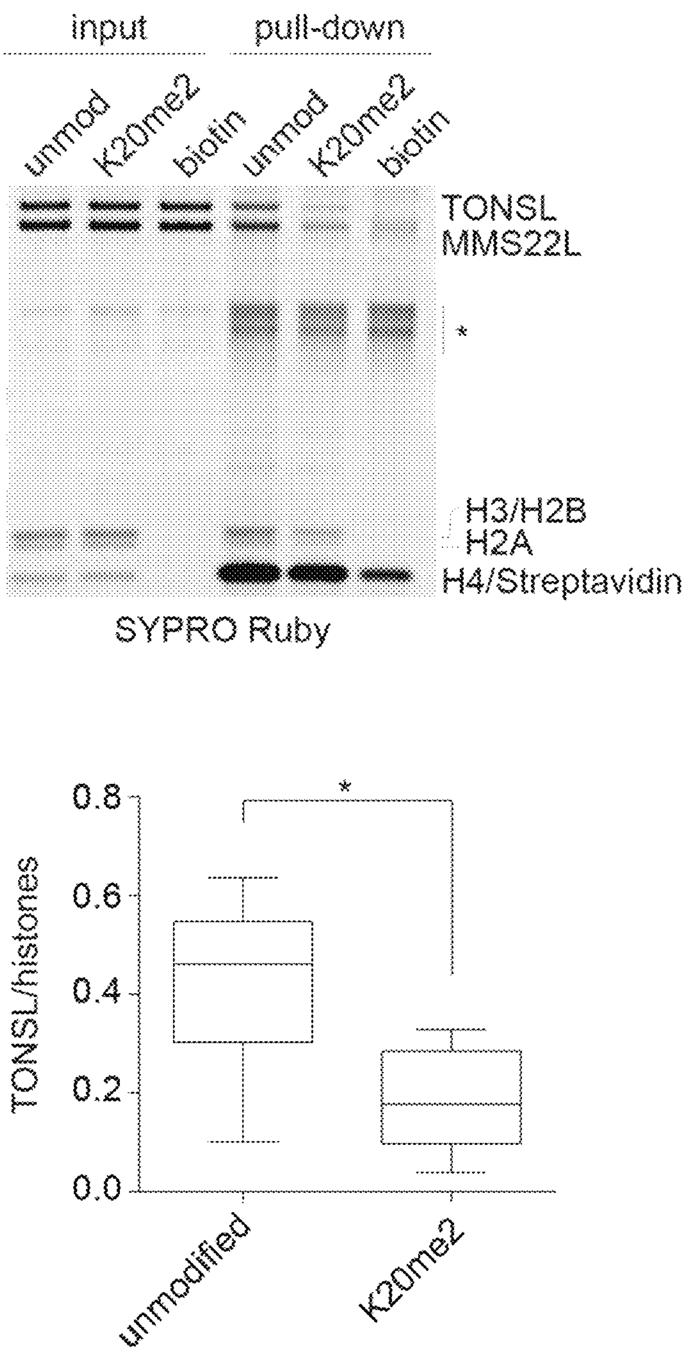
FIG. 16 shows in vitro pull-down of recombinant TONSL-MMS22L heterodimer with biotinylated recombinant mononucleosomes, unmodified or di-methylated at K20. * indicates an unspecific band. (bottom) TONSL binding quantified relative to histones. Unpaired t-test: *, $P<0.05$; mean of 6 independent experiments is shown; whiskers, outliers.
Figure 17:
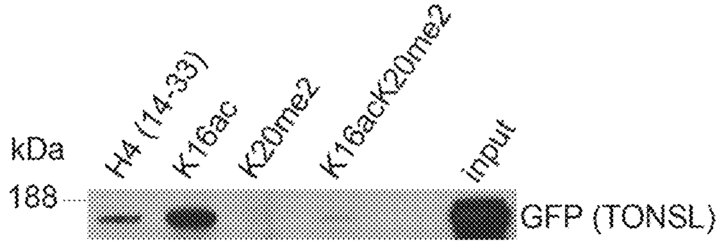
FIG. 17 shows a pull-down of GFP-TONSL from cell extracts with biotinylated H4 tail peptides.
Figure 18:
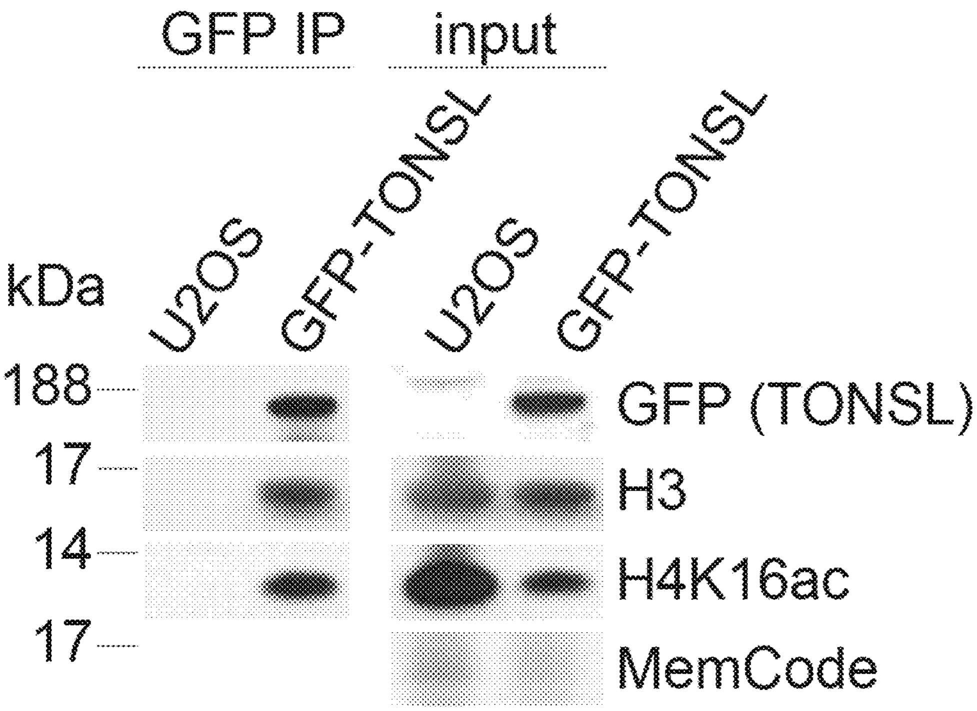
FIG. 18 shows immunoprecipitation of GFP-TONSL from solubilized chromatin of GFP-TONSL U-2-OS cells.
Figure 19:
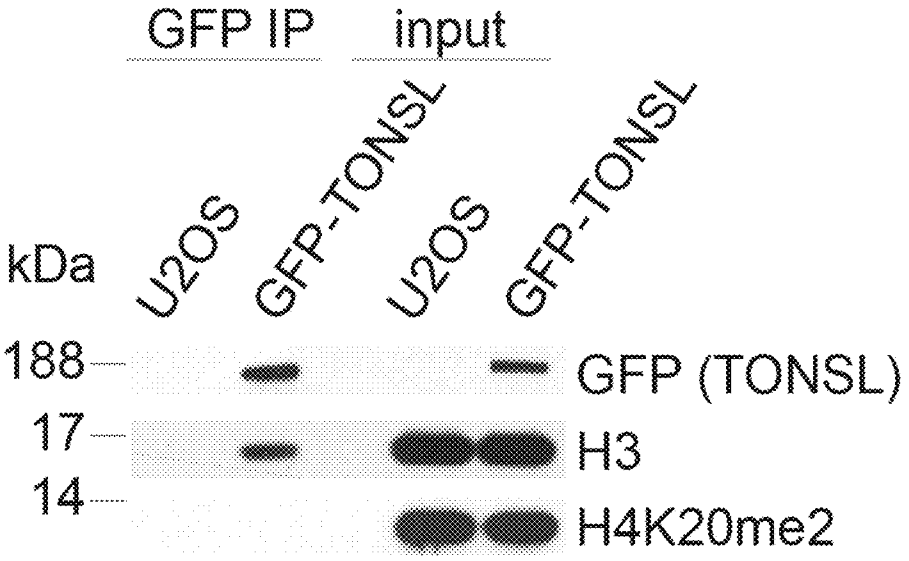
FIG. 19 shows immunoprecipitation of GFP-TONSL from solubilized chromatin of GFP-TONSL U-2-OS cells.

Further, in vitro pull-down of full-length recombinant TONSL-MMS22L with modified reconstituted mononucleosomes showed that H4K20me2 significantly reduced TONSL-MMS22L binding (FIG. 16).

The term "H4 tail binding surface of TONSL ARD" as used herein refers to the part of TONSL ARD binding the H4 tail. Amino acids of TONSL ARD involved in the binding of the H4 tail are described in detail above in this section, and the "H4 tail binding surface of TONSL ARD" may be comprise any of these amino acids. In particular, the "H4 tail binding surface of TONSL ARD" may comprise amino acids Asp527, Met528, Glu530, Asp559, Tyr560, Cys561, Trp563, Glu568, Asn571, Tyr572, Gly595, Glu597, Asp604, Asn607, Cys608, Trp641, Tyr645 and Leu649 of SEQ ID NO:16.

Our data establish that the methylation of H4K20 hinders binding with TONSL ARD.

A previous study found that the ARD of the G9a/GLP methyltransferases specifically recognize H3K9me1/2, but the TONSL ARD showed no binding to H3K9me1 peptides.

Figure 10:
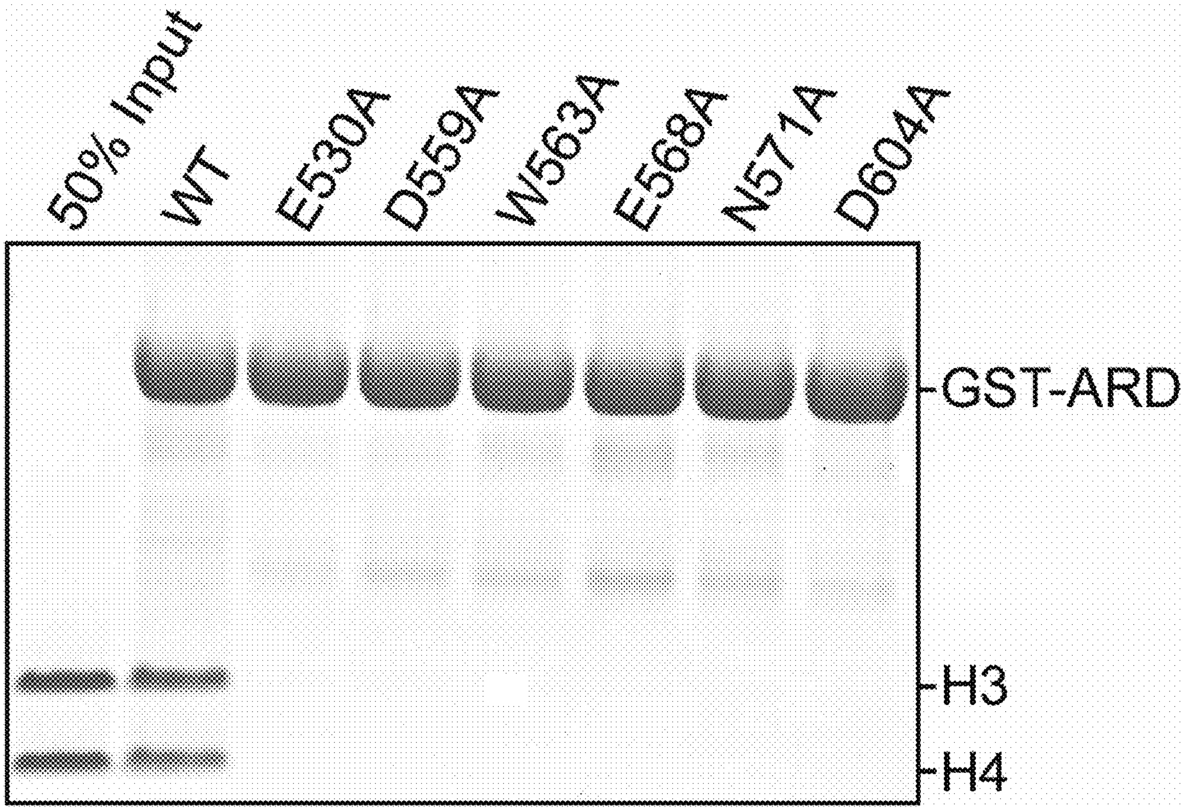
FIG. 10 shows in vitro pull-down of recombinant histones H3-H4 with recombinant GST-TONSL ARD wild type or indicated mutants.
Figure 11:
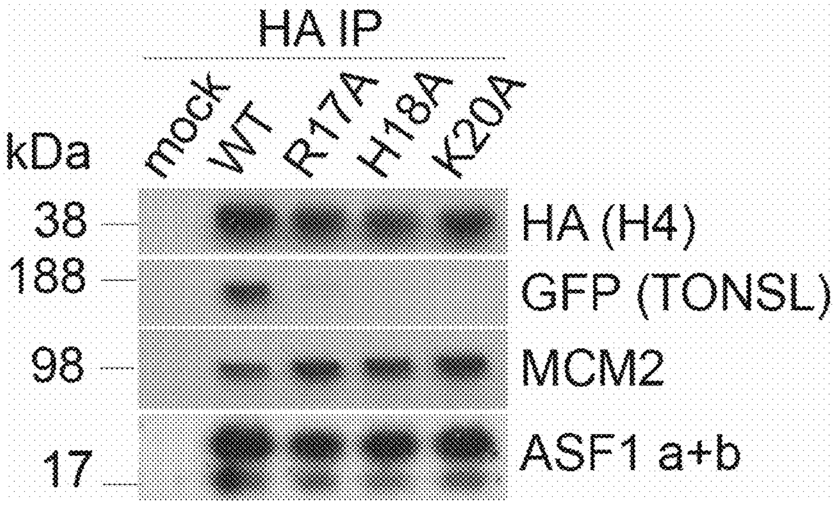
FIG. 11 shows immunoprecipitation of HA-SNAP-H4 wild-type (WT) and indicated mutants transiently transfected into GFP-TONSL U-2-OS cells.
Figure 12:
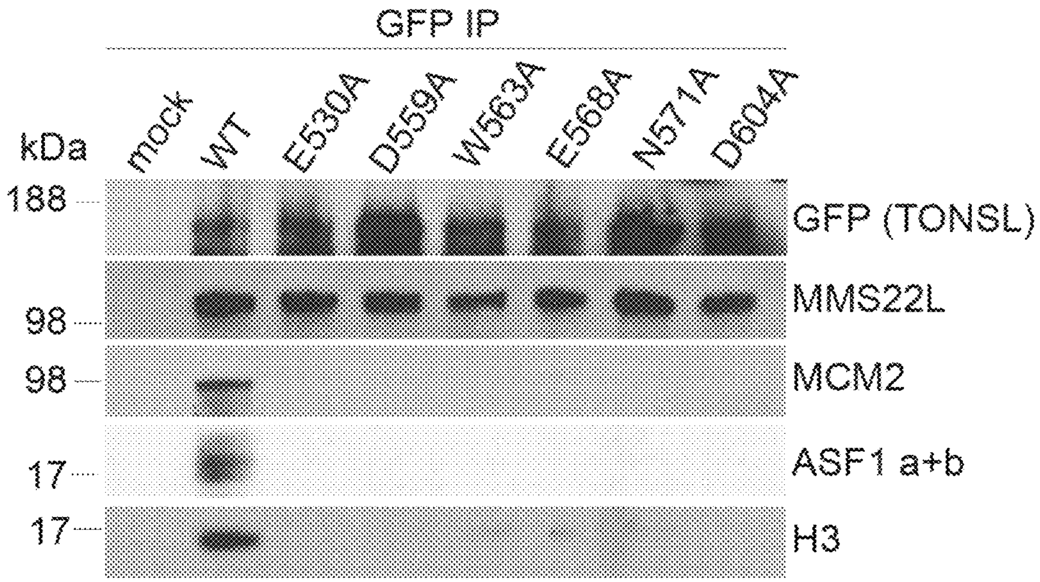
FIG. 12 shows immunoprecipitation of GFP-TONSL WT or indicated mutants from transiently transfected HeLa S3 cells.

Consistent with the structural data, histone H4 mutations H18A and K20A disrupted binding to TONSL in cell extracts (FIG. 11). Conversely, mutation of 6 conserved TONSL residues lining the H4 His18 and Lys20 binding pockets disrupted binding to H3-H4 and MCM2, both in vivo and in vitro without affecting binding to MMS22L, previously shown to bind to the C-terminal part of TONSL (FIGS. 10, 12). In vivo, these mutants abrogated binding to soluble H3-H4 and, consequentially, association with ASF1 and MCM2 was lost without affecting MMS22L binding to the C-terminal part of TONSL (FIG. 12).

Taken together, these results show that TONSL binds to free histones and nucleosomes via ARD recognition of H4 tails, with the important residues His18 and Lys20 fitting within two adjacent pockets. It is also shown that aa 9 to 25 of SEQ ID NO:23 can bind TONSL ARD (aa512-692 of SEQ ID NO: 16), but that the mutants are strongly impaired in H4 tail peptide binding.

It is apparent that a small molecule that could bind to the His18-binding pocket or the Lys20-binding pocket, as well as either single or covalently-linked small molecules that target both pockets on TONSL ARD, would disrupt the interactions between H4 and TONSL.

Drug Design

In the most basic sense, the drug design of the present invention involves the design of single or linked small molecules that are complementary in shape and charge to the molecular target of the present invention. The invention also relates to peptides or polypeptides designed to bind to the target.

The drug design of the present invention relies on the knowledge of the three-dimensional structure presented herein. In addition to small molecules, biopharmaceuticals are an increasingly important class of drugs and computational methods for improving the affinity, selectivity, and stability of these protein-based therapeutics are also embodiments of the present invention.

The small molecules of the present invention are preferably designed so as not to affect any other important "off-target" molecules (often referred to as anti-targets), since drug interactions with off-target molecules may lead to undesirable side effects.

The term "small molecule" as used herein refers to any molecule with a molecular weight below 1000 Da, for example below 500 Da. Preferably, the "small molecule" may be an organic molecule having a molecular weight below 500 Da.

Another class of small molecules that constitute an embodiment of the invention are aptamers, which can be made up of DNA, RNA, or peptide units. Aptamers bind to a specific target molecule, and may be designed as described herein in this section. Alternatively, they may be created by selecting them from a large random sequence pool. Thus, aptamer may be any aptamer having the binding properties described herein.

In contrast to traditional methods of drug discovery (known as forward pharmacology), which rely on trial-and-error testing of chemical substances on cultured cells or animals, and matching the apparent effects to treatments, rational drug design (also called reverse pharmacology) begins with a hypothesis that modulation of a specific biological target may have therapeutic value.

In order for a small molecule to be selected as a drug target according to the present invention, one essential piece of information is required, namely the evidence that modulation of the target by the small molecule of the present invention will be disease modifying. This knowledge comes from disease linkage studies that show an association between e.g. mutations in the biological target and certain disease states.

The search for small molecules may begin by screening libraries of potential drug compounds. This may be done by using a virtual screen of existing and available small molecule libraries. The atomic co-ordinate data of the present invention or data derivable therefrom are useful in selecting and/or designing small molecules capable of interfering with the adjacent histone H4H18 and H4K20 binding pockets on the surface of the Ankyrin repeats of TONSL.

Thus, in one aspect, the present invention relates to methods for selecting and/or designing such small molecules, wherein for e.g. the method involves the use of a computer modelling or a computer program to model all or part of the structure disclosed in the PDB Protein Databank under the PDB ID 5JA4, DOI: 10.2210/pdb5ja4/pdb or data derivable therefrom, identifying a potential small molecule based on its likely ability to interact with the modelled structure, synthesising or obtaining the small molecule from a commercial source and carrying out in vitro testing of the functionality.

In one embodiment, the present invention relates to a computer-based method for identifying a small molecule capable of interfering with the adjacent histone H4H18 and H4K20 binding pocket on the surface of the Ankyrin repeats of TONSL, comprising the steps of:

a) providing a 3D structural representation of the histone H4H18 and H4K20 binding pocket on the surface of the Ankyrin repeats of TONSL in a storage medium on a computer, wherein the 3D structural representation is derived from the atomic co-ordinates available in the PDB Protein Databank under the PDB ID 5JA4, DOI: 10.2210/pdb5ja4/pdb or a variant thereof in which the r.m.s. deviation of the x, y and z co-ordinates for all heavy atoms is less than 1.0 Å, and b) using the computer to apply structure-based drug design techniques to the structural representation.

In one embodiment, the structure-based drug design includes one or more steps of docking, such as but not limited to docking steps which screens members of a structural library.

In another embodiment, the invention relates to a computer-based method for identifying a small molecule capable of interfering with the adjacent histone H4H18 and H4K20 binding pocket on the surface of the Ankyrin repeats of TONSL, comprising the steps of:

a) providing a 3D structural representation of the histone H4H18 and H4K20 binding pocket on the surface of the Ankyrin repeats of TONSL in a storage medium on a computer, wherein the 3D structurel representation is derived from the atomic co-ordinates of available in the PDB Protein Databank under the PDB ID 5JA4, DOI: 10.2210/pdb5ja4/pdb or a variant thereof in which the r.m.s. deviation of the x, y and z co-ordinates for all heavy atoms is less than 1.0 Å, and b) using the computer to apply structure-based drug design techniques to the structural representation, and c) providing a compound identified by said structure based drug design technique, and d) contacting said compound with the binding pocket on the surface of the Ankyrin repeats of TONSL and assaying the interaction between them.

In another embodiment, the invention relates to method of identifying a small molecule capable of interfering with the histone H4H18 and H4K18 binding pocket on the surface of the Ankyrin repeats of TONSL, or a fragment or variant thereof, said method comprising the steps of:

a. generating the spatial structure of the pocket on a computer screen using atomic coordinates as presented in the PDB Protein Databank under the PDB ID 5JA4, DOI: 10.2210/pdb5ja4/pdb, data derivable therefrom, or by a root mean square deviation over protein backbone atoms of not more than 1.0 Å, b. generating potential small molecules with their spatial structure on the computer screen, and c. selecting small molecules that can bind to at least one amino acid residue of the set of binding interaction sites.

In another embodiment, the invention relates to a computer-assisted method for identifying a small molecule capable of interfering with the histone H4H18 and H4K20 binding pocket on the surface of the Ankyrin repeats of TONSL, or a fragment or variant thereof, using a programmed computer comprising a processor, a data storage system, a data input device and a data output device, comprising the following steps:

a. inputting into the programmed computer through said input device data comprising; atomic coordinates of a subset of the atoms according to the present invention, thereby generating a criteria data set; wherein said atomic coordinates are selected from the atomic coordinates as presented in the PDB Protein Databank under the PDB ID 5JA4, DOI: 10.2210/pdb5ja4/pdb, data derivable therefrom, or by a root mean square deviation over protein backbone atoms of not more than 1.0 Å, b. comparing, using said processor, the criteria data set to a computer data base of low-molecular weight organic chemical structures and peptide fragments stored in the data storage system, and c. selecting from said data base, using computer methods, a chemical structure having a portion that is structurally complementary to the criteria data set.

In another embodiment, the invention relates to a method for identifying a ligand, comprising the steps of:

a. selecting a potential ligand using atomic coordinates in conjunction with computer modelling, wherein said atomic coordinates are the atomic coordinates as presented in the PDB Protein Databank under the PDB ID 5JA4, DOI: 10.2210/pdb5ja4/pdb, data derivable therefrom, or by a root mean square deviation over protein backbone atoms of not more than 1.0 Å, by docking potential ligands into a set of binding interaction sites, said binding interaction generated by computer modelling and selecting a potential ligand capable of binding to at least one amino acid in said set of binding interaction sites of TONSL, b. providing said potential ligand and said TONSL, c. contacting the potential ligand with said TONSL, and d. detecting binding of said potential ligand with TONSL.

A non-limiting Example of methods for identifying small molecules or inhibitors according to the invention is provided in Example 16 herein below.

SCHRODINGER Analysis

The small molecule drug discovery suite by SCHRODINGER contains a comprehensive set of programs aimed at state-of-the-art support of every step of drug discovery and optimization. This represents one type of structure-based docking programs for small molecule inhibitor design, other could also be applied. The essence of drug discovery is in (1) finding key adjacent pocket(s) on a target protein that affects or controls its function and (2) finding covalently linked small molecules with high-affinity binding to the adjacent pocket(s) in the known databases followed by iterative optimization through addition/deletion of substituents while maximizing shape, hydrogen bonding and electrostatic complementarity.

The most effective definition of a binding pocket is possible when a crystal structure of a protein-ligand complex is known. In this case, the high precision GLIDE algorithm is applied to calculate the grid, which is subsequently used for high-throughput docking of commercially available small molecules. This grid represents the three-dimensional spatial information about essential components of binding surfaces such as all lipophilic atoms, all hydrogen-bonding atoms with a score accounting for orientation of hydrogen bonds, metal atoms if present in the protein, distribution of charges, as well as van der Waals atomic interactions. The ligand conformations are also pre-computed in SCHRODINGER through application of LigPrep procedure that filters out the least probable configurations and accounts for various pH-dependent ionization states of the prospective ligands.

Docking computations for two interacting components thus represented are highly precise and can be performed on high scale and with various degrees of controlled flexibility within the protein component. The protein-ligand complexes with ligands screened from databases can next be ranked using advantages of post-docking Embrace minimizations and prime MM GBSA of the SCHRODINGER suite. These procedures give estimates of free binding energy and thus are suitable tools for ligand ranking based on the computed binding affinity.

When the crystal structure of a drug-protein complex is not known, as is the case in TONSL-H4 tail complex, the protein binding pocket(s) and corresponding grid(s) can be computed from the assumption that binding of the prospective ligand(s) should outcompete the most critical aspects for interacting such as for e.g. amino acid residues H18 and K20 on histone H4 tail or any of the above listed interactions.

In this case, the docking grid(s) are computed for the TONSL pocket(s) as defined by the cavities that incorporate these two residues: individually or through being covalently connected together. The scoring function for the competing small molecules in this case is compared with that of the original binding targets. Optimization of identified small molecule leads is achieved by introduction/deletion of R-groups and computing the resulting effect on their affinity by isothermal titration calorimetry, prior to chemical synthesis of the most promising candidates.

Prospective drug candidates are generated in an iterative process of x-ray structure determination and ligand optimization, with the goal of identifying covalently linked optimized ligands that simultaneously target the H4H18 and H4K20 pockets on the TONSL scaffold.

The route to effective compounds according to the present invention is to

1. Determine by the use of the structure scaffold/coordinates in-silico and standard binding/scoring algorithms in-silico molecules with high binding affinity to the TONSL/H4 crystal structure disclosed herein 2. Modify the small molecule structures (with R-substitutions) in silico to represent drug-like compounds 3. Synthesize such structures by standard chemistry 4. Test the resulting synthesized structures in the assays of the invention 5. Select, modify and optimize the most promising compounds.

An alternative to this approach is to screen existing libraries in the assays, and optionally optimize these so as bind in the space as described.

Thus, in one embodiment the present invention relates to a method of selecting or designing a small molecule capable of interfering with the histone H4H18 and H4K20 binding pocket on the surface of the Ankyrin repeats of TONSL, said method comprises use of at least part of the atomic coordinates data contained in the PDB Protein Databank under the PDB ID 5JA4, DOI: 10.2210/pdb5ja4/pdb or data derivable therefrom, wherein said method involves use of a computer modelling package or a computer program to model all or part of the structure of MCM2 HBD-G4-TONSL ARD in complex with H3 (57-135) and H4, identifying such small molecule based on its likely ability to prevent or disrupt the H4 tail with the Ankyrin repeats of TONSL in the modelled structure.

In one embodiment, the invention relates to a fusion protein, MCM2 HBD-$G_4$-TONSL ARD (SEQ ID NO: 15) or variants thereof (e.g. $G_x$ linker=$G_{12}$, $G_{11}$, $G_{10}$, $G_9$, $G_8$, $G_7$, $G_6$, or $G_5$), which are instrumental for determining the structural details of TONSL binding small molecule inhibitors.

In another embodiment, the invention relates to the TONSL and H4 mutants that disrupt interaction between TONLS and TONSL ARD with histone H4 (FIGS. 10-13, Examples 2-4). The mutant data identify key intermolecular interactions contributing to the specificity and stability of complex formation. The verified TONSL histone-binding mutants are instrumental for biochemical and biological assay design to assess the efficiency of screened small molecule inhibitors in blocking TONSL-histone interaction and TONSL function.

In one embodiment the invention relates to compounds having a 3-[(3-Aminocyclopentyl)carbonyl]-1H-quinolin-4-one core. Such compounds may be any compound, preferably any small organic compound comprising the 3-[(3-Aminocyclopentyl)carbonyl]-1H-quinolin-4-one, wherein one or more positions may be substituted with a substituent. Thus, the compound may be a 3-[(3-Aminocyclopentyl) carbonyl]-1H-quinolin-4-one, wherein one or more —H have been substituted for another group.

Peptide Inhibitors of TONSL

The invention also provides inhibitors of TONSL, in particular such inhibitors, which can inhibit binding of TONSL ARD to histone H4. In preferred embodiments the inhibitor may be a compound binding the histone H4 tail binding surface of TONSL ARD.

Methods for identifying such inhibitors are provided herein elsewhere.

The inhibitor may be any useful compound for example a peptide inhibitor or a small molecule. In one embodiment of the invention, the inhibitor is a peptide inhibitor. The peptide inhibitor may for example be useful in the treatment of cancer.

As used herein the term "peptide inhibitor" refers to a compound comprising a peptide or a polypeptide optionally linked to a conjugated moiety. The peptide or polypeptide part of the peptide inhibitor is in the following referred to as "peptide".

The peptide inhibitor may thus be a peptide, which is capable of binding the TONSL ARD. Thus, the peptide inhibitors may be any of the peptides described herein below, wherein said peptide is capable of binding to TONSL ARD (e.g. to a peptide consisting of amino acids 512 to 692 of SEQ ID NO:16) with a Kd of at the most 10 μM, preferably a Kd of at the most 5 μM, such as with a Kd of at the most 3 μM. Said Kd may for example be determined as described in Example 10 and 15 below.

In one embodiment the peptide may comprise the sequence motif I: Arg-His-Xaa-Lys (SEQ ID NO:26), wherein Xaa may be any amino acid.

In one embodiment the peptide may comprise the sequence motif II: Arg-His-Xaa-Lys-Val-Leu (SEQ ID NO:27), wherein Xaa may be any amino acid.

In one embodiment the peptide may comprise the sequence motif III: Val-Leu-Arg.

In one embodiment the peptide may comprise the sequence motif IV: Arg-His-Xaa-Lys-Val-Leu-Arg (SEQ ID NO:28), wherein Xaa may be any amino acid.

In particular, the peptide may be a peptide consisting of in the range of 4 to 40 amino acids comprising the sequence Arg-His-Xaa-Lys, and/or one or more of the sequence motifs I, II, III or IV. The peptide may also be a peptide consisting of in the range of 4 to 25 amino acids, such as in the range of 4 to 15 amino acids, preferably in the range of 7 to 15 amino acids, such as in the range of 7 to 12 amino acids, such as in the range of 4 to 10 amino acids, for example in the range of 6 to 9 amino acids comprising the sequence Arg-His-Xaa-Lys, and/or one or more of the sequence motifs I, II, III or IV. The peptide may also be a peptide consisting of at the most 25 amino acids, preferably at the most 15 amino acids, such as at the most 12 amino acids, for example at the most 9 amino acids, wherein the peptide comprises one or more of the sequence motifs I, II, III or IV. Said Lys is preferably unmethylated. Said Xaa may be any amino acid, for example it may be selected from the group consisting of Ala and Arg. In one embodiment of the invention Xaa is not Arg.

In one embodiment the peptide comprises or consists of:

I. a sequence consisting of amino acid 12 to 23 of SEQ ID NO:23 or of SEQ ID NO:34; or II. a functional homologue thereof consisting of a sequence of amino acid 12 to 23 of SEQ ID NO:23 or of SEQ ID NO:34, wherein up to 5 amino acids, for example up to 4 amino acids, for example up to 3 amino acids, such as up to 2 amino acids, for example 1 amino acids may be substituted, and wherein said peptide comprises at least Arg17, His18 and Lys20 of SEQ ID NO:23 or of SEQ ID NO:34, III. a functional homologue thereof consisting of a sequence of amino acid 12 to 23 of SEQ ID NO:23, wherein up to 6 amino acids, such as up to 5 amino acids, for example up to 4 amino acids, such as up to 3 amino acids, for example up to 2 amino acids may be substituted may be substituted, with the proviso that the inhibitor is different to histone H4 of SEQ ID NO:23.

In one embodiment the peptide comprises or consists of:

IV. a sequence consisting of amino acid 9 to 25 of SEQ ID NO:23 or of SEQ ID NO:34; or V. a functional homologue thereof consisting of a sequence of amino acid 9 to 25 of SEQ ID NO:23 or of SEQ ID NO:34, wherein up to 5 amino acids, for example up to 4 amino acids, for example up to 3 amino acids, such as up to 2 amino acids, for example 1 amino acids may be substituted, and wherein said peptide comprises at least Arg17, His18 and Lys20 of SEQ ID NO:23 or of SEQ ID NO:34, VI. a functional homologue thereof consisting of a sequence of amino acid 9 to 25 of SEQ ID NO:23 or of SEQ ID NO:34, wherein up to 6 amino acids, such as up to 5 amino acids, for example up to 4 amino acids, such as up to 3 amino acids, for example up to 2 amino acids may be substituted with the proviso that the inhibitor is different to histone H4 of SEQ ID NO:23.

In one embodiment the peptide comprises or consists of:

VII. a sequence consisting of amino acid 14 to 33 of SEQ ID NO:23 or of SEQ ID NO:34; or VIII. a functional homologue thereof consisting of a sequence of amino acid 14 to 33 of SEQ ID NO:23 or of SEQ ID NO:34, wherein up to 5 amino acids, for example up to 4 amino acids, for example up to 3 amino acids, such as up to 2 amino acids, for example 1 amino acids may be substituted, and wherein said peptide comprises at least Arg17, His18 and Lys20 of SEQ ID NO:23, IX. a functional homologue thereof consisting of a sequence of amino acid 14 to 33 of SEQ ID NO:23 or of SEQ ID NO:34, wherein up to 6 amino acids, such as up to 5 amino acids, for example up to 4 amino acids, such as up to 3 amino acids, for example up to 2 amino acids may be substituted with the proviso that the inhibitor is different to histone H4 of SEQ ID NO:23.

In embodiments of the invention where the peptide comprises a functional homologue as described under III., VI. or IX herein above it may be preferred that:

I. the amino acid corresponding to amino acid 17 of SEQ ID NO:23 or of SEQ ID NO:34 is a charged amino acid, such as a positively charged amino acid, for example an amino acid selected from the group consisting of Lys and Arg II. the amino acid corresponding to amino acid 18 of SEQ ID NO:23 or of SEQ ID NO:34 is a charged amino acid, such as a positively charged amino acid, for example His III. the amino acid corresponding to amino acid 20 of SEQ ID NO:23 or of SEQ ID NO:34 is a charged amino acid, such as a positively charged amino acid, for example an amino acid selected from the group consisting of Lys and Arg.

In one embodiment, the peptide inhibitors may be identified based on the sequence of histone H4 of SEQ ID NO:23 or a fragment thereof, i.e. by systematically or randomly replacing one or more amino acids of an H4 peptide, or certain parts of H4 native peptide, with other amino acids.

In general the peptide inhibitor should not be too large. Accordingly, it may be preferred that the peptide consists of at the most 40 amino acids, such as at the most 25 amino acids, for example at the most 20 amino acids, such as at the most 15 amino acids, for example at the most 12 amino acids. For example, the peptide may comprise or consist of in the range of 4 to 40, for example in the range of 4 to 25, for example in the range of 4 to 20, such as in the range of 4 to 15, such as in the range of 4 to 12, for example in the range of 7 to 15 amino acids, such as in the range of 7 to 12 amino acids, such as in the range of 5 to 10 or such as in the range of 6 to 9 consecutive amino acids of SEQ ID NO:23.

In one embodiment, the peptide may comprise or consist of in the range of 4 to 40, for example in the range of 4 to 25, for example in the range of 4 to 20, such as in the range of 4 to 15, such as in the range of 4 to 12, for example in the range of 7 to 15 amino acids, such as in the range of 7 to 12 amino acids, such as in the range of 5 to 10 or such as in the range of 6 to 9 consecutive amino acids of SEQ ID NO:23, wherein up to 3, such as up to 2, for example at the most one amino acid may have been substituted for another amino acid, and wherein the peptide comprises one or more of the sequence motifs I, II, III or IV.

Said functional homologues of fragments of SEQ ID NO:23 are preferably peptides, comprising above defined sequence, and which are capable of binding TONSL.

As described above the peptide may comprise one or more Lys residues. It may be preferred that at least one Lys residue, for example all Lys residues are unmethylated. In particular, when the peptide comprises a fragment of SEQ ID NO:23 it may be preferred that the amino acid corresponding to Lys20 of SEQ ID NO:23 is unmethylated.

In some embodiments of the invention, the C-terminal of the peptide is amidated, i.e. having the chemical structure $—C(O)NH_2$.

In some embodiments of the invention, the C-terminal of the peptide is alkylated e.g methylated i.e. having the chemical structure $—C(O)OCH_3$.

In some embodiments of the invention, the N-terminal of the peptide is acetylated i.e. having the chemical structure $CH_3C(O)N(H)—$.

In some embodiments of the invention, the N-terminal of the peptide is formylated i.e. having the chemical structure $HC(O)N(H)—$.

It is understood that a peptide consisting of a given sequence may have a C-terminal, which is amidated or alkylated and/or an N-terminal, which is acetylated or formylated.

The peptide inhibitor may in particular be a peptide comprising or consisting of a peptide selected from the group consisting of:

Ala-Lys-Arg-His-Arg-Lys-Val-Leu-Arg-$NH_2$,

Lys-Gly-Gly-Ala-Lys-Arg-His-Arg-Lys-Val-Leu-Arg-$NH_2$,

Lys-Gly-Gly-Ala-Lys-Arg-His-Ala-Lys-Val-Leu-Arg-$NH_2$ and

Lys-Gly-Gly-Ala-Ala-Arg-His-Arg-Lys-Val-Leu-Arg-$NH_2$.

The moiety "—$NH_2$" indicated in the sequence above indicates that the C-terminal of the peptides are amidated. The invention however also encompass peptides which are not amidated. Accordingly, in one embodiment, the invention relates to peptide inhibitors comprising or consisting of at the most 40, for example at the most 25, for example at the most 20, such as at the most 15, such as at the most 12 amino acids, wherein the peptide comprises a sequence selected from the group consisting of SEQ ID NO:29, SEQ ID NO:30, SEQ ID NO:31, SEQ ID NO:32 and SEQ ID NO:33.

In some embodiments of the invention, the peptide is a TONSL mutant polypeptide, for example any of the TONSL mutant polypeptides described herein below in the section "TONSL mutant polypeptides". For example, the peptide may be selected from the group consisting of polypeptides of SEQ ID NO:17, SEQ ID NO:18, SEQ ID NO:19, SEQ ID NO:20, SEQ ID NO:21 and SEQ ID NO:22.

In some embodiments of the invention the inhibitor is a fragment of TONSL, in particular a fragment of TONSL capable of binding histone H4, but incapable of binding at least one other binding partner of TONSL, e.g. incapable of binding MMS22L. Said fragment of TONSL, may for example be a fragment comprising the H4 tail binding surface of TONSL. In one embodiment, the fragment comprises or consists of amino acids 512 to 692 of SEQ ID NO: 16 or a functional homologue thereof sharing at least 70%, such as at least 80%, for example at least 85%, such as at least 90%, for example at least 95% sequence identity therewith.

The peptide described herein may in some embodiments be linked to a conjugated moiety, for example the peptide may be covalently linked to a conjugated moiety. Said conjugated moiety may for example be any of the moieties described herein below.

In one embodiment the conjugated moiety may be a peptide, a sugar, a lipid, a polymeric molecule or any other chemical group that can be covalently linked to a peptide. For example, the conjugated moiety may improve the physical properties of the peptide, such as its solubility, stability or half-life.

In one embodiment the conjugated moiety is a polymeric molecule, such as polyethylene glycol (PEG) and polyvinylpyrrolidone (PVP). The polymeric molecule may also be a modified PEG, for example NPEG.

Assays Validating the Small Molecules of the Present Invention

Molecules identified according to the present invention are tested in biochemical and cell biology assays listed below. Molecules that show activity in these assays towards inhibiting TONSL function similar to TONSL ARD mutants are further tested in high-throughput biological assay for efficacy in killing cancer cells and ultimately in pre-clinical and clinical trials.

Biochemical Screening and Biophysical Testing (Assays)

The key components in the assays are:

a) Recombinant human TONSL ARD (residues 512-692, point 1)

b) Recombinant human TONSL ARD mutants E530A, D559A, W563A, E568A, N571A, D604A (point 2)

c) Histone H4 peptide-containing K20me0 with or without acetylation at K16 (H4 tail covering the critical residues for TONSL binding, for example 9-25 or 14-33) coupled to fluorescent molecule or biotin d) Histone H4 peptide containing K20me2 with or without acetylation at K16 as a control for no binding to TONSL ARD H4 tail covering the critical residues for TONSL binding, for example 9-25 or 14-33) coupled to fluorescent molecule or biotin e) Human cells expressing tagged TONSL ARD wild type (WT) or histone-binding mutant (e.g. any of the mutants described herein in the section "TONSL mutant polypeptide", for example any of E530A, D559A, W563A, E568A, N571 A, or D604A).

We generated and verified expression constructs for GFP-fusion proteins for mutants and inducible cell lines for WT, E568A and N571A Assay 1: High-Throughput (HT) Measurements of Small Molecule Dependent Disruption of the TONSL ARD—H4 Tail Interaction Detailed in Point 2.

Figure 13:
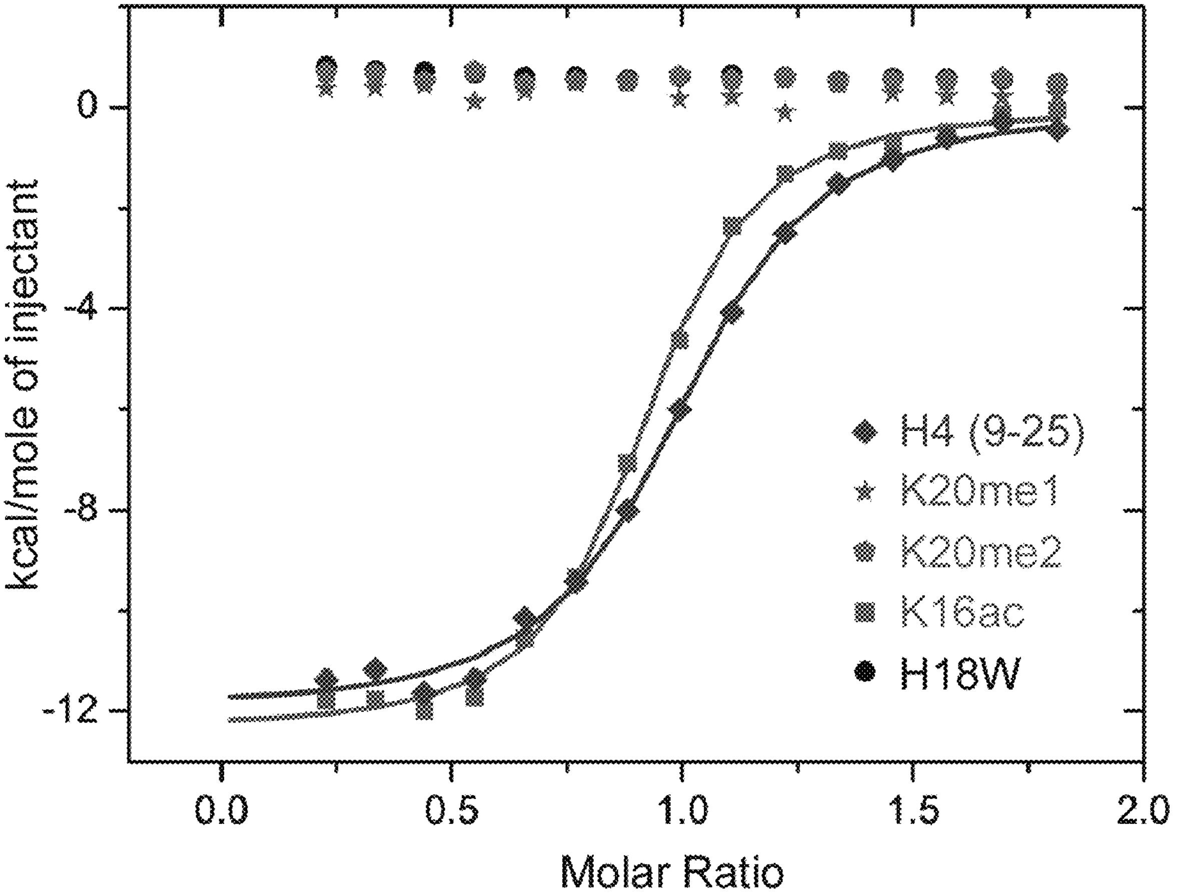
FIG. 13 shows ITC analysis of TONSL ARD binding to H4 tail peptides with the indicated modifications.
Figure 14:
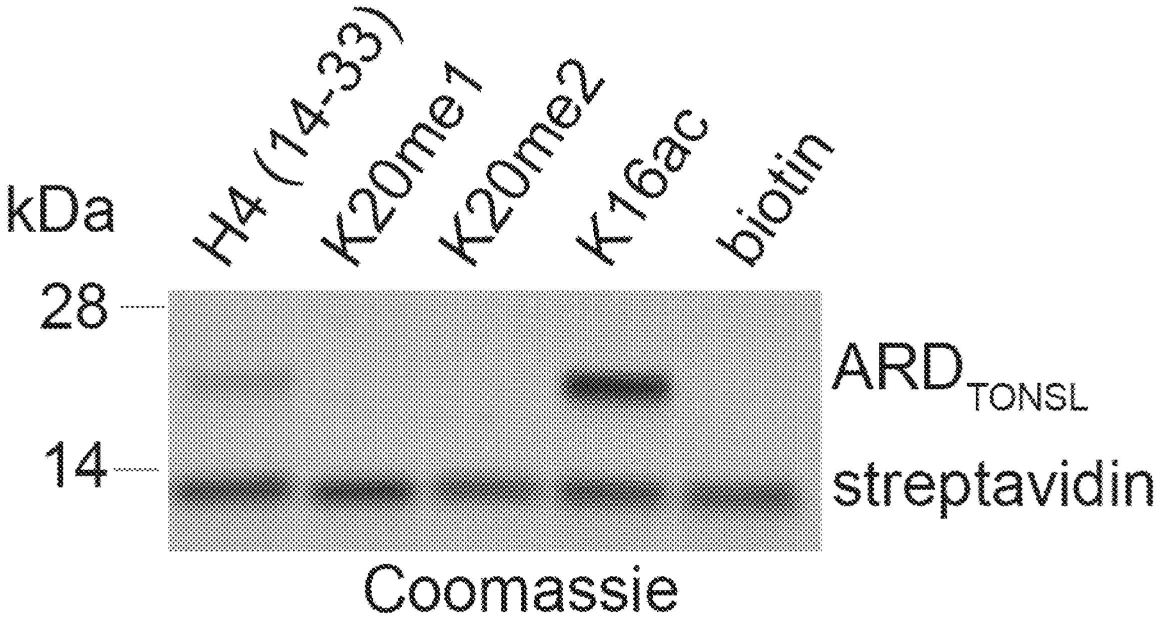
FIG. 14 shows in vitro pull-down of recombinant TONSL ARD with biotinylated H4 tail peptides.
Figure 15:
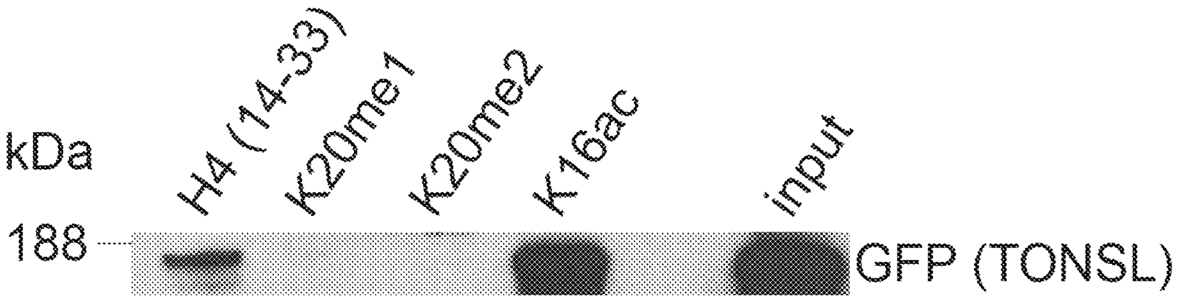
FIG. 15 shows in vivo pull-down of GFP-TONSL from cell extracts with biotinylated H4 tail peptides.

First line screening may be based on Fluorescence anisotropy measurements using histone H4 peptides conjugated with a fluorescent probe. Assay conditions are as detailed below in our demonstrated ITC assay (Example 2), with the critical criteria that ARD binding being observed to H4 (residues 9-25), but not H4K20me2 (residues 9-25, dimethylated at K20) (FIG. 13).

Assay 2: Measurement of Binding Properties of Small Molecule Inhibitors to ARD

Second line screening may involve Isothermal titration calorimetry (ITC) to determine binding affinity/association constants (Ka) and Surface plasmon resonance (SPR) assays to determine rate constants. The resulting molecules yielding higher binding affinity to TONSL than unmodified histone H4 peptide (Example 2) are further shortlisted to identify those with μM to nM effective range.

Assay 3. Crystallization and Optimization

Candidate small molecules may be crystallized with TONSL ARD (using our demonstrated crystallization conditions outlined in point 1, Example 1), providing further possibility for drug optimization.

Assay 4. Competition Assay Based on Peptide Pulldown a. Selected small molecules are validated for their ability to compete out binding of recombinant ARD to H4K20me0 peptides (H4K20me2 and ARD mutants are used as negative controls, assay conditions as in Example 3).

b. Selected small molecules are validated for their ability to compete out binding of GFP-TONSL-MMS22L to H4K20me0 peptides in cell extracts.

Grow cells expressing tagged TONSL WT or ARD mutant (as control for no histone H4 binding). Prepare whole-cell extracts according to standard protocols (documented conditions for this assay in Example 4). Incubate the cell extracts with surface-bound biotinylated-histone H4 peptides (e.g. H4K20me0 vs. H4K20me2 as a control for no binding to WT TONSL). Dose-response analysis with small molecule inhibitors assaying loss of WT TONSL binding to H4K20me0 peptides by ELISA, western blotting or similar approaches.

HT Biological Assays to Screen for Small Molecule Inhibitors

The present inventors have demonstrated that TONSL binds to chromatin via ARD recognition of the tails of nucleosomal histone H4 unmethylated at K20 (FIG. 21). The biological function of a small molecule inhibitor is thus to prevent TONSL from binding histone H4 and displace TONSL-MMS22L complex from chromatin.

The present inventors have developed high-content microscopy based assays, which are used for drug screening (Example 5).

Figure 20:
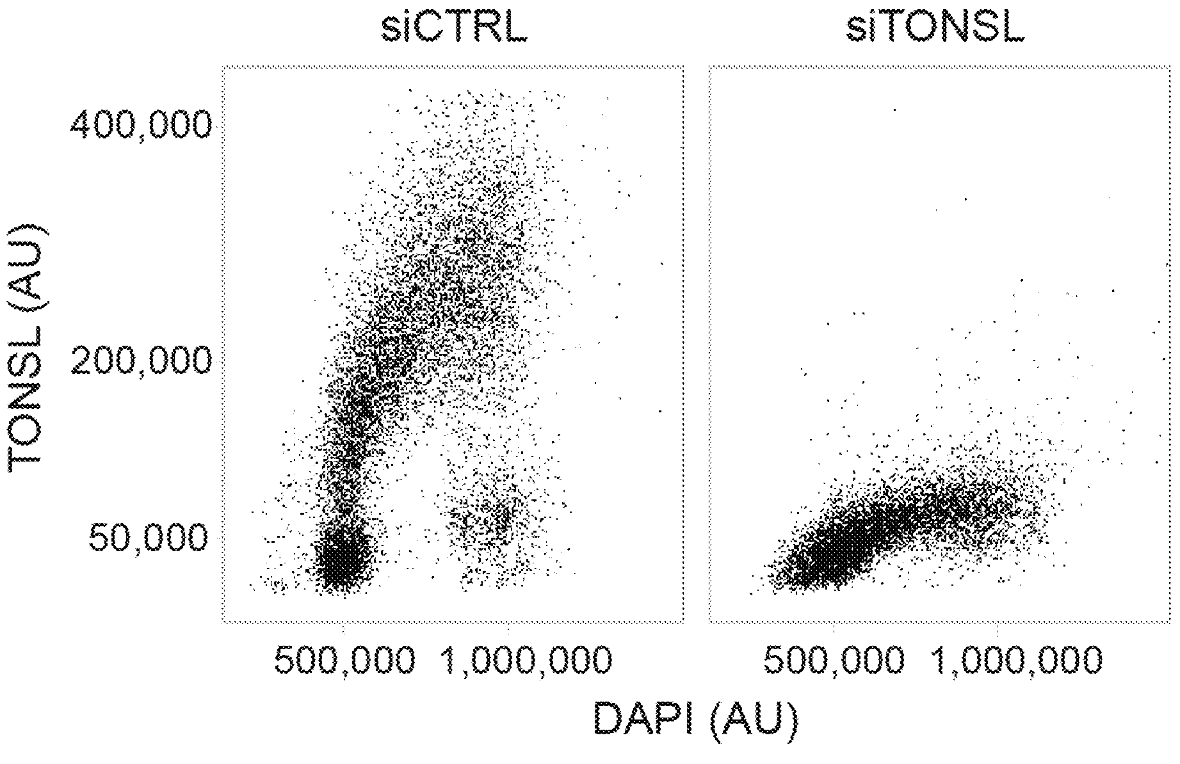
FIG. 20 shows high-content quantitative imaging of TONSL in pre-extracted U-2-OS fibroblasts. Plots show total TONSL and DAPI intensities in cells treated with control or TONSL siRNAs, confirming the specificity of TONSL antibody. Dots represent measured intensities of individual cell nuclei.

1) Immunofluorescence staining of endogenous TONSL shows binding to post-replicative chromatin, which is lost upon depletion of TONSL with RNAi (FIG. 20).

2) binding of GFP-TONSL to chromatin is disrupted by ARD mutants that disrupt H4 binding (FIG. 21).

The present invention covers small molecule inhibitors that displace TONSL and TONSL-MMS22L complex from post-replicative chromatin and mimic TONSL ARD mutants.

Key Components:

a) Anti-TONSL antibody (Sigma, ref. nr. HPA0244679), tested in our high-content assay (Example 5)
b) Pre-extraction conditions to remove soluble TONSL (Example 5)
c) Condition for TONSL depletion (negative control) (Example 5)
d) GFP-TONSL WT and ARD mutant cell lines Rationale of HT Assays:

1. High-content imaging to identify small molecules that remove endogenous TONSL and TONSL-MMS22L complex from chromatin (FIG. 21)
2. High-content imaging of TONSL binding to chromatin using cells expressing GFP-TONSL WT and ARD mutant (N571A, point 2) upon incubation with TONSL inhibitors by high-content imaging Assay 1: HT Imaging of Chromatin-Bound Endogenous TONSL Cells are grown in a HT format (96 or 384 well-plates). Incubated with small molecule TONSL inhibitors in a dose-response and time-course set-up. Soluble proteins are removed by cell pre-extraction followed by cell fixation according to standard protocols. Detect chromatin-bound TONSL with commercial antibody (Sigma, ref. nr. HPA0244679) documented by us for specificity (Example 5). TONSL siRNA are used as control. Chromatin-bound TONSL may be quantified by conventional methods, for example using standard high content imaging (Example 5) or alternatively by FACS analysis.

Assay 2: HT Imaging of GFP-TONSL

Grow cells with expression of GFP-TONSL WT and ARD mutant (N571A, point 2: negative control for binding) in a HT format (96 or 384 well-plates). Incubate with small molecule TONSL inhibitors in a dose-response and time-course set-up. Remove soluble proteins by pre-extraction cells and fix cells according to standard protocols. Quantify GFP-TONSL levels on chromatin by standard high content imaging (Example 5).

Biological Assays to Measure HR Inhibition

TONSL is required for HR of damaged replication forks and DNA double strand breaks (Duro et al. 2010 Mol Cell 40:619; O'Donnell et al. 2010 Mol Cel 40:619; O'Connell et al. 2010 Mol Cell 40:645; Piwko et al. EMBO J 2010 29:4210). Thus, small molecule inhibitors preventing TONSL or MMS22L recruitment to chromatin phenocopy the loss of TONSL or MMS22L.

To test the capacity of small molecule inhibitors to compromise HR, published assays to monitor recruitment of repair proteins (e.g., Duro et al. 2010 Mol Cell 40:619; O'Donnell et al. 2010 Mol Cel 40:619; O'Connell et al. 2010 Mol Cell 40:645; Piwko et al. EMBO J 2010 29:4210) and HR reporter cell lines are used (e.g., Pierce et al., Genes Dev 13:2633, 1999). In those assays, the cells are treated with small molecule TONSL inhibitors in a time and dose-dependent manner and efficiency of HR repair is assayed by high-content microscopy TONSL Mutant Polypeptide In one embodiment the invention relates to a TONSL mutant polypeptide. Said TONSL mutant polypeptide is preferably a TONSL mutant polypeptide, which is incapable of binding histone H4, but which retains other TONSL functions. Preferably, said TONSL mutant polypeptide is capable of binding MMS22L and wherein said TONSL mutant does not bind histone H4. Such TONSL mutant polypeptides will function as dominant negative mutants, because they will bind MMS22L and other members of the complex, preferably with the same or similar affinity as the wild type TONSL polypeptide, but they will not bind the post-replicative chromatin to any significant extent.

In one embodiment the TONSL mutant polypeptide is a polypeptide of SEQ ID NO: 16 carrying one or more mutations, preferably one or more mutations in amino acid(s) contributing to the H4 tail binding surface of TONSL ARD. Thus, the TONSL mutant polypeptide may comprise at least one mutation in an amino acid of the histone H4 tail binding surface of the TONSL ARD, wherein said TONSL mutant polypeptide apart from said mutation is identical to SEQ ID NO:16 or shares a sequence identity with SEQ ID NO:16 of at least 70%, wherein said TONSL mutant polypeptide is capable of binding MMS22L and wherein said TONSL mutant does not bind histone H4.

In particular said TONSL mutant polypeptide may be a polypeptide of SEQ ID NO: 16 carrying a mutation in at least one amino acid selected from the group consisting of amino acid number 527, 528, 530, 559, 560, 561, 563, 568, 571, 572, 595, 597, 604, 607, 608, 641, 645 and 649 of SEQ ID NO:16.

In one embodiment the TONSL mutant polypeptide carries a mutation in one or more of the amino acids selected from the group consisting of: Glu530, Asp559, Trp563, Glu568, Gln571 and D604 of SEQ ID NO:16.

In one embodiment TONSL mutant polypeptide may comprise or even consist of a sequence selected from the group consisting of SEQ ID NO: 17, SEQ ID NO: 18, SEQ ID NO:19, SEQ ID NO:20, SEQ ID NO:21 and SEQ ID NO:22.

The TONSL mutant polypeptide may be linked to a conjugated moiety, for example the TONSL mutant polypeptide may be linked to a detectable marker. Said detectable marker may be a peptide or a polypeptide, e.g. a fluorescent protein, such as GFP.

A Method for Predicting the Effect of Inhibition of TONSL

The invention also provides methods for predicting the effect of inhibition of TONSL. As described herein above, the TONSL mutant polypeptides described herein may be dominant negative mutant. Expression of such mutants may phenocopy TONSL/MMS22L depletion, and thus mimic the actions of an inhibitor of TONSL binding to histone H4.

Thus, in one embodiment the invention relates to methods for predicting the effect of inhibition of TONSL, said method comprising the steps of expressing a TONSL mutant polypeptide in an organism and/or cells of an organism, wherein said polypeptide optionally is expressed conditionally, determining the effect of said polypeptide in said organism and/or cells wherein said effect of expressing said polypeptide in said organism and/or cells indicates the effect of inhibition of TONSL in said organism and/or cells.

In particular, said TONSL mutant polypeptide may be any of the TONSL mutant polypeptides described herein above in the section “TONSL mutant polypeptide”. The organism and/or cells may comprise a heterologous nucleic acid encoding any of said TONSL mutant polypeptides.

Thus, the effect obtained after expression of a dominant negative TONSL mutant polypeptide may mimic the effect of inhibition of TONSL in said organism and/or cells. Thus, the effect observed is indicative of the effect expected to be obtained, if the organism/cells were treated with an inhibitor of TONSL, in particular with an inhibitor inhibiting binding between TONSL ARD and the histone H4.

The organism or the cells may represent a disease model, and thus the method may be used to predict the efficacy of treating said disease with an inhibitor or TONSL, e.g. an inhibitor inhibiting binding between TONSL ARD and the histone H4.

The organism may be any organism, e.g. a mammal, for example a mouse, a rat or a rabbit. The organism may be genetically modified to contract a particular disease, for example cancer. Thus, the organism may be a mouse genetically engineered to contract cancer.

The cells may also represent a disease model. The cells may be any cells, such as mammalian cells, e.g. human cells. The cells may be cultivated using any conventional method. For example, the cells may be cultured in a 3D culture, which more closely may mimic in vivo conditions.

Since expression of TONSL mutant polypeptide may be toxic to cells, it may be preferred that said TONSL mutant polypeptide is expressed only conditionally. Thus, the TONSL mutant polypeptide may be expressed only in specific cells of said organism and/or said TONSL mutant polypeptide may be induced to be expressed at specific times. Thus, the organisms and/or cells may comprise a heterologous nucleic acid encoding any of the TONSL mutant polypeptides described herein above in the section “TONSL mutant polypeptide” operably linked to an inducible promoter. In that manner expression of said TONSL mutant polypeptide may be induced at any specific time. Inducible promoters and well known in the art and the skilled person will be able to select a useful promoter. The organism may also comprise a heterologous nucleic acid encoding any of said TONSL mutant polypeptides operably linked to a promoter directing expression in only some cell types. Such promoters are also known in the art.

Method for Determining TONSL Inhibitory, Effect

The invention also provides methods of identifying the TONSL inhibitory effect of a putative inhibitor of TONSL. In particular said methods can be used to determine whether a compound is capable of inhibiting binding between TONSL and histone H4. Such methods are useful for screening for inhibitors of TONSL. However, the methods are also useful for validating whether a putative inhibitor in fact is capable of inhibiting TONSL. Thus, the methods can be used for determining biosimilarity between a known TONSL inhibitor and a similar compound, which is a putative TONSL inhibitor. The methods may also be used in quality control of TONSL inhibitors. The methods may also be used to validate the inhibitory effect of an inhibitor identified by computer aided techniques using the atomic coordinates provided in the PDB Protein Databank under the PDB ID 5JA4, DOI: 10.2210/pdb5 ja4/pdb.

Said methods may comprise the steps of a) providing a test compound, which is a putative inhibitor of TONSL b) providing an host organism expressing TONSL of SEQ ID NO: 16, TONSL ARD consisting of amino acids 512 to 692 of SEQ ID NO: 16 or a functional homologue of any of the aforementioned sharing at least 90% sequence identity to amino acids 512 to 692 of SEQ ID NO:16;

c) contacting said host organism with said putative inhibitor d) detecting chromatin associated TONSL, TONSL ARD or functional homologue thereof in said host organism, wherein reduction of chromatin associated TONSL, TONSL ARD or a functional homologue thereof is indicative of said test compound being an inhibitor of TONSL.

Said reduction of chromatin associated TONSL, TONSL ARD or a functional homologue thereof is preferably a reduction compared to said level in said host organism in the absence of said inhibitor. In particular, said reduction may be a reduction to less than 50%, such as a reduction to less than 30%, such as a reduction to less than 20%, for example a reduction to less than 10% of the chromatin associated TONSL, TONSL ARD or a functional homologue thereof in said host organism in the absence of said inhibitor. In one embodiment, the reduction is that there is no detectable chromatin associated TONSL, TONSL ARD or a functional homologue thereof.

The host organism may be any useful host organism including cells, e.g. mammalian cells maintained in a tissue culture. Thus, the term “cells of the host organism” may refer to part of a multicellular host organism or it may refer to the host organism per se, when the host organism is cells. The host organism may endogenously express TONSL, in which case the method may involve detecting chromatin associated endogenous TONSL. Endogenous TONSL may be detected by various means, but frequently, endogenous TONSL is detected by means of an antibody, a binding fragment of an antibody or another binding molecule specifically recognising and binding TONSL. The antibody, fragment or binding molecule may be directly labelled with a detectable label. It is also possible that the methods involve use of a secondary antibody, fragment or binding molecule binding the first antibody, fragment or binding molecule, wherein the secondary antibody, fragment or binding molecule is labelled with a detectable label. Other methods for detecting binding of an antibody, fragment or binding molecule are also available and may be used with the methods.

The detectable label may be any detectable label including but not limited to fluorophores, bioluminescents, chemoluminescents, dyes, enzymes, heavy metals, or radioactive compounds. In preferred embodiments the detectable label is a fluorophore, i.e. a fluorescent moiety.

It is also comprised within the invention that said host organism comprises a heterologous nucleic acid encoding said TONSL, TONSL ARD or functional homologue thereof. In such embodiments the methods may involve detecting chromatin associated heterologous TONSL, TONSL ARD or functional homologue thereof. The heterologous TONSL, TONSL ARD or functional homologue thereof may be linked to a detectable label, for example to a fluorescent polypeptide, such as GFP. Thus, the step of detection, may be a step of detecting the detectable label. Heterologous TONSL, TONSL ARD or functional homologue thereof may also be detected used the same methods useful for detection of endogenous TONSL.

The detectable label may be detected using any technical means useful for detecting the particular detectable label. In embodiments of the invention, where the detectable label is fluorescent, then the detectable label may be detected by means of FACS, fluorescent microscopy or high content microscopy.

Step d) of the method may comprise a step of extracting soluble proteins from the cells of said host organism. This step may ensure that all TONSL, TONSL ARD or functional homologues thereof, which is not chromatin associated is extracted from the cells of said host organism. Following extraction of soluble proteins all remaining TONSL, TONSL ARD or functional homologues thereof may be regarded as chromatin associated TONSL, TONSL ARD or functional homologues thereof.

Extracting soluble protein may be done in any conventional manner, e.g. by permeabilising cell membranes, e.g. by use of a detergent optionally followed by one or multiple washing steps. Any detergent may be used for permeabilisation, e.g. Triton (e.g. Triton X-100), NP-40, saponin, Tween (e.g. Tween-20), Digitonin or Leucoperm. After extraction the cells may be fixed prior to detection. Fixation reagents are well known in the art and includes for example aldehydes, e.g. formaldehyde, paraformaldehyde or glutaraldehyde.

One useful method for determining chromatin associated TONSL, TONSL ARD or functional homologues thereof is described in Example 5 herein. Other useful methods for determining chromatin associated TONSL, TONSL ARD or functional homologues thereof are described in the section "High-throughput (HT) biological assays for efficacy of small molecule inhibitors in killing cancer cells", for example in Assay 1 and 2 of that section. The methods for determining TONSL inhibitory effect may also be any of the methods described herein in the section "Assays validating the small molecules of the present invention", for example any of the assays 1, 2, 3 or 4. Thus, these methods may not only be used for validating small molecules, but can also generally be used for determining TONSL inhibitory effect of a compound.

In one embodiment the method comprises the steps of:

a) Providing histone H4 or a fragment thereof comprising at least amino acids 17 to 20, such as at least amino acids 12 to 23, for example at least amino acids 9 to 25, such as at least amino acids 14 to 33 of SEQ ID NO:23, wherein said histone H4 or fragment thereof optionally may be linked to a detectable label;

b) providing TONSL of SEQ ID NO: 16, TONSL ARD consisting of amino acids 512 to 692 of SEQ ID NO: 16 or a functional homologue of any of the aforementioned sharing at least 90% sequence identity to amino acids 512 to 692 of SEQ ID NO: 16 c) Incubating said histone H4 or fragment thereof with said TONSL, TONSL ARD or functional homologue thereof in the presence of a putative inhibitor of TONSL d) Determining whether binding between said histone H4 or fragment thereof with said TONSL, TONSL ARD or functional homologue thereof wherein reduction in binding of said histone H4 or fragment thereof with said TONSL, TONSL ARD or functional homologue thereof is indicative of that said putative inhibitor of TONSL is capable of inhibiting TONSL.

Said reduction in binding may in particular be a reduction to at the most 50%, such as a reduction to less than 30%, such as a reduction to less than 20%, for example a reduction to less than 10% of the binding of said histone H4 or fragment thereof with said TONSL, TONSL ARD or functional homologue thereof observed in the absence of said putative inhibitor. In one embodiment, the reduction is that there is no detectable binding between said histone H4 or fragment thereof and said TONSL, TONSL ARD or a functional homologue thereof.

High-Throughput (HT) Biological Assays for Efficacy of Small Molecule Inhibitors in Killing Cancer Cells Loss of TONSL leads to accumulation of replication associated DNA damage and sensitizes cells to camptothecin (CPT)-induced DNA damage (Duro et al. 2010 Mol Cell 40:619; O'Donnell et al. 2010 Mol Cell 40:619; O'Connell et al. 2010 Mol Cell 40:645; Piwko et al. EMBO J 2010 29:4210). Further it is well established that loss of HR sensitizes cells to PARP inhibition. The prediction is thus that TONSL inhibition alone or in combination with CPT-like drugs or PARP inhibitors will be toxic to cancer cells.

Key Components:

a) Panel of cancer cell lines and primary cells b) Campthotecin, PARP inhibitors, conventional chemotherapy drugs targeting DNA Replication Rationale of HT Assays:

i. Assay the cell cytotoxicity of TONSL inhibitors by screening a panel of cancer cell lines and primary cells.

ii. Assay the synergy of TONSL inhibitors and other cancer drugs (conventional chemotherapy, CPT and derivatives, PARP inhibitors) in killing cancer cells.

Typical Cell Toxicity Assay: Grow cells in any HT format (e.g. 96 or 384 plates) and incubate with small molecule inhibitors in a dose and time dependent manner. Impact on cell proliferation and cell death may be analysed using any suitable method available, e.g. colorimetric assays or HT microscopy.

In Vivo Models for Drug Testing

Pre-clinical animal testing of TONSL inhibitors with the aim of starting clinical trials.

Small Molecules of the Invention

The small molecules of the present invention are useful for impairing homologous recombination. These could also involve both short linear and cyclic peptides and peptidomimetics, whose low molecular weights allows cell permeability.

By use of the structural data presented in the present application and the proof of concept assays above, the present inventors have identified pharmacophore targeted molecules, including small molecules, covalently linked small molecules, peptides or cyclic counterparts, interfering with the adjacent histone H4H18 and H4K20 binding pocket on the surface of the Ankyrin repeats of TONSL.

Structure Properties of the Small Molecule Inhibitor

The present invention relates to small molecule inhibitors, which target the conformational space of the TONSL ARD occupied by the histone H4 tail encompassing residues K12-R23 and act to disrupt the binding of the H4 tail K12-R23 with the TONSL ARD via direct competition or via allosteric disruption of the binding pocket.

In one embodiment, the present invention relates to a small molecule, which targets or interferes with the conformational space of the TONSL ARD occupied by the histone H4 tail encompassing residues K12-R23 and acting to prevent or disrupt the binding of the H4 tail K12-R23 with the TONSL ARD via direct competition or via allosteric disruption of the binding pocket.

As the skilled addressee would know, it's apparent that a small molecule that could bind to the His18-binding pocket or the Lys20-binding pocket or both pockets on TONSL ARD, would disrupt the interactions between H4 and TONSL.

In one embodiment, the present invention relates to a small molecule that targets the H4 tail spanning residues Lys12 to Arg23 through intermolecular hydrogen-bonding, electrostatic and/or van der Waals interactions.

In a more preferred embodiment, the present invention relates to a small molecule, wherein the molecule targets the intermolecular contacts spanning the Lys12-Gly13-Gly14-Ala15 segment of H4.

In another preferred embodiment the present invention relates to a small molecule, wherein the molecule targets the hydrophobic interactions between residues Gly13, Gly14 and Ala15 of H4 and residues Asn507, Cys508, Trp641, Tyr645 and Leu649 of ARD.

In one embodiment, the present invention relates to a small molecule, wherein the molecule targets the hydrogen bonds between the main-chain O of H4 Gly14 and Nε of ARD Trp641, and between the main-chain N of H4 Ala15 and Oη of ARD Tyr645.

In one embodiment, the present invention relates to a small molecule, wherein the molecule targets the main-chain O of H4 Lys16 hydrogen bonds with the Nδ2 of ARD Asn571.

In one embodiment, the present invention relates to a small molecule, wherein the molecule targets and/or associates with the conformational space of the TONSL ARD occupied by the side-chain of H4 Arg17, which stacks over the side-chains of ARD Tyr572 and Cys608, while its Nη1 atom forms two hydrogen bonds with main-chain O and Oδ1 of ARD Asn571. Thus, in one embodiment the invention relates to a compound, e.g. a TONSL inhibitor capable of associating with the side-chains of ARD Tyr572 and Cys608, and forming hydrogen bonds with the main-chain O and 061 of ARD Asn571.

In one embodiment, the present invention relates to a small molecule, wherein the molecule targets and/or associates with the conformational space of the TONSL ARD occupied by the side-chain of H4 H18, which penetrates into a pocket lined by four strictly conserved residues (Trp563, Glu568, Asn571 and Asp604) and is positioned over His567 of ARD. Thus, in one embodiment the invention relates to a compound, e.g. a TONSL inhibitor capable of associating with Trp563, Glu568, Asn571, Asp604 and His567 of TONSL ARD.

In one embodiment, the present invention relates to a small molecule, wherein the molecule targets and/or associates with the conformational space of the TONSL ARD occupied by the side chain of H4 His18, which is stacked between Trp563 and Asn571 and forms hydrogen bonds to Glu568 and Asp604 of ARD. Thus, in one embodiment the invention relates to a compound, e.g. a TONSL inhibitor capable of associating with Trp563 and Asn571 and forming hydrogen bonds to Glu568 and Asp604 of TONSL ARD.

In one embodiment, the present invention relates to a small molecule, wherein the molecule targets and/or associates with the conformational space of the TONSL ARD occupied by the main-chain O of H4 Arg19 that forms a hydrogen bond with Nε1 of Trp563 and its side-chain forms contacts with Cys561 and Gly595 of ARD. Thus, in one embodiment the invention relates to a compound, e.g. a TONSL inhibitor capable of associating with the Nε1 of Trp563 and with Cys561 and Gly595 of TONSL ARD.

In one embodiment, the present invention relates to a small molecule, wherein the molecule targets and/or associates with the conformational space of the TONSL ARD occupied by the H4 Lys20 residue, which is bound within an acidic surface pocket on ARD adjacent to the H4 His18 binding pocket.

In one embodiment, the present invention relates to a small molecule, wherein the molecule targets and/or associates with the conformational space of the TONSL ARD occupied by side-chain of H4 Lys20, which interacts with the side-chain of Met528 and contacts the edge of Trp563 of ARD, while the main-chain atoms of H4 Lys20 packs against Cys561 of ARD. Thus, in one embodiment the invention relates to a compound, e.g. a TONSL inhibitor capable of associating with the side-chain of Met528 and Trp563 and Cys561 of TONSL ARD.

In one embodiment, the present invention relates to a small molecule, wherein the molecule targets and/or associates with the conformational space of the TONSL ARD occupied by the Ni atom of H4 Lys20, which forms three strong hydrogen bonds (distance <3 Å) with the side-chains of strictly conserved residues Glu530, Asp559 and Glu568 of ARD, which surround H4 Lys20 within a regular triangle-like alignment. Thus, in one embodiment the invention relates to a compound, e.g. a TONSL inhibitor capable of forming hydrogen bonds with the side chains of Glu530, Asp559 and Glu568 of TONSL ARD.

In one embodiment, the present invention relates to a small molecule, wherein the molecule targets the intermolecular contacts spanning the Val21-Leu22-Arg23 segment of H4, which include contacts between side-chains of H4 Val21 with Tyr560 and Cys561 of ARD, while H4 Leu22 interacts with Asp527 and Met528 of ARD.

In one embodiment, the present invention relates to a small molecule, wherein the molecule targets and/or associates with the conformational space of the TONSL ARD occupied by the main-chain N of H4 Arg23, which forms a hydrogen bond with the main-chain O of Asp527 of ARD, while the side-chain packs against the side-chain of Tyr560 of ARD. Thus, in one embodiment the invention relates to a compound, e.g. a TONSL inhibitor capable of forming hydrogen bond(s) with the main-chain O of Asp527 of ARD, while the binding the side-chain of Tyr560 of TONSL ARD.

In one embodiment, the present invention relates to a small molecule according to the present invention capable of blocking histone reader domains in a protein selected from the group consisting of TONSL, BARD1 and ANKRD11.

Such molecules are typically identified and validated by the SCHRODINGER package to identify and validate covalently linked small molecule drugs targeted to the adjacent histone H4H18 and H4K20 binding pockets on the surface of the Ankyrin repeats of TONSL.

Relationship with BARD1

Figure 22:
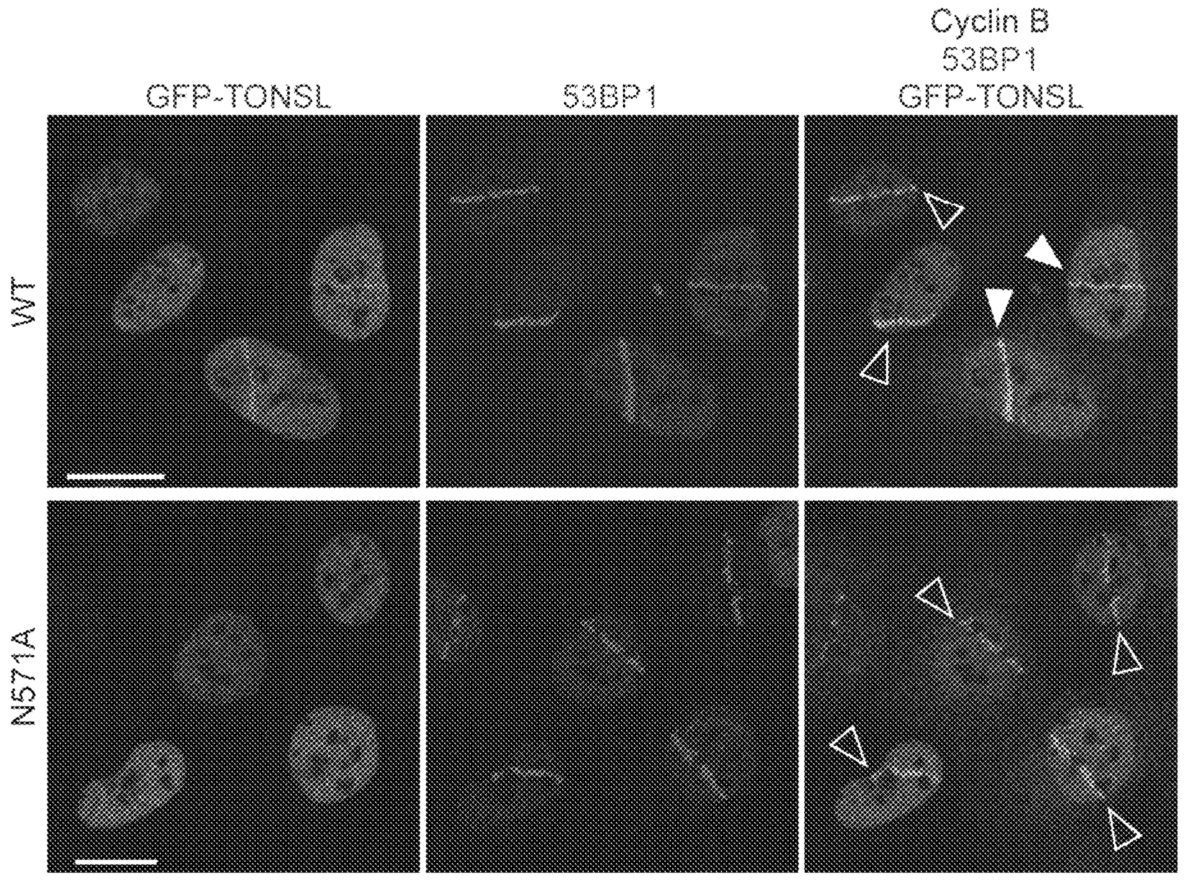
FIG. 22 shows TONSL recruitment to DNA lesions requires recognition of H4K20me0. (top) U-2-OS cells conditional for GFP-TONSL WT or N571A were laser-irradiated and co-stained for 53BP1 and cyclin B to mark DNA damage and identify S/G2 cells, respectively. Full arrowheads, GFP-TONSL recruitment; empty arrowheads, no recruitment. Scale bar, 10 μm. (bottom) Quantification of GFP-TONSL cells showing recruitment to laser tracks (error bars, SD; n=3)
Figure 22:
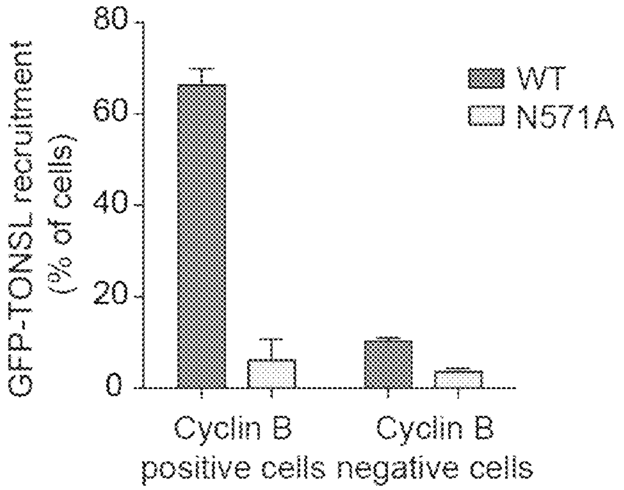
Figure 23:
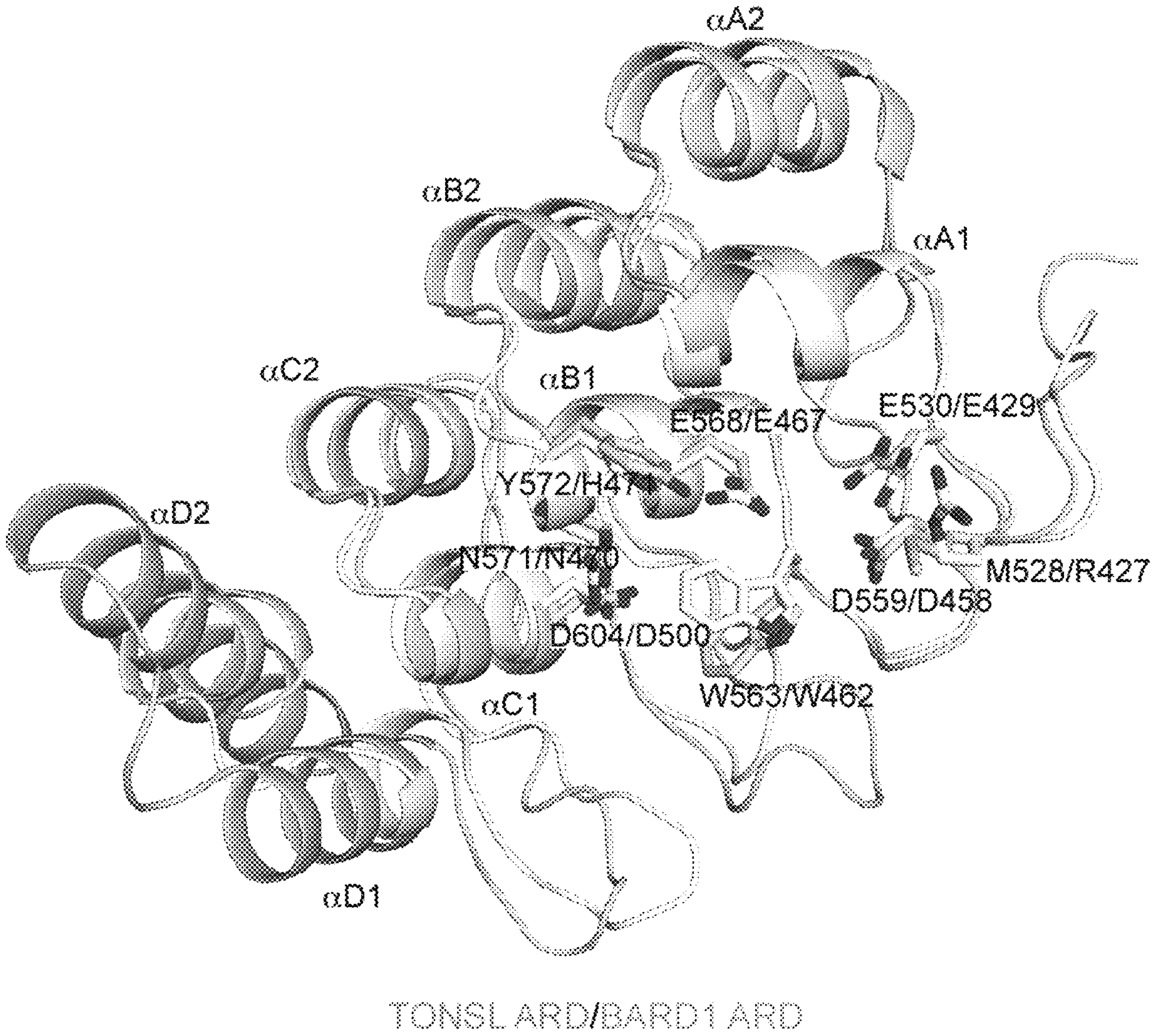
FIG. 23 shows the superposition of the structure of TONSL ARD and BARD1 ARD. The main residues involved in TONSL ARD interactions with the H4 tail are compared to the corresponding residues of BARD1 ARD. The two ARDs show highly similar topology and conservation of the histone-binding surface.

The topology of TONSL ARD domain including the histone-binding surface is highly similar to the ARD of BARD1 (FIG. 23). BARD1 is an obligate binding partner of BRCA1 and is required for most cellular and tumour-suppressor functions of BRCA1. The key residues involved in histone H4 binding are conserved in ARD of BARD1. Furthermore, N571 residue of TONSL ARD that is essential for histone H4 binding (FIGS. 10, 12) and recruitment of TONSL to chromatin (FIG. 21) and sites of DNA damage (FIG. 22) and viability (Figure) corresponds to the BARD1 N470S cancer mutation (FIG. 23). Therefore, small molecule inhibitors against TONSL ARD are predicted to target BARD1 ARD domain as well. Given that both TONSL and BARD1 function in the same DNA repair pathway, small molecule inhibitors designed based on our invention that would target both TONSL and BARD ARD would predictably inhibit HR more efficiently and show more potent anti-cancer activity as compared to inhibitors specific for TONSL ARD only.

General

It should be understood that any feature and/or aspect discussed above in connections with the compounds according to the invention apply by analogy to the crystal structures and/or methods described herein.

The atomic coordinate's variation of the crystal structures of the present invention such e.g. 1 Å up to 3 Å are used interchangeably.

The following sequence data, structures, figures and examples are provided below to illustrate the present invention. They are intended to be illustrative and are not to be construed as limiting in any way.

EXAMPLES

Example 1—The Crystal Structure

Protein production: All proteins described in the Examples herein, unless otherwise indicated, were expressed in BL21(DE3)-RIL cell strain (Stratagene). The GST-tagged TONSL ARD and its mutants including E530A, D559A, W563A, E568A, N571A and D604A were cloned into pGEX-6P-1 vector (GE Healthcare). The expressed proteins were first purified using Glutathione Sepharose 4B, then further purified by gel-filtration step. In some case, the GST-tag was removed with 3C protease before gel-filtration step. For purification of GST-H3 tail and GST-H4 tail proteins, the human histones H3 fragment 1-59 and H4 fragment 1-31 were cloned into pGEX-6P-1 vector respectively. The proteins were expressed and purified in the same way.

For production of recombinant full-length TONSL-MMS22L heterodimer, the sequence coding for full-length MMS22L was fused with a MBP tag at the 5' end and 10×His tag at the 3' end. The sequence coding for full-length TONSL was fused with GST tag at the 5' end. Both MMS22L and TONSL constructs were cloned into a pFastBac1 vector. The complex was expressed in Sf9 cells by co-infection with both recombinant baculoviruses according to manufacturer's recommendation (Invitrogen). The proteins were extracted from Sf9 cells and purified similarly as described previously for Sgs1. Briefly, the complex was purified on amylose resin, and MBP and GST tags were subsequently cleaved with PreScission protease. The heterodimer was then further purified using a Ni-NTA affinity resin. Washes were performed with 300 mM NaCl buffer.

For crystallization: The human TONSL Ankyrin Repeat Domain (ARD, residues 512-692) and MCM2 Histone-binding Domain (HBD, residues 61-130) were covalently linked through a four-Glycine linker (G4 linker) into a single expression cassette (SEQ ID NO: 15).

The MCM2 HBD-G4-TONSL ARD expression cassette was cloned into a modified RSFDuet-1 vector (Novagen), with an N-terminal His6-SUMO tag. The resulting plasmid was coexpressed with a pETDuet plasmid harboring human histone genes H3.3(57-135) and H4(1-102) in BL21(DE3)-RIL cell strain (Stratagene).

The *E. coli* was cultured at 37° C. using LB media with 50 μg/ml Kanamycin, 100 μg/ml Ampicillin and 34 μg/ml Chloramphenicol.

When the *E. coli* reached cell density of $OD_{600}$~1.0, 0.5 mM IPTG was added into the LB media which was further incubated at 20° C. overnight.

The expressed protein complex was first purified on HisTrap HP column (GE Healthcare). After removing the His6-SUMO tag by using Ulp1 (SUMO protease), the protein complex was further purified on HiLoad 16/600 Superdex 200 column (GE Healthcare) in the buffer of 20 mM Tris pH 7.5 and 500 mM NaCl.

The purified G4 linker complex, MCM2 HBD-G4-TONSL ARD cassette-H3.3(57-135)-H4(1-102) complex (herein designated as TONSL ARD-MCM2 HBD-H3-H4 tetramer complex) with a concentration of 23 mg $ml^{-1}$ in the buffer of 20 mM Tris pH 7.5 and 1 M NaCl, was crystallized in the condition of 100 mM MES pH 5.6-6.6, 5-10% isopropanol using setting-drop vapor-diffusion method at 20° C. All the crystals were soaked in a cryoprotectant made from the mother liquor supplemented with 25% glycerol before flash freezing in liquid nitrogen.

The data set for the TONSL ARD-MCM2 HBD-H3-H4 tetramer complex was collected at 0.979 Å on 24-ID-C/E NE-CAT (Advanced Photo Source, Argonne National Laboratory). The data was processed using the HKL 2000 program. The initial structure for the complex was solved by molecular replacement in PHASER with our previous structure of the MCM2 HBD-H3-H4 tetramer complex as a search model and manually refined and built using Coot. The final structure of this complex was refined to 2.43 Å resolution using PHENIX. Table 1 summarizes the statistics for data collection and structural refinement

TABLE 1

Data collection and refinement statistics

| | TONSL ARD-MCM2 HBD-H3-H4 Tetramer Complex |
|---|---|
| Data collection | |
| Space group | P3 2 1 |
| Cell dimensions□□ | |
| a, b, c (Å) | 139.5, 139.5, 72.9 |
| □□□□□□□□□□□□□ (°) | 90, 90, 120 |
| Resolution (Å) | 50-2.43 (2.95-2.43)[a] |
| $R_{pim}$ (%) | 3.8 (46.8) |
| I/□I | 23.1 (1.8) |
| Completeness (%) | 99.8 (99.7) |
| Redundancy | 5.5 (5.5) |
| Refinement | |
| Molecules per asymmetric unit | 1 |
| No. reflections (total/unique) | 171,308/31,146 |
| $R_{work}/R_{free}$ (%) | 20.1/24.6 |
| No. atoms | |
| Protein | 2,908 |
| MES | 17 |
| Glycerol | 12 |
| Water | 87 |
| B-factors | |
| Protein | 81.8 |
| MES | 108.5 |
| Glycerol | 92.6 |
| Water | 59.8 |
| R.m.s deviations | |
| Bond lengths (Å) | 0.009 |
| Bond angles (°) | 1.316 |
| Ramachandran plot[b] | |
| Favored (%) | 95.9 |
| Allowed (%) | 4.1 |

[a]Highest resolution shell is shown in parenthesis.
[b]Calculated using MolProbity in PHENIX.

The structural data obtained are described below in Annex 1.

One molecule of each protein MCM2 HBD-TONSL ARD cassette, H3 and H4 is present in the asymmetric unit. The crystallographic symmetric operation reconstitutes a tetramer of H3-H4, thus resulting in formation of an intact complex with two copies of MCM2 HBD-TONSL ARD cassette in complex with an H3-H4 tetramer (named TONSL ARD-MCM2 HBD-H3-H4 tetramer complex), which is consistent with our previous finding that MCM2 HBD binds and stabilizes an H3-H4 tetramer under physiological conditions. The TONSL ARD-MCM2 HBD-H3-H4 tetramer complex is also highly similar to our previous structure of the MCM2 HBD-H3-H4 complex, with a pair of MCM2 HBDs wrapping around the lateral surface of the H3-H4 tetramer, while the two TONSL ARDs interact with each of the H4 tails. The TONSL ARD forms no intermolecular interactions with the MCM2 HBD, consistent with the H3-H4 tetramer bridging the interaction between TONSL and MCM2 in cells. The TONSL ARD forms extensive contacts with a segment of the H4 tail (residues 12-23), but shows only minimal contacts with the core of the H3-H4 tetramer. The TONSL ARD could be modeled to bind the H4 tail in the context of the nucleosome without steric clashes and a conserved positive patch may interact with the nucleosomal DNA, suggesting that the extensive interactions between TONSL ARD and the H4 tail could describe TONSL binding to both soluble non-nucleosomal histones H3-H4 together with MCM2 and also to H3-H4 in nucleosomes.

The Ankyrin (ANK) repeat fold contains two antiparallel helices named the inner and outer helix respectively, followed by a hairpin loop named the finger. The TONSL ARD consists of four ANK repeats, three of which adopt the canonical ANK repeat fold (ANK1-3), while the remaining one is an atypical and capping repeat (ANK4). Besides the internal fingers 1-3, the TONSL ARD contains an extra loop preceding ANK1, designated finger 0. The TONSL ARD uses its elongated concave surface composed of inner helices (αA1, αB1, αC1 and αD1) and fingers 0-4 to form extensive intermolecular contacts with the extended β-strand like conformation of the H4 tail. It is notable that 15 out of 18 residues that constitute the H4 tail-binding surface of TONSL ARD are highly conserved. The TONSL ARD targets the H4 tail spanning residues Lys12 to Arg23, primarily through intermolecular hydrogen-bonding, electrostatic and van der Waals interactions.

Example 2—Determination of TONSL ARD Binding to Histone H4 Peptides by Isothermal Titration Calorimetry (ITC)

All the ITC titrations were performed on a Microcal ITC 200 calorimeter at 25° C. The peptides of histone H4 (residues 9-25) and its modified peptides K16ac (with acetylation on Lys16), H18W (with His18 mutated to Trp18), H4K20me1 (mono-methylation on Lys20) and H4K20me2 (di-methylation on Lys20), and peptide of histone H3(1-19) K9me1 (mono-methylation on Lys9) were all synthesized at Tufts University Core Facility. The exothermic heat of the reaction was measured by 17 sequential 2.2 μl injections of the peptides (1.41 mM in buffer 20 mM Tris pH 7.5 and 0.5 M NaCl) into 200 μl of the TONSL ARD solution (145 μM in the same buffer), spaced at intervals of 150 s. The data were processed with Microcal Origin software and the curves were fit to a single size binding model.

Example 3—Assaying Binding of Recombinant TONSL ARD to Histone H4 Peptides In Vitro Purified recombinant TONSL ARD (residues 512-692) was stored at 400 μM concentration in 1 M NaCl, 20 mM Tris HCl pH 7.5 at −80° C. For each pull-down, 400 pmol of the ARD stock (1 μl, 400 μM) was diluted with 99 μl of binding buffer (150 mM NaCl, 50 mM Tris HCl pH 7.5, 5% Glycerol, 0.25% NP-40, 0.2 mM EDTA, 0.5 mM DTT, 0.2 mM PMSF, 1 mM Leupeptin, 1 mM Pepstatin). ARD input material was scaled to the number of pull-downs performed. For each pull-down, a histone H4 peptide (JPT Peptide Technologies GmbH) spanning residues 14-33 (2.5 μl, 250 μM) with a C-terminal biotinoyl-lysine residue or biotin (2.5 μl, 400 μM) was added to 1.1 ml of binding buffer in addition to 100 μl of the ARD input material and the mixture incubated overnight rotating at 4° C. The next day 25 μl of MyOne Streptavidin C1 beads (Life Technologies) was washed in binding buffer (3×500 μl) for each pull-down removing the final wash from the beads. The ARD/peptide or ARD/biotin mixture was added to an aliquot of pre-washed MyOne Streptavidin C1 beads and incubated with rotation at 4° C. for 3 hours. Finally the beads were washed (2×300 μl and 1×200 μl of 300 mM NaCl, 50 mM Tris HCl pH 7.5, 5% Glycerol, 0.25% NP-40, 0.2 mM EDTA, 0.5 mM DTT, 0.2 mM PMSF, 1 mM Leupeptin, 1 mM Pepstatin) and pulldown material visualized by Coomassie staining after SDS PAGE separation of proteins on a NuPAGE 4-12% gel.

Example 4—Measuring GFP-TONSL Binding to Histone H4K20Me0 Peptides in Cell Extracts For detergent-soluble extracts (NP40/NaCl), U-2-OS cells expressing GFP-TONSL WT or ARD mutants were washed with cold PBS, scraped and incubated for 15 min on ice in HS buffer supplemented with trichostatin A (TSA) and protease and phosphatase inhibitors (5 mM sodium fluoride, 10 mM μ-glycerolphosphate, 0.2 mM sodium vanadate, 10 μg/ml leupeptin, 10 μg/ml pepstatin, 0.1 mM PMSF, Sigma). After centrifugation at 16.000 g for 15 min at 4° C., the supernatant was collected.

For pull-downs from cell extracts, MyOne T1 beads were incubated O/N with 1 μg of biotinylated histone peptides in High Salt (HS; 300 mM NaCl, 0.5% NP40, Tris HCl, EDTA, 5% glycerol) buffer and subsequently washed 2 times with PBS. 1 mg of NP40/NaCl extract from GFP-TONSL U-2-OS cells was added to the beads and incubated for 2 hrs rotating at 4° C. The beads were then washed 5 times with HS buffer, 2 min rotating at 4° C. After washing, the beads were resuspended in 1×LSB and boiled for 10 min. The eluted proteins were loaded on a 4-12% Bis-Tris NuPage gel (LifeTechnologies). Proteins were then transferred to a 0.2 μm nitrocellulose membrane by O/N wet transfer at 20V and detected by western blotting.

Example 5—Quantifying Chromatin-Bound TONSL in Human Cells by HT Microscopy

U-2-OS and TIG3 cells were grown on 6-well plates ($1\times10^5$ cells seeded/well 1 day prior to analysis). To analyse only chromatin-bound TONSL, soluble proteins were removed (pre-extracted) by 5 min incubation on ice with CSK buffer 0.5% Triton (CSK buffer: 10 mM PIPES pH 7, 100 mM NaCl, 300 mM sucrose, 3 mM MgCl2 plus protease and phosphatase inhibitors 1 mM DTT, 10 ug/ml leupeptin, 10 ug/ml pepstatin, 0.1 mM PMSF, 0.2 mM sodium vanadate, 5 mM sodium fluoride, 10 mM beta-glycerolphosphate). Cells were then rinsed with CSK and PBS before fixation in 4% formaldehyde for 10 min and staining with TONSL antibody.

For detection, cells were blocked with PBS containing 5% BSA and 0.1% Tween20 for 1 h, and incubated with TONSL antibody (Sigma, ref. nr. HPA0244679) overnight at 4° C. (1:400 in blocking buffer). After washing 3 times with PBS containing 5% BSA and 0.1% Tween 20, anti-rabbit-Alexa488 (LifeTechnologies 1:1000 in blocking buffer) was applied and let to incubate for 30 min. Cells were washed 3 times and DNA was counterstained with DAPI (Sigma). Images were acquired on ScanR high-content imaging system (Olympus) and analysed using ScanR software. Relative fluorescence intensity TONSL was quantified relative to cells depleted for TONSL using the specific siRNAs (O'Donnell et al. 2010 Mol Cel 40:619, synthesized by Sigma) for 30 h at 100 nM concentration.

Example 6

Figure 24A:
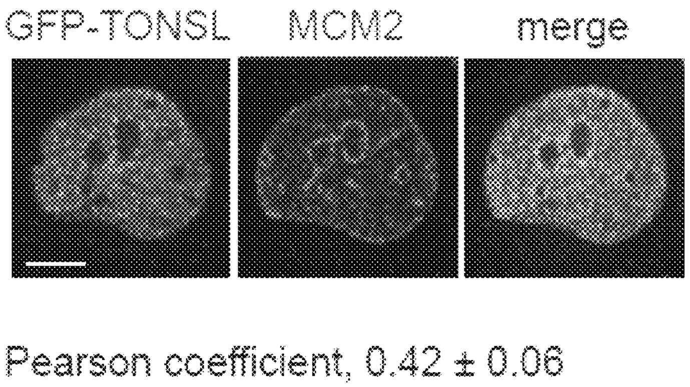
FIGS. 24A and 24B show co-localizationanalysis of chromatin-bound GFP-TONSL with MCM2 (FIG. 24A) and EdU (FIG. 24B) in inducible cell lines. Cells were either pulsed with EdU (left) or released into S phase in continuous presence of EdU (right). Co-localization analysed by deconvolution microscopy and measurement of Pearson coefficient in single cells ($n>15$, two independent experiments). Representative images.
Figure 24B:
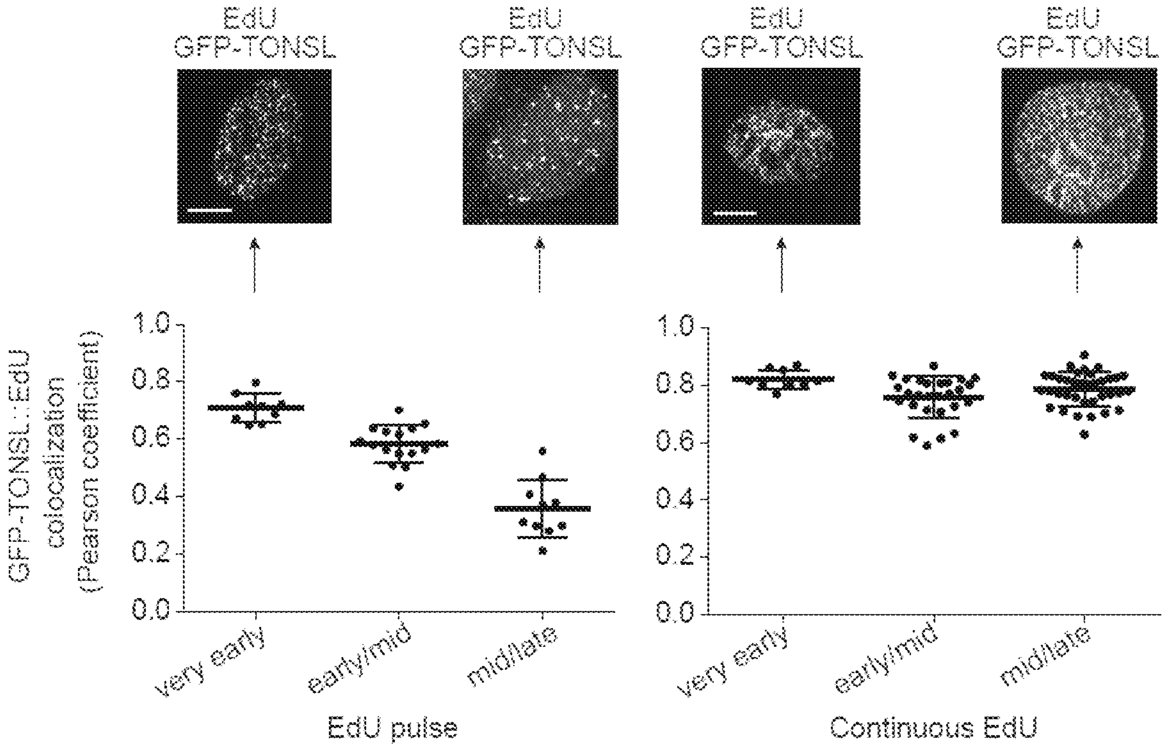
Figure 25:
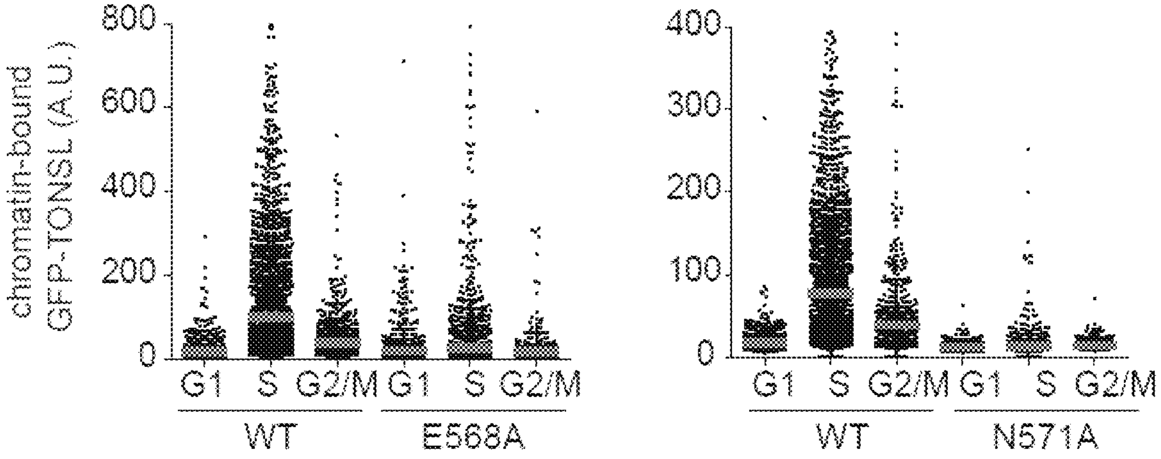
FIG. 25 shows chromatin-binding of GFP-TONSL WT and ARD mutants analysed across the cell cycle (representative of 2 experiments)

Given that TONSL-MMS22L binds histones in a pre-deposition complex with ASF1 and MCM2, TONSL-MMS22L could be loaded onto replicating DNA together with new histones. It is shown herein that in nascent chromatin, new histones were exclusively unmethylated at H4K20 (98% H4K20me0), while old recycled histones were almost fully methylated at H4K20 (me1, 7%; me2, 88%; me3, 2%). New histones became methylated in late G2/M, rendering G1 chromatin devoid of H4K20me0. This identifies H4K20me0 on new histones as a signature of post-replicative chromatin, implying that TONSL-MMS22L can bind H4 tails on new histones at replication forks and sister chromatids until late G2/M. Confirming this prediction, TONSL accumulated on chromatin in S phase, remained chromatin-bound in a population of G2 cells and was excluded from chromatin in G1 (FIG. 20). To discriminate pre- and post-replicative chromatin, we labeled replicating DNA with EdU (pulse to mark ongoing replication, continuous labeling to identify post-replicative chromatin) and marked pre-replicative chromatin with MCM2, and analyzed co-localization with TONSL. TONSL staining was mutually exclusive with MCM2 (FIG. 24A), but co-localized with EdU pulse labeling in very early S phase and with replicated DNA (continuous EdU labeling) throughout S phase (FIG. 24B). TONSL was present at sites of ongoing DNA replication throughout S phase, but the degree of co-localization declined in mid/late S (FIG. 24B, left panel), consistent with TONSL binding to post-replicative chromatin also after fork passage (FIG. 24B, right panel). Mutation of the TONSL ARD abrogated recruitment of TONSL to chromatin, including DNA replication sites (FIG. 25). Together, this demonstrates that TONSL is recruited to replication forks and post-replicative chromatin via ARD recognition of H4K20me0 on new histones. TONSL ARD recognition of the H4 tail is required for binding to post-replicative chromatin and recruitment of damaged forks and DNA lesions.

Figure 26:
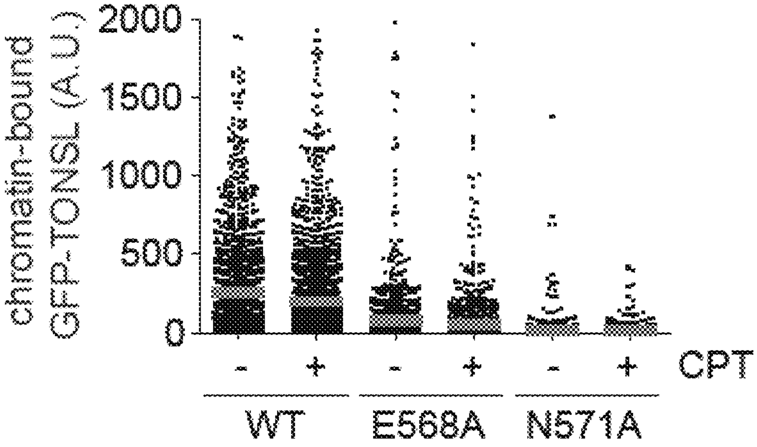
FIG. 26 shows chromatin-binding of GFP-TONSL ARD WT and mutant analysed by high-content imaging of pre-extracted inducible U-2-OS cells treated with CPT (3 hours, 1 μM CPT) as indicated (representative of 3 experiments)
Figure 27A:
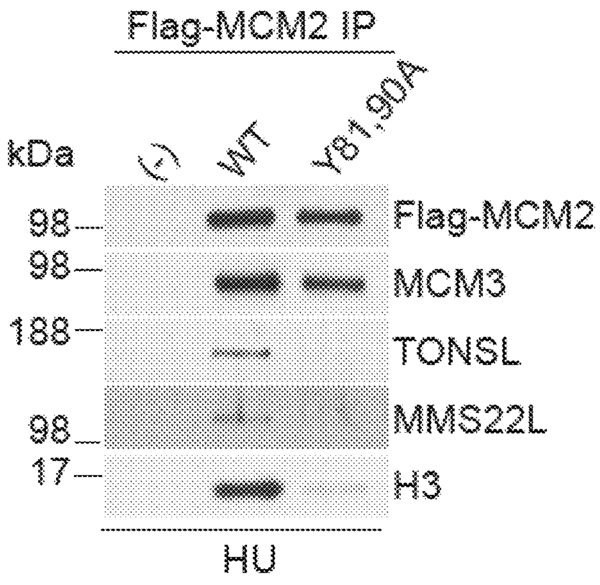
FIG. 27A shows co-immunoprecipitation analysis of TONSL-MMS22L with Flag-HA-MCM2 WT or histone binding mutant of MMS22L(Y81A, Y90A) isolated from solubilized chromatin from HUtreated cells (2 hours, 3 mM) (representative of 2 experiments)
Figure 27B:
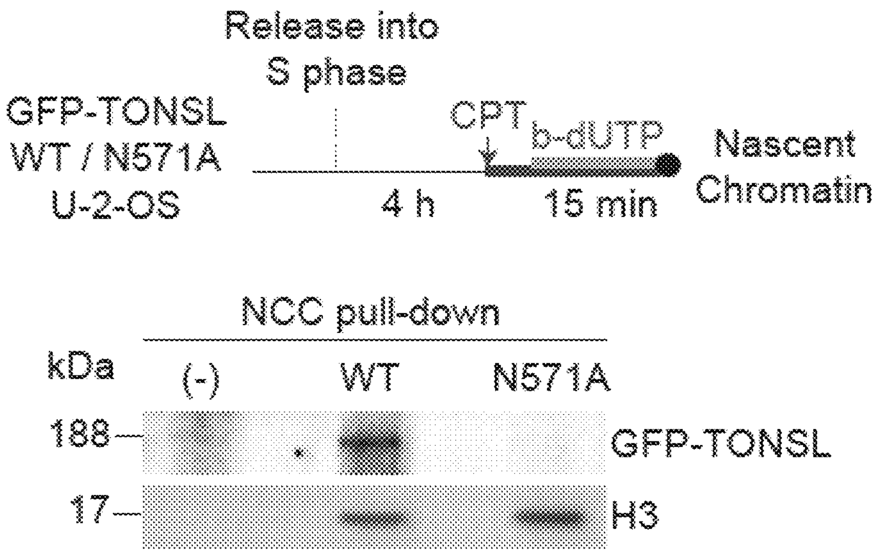
FIG. 27B shows analysis of GFPTONSL ARD WT and mutant recruitment to CPT-challenged replication forks by NCC as illustrated (CPT, 1 μM). (−), no biotin-dUTP.
Figure 28:
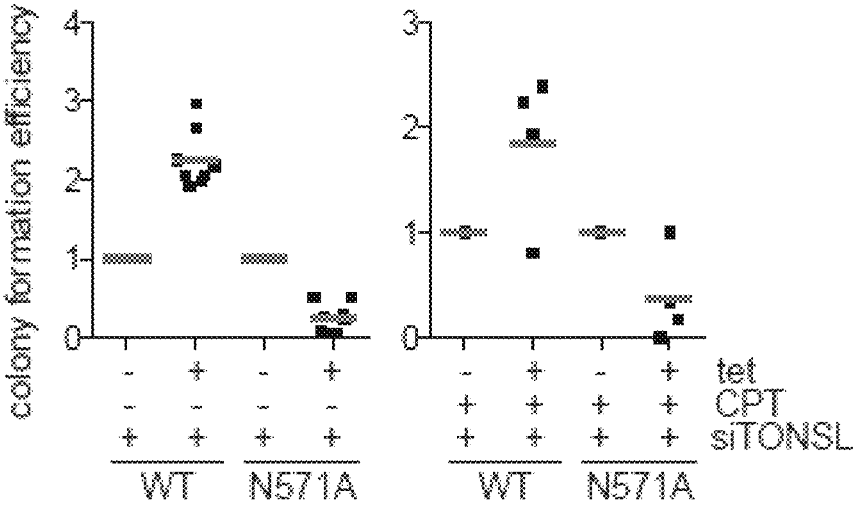
FIGS. 28 and 29 show colony formation upon GFP-TONSL expression induced by tetracycline in TONSL depleted (FIG. 28) and control cells (FIG. 29). Cells were siRNA treated and induced to express siRNA-resistant GFP-TONSL ARD WT and mutant by tetracycline (tet) and treated with CPT (24 hours, 50 nM) as indicated. Rescue efficiency determined by colony forming efficiency of TONSL depleted cells (A). Dominant negative effect of TONSL ARD mutant determined by colony forming efficiency of cells treated with control siRNA (B). Data points represent two different cell concentrations in technical triplicate from two or four (28, left panel) independent biological replicates.
Figure 29:
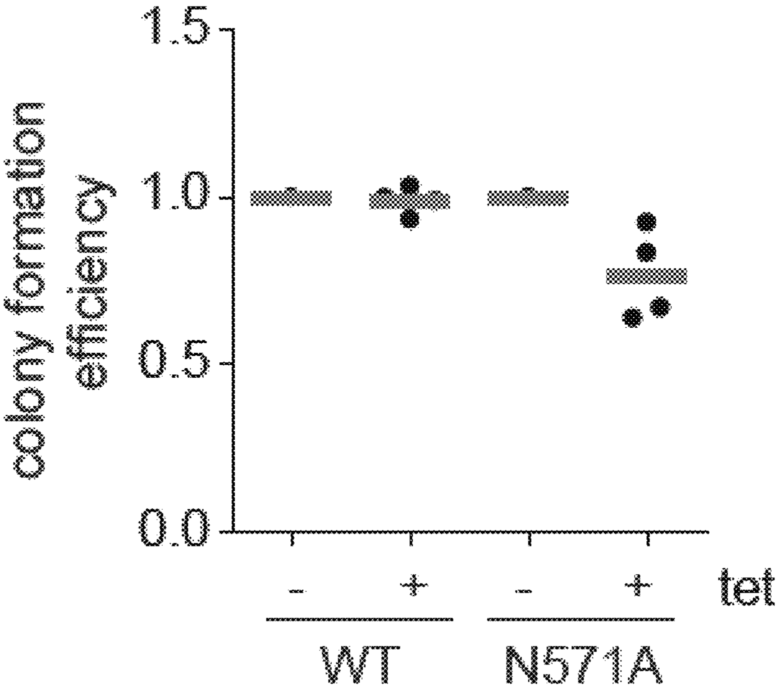
Figure 31:
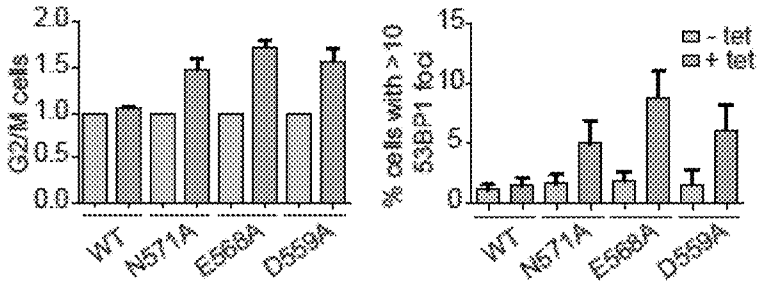
FIG. 31 shows cells were treated as in FIG. 29 and analysed for cell cycle distribution using EdU and Dapi (left) and 53BP1 foci (right). Error bars, mean with S.D (four (left) or five (right) biological replicates in technical triplicates)
Figure 32A:
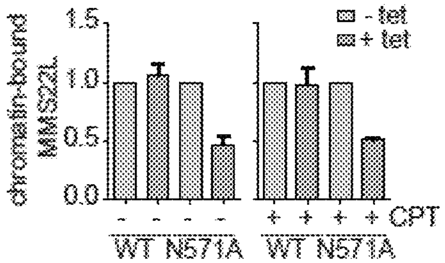
FIGS. 32A and 32B show chromatin-binding of MMS22L. The chromatin-bound fraction was analyzed by western blotting (FIG. 32B) and quantified relative to total MMS22L (FIG. 32A) (untreated: error bar, SD, n=3; CPT: error bar, mean with range, n=2)
Figure 32B:
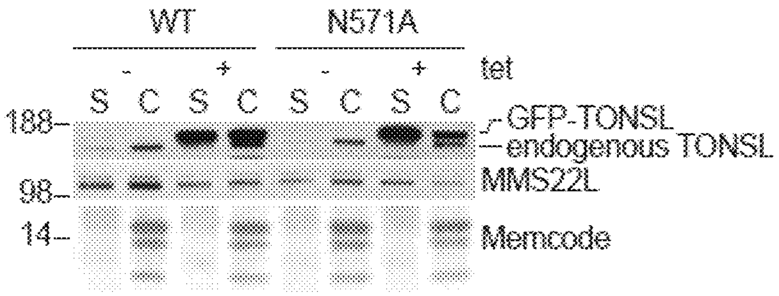
Figure 33:
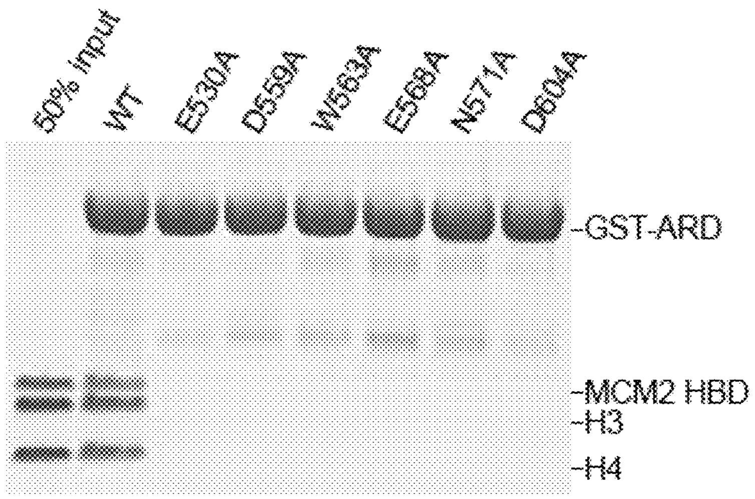
FIG. 33 shows pull-down of recombinant histones H3-H4 and MCM histone binding domain (HBD) with GST-TONSL ARD WT or indicated mutants.

Mutation of TONSL ARD also abrogated chromatin binding (FIG. 26) and recruitment to replication forks in the presence of replication poisons like camptothecin (CPT) and hydroxyurea (HU) (FIGS. 27A and B). Furthermore, ARD mutation prevented accumulation of TONSL at site-specific DSBs (FIG. 28) and microlaser-generated DNA damage. Co-staining with cell cycle markers confirmed that TONSL is recruited to DNA repair sites only in S and G2 cells as expected. H4K20me0 binding is required for TONSL accumulation at damaged forks and DNA lesions in post-replicative chromatin. However, this was not due to increased H4K20me0, suggesting that unmasking of H4 tails upon chromatin decompaction and/or interaction with repair factors contribute to TONSL-MMS22L accumulation at repair sites. Consistent with the latter, MMS22L interaction with Rad51 can stabilize the complex at challenged forks (P. Cejka and M. Peter, personal communication). Our data argue that this is subsequent to H4K20 binding (FIG. 26 to 28). In complementation analysis, TONSL WT partially rescued viability of TONSL depleted cells in the presence and absence of CPT (FIG. 28, FIGS. 30A and B), whereas TONSL ARD mutants were highly toxic (FIG. 28, FIGS. 30A and B). In control cells, TONSL ARD mutants also reduced viability and caused G2/M arrest accompanied by replication-associated DNA damage (FIG. 29 and FIG. 31). Further, the TONSL ARD mutant titrated MMS22L away from chromatin, explaining the dominant negative phenotype that mimics TONSL-MMS22L depletion (FIGS. 32A and B). Collectively, this indicates that recognition of H4K20me0 is central to TONSL-MMS22L function in safeguarding genome stability.

The cell viability was assayed by clonogenic assay (see Example 8 herein below for details of the assay) using inducible U2OS cells that express siRNA resistant GFP-TONSL WT or ARD mutant (D559A, E568A, N571A), in the presence or absence of CPT. Aforementioned results shows that GFP-TONSL WT can partially complement the growth defect and CPT sensitivity of TONSL depleted cells, while expression of GFP-TONSL ARD mutants further impairs cell viability and survival to CPT. Also, it show that expression of GFP-TONSL ARD mutants in control cells has a dominant negative effect on cell growth.

Accumulation of the genome instability marker 53BP1 and cell cycle arrest in G2/M in cells expressing GFP-TONSL ARD mutants was determined. Inducible U2OS cells were induced to express resistant GFP-TONSL WT or ARD mutant (D559A, E568A, N571A) for 24 hours and then fixed and stained for 53BP1 and EdU after an additional 24 hours. Images were acquired by high-throughput microscopy. This shows that expression of the TONSL ARD mutants phenocopies TONSL/MMS22L depletion. Accordingly, these mutants are useful for testing the effect of inhibitors of TONSL in various disease models. The demonstrated titration of MMS22L away from chromatin in cells expressing GFP-TONSL ARD mutants, both in the absence and presence of CPT may explain why expression of TONSL ARD phenocopies TONSL/MMS22L depletion.

It is revealed that post-replicative chromatin has a distinct histone modification signature, read by the TONSL-MMS22L effector protein. This opens a new avenue to understand how DNA repair and other chromosomal transactions can be directly linked to the replication state of a genomic locus. Intriguingly, it is the new histones that make post-replicative chromatin distinct. It is presented that TONSL-MMS22L is delivered to nascent chromatin with new histones via the pre-deposition complex with MCM2 and ASF1. TONSL may thus have a dual function as a histone chaperone and histone reader. The structural work proposes that TONSL acts in a histone chaperone-like capacity by sequestering the H4 tail to prevent spurious contacts with DNA during H3-H4 deposition. Further, TONSL ARD may counteract chromatin compaction by preventing association of the H4 tail with the H2A-H2B acidic patch on neighboring nucleosomes. Thus, TONSL changes our perception of a histone chaperone by binding both soluble and nucleosomal histones. In its function as a histone reader, TONSL localizes MMS22L to post-replicative chromatin via H4K20me0 and allows TONSL-MMS22L to accumulate at damaged forks and DNA lesions. We envision that H4K20me0 works as an affinity trap, making TONSL-MMS22L readily available to support Rad51 loading during HR. This provides a new angle to understand the role of H4K20 in DNA repair, complementing the well-described role of H4K20me1/2 in recruiting 53BP1 to promote NHEJ in competition with BRCA1-

BARD1. In post-replicative chromatin, H4K20me1/2 on old histones will support 53BP1 recruitment. Whether H4K20me0 on new histones also influences DNA repair pathway choice will be of interest to future investigations. It is notable that the structure of the TONSL ARD, including the histone-binding surface, is highly similar to the ARD of BARD1, required for BRCA1 tumor suppressor function and HR. Multiple mutations in the TONSL ARD are reported in cancer (C608G, COSM4879909; P557S, COSM4565032; E597K, COSM3382163) and the N571 residue, key to H4 binding, corresponds to the BARD1 N470S cancer mutation. This underscores that the tumor suppressor function of H4K20me0 recognition and the possibilities it brings for targeted cancer therapy should be explored in the future.

Figure 34:
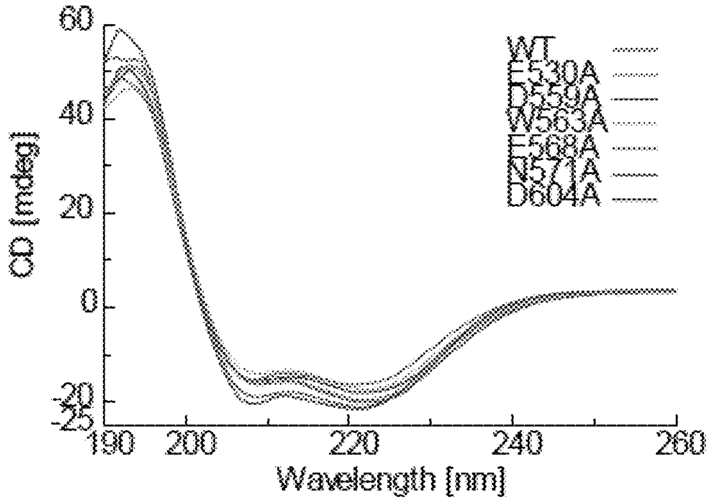
FIG. 34 shows circular dichroism (CD) analysis of TONSL ARD WT and the indicated ARD mutants. The indicated ARD point mutations do not destabilize the overall structure of the ARD.
Figure 35:
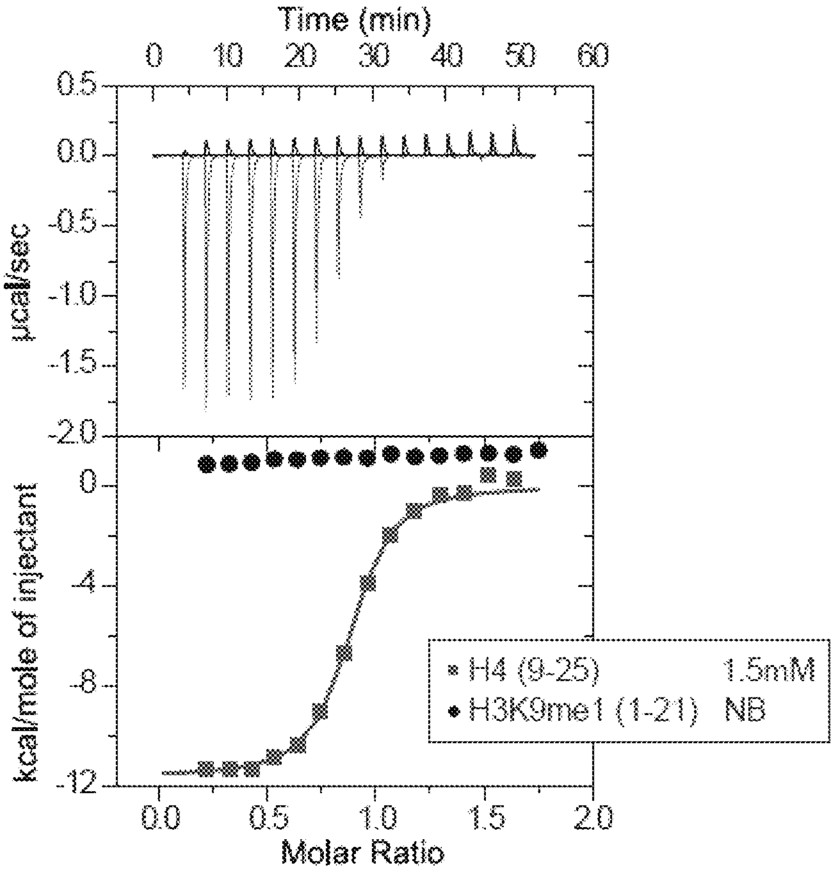
FIG. 35 shows ITC analysis of TONSL acidic stretch and ARD (aa. 450-692) with H3K9me1 (aa. 1-21) and H4 (aa. 9-25)
Figure 36:
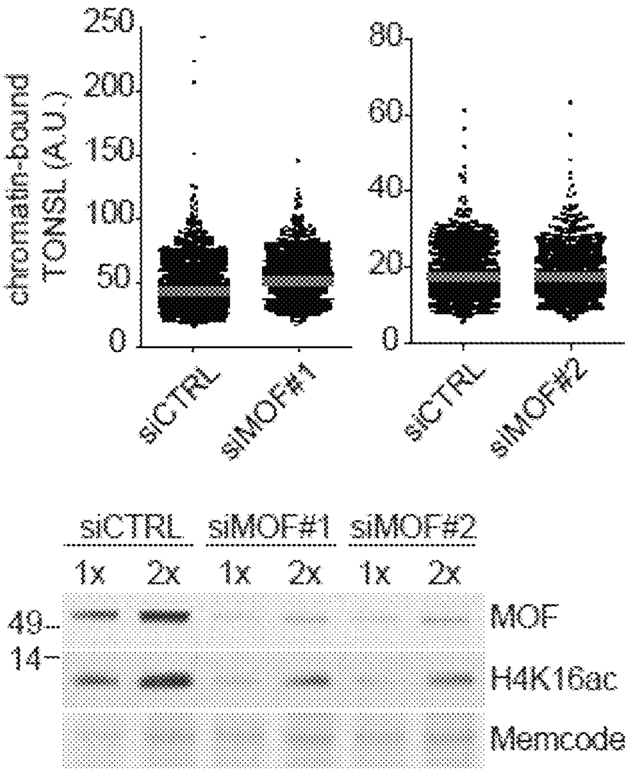
FIG. 36 shows analysis of TONSL chromatin-binding in MOF-depleted cells. Chromatin-bound TONSL was quantified by high content imaging of pre-extracted cells stained for endogenous TONSL. Mean TONSL intensity is shown. A.U., arbitrary units. Knock-down efficiency and expected effect on histone modification were confirmed by western blotting (representative of 2 experiments)
Figure 37:
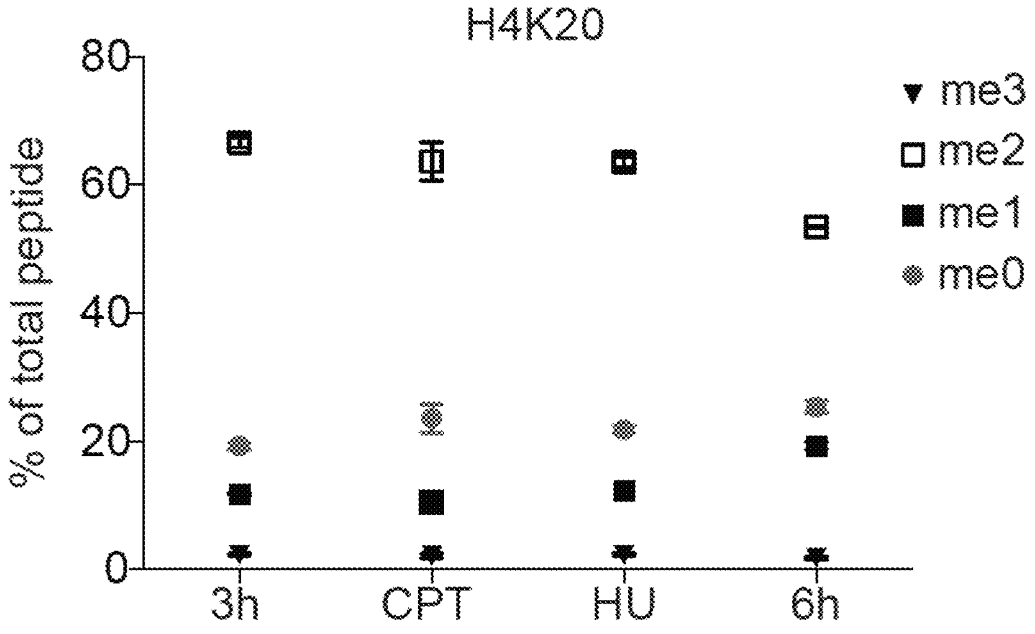
FIG. 37 shows H4K20 methylation levels measured by mass spectrometry in synchronized TIG3 cells. Cell were treated with HU (3 mM) or CPT (1 μM) from 3-6 hours after release or left untreated (6 hours) (error bars, range; n=2).

Circular dichroism analysis of TONSL ARD WT or mutants stability (FIG. 34), show that the indicated ARD point mutations do not destabilize the overall structure of the ARD. ITC analysis of TONSL acidic stretch and ARD (450-692) with H4 tail (9-25) and H3K9me1 (1-21) peptides (FIG. 35) show that TONSL (450-692) does not bind to H3K9me1, but recognizes H4 peptides.

The methods used for immunofluorescence, microscopy and laser microirradiation are described below in Example 7.

Example 7

Immunofluorescence, Microscopy and Laser Microirradiation

U-2-OS, HeLa S3, and TIG-3 cells were grown in DMEM (Gibco) containing 10% FBS (Hyclone) and 1% penicillin/streptomycin and drugs for selection. The construct for siRNA resistant GFP-TONSL was described (O'Donnell et al., Mol Cell 40, 619-631 (2010)) and ARD mutation were introduced in this construct by site-directed mutagenesis. Cells inducible for GFP-TONSL WT and ARD mutants were generated in Flp-In T-Rex U-2-OS cells (Invitrogen) by transfection of pcDNA5/FRT/TO-GFP-TONSL plasmids with Lipofectamine 2000, according to the manufacturer's protocol, and selection with hygromycin (200 μg/ml). All cell lines were authenticated by western blotting and immunofluorescence. Expression of GFP-TONSL was induced by addition of 1 μg/ml of tetracycline for 24 hours. U-2-OS and TIG3 cells were synchronized by a single thymidine block (2 mM) and released into S phase in the presence of 24 □M dCTP. For transient expression of GFP-TONSL, expression plasmids were introduced by transfection with Lipofectamine 2000 (Invitrogen) according to the manufacturer's protocol and cells harvested 24 hours after transfection. siRNA transfection was performed with RNAiMax reagent (Invitrogen) according to the manufacturer's protocol.

siRNA sequences: siSET8#1: 5'-GUACGGAGCGCCAUGAAGU-3'; siSET8#2: 5'-ACUUCAUGGCGCUCCGUACUU-3'; siMOF #1: 5'-GUGAUCCAGUCUCGAGUGA-3'; siMOF #2: 5'-GUGAUCCAGUCUCGAGUGA-3': siTONSL: 5'-GAGCUGGACUUAAGCAUGA-3'. All cell lines used in this study tested negative for mycoplasma contamination.

U-2-OS cells conditional for GFP-TONSL were grown on glass coverslips and either directly fixed in 4% paraformaldehyde (PAF) for 10 mins or washed in CSK, pre-extracted 5 min with CSK/0.5% Triton X-100 and rinsed with CSK and PBS before fixation in 4% PAF for 10 mins. Coverslips were mounted on glass slides with Mowiol mounting medium (Sigma Aldrich) containing DAPI. Fluorescence images were collected on a DeltaVision system with a 40× or 60× oil immersion objective. For deconvolution microscopy, z-stacks were acquired (step of 0.2 □m), deconvolved and analyzed by SoftWoRX 5.0.0. Pearson coefficient correlation analysis was performed on single cells using SoftWoRX 5.0.0. Brightness and contrast were adjusted using Adobe Photoshop CS6. For high content quantitative analysis, fluorescence images were acquired using an Olympus ScanR high-content microscope and processed on the ScanR analysis software. More than 5000 cells per sample were analyzed. Graphs were generated with TIBCO Spotfire software. For microirradiation experiments, cells grown on glass coverslips were fixed in 4% formaldehyde for 15 min, permeabilized with PBS containing 0.2% Triton X-100 for 5 min and incubated with primary antibodies diluted in DMEM for 1 hour at room temperature. Following staining with secondary antibodies (Alexa Fluor 488, 568 and 647; Life Technologies) for 30 min, coverslips were mounted on glass slides in Vectashield mounting medium (Vector Laboratories) containing the nuclear stain DAPI. For detection of nucleotide incorporation during DNA replication, an EdU-Plus labeling kit (Life Technologies) was used according to the manufacturer's instructions. Confocal images were acquired on an LSM-780 (Carl Zeiss) mounted on a Zeiss-AxioObserver Z1 equipped with a Plan-Neofluar 40×/1.3 oil immersion objective. Image acquisition and analysis was carried out with LSM-ZEN software. Laser microirradiation of cells was performed essentially as described.

Example 8

Clonogenic Assay

U-2-OS inducible for GFP-TONSL ARD WT and mutant were transfected with siRNA, trypsinized 24 hours later and seeded in technical triplicates of 1000 or 3000 cells in the presence or absence of tetracycline. After 24 hours, the cells were washed and left in fresh medium for 12-15 days before fixation and staining with MeOH/Crystal Violet. Colony formation efficiency was determined by manual colony counting or quantification of Crystal Violet staining by ImageJ software and normalized to non-induced control.

Example 9

Nascent Chromatin Capture (NCC)

The NCC protocol from (Alabert et al., *Nat Cell Biol* 16, 281-293 (2014)) was adjusted for adherent U-2-OS cells. CPT (1 μM) was added 5 minutes prior to b-dUTP labelling and was included in all steps until fixation. Cells were incubated for 5 minutes in a hypotonic buffer (50 mM KCl, 10 mM Hepes) containing biotin-dUTP and resuspended into fresh cell culture medium for an additional 15 minutes. Cells were fixed 15 minutes in 1% formaldehyde, rinsed twice in PBS and collected by scraping in cold room. Nuclei were mechanically isolated in sucrose buffer (0.3 M sucrose, 10 mM HEPES-NaOH at pH 7.9, 1% Triton X-100 and 2 mM MgOAc). Chromatin was solubilized by 28 cycles 30 sec ON, 90 sec OFF in sonication buffer (10 mM HEPES-NaOH at pH 7.9, 100 mM NaCl, 2 mM EDTA at pH 8, 1 mM EGTA at pH 8, 0.2% SDS, 0.1% sodium sarkosyl and 1 mM phenylmethylsulphonylfluoride) using a Bioruptor at 4° C. Solubilized chromatin was pre-cleared using streptavidin-coated magnetic beads (MyC1 Streptavidin beads) pre-incubated with biotin. b-dUTP labelled chromatin was next purified over night at 4° C. using streptavidin-coated magnetic beads. Beads were washed 5 times for 2 minutes in wash buffer (10 mM HEPES-NaOH pH 7.9; 200 mM NaCl; 2 mM EDTA pH 8; 1 mM EGTA pH 8; 0.1% SDS; 1 mM PMSF). Total chromatin (input) and isolated nascent chromatin were boiled 40 min on beads in LSB 1× (50 mM Tris-HCl pH 6.8, 100 mM DTT, 2% SDS, 8% Glycerol, Bromophenol blue) and separated by SDS-PAGE for western blotting. An alternative method which may be used in place of NCC is iPOND (Sirbu et al., Nat Protoc 3, 594-605 (2012)).

Example 10

Native MS Analysis of Protein-Peptide Complexes

Various peptides were obtained including the peptides described in Examples 11, 12, 13, 14 and 15. If the peptide was in the form of a trifluoroacetate salt (TFA salt), it was desalted on a polymeric weak cation exchange sorbent (Strata X-CW, Phenomenex, Sartrouville, France): Dry peptide (1-3 μmol) were solubilized in 200 μL pure water (Sigma-Aldrich, Lyon, France). The pH of the solution was adjusted to 7-7.5 by addition of 1 mM aqueous ammonium hydroxide solution (solution freshly prepared from 20% concentrated ammonium hydroxide). The exchange column was conditioned with 1 mL methanol (Sigma-Aldrich, Lyon, France) followed by 1 mL water. The solution was injected and the column was washed twice with 500 μL pure water. Finally the peptide was eluted by gravity with 2 times 500 μL of a 20:80:5 acetonitrile/water/formic acid mixture. The elution fraction containing the expected peptide was identified by mass spectrometry. The TFA-free solution was freeze-dried to get a white solid. The solid was dissolved in 300 μL pure water and the solution was freeze-dried for a second time.

A stock solution of the peptide was prepared by adding 300 μL of pure water to the resulting solid and the concentration of the solution was measured by UV at a wavelength of 205 nm. The extinction coefficient for the corresponding peptide sequence was calculated using the Nick Anthis online protein parameter calculator script (http://nickanthis.com/tools/a205.html). The absence of TFA adducts was confirmed by mass spectrometry with infusion of the protein-peptide mixture at low acceleration voltage (Vc 25 V) in native conditions.

Purified TONSL ARD (i.e. amino acid 512-692 of TONSL of SEQ ID NO: 16) was buffer exchanged against 500 mM $NH_4OAc$ pH 7.5 using a NAP 5 column (NAP™-5, GE Healthcare). Bradford protein quantitation was performed on buffer exchanged protein. Protein was diluted in water to a final concentration of 10 μM and kept on ice until native MS analyses were performed.

The mass spectrometry (MS) analysis were carried out on an electrospray time-of-flight mass spectrometer (LCT, Waters, Manchester, UK) equipped with an automated chip-based nanoESI device (Triversa Nanomate, Advion Biosciences, Ithaca, N.Y.). External calibration was done in the positive ion mode over the mass range m/z 200-6000 using the multiply charged ions produced by 0.4 μM horse heart myoglobin solution diluted in water/acetonitrile 50/50 mixture acidified with 0.5% (v/v) formic acid. Homogeneity and purity of TONSL-ARD was first checked under denaturing conditions by diluting the protein to 1 μM in 50/50 water/acetonitrile mixture acidified with 0.5% (v/v) formic acid. Mass measurement revealed mainly the presence of a species with a molecular weight of 20747.18±0.34 Da. Characterization of peptide binding to TONSL-ARD under native conditions was performed in 50 mM $NH_4OAc$ pH 7.5 keeping a constant 5% amount of EtOH (v/v). The protein concentration was set to 10 μM and different peptide concentrations ranging from 1 to 5 molar equivalents were added. Incubations were performed at room temperature for 15 min. Mass spectra were recorded using reduced cone voltage (Vc=50 V) and elevated interface pressure (Pi=5 mbar) which correspond to fine-tuned instrumental settings providing sufficient ion desolvation while preserving the integrity of weak non-covalent complexes in the gas phase. Micromass MassLynx 4.1 was used for data acquisition and processing. Native MS analysis of protein-peptide complexes were attempted by incubation of 10 μM TONSL-ARD with several peptide concentrations (10, 20, 30, 40, 50 μM).

For data processing under native conditions, protein-peptide complex abundance (% PL) was estimated from the peak heights of $9^+$ and $8^+$ charge states of free and bound TONSL-ARD, assuming that compound binding does not alter protein response factor. The proportion of 1:1 stoichiometry complex is calculated according to the following equation:

$$\%\ P1L1 = \frac{I_{P1L1}}{I_{P1L1} + I_P}$$

To estimate the binding affinities (Kd) of peptides for TONSL-ARD, a mixture of protein/peptide was analyzed at a constant peptide to protein ratio with decreasing protein concentration until the lowest detection limit was reached. For data processing under native conditions, protein-peptide complex abundance (% PL) was estimated from the peak heights of $9^+$ and $8^+$ charge states of free and bound TONSL-ARD. This protein proportion is used to calculate the bound protein, the free protein and the free peptide concentrations. The Kd is calculated by using the following equation for each protein/peptide concentration. The final Kd for each peptide is the average of the Kd at different protein/peptide ratio.

$$Kd = \frac{[P\text{ free}][Lfree]}{[PL]}$$

Test Compounds

Example 11

Leu-Gly-Lys-Gly-Gly-Ala-Lys-Arg-His-Arg-Lys-Val-Leu-Arg-Asp-Asn-Ile-$NH_2$ (Histone H4 Peptide)

Purchased from JPT Peptide Technologies GmbH, Berlin, Germany

The following peptides were obtained from Schafer-N Aps, Copenhagen, Denmark and were prepared by using Fmoc-chemistry on chlorotrityl resins, a method known to those skilled in the art.

Example 12

Ala-Lys-Arg-His-Arg-Lys-Val-Leu-Arg-$NH_2$

Example 13 Lys-Gly-Gly-Ala-Lys-Arg-His-Arg-Lys-Val-Leu-Arg-$NH_2$

Example 14 Lys-Gly-Gly-Ala-Lys-Arg-His-Ala-Lys-Val-Leu-Arg-$NH_2$

Example 15 Lys-Gly-Gly-Ala-Ala-Arg-His-Arg-Lys-Val-Leu-Arg-$NH_2$

Using the assays described in Examples 10, the following values were obtained.

| Example | % P1L1 | Apparent $K_d$ (μM) | Titration $K_d$ (μM) |
|---|---|---|---|
| 11 | | | 0.077 |
| 12 | 62.6 | 2.2 | 1.95 |
| 13 | 89.9 | 0.1 | 0.31 |
| 14 | 73.3 | 1.0 | 0.96 |
| 15 | 81.4 | 0.4 | not determined* |

*A Kd value could not be measured by titration

Example 16

Structure Based Design of Small Molecule and Peptide Inhibitors:

Using the structural information of the present invention, we conducted a large scale virtual screening of the collective repertoire of world vide vendor chemical libraries of available screening compounds (small molecules and peptides) directly related to drug discovery applications of ligands, which can be developed into potent and efficacious TONSL inhibitors. The screened (in silico) chemical libraries and the virtual screening protocol is described below.

Chemical Vendor Libraries:

The 'In Stock'subset of the ZINC database containing 12,782,590 biologically relevant screening molecules, that are stripped for counter ions and assigned tautomers, protonation states, charges and 3D conformations, was obtained from http://zinc.docking.org and stored in SDF files.

Preparation of the TONSL Structure for Docking:

a. The histone H4 tail (K12-D24) and crystallographic water molecules was removed from the TONSL ARD complex structure (see Example 1).

b. All hydrogen atoms were built and optimized using ICM (Molsoft L.L.C., San Diego, Calif., USA)

c. A box of interactions grids (20×20×20 Å) centered around E530, D559, E568 and D604 was calculated using ICMs (Molsoft L.L.C., San Diego, Calif., USA) docking tools.

d. Full flexible 'ligand' docking of the 12,782,590 screening molecules (default parameters) was performed using ICM (Molsoft L.L.C., San Diego, Calif., USA).

e. The chemical structures and predicted binding conformations of the top 0.001% scored compounds with MW<500 Da, 0.2<drug-like score <1, c log P<5, number of rotatable bonds <12, compound strain <10 were manually assessed.

f. Initially, a total of 49 high scored compounds were acquired and of those 27 were tested for TONSL ARD binding using a standard native MS binding experiment. A protocol for an MS binding experiment is outlined in Example 10.

Discovery of TONSL-ARD Hits in Primary Binding Screen

Among the compounds tested in competition binding experiments with an unmodified histone H4 peptide tail (SEQ ID NO), weak binding to TONSL ARD (amino acids 512-692 of SEQ ID NO: 16) were observed for at least one chemo type based on a "3-[(3-Aminocyclopentyl)carbonyl]-1H-quinolin-4-one" scaffold. AG100021 (MW 317) was the best binding compound in this first binding experiment forming ~20% complex at 20 μM.

Structural Data

Annex I—Structure Data of TONSL-GFP

The structure data including the coordinates of the "Crystal structure of Human TONSL and MCM2 HBDS binding to a histone H3-H4 tetramer" are provided in the PDB database under the PDB ID 5JA4. As used herein the term "PDB ID 5JA4" refers to the PDB ID 5JA4 as deposited with PDB on 11 Apr. 2016. The PDB ID 5JA4 has the DOI: 10.2210/pdb5ja4/pdb, and is accessible at http://www.rcsb.org/pdb/explore/explore.do?structureId=5JA4. The structure data including the same coordinates as PDB ID 5JA4 are also provided in Annex 1 of Danish patent application PA 2015 00605 and in Annex 1 of U.S. patent application 62/324,257.

SEQUENCE DATA

SEQ ID NO: 1 - TONSL WT / GFP

```
atggtgagcaagggcgaggagctgttcaccggggtggtgcccatcctggtcgagctggacggcgacgtaaacggccacaagttca
gcgtgtccggcgagggcgagggcgatgccacctacggcaagctgaccctgaagttcatctgcaccaccggcaagctgcccgtgc
cctggcccaccctcgtgaccaccctgacctacggcgtgcagtgcttcagccgctaccccgaccacatgaagcagcacgacttcttca
agtccgccatgcccgaaggctacgtccaggagcgcaccatcttcttcaaggacgacggcaactacaagacccgcgccgaggtgaa
gttcgagggcgacaccctggtgaaccgcatcgagagaagggcatcgacttcaaggaggacggcaacatcctggggcacaagct
ggagtacaactacaacagccacaacgtctatatcatggccgacaagcagaagaacggcatcaaggtgaacttcaagatccgccaca
acatcgaggacggcagcatgcagctcgccgaccactaccagcagaacacccccatcggcgacggccccgtgctgctgcccgac
aaccactacctgagcacccagtccgccctgagcaaagaccccaacgagaagcgcgatcacatggtcctgctggagttcgtgaccg
ccgccgggatcactctcggcatggacgagctgtacaagggcgcgccaATGAGCCtGGAGCGCGAGCTTCG
CCAGCTGAGCAAGGCGAAAGCCAAGGCGCAGAGGGCCGGGCAGCGGCGCGAA
GAGGCCGCGCTGTGCCACCAGCTGGGGGAGCTCCTGGCCGGCCATGGCCGCTAC
GCCGAGGCTCTGGAGCAGCACTGGCAGGAGCTGCAGCTTCGGGAGCGCGCTGA
CGACCCTCTGGGCTGTGCCGTGGCCCACCGCAAGATCGGAGAGCGCCTGGCCGA
GATGGAGGACTACCCGGCTGCCTTGCAGCACCAGCACCAGTACCTGGAGCTGGC
ACATTCCCTGCGCAACCACACGGAGCTGCAGAGGGCCTGGGCCACCATCGGCCG
CACCCACCTGGACATCTATGACCACTGCCAGTCGAGGGATGCTTTGCTGCAGGC
ACAGGCTGCCTTTGAGAAGAGCTTGGCTATTGTGGATGAGGAGCTGGAGGGGA
CACTGGCCCAGGGAGAGCTGAATGAGATGAGGACCCGCCTCTATCTCAACCTGG
GCCTCACCTTTGAGAGCCTGCAGCAGACAGCCCTGTGCAACGATTACTTCAGGA
AGAGCATCTTCCTTGCGGAGCAGAACCACCTTTACGAGGACCTATTCCGCGCCC
GCTACAACCTGGGCACCATCCACTGGCGCGCGGGCCAGCACTCCCAGGCTATGC
GCTGCTTGGAGGGTGCCCGGGAGTGTGCGCACACCATGAGGAAGCGGTTCATG
GAGAGCGAGTGCTGCGTGGTTATTGCACAGGTCCTCCAAGACCTGGGAGACTTT
TTGGCTGCCAAGCGAGCCCTGAAGAAGGCCTACAGGCTGGGCTCCCAGAAGCCT
GTGCAGAGGGCAGCCATCTGTCAGAACCTCCAGCATGTGCTGGCAGTGGTCCGG
CTGCAGCAACAGCTGGAAGAGGCTGAGGGCAGAGACCCTCAGGGTGCCATGGT
CATCTGTGAGCAGCTAGGGGACCTCTTCTCCAAGGCAGGAGACTTTCCCAGGGC
AGCTGAGGCTTACCAGAAGCAGCTGCGTTTTGCTGAGCTGCTGGACAGACCGGG
TGCTGAGCGGGCCATCATCCACGTGTCCCTGGCCACCACACTGGGAGACATGAA
GGACCACCATGGGGCCGTGCGCCACTATGAGGAGGAACTGAGGCTGCGCAGCG
GCAACGTGCTGGAGGAGGCCAAGACCTGGCTGAACATTGCACTGTCCCGCGAG
```

-continued

SEQUENCE DATA

GAGGCCGGCGATGCCTACGAGCTGCTGGCCCCGTGCTTCCAGAAAGCGCTCAGC
TGTGCCCAGCAGGCCCAGCGTCCCCAGCTGCAGAGGCAGGTCTTGCAGCATCTC
CATACCGTGCAGCTGAGGCTGCAGCCCCAGGAGGCCCCTGAGACCGAAACCAG
ACTGCGGGAGCTCAGTGTAGCTGAAGATGAAGATGAGGAGGAGGAGGCGGAGG
AGGCGGCAGCCACAGCGGAGAGCGAAGCCCTGGAGGCCGGCGAGGTGGAGCTC
TCAGAGGGCGAGGACGACACCGATGGCCTGACCCCGCAGCTGGAGGAGGACGA
GGAGCTTCAGGGCCACCTGGGCCGGCGGAAGGGGAGCAAGTGGAACCGGCGAA
ACGACATGGGGGCGACCCTGCTGCACCGAGCCTGCATCGAGGGCCAGCTGCGC
CGCGTCCAGGACCTTGTGAGGCAGGGCCACCCCCTTAACCCTCGGGACTACTGT
GGCTGGACACCTCTGCACGAGGCCTGCAACTACGGGCATCTAGAAATTGTCCGC
TTCCTGCTGGACCACGGGGCCGCAGTGGACGACCCAGGTGGCCAGGGCTGCGA
AGGCATCACCCCCCTCCACGATGCCCTCAACTGTGGCCACTTCGAGGTGGCTGA
GCTGCTGCTTGAACGGGGGGCGTCCGTCACCCTCCGCACTCGAAAGGGCCTCAG
CCCGCTGGAGACGCTGCAGCAGTGGGTGAAGCTGTACCGCAGGGACCTGGACC
TGGAGACGCGGCAGAAGGCCAGGGCCATGGAGATGCTGCTCCAGGCGGCTGCC
TCGGGCCAAGATCCCCACAGCTCCCAGGCCTTCCACACCCCAAGCAGCCTTCTG
TTTGACCCCGAGACCTCTCCTCCTTTGAGCCCCTGCCCAGAACCCCCCTCTAATA
GCACTAGAACTCCCAGAGGCCTCTCAGGTCCATGTCAGGGTCTCCCCAGGGCAGG
CGGCACCAGCCATGGCCAGGCCTCGGAGGAGCAGGCATGGGCCAGCCAGCAGC
AGCAGCAGCTCAGAAGGCGAGGACAGCGCAGGCCCCGCACGGCCGTCCCAGAA
GAGGCCTCGGTGCTCGGCCACAGCACAACGGGTGGCAGCCTGGACGCCTGGCC
CCGCCAGCAACAGGGAAGCAGCCACAGCCAGCACCAGCCGGGCAGCCTACCAG
GCAGCCATCCGGGGTGTGGGCAGTGCTCAGAGCCGGCTGGGGCCTGGCCCACC
GCGGGGCCACAGCAAAGCCCTTGCCCCCCAGGCAGCGCTCATCCCGGAGGAGG
AGTGCCTGGCTGGGGACTGGCTGGAGCTGGACATGCCCCTGACCCGCAGCCGCC
GGCCCCGCCCCCGGGGCACTGGAGACAACCGCAGGCCCAGTAGTACCTCTGGGT
CGGACAGTGAGGAGAGCAGGCCCCGTGCCCGAGCCAAGCAGGTCCGCCTGACC
TGCATGCAGAGTTGCAGTGCGCCAGTTAACGCAGGGCCCAGCAGCCTGGCTTCA
GAACCTCCAGGGAGCCCCAGCACCCCCAGGGTCTCAGAGCCCAGTGGGGACAG
CTCTGCGGCAGGCCAGCCCTTGGGTCCGGCCCCGCCCCCTCCCATCCGGGTTCG
AGTTCAAGTTCAGGATCATCTCTTCCTCATCCCTGTCCCACACAGCAGTGACACC
CACTCTGTGGCCTGGCTGGCCGAGCAGGCGGCCCAGCGCTACTACCAGACCTGC
GGGCTGCTGCCCAGGCTCACCCTACGGAAAGAGGGGGCCCTGCTGGCCCCACA
GGACCTCATCCCTGATGTGCTGCAGAGCAATGACGAGGTGTTGGCTGAGGTGAC
TTCGTGGGACCTGCCCCCGTTGACTGACCGCTACCGCAGGGCCTGCCAGAGCCT
GGGGCAAGGGGAGCACCAACAGGTGCTGCAGGCCGTGGAGCTCCAGGGCTTGG
GCCTCTCGTTCAGCGCCTGCTCCCTGGCCCTGGACCAGGCCCAGCTTACACCCCT
GCTGCGGGCCCTCAAGCTGCACACAGCACTCCGGGAGCTGCGCCTGGCAGGGA
ACCGGCTGGGGGACAAGTGTGTGGCTGAGCTGGTGGCTGCCCTGGGCACCATGC
CCAGCCTGGCCCTCCTTGACCTCTCCTCCAATCACCTGGGTCCCGAAGGCCTGCG
CCAGCTTGCCATGGGGCTCCCAGGCCAAGCCACCTTGCAGAGTTTGGAGgaattagat
ctatcgatgaACCCCCTGGGGGACGGCTGTGGCCAGTCCCTGGCCTCCCTCCTGCACG
CCTGCCCCTTACTCAGCACCCTGCGCCTGCAGGCGTGTGGCTTCGGCCCCAGCTT
CTTTCTGAGCCACCAGACAGCACTGGGTAGTGCTTTCCAAGATGCTGAGCACCT
GAAGACCCTGTCCCTGTCCTACAACGCCCTGGGAGCCCCTGCCCTGGCCAGGAC
CCTGCAGAGCCTGCCCGCCGGCACCCTCCTGCACTTAGAGCTCAGCTCCGTGGC
AGCCGGCAAGGGTGATTCGGACCTCATGGAGCCTGTATTCCGATACCTGGCCAA
GGAAGGCTGTGCTCTAGCCCACCTGACCCTGTCTGCAAACCACCTGGGGGACAA
GGCTGTTAGAGACCTGTGCAGATGTCTCTCTCTGTGCCCCTCACTCATCTCACTG
GATCTGTCTGCCAACCCTGAGATCAGCTGTGCCAGCTTGGAAGAGCTCCTGTCC
ACCCTCCAAAAGCGGCCCCAAGGCCTTAGCTTCCTTGGCCTGTCAGGCTGCGCC
GTCCAGGGTCCCCTGGGCCTGGGCCTGTGGGACAAGATAGCCGCGCAGCTCCGG
GAACTGCAGCTGTGCAGCAGACGCCTCTGCGCTGAGGACAGGGACGCCCTGCG
CCAGCTGCAGCCCAGTCGGCCGGGCCCCGGCGAGTGCACGCTGGACCACGGCTC
CAAGCTCTTCTTTCGGCGCCTCTAG SEQ ID NO: 2 - TONSL WT
ATGAGCCTGGAGCGCGAGCTTCGCCAGCTGAGCAAGGCGAAAGCCAAGGCGCA
GAGGGCCGGGCAGCGGCGCGAAGAGGCCGCGCTGTGCCACCAGCTGGGGGAGC
TCCTGGCCGGCCATGGCCGCTACGCCGAGGCTCTGGAGCAGCACTGGCAGGAGC
TGCAGCTTCGGGAGCGCGCTGACGACCCTCTGGGCTGTGCCGTGGCCCACCGCA
AGATCGGAGAGCGCCTGGCCGAGATGGAGGACTACCCGGCTGCCTTGCAGCAC
CAGCACCAGTACCTGGAGCTGGCACATTCCCTGCGCAACCACACGGAGCTGCAG
AGGGCCTGGGCCACCATCGGCCGCACCCACCTGGACATCTATGACCACTGCCAG
TCGAGGGATGCTTTGCTGCAGGCACAGGCTGCCTTTGAGAAGAGCTTGGCTATT
GTGGATGAGGAGCTGGAGGGGACACTGGCCCAGGGAGAGCTGAATGAGATGAG
GACCCGCCTCTATCTCAACCTGGGCCTCACCTTTGAGAGCCTGCAGCAGACAGC
CCTGTGCAACGATTACTTCAGGAAGAGCATCTTCCTTGCGGAGCAGAACCACCT
TTACGAGGACCTATTCCGCGCCCGCTACAACCTGGGCACCATCCACTGGCGCGC
GGGCCAGCACTCCCAGGCTATGCGCTGCTTGGAGGGTGCCCGGGAGTGTGCGCA
CACCATGAGGAAGCGGTTCATGGAGAGCGAGTGCTGCGTGGTTATTGCACAGGT
CCTCCAAGACCTGGGAGACTTTTTGGCTGCCAAGCGAGCCCTGAAGAAGGCCTA
CAGGCTGGGCTCCCAGAAGCCTGTGCAGAGGGCAGCCATCTGTCAGAACCTCCA
GCATGTGCTGGCAGTGGTCCGGCTGCAGCAACAGCTGGAAGAGGCTGAGGGCA
GAGACCCTCAGGGTGCCATGGTCATCTGTGAGCAGCTAGGGGACCTCTTCTCCA
AGGCAGGAGACTTTCCCAGGGCAGCTGAGGCTTACCAGAAGCAGCTGCGTTTTG
CTGAGCTGCTGGACAGACCGGGTGCTGAGCGGGCCATCATCCACGTGTCCCTGG -continued

SEQUENCE DATA

CCACCACACTGGGAGACATGAAGGACCACCATGGGGCCGTGCGCCACTATGAG
GAGGAACTGAGGCTGCGCAGCGGCAACGTGCTGGAGGAGGCCAAGACCTGGCT
GAACATTGCACTGTCCCGCGAGGAGGCCGGCGATGCCTACGAGCTGCTGGCCCC
GTGCTTCCAGAAAGCGCTCAGCTGTGCCCAGCAGGCCCAGCGTCCCCAGCTGCA
GAGGCAGGTCTTGCAGCATCTCCATACCGTGCAGCTGAGGCTGCAGCCCCAGGA
GGCCCCTGAGACCGAAACCAGACTGCGGGAGCTCAGTGTAGCTGAAGATGAAG
ATGAGGAGGAGGAGGCGGAGGAGGCGGCAGCCACAGCGGAGAGCGAAGCCCT
GGAGGCCGGCGAGGTGGAGCTCTCAGAGGGCGAGGACGACACCGATGGCCTGA
CCCCGCAGCTGGAGGAGGACGAGGAGCTTCAGGGCCACCTGGGCCGGCGGAAG
GGGAGCAAGTGGAACCGGCGAAACGACATGGGGGCGACCCTGCTGCACCGAGC
CTGCATCGAGGGCCAGCTGCGCCGCGTCCAGGACCTTGTGAGGCAGGGCCACCC
CCTTAACCCTCGGGACTACTGTGGCTGGACACCTCTGCACGAGGCCTGCAACTA
CGGGCATCTAGAAATTGTCCGCTTCCTGCTGGACCACGGGGCCGCAGTGGACGA
CCCAGGTGGCCAGGGCTGCGAAGGCATCACCCCCCTCCACGATGCCCTCAACTG
TGGCCACTTCGAGGTGGCTGAGCTGCTGCTTGAACGGGGGGCGTCCGTCACCCT
CCGCACTCGAAAGGGCCTCAGCCCGCTGGAGACGCTGCAGCAGTGGGTGAAGC
TGTACCGCAGGGACCTGGACCTGGAGACGCGGCAGAAGGCCAGGGCCATGGAG
ATGCTGCTCCAGGCGGCTGCCTCGGGCCAAGATCCCCACAGCTCCCAGGCCTTC
CACACCCCAAGCAGCCTTCTGTTTGACCCCGAGACCTCTCCTCCTTTGAGCCCCT
GCCCAGAACCCCCCTCTAATAGCACTAGACTCCCAGAGGCCTCTCAGGTCCATG
TCAGGGTCTCCCCAGGGCAGGCGGCACCAGCCATGGCCAGGCCTCGGAGGAGC
AGGCATGGGCCAGCCAGCAGCAGCAGCAGCTCAGAAGGCGAGGACAGCGCAG
GCCCCGCACGGCCGTCCCAGAAGAGGCCTCGGTGCTCGGCCACAGCACAACGG
GTGGCAGCCTGGACGCCTGGCCCCGCCAGCAACAGGGAAGCAGCCACAGCCAG
CACCAGCCGGGCAGCCTACCAGGCAGCCATCCGGGGTGTGGGCAGTGCTCAGA
GCCGGCTGGGGCCTGGCCCACCGCGGGGCCACAGCAAAGCCCTTGCCCCCCAG
GCAGCGCTCATCCCGGAGGAGGAGTGCCTGGCTGGGGACTGGCTGGAGCTGGA
CATGCCCCTGACCCGCAGCCGCCGGCCCCGCCCCCGGGGCACTGGAGACAACCG
CAGGCCCAGTAGTACCTCTGGGTCGGACAGTGAGGAGAGCAGGCCCCGTGCCC
GAGCCAAGCAGGTCCGCCTGACCTGCATGCAGAGTTGCAGTGCGCCAGTTAACG
CAGGGCCCAGCAGCCTGGCTTCAGAACCTCCAGGGAGCCCCAGCACCCCCAGG
GTCTCAGAGCCCAGTGGGGACAGCTCTGCGGCAGGCCAGCCCTTGGGTCCGGCC
CCGCCCCCTCCCATCCGGGTTCGAGTTCAAGTTCAGGATCATCTCTTCCTCATCC
CTGTCCCACACAGCAGTGACACCCACTCTGTGGCCTGGCTGGCCGAGCAGGCGG
CCCAGCGCTACTACCAGACCTGCGGGCTGCTGCCCAGGCTCACCCTACGGAAAG
AGGGGGCCCTGCTGGCCCCACAGGACCTCATCCCTGATGTGCTGCAGAGCAATG
ACGAGGTGTTGGCTGAGGTGACTTCGTGGGACCTGCCCCCGTTGACTGACCGCT
ACCGCAGGGCCTGCCAGAGCCTGGGGCAAGGGGAGCACCAACAGGTGCTGCAG
GCCGTGGAGCTCCAGGGCTTGGGCCTCTCGTTCAGCGCCTGCTCCCTGGCCCTG
GACCAGGCCCAGCTTACACCCCTGCTGCGGGCCCTCAAGCTGCACACAGCACTC
CGGGAGCTGCGCCTGGCAGGGAACCGGCTGGGGGACAAGTGTGTGGCTGAGCT
GGTGGCTGCCCTGGGCACCATGCCCAGCCTGGCCCTCCTTGACCTCTCCTCCAAT
CACCTGGGTCCCGAAGGCCTGCGCCAGCTTGCCATGGGGCTCCCAGGCCAAGCC
ACCTTGCAGAGTTTGGAGaaattagatctatcgataaACCCCCTGGGGGACGGCTGTGGCCA
GTCCCTGGCCTCCCTCCTGCACGCCTGCCCCTTACTCAGCACCCTGCGCCTGCAG
GCGTGTGGCTTCGGCCCCAGCTTCTTTCTGAGCCACCAGACAGCACTGGGTAGT
GCTTTCCAAGATGCTGAGCACCTGAAGACCCTGTCCCTGTCCTACAACGCCCTG
GGAGCCCCTGCCCTGGCCAGGACCCTGCAGAGCCTGCCCGCCGGCACCCTCCTG
CACTTAGAGCTCAGCTCCGTGGCAGCCGGCAAGGGTGATTCGGACCTCATGGAG
CCTGTATTCCGATACCTGGCCAAGGAAGGCTGTGCTCTAGCCCACCTGACCCTG
TCTGCAAACCACCTGGGGGACAAGGCTGTTAGAGACCTGTGCAGATGTCTCTCT
CTGTGCCCCTCACTCATCTCACTGGATCTGTCTGCCAACCCTGAGATCAGCTGTG
CCAGCTTGGAAGAGCTCCTGTCCACCCTCCAAAAGCGGCCCCAAGGCCTTAGCT
TCCTTGGCCTGTCAGGCTGCGCCGTCCAGGGTCCCCTGGGCCTGGGCCTGTGGG
ACAAGATAGCCGCGCAGCTCCGGGAACTGCAGCTGTGCAGCAGACGCCTCTGC
GCTGAGGACAGGGACGCCCTGCGCCAGCTGCAGCCCAGTCGGCCGGGCCCCGG
CGAGTGCACGCTGGACCACGGCTCCAAGCTCTTCTTTCGGCGCCTCTAG SEQ ID NO: 3 - TONSL E530A
ATGAGCCTGGAGCGCGAGCTTCGCCAGCTGAGCAAGGCGAAAGCCAAGGCGCA
GAGGGCCGGGCAGCGGCGCGAAGAGGCCGCGCTGTGCCACCAGCTGGGGGAGC
TCCTGGCCGGCCATGGCCGCTACCTCCGAGGCTCTGGAGCAGCACTGGCAGGAGC
TGCAGCTTCGGGAGCGCGCTGACGACCCTCTGGGCTGTGCCGTGGCCCACCGCA
AGATCGGAGAGCGCCTGGCCGAGATGGAGGACTACCCGGCTGCCTTGCAGCAC
CAGCACCAGTACCTGGAGCTGGCACATTCCCTGCGCAACCACACGGAGCTGCAG
AGGGCCTGGGCCACCATCGGCCGCACCCACCTGGACATCTATGACCACTGCCAG
TCGAGGGATGCTTTGCTGCAGGCACAGGCTGCCTTTGAGAAGAGCTTGGCTATT
GTGGATGAGGAGCTGGAGGGGACACTGGCCCAGGGAGAGCTGAATGAGATGAG
GACCCGCCTCTATCTCAACCTGGGCCTCACCTTTGAGAGCCTGCAGCAGACAGC
CCTGTGCAACGATTACTTCAGGAAGAGCATCTTCCTTGCGGAGCAGAACCACCT
TTACGAGGACCTATTCCGCGCCCGCTACAACCTGGGCACCATCCACTGGCGCGC
GGGCCAGCACTCCCAGGCTATGCGCTGCTTGGAGGGTGCCCGGGAGTGTGCGCA
CACCATGAGGAAGCGGTTCATGGAGAGCGAGTGCTGCGTGGTTATTGCACAGGT
CCTCCAAGACCTGGGAGACTTTTTGGCTGCCAAGCGAGCCCTGAAGAAGGCCTA
CAGGCTGGGCTCCCAGAAGCCTGTGCAGAGGGCAGCCATCTGTCAGAACCTCCA
GCATGTGCTGGCAGTGGTCCGGCTGCAGCAACAGCTGGAAGAGGCTGAGGGCA
GAGACCCTCAGGGTGCCATGGTCATCTGTGAGCAGCTAGGGGACCTCTTCTCCA -continued

| SEQUENCE DATA |
| --- |

AGGCAGGAGACTTTCCCAGGGCACTCTGAGGCTTACCAGAAGCAGCTGCGTTTTG
CTGAGCTGCTGGACAGACCGGGTGCTGAGCGGGCCATCATCCACGTGTCCCTGG
CCACCACACTGGGAGACATGAAGGACCACCATGGGGCCGTGCGCCACTATGAG
GAGGAACTGAGGCTGCGCAGCGGCAACGTGCTGGAGGAGGCCAAGACCTGGCT
GAACATTGCACTGTCCCGCGAGGAGGCCGGCGATGCCTACGAGCTGCTGGCCCC
GTGCTTCCAGAAAGCGCTCAGCTGTGCCCAGCAGGCCCAGCGTCCCCAGCTGCA
GAGGCAGGTCTTGCAGCATCTCCATACCGTGCAGCTGAGGCTGCAGCCCCAGGA
GGCCCCTGAGACCGAAACCAGACTGCGGGAGCTCAGTGTAGCTGAAGATGAAG
ATGAGGAGGAGGAGGCCTGAGGAGGCGGCAGCCACAGCGGAGAGCCTAAGCCCT
GGAGGCCGGCGAGGTGGAGCTCTCAGAGGGCGAGGACGACACCGATGGCCTGA
CCCCGCAGCTGGAGGAGGACGAGGAGCTTCAGGGCCACCTGGGCCGGCGGAAG
GGGAGCAAGTGGAACCGGCGAAACGACATGGGGGCGACCCTGCTGCACCGAGC
CTGCATCGAGGGCCAGCTGCGCCGCGTCCAGGACCTTGTGAGGCAGGGCCACCC
CCTTAACCCTCGGGACTACTGTGGCTGGACACCTCTGCACCTAGGCCTGCAACTA
CGGGCATCTAGAAATTGTCCGCTTCCTGCTGGACCACGGGGCCGCAGTGGACGA
CCCAGGTGGCCAGGGCTGCGAAGGCATCACCCCCCTCCACGATGCCCTCAACTG
TGGCCACTTCGAGGTGGCTGACTCTGCTGCTTGAACGGGGGGCGTCCGTCACCCT
CCGCACTCGAAAGGGCCTCAGCCCGCTGGAGACGCTGCAGCAGTGGGTGAAGC
TGTACCGCAGGGACCTGGACCTGGAGACGCGGCAGAAGGCCAGGGCCATGGAG
ATGCTGCTCCAGGCGGCTGCCTCGGGCCAAGATCCCCACAGCTCCCAGGCCTTC
CACACCCCAAGCAGCCTTCTGTTTGACCCCGAGACCTCTCCTCCTTTGAGCCCCT
GCCCAGAACCCCCCTCTAATAGCACTAGACTCCCAGAGGCCTCTCAGGTCCATG
TCAGGGTCTCCCCAGGGCAGGCG-GCACCAGCCATGGCCAGGCCTCGGAGGAGC
AGGCATGGGCCAGCCAGCAGCAGCAGCAGCTCAGAAGGCGAGGACAGCGCAG
GCCCCGCACGGCCGTCCCAGAAGAGGCCTCGGTGCTCGGCCACAGCACAACGG
GTGGCAGCCTGGACGCCTGGCCCCGCCAGCAACAGGGAAGCAGCCACAGCCAG
CACCAGCCGGGCAGCCTACCAGGCAGCCATCCGGGGTGTGGGCAGTGCTCAGA
GCCGGCTGGGGCCTGGCCCACCGCGGGGCCACAGCAAAGCCCTTGCCCCCCAG
GCAGCGCTCATCCCGGAGGAGGAGTGCCTGGCTGGGGACTGGCTGGAGCTGGA
CATGCCCCTGACCCGCAGCCGCCGGCCCCGCCCCCGGGGCACTGGAGACAACCG
CAGGCCCAGTAGTACCTCTGGGTCGGACAGTGAGGAGAGCAGGCCCCGTGCCC
GAGCCAAGCAGGTCCGCCTGACCTGCATGCAGAGTTGCAGTGCGCCAGTTAACG
CAGGGCCCAGCAGCCTGGCTTCAGAACCTCCAGGGAGCCCCAGCACCCCCAGG
GTCTCAGAGCCCAGTGGGGACAGCTCTGCGGCAGGCCAGCCCTTGGGTCCGGCC
CCGCCCCCTCCCATCCGGGTTCGAGTTCAAGTTCAGGATCATCTCTTCCTCATCC
CTGTCCCACACAGCAGTGACACCCACTCTGTGGCCTGGCTGGCCGAGCAGGCGG
CCCAGCGCTACTACCAGACCTGCGGGCTGCTGCCCAGGCTCACCCTACGGAAAG
AGGGGGCCCTGCTGGCCCCACAGGACCTCATCCCTGATGTGCTGCAGAGCAATG
ACGAGGTGTTGGCTGAGGTGACTTCGTGGGACCTGCCCCCGTTGACTGACCGCT
ACCGCAGGGCCTGCCAGAGCCTGGGGCAAGGGGAGCACCAACAGGTGCTGCAG
GCCGTGGAGCTCCAGGGCTTGGGCCTCTCGTTCAGCGCCTGCTCCCTGGCCCTG
GACCAGGCCCAGCTTACACCCCTGCTGCGGGCCCTCAAGCTGCACACAGCACTC
CGGGAGCTGCGCCTGGCAGGGAACCGGCTGGGGGACAAGTGTGTGGCTGAGCT
GGTGGCTGCCCTGGGCACCATGCCCAGCCTGGCCCTCCTTGACCTCTCCTCCAAT
CACCTGGGTCCCGAAGGCCTGCGCCAGCTTGCCATGGGGCTCCCAGGCCAAGCC
ACCTTGCAGAGTTTGGAGgaattagatctatcgatgaACCCCCTGGGGGACGGCTGTGGCCA
GTCCCTGGCCTCCCTCCTGCACGCCTGCCCCTTACTCAGCACCCTGCGCCTGCAG
GCGTGTGGCTTCGGCCCCAGCTTCTTTCTGAGCCACCAGACAGCACTGGGTAGT
GCTTTCCAAGATGCTGAGCACCTGAAGACCCTGTCCCTGTCCTACAACGCCCTG
GGAGCCCCTGCCCTGGCCAGGACCCTGCAGAGCCTGCCCGCCGGCACCCTCCTG
CACTTAGAGCTCAGCTCCGTGGCAGCCGGCAAGGGTGATTCGGACCTCATGGAG
CCTGTATTCCGATACCTGGCCAAGGAAGGCTGTGCTCTAGCCCACCTGACCCTG
TCTGCAAACCACCTGGGGGACAAGGCTGTTAGAGACCTGTGCAGATGTCTCTCT
CTGTGCCCCTCACTCATCTCACTGGATCTGTCTGCCAACCCTGAGATCAGCTGTG
CCAGCTTGGAAGAGCTCCTGTCCACCCTCCAAAAGCGGCCCCAAGGCCTTAGCT
TCCTTGGCCTGTCAGGCTGCGCCGTCCAGGGTCCCCTGGGCCTGGGCCTGTGGG
ACAAGATAGCCGCGCAGCTCCGGGAACTGCAGCTGTGCAGCAGACGCCTCTGC
GCTGAGGACAGGGACGCCCTGCGCCAGCTGCAGCCCAGTCGGCCGGGCCCCGG
CGAGTGCACGCTGGACCACGGCTCCAAGCTCTTCTTTCGGCGCCTCTAG SEQ ID NO: 4 - TONSL E530A / GFP
atggtgagcaagggcgaggagctgttaccggggtggtgcccatcctggtcgagctggacggcgacgtaaacggccacaagttca
gcgtgtccggcgagggcgagggcgatgccacctacggcaagctgaccctgaagttcatctgcaccaccggcaagctgcccgtgc
cctggcccaccctcgtgaccaccctgacctacggcgtgcagtgcttcagccgctaccccgaccacatgaagcagcacgacttcttca
agtccgccatgcccgaaggctacgtccaggagcgcaccatcttcttcaaggacgacggcaactacaagacccgcgccgaggtgaa
gttcgagggcgacaccctggtgaaccgcatcgagctgaagggcatcgacttaaggaggacggcaacatcctggggcacaagct
ggagtacaactacaacagccacaacgtctatatcatggccgacaagcagaagaacggcatcaaggtgaacttcaagatccgccaca
acatcgaggacggcagcgtgcagctcgccgaccactaccagoagaacacccccatcggcgacggccccgtgctgctgcccgac
aaccactacctgagcacccagtccgccctgagcaaagaccccaacgagaagcgcgatcacatggtcctgctggagttcgtgaccg
ccgccgggatcactctcggcatggacgagctgtacaagggcgcgccaATGAGCCTGGAGCGCGAGCTTCG
CCAGCTGAGCAAGGCGAAAGCCAAGGCGCAGAGGGCCGGGCAGCGGCGCGAA
GAGGCCGCGCTGTGCCACCAGCTGGGGGAGCTCCTGGCCGGCCATGGCCGCTAC
GCCGAGGCTCTGGAGCAGCACTGGCAGGAGCTGCAGCTTCGGGAGCGCGCTGA
CGACCCTCTGGGCTGTGCCGTGGCCCACCGCAAGATCGGAGAGCGCCTGGCCGA
GATGGAGGACTACCCGGCTGCCTTGCAGCACCAGCACCAGTACCTGGAGCTGGC
ACATTCCCTGCGCAACCACACGGAGCTGCAGAGGGCCTGGGCCACCATCGGCCG
CACCCACCTGGACATCTATGACCACTGCCAGTCGAGGGATGCTTTGCTGCAGGC -continued

| SEQUENCE DATA |
|---|

ACAGGCTGCCTTTGAGAAGAGCTTGGCTATTGTGGATGAGGAGCTGGAGGGGA
CACTGGCCCAGGGAGAGCTGAATGAGATGAGGACCCGCCTCTATCTCAACCTGG
GCCTCACCTTTGAGAGCCTGCAGCAGACAGCCCTGTGCAACGATTACTTCAGGA
AGAGCATCTTCCTTGCGGAGCAGAACCACCTTTACGAGGACCTATTCCGCGCCC
GCTACAACCTGGGCACCATCCACTGGCGCGCGGGCCAGCACTCCCAGGCTATGC
GCTGCTTGGAGGGTGCCCGGGAGTGTGCGCACACCATGAGGAAGCGGTTCATG
GAGAGCGAGTGCTGCGTGGTTATTGCACAGGTCCTCCAAGACCTGGGAGACTTT
TTGGCTGCCAAGCGAGCCCTGAAGAAGGCCTACAGGCTGGGCTCCCAGAAGCCT
GTGCAGAGGGCAGCCATCTGTCAGAACCTCCAGCATGTGCTGGCAGTGGTCCGG
CTGCAGCAACAGCTGGAAGAGGCTGAGGGCAGAGACCCTCAGGGTGCCATGGT
CATCTGTGAGCAGCTAGGGGACCTCTTCTCCAAGGCAGGAGACTTTCCCAGGGC
AGCTGAGGCTTACCAGAAGCAGCTGCGTTTTGCTGAGCTGCTGGACAGACCGGG
TGCTGAGCGGGCCATCATCCACGTGTCCCTGGCCACCACACTGGGAGACATGAA
GGACCACCATGGGGCCGTGCGCCACTATGAGGAGGAACTGAGGCTGCGCAGCG
GCAACGTGCTGGAGGAGGCCAAGACCTGGCTGAACATTGCACTGTCCCGCGAG
GAGGCCGGCGATGCCTACGAGCTGCTGGCCCCGTGCTTCCAGAAAGCGCTCAGC
TGTGCCCAGCAGGCCCAGCGTCCCCAGCTGCAGAGGCAGGTCTTGCAGCATCTC
CATACCGTGCAGCTGAGGCTGCAGCCCCAGGAGGCCCCTGAGACCGAAACCAG
ACTGCGGGAGCTCAGTGTAGCTGAAGATGAAGATGAGGAGGAGGAGGCGGAGG
AGGCGGCAGCCACAGCGGAGAGCGAAGCCCTGGAGGCCGGCGAGGTGGAGCTC
TCAGAGGGCGAGGACGACACCGATGGCCTGACCCCGCAGCTGGAGGAGGACGA
GGAGCTTCAGGGCCACCTGGGCCGGCGGAAGGGGAGCAAGTGGAACCGGCGAA
ACGACATGGGGGCGACCCTGCTGCACCGAGCCTGCATCGAGGGCCAGCTGCGC
CGCGTCCAGGACCTTGTGAGGCAGGGCCACCCCCTTAACCCTCGGGACTACTGT
GGCTGGACACCTCTGCACGAGGCCTGCAACTACGGGCATCTAGAAATTGTCCGC
TTCCTGCTGGACCACGGGGCCGCAGTGGACGACCCAGGTGGCCAGGGCTGCGA
AGGCATCACCCCCCTCCACGATGCCCTCAACTGTGGCCACTTCGAGGTGGCTGA
GCTGCTGCTTGAACGGGGGGCGTCCGTCACCCTCCGCACTCGAAAGGGCCTCAG
CCCGCTGGAGACGCTGCAGCAGTGGGTGAAGCTGTACCGCAGGGACCTGGACC
TGGAGACGCGGCAGAAGGCCAGGGCCATGGAGATGCTGCTCCAGGCGGCTGCC
TCGGGCCAAGATCCCCACAGCTCCCAGGCCTTCCACACCCCAAGCAGCCTTCTG
TTTGACCCCGAGACCTCTCCTCCTTTGAGCCCCTGCCCAGAACCCCCCTCTAATA
GCACTAGACTCCCAGAGGCCTCTCAGGTCCATGTCAGGGTCTCCCCAGGGCAGG
CGGCACCAGCCATGGCCAGGCCTCGGAGGAGCAGGCATGGGCCAGCCAGCAGC
AGCAGCAGCTCAGAAGGCGAGGACAGCGCAGGCCCCGCACGGCCGTCCCAGAA
GAGGCCTCGGTGCTCGGCCACAGCACAACGGGTGGCAGCCTGGACGCCTGGCC
CCGCCAGCAACAGGGAAGCAGCCACAGCCAGCACCAGCCGGGCAGCCTACCAG
GCAGCCATCCGGGGTGTGGGCAGTGCTCAGAGCCGGCTGGGGCCTGGCCCACC
GCGGGGCCACAGCAAAGCCCTTGCCCCCCAGGCAGCGCTCATCCCGGAGGAGG
AGTGCCTGGCTGGGGACTGGCTGGAGCTGGACATGCCCCTGACCCGCAGCCGCC
GGCCCCGCCCCCGGGGCACTGGAGACAACCGCAGGCCCAGTAGTACCTCTGGGT
CGGACAGTGAGGAGAGCAGGCCCCGTGCCCGAGCCAAGCAGGTCCGCCTGACC
TGCATGCAGAGTTGCAGTGCGCCAGTTAACGCAGGGCCCAGCAGCCTGGCTTCA
GAACCTCCAGGGAGCCCCAGCACCCCCAGGGTCTCAGAGCCCAGTGGGGACAG
CTCTGCGGCAGGCCAGCCCTTGGGTCCGGCCCCGCCCCCTCCCATCCGGGTTCG
AGTTCAAGTTCAGGATCATCTCTTCCTCATCCCTGTCCCACACAGCAGTGACACC
CACTCTGTGGCCTGGCTGGCCGAGCAGGCGGCCCAGCGCTACTACCAGACCTGC
GGGCTGCTGCCCAGGCTCACCCTACGGAAAGAGGGGGCCCTGCTGGCCCCACA
GGACCTCATCCCTGATGTGCTGCAGAGCAATGACGAGGTGTTGGCTGAGGTGAC
TTCGTGGGACCTGCCCCCGTTGACTGACCGCTACCGCAGGGCCTGCCAGAGCCT
GGGGCAAGGGGAGCACCAACAGGTGCTGCAGGCCGTGGAGCTCCAGGGCTTGG
GCCTCTCGTTCAGCGCCTGCTCCCTGGCCCTGGACCAGGCCCAGCTTACACCCCT
GCTGCGGGCCCTCAAGCTGCACACAGCACTCCGGGAGCTGCGCCTGGCAGGGA
ACCGGCTGGGGGACAAGTGTGTGGCTGAGCTGGTGGCTGCCCTGGGCACCATGC
CCAGCCTGGCCCTCCTTGACCTCTCCTCCAATCACCTGGGTCCCGAAGGCCTGCG
CCAGCTTGCCATGGGGCTCCCAGGCCAAGCCACCTTGCAGAGTTTGGAGgaattagat
ctatcgatgaACCCCCTGGGGGACGGCTGTGGCCAGTCCCTGGCCTCCCTCCTGCACG
CCTGCCCCTTACTCAGCACCCTGCGCCTGCAGGCGTGTGGCTTCGGCCCCAGCTT
CTTTCTGAGCCACCAGACAGCACTGGGTACTTGCTTTCCAAGATGCTGAGCACCT
GAAGACCCTGTCCCTGTCCTACAACGCCCTGGGAGCCCCTGCCCTGGCCAGGAC
CCTGCAGAGCCTGCCCGCCGGCACCCTCCTGCACTTAGAGCTCAGCTCCGTGGC
AGCCGGCAAGGGTGATTCGGACCTCATGGAGCCTGTATTCCGATACCTGGCCAA
GGAAGGCTGTGCTCTAGCCCACCTGACCCTGTCTGCAAACCACCTGGGGGACAA
GGCTGTTAGAGACCTGTGCAGATGTCTCTCTCTGTGCCCCTCACTCATCTCACTG
GATCTGTCTGCCAACCCTGAGATCAGCTGTGCCAGCTTGGAAGAGCTCCTGTCC
ACCCTCCAAAAGCGGCCCCAAGGCCTTAGCTTCCTTGGCCTGTCAGGCTGCGCC
GTCCAGGCTTCCCCTGGGCCTGGGCCTGTGGGACAAGATAGCCGCGCACTCTCCGG
GAACTGCAGCTGTGCAGCAGACGCCTCTGCGCTGAGGACAGGGACGCCCTGCG
CCAGCTGCAGCCCAGTCGGCCGGGCCCCGGCGAGTGCACGCTGGACCACGGCTC
CAAGCTCTTCTTTCGGCGCCTCTAG SEQ ID NO: 5 - TONSL D559_4
ATGAGCCTGGAGCGCGAGCTTCGCCAGCTGAGCAAGGCGAAAGCCAAGGCGCA
GAGGGCCGGGCAGCGGCGCGAAGAGGCCGCGCTGTGCCACCAGCTGGGGGAGC
TCCTGGCCGGCCATGGCCGCTACCTCCGAGGCTCTGGAGCAGCACTGGCAGGAGC
TGCAGCTTCGGGAGCGCGCTGACGACCCTCTGGGCTGTGCCGTGGCCCACCGCA
AGATCGGAGAGCGCCTGGCCGAGATGGAGGACTACCCGGCTGCCTTGCAGCAC -continued

| SEQUENCE DATA |
|---|
| CAGCACCAGTACCTGGAGCTGGCACATTCCCTGCGCAACCACACGGAGCTGCAG<br>AGGGCCTGGGCCACCATCGGCCGCACCCACCTGGACATCTATGACCACTGCCAG<br>TCGAGGGATGCTTTGCTGCAGGCACAGGCTGCCTTTGAGAAGAGCTTGGCTATT<br>GTGGATGAGGAGCTGGAGGGGACACTGGCCCAGGGAGAGCTGAATGAGATGAG<br>GACCCGCCTCTATCTCAACCTGGGCCTCACCTTTGAGAGCCTGCAGCAGACAGC<br>CCTGTGCAACGATTACTTCAGGAAGAGCATCTTCCTTGCGGAGCAGAACCACCT<br>TTACGAGGACCTATTCCGCGCCCGCTACAACCTGGGCACCATCCACTGGCGCGC<br>GGGCCAGCACTCCCAGGCTATGCGCTGCTTGGAGGGTGCCCGGGAGTGTGCGCA<br>CACCATGAGGAAGCGGTTCATGGAGAGCGAGTGCTGCGTGGTTATTGCACAGGT<br>CCTCCAAGACCTGGGAGACTTTTTGGCTGCCAAGCGAGCCCTGAAGAAGGCCTA<br>CAGGCTGGGCTCCCAGAAGCCTGTGCAGAGGGCAGCCATCTGTCAGAACCTCCA<br>GCATGTGCTGGCAGTGGTCCGGCTGCAGCAACAGCTGGAAGAGGCTGAGGGCA<br>GAGACCCTCAGGGTGCCATGGTCATCTGTGAGCAGCTAGGGGACCTCTTCTCCA<br>AGGCAGGAGACTTTCCCAGGGCAGCTGAGGCTTACCAGAAGCAGCTGCGTTTTG<br>CTGAGCTGCTGGACAGACCGGGTGCTGAGCGGGCCATCATCCACGTGTCCCTGG<br>CCACCACACTGGGAGACATGAAGGACCACCATGGGGCCGTGCGCCACTATGAG<br>GAGGAACTGAGGCTGCGCAGCGGCAACGTGCTGGAGGAGGCCAAGACCTGGCT<br>GAACATTGCACTGTCCCGCGAGGAGGCCGGCGATGCCTACGAGCTGCTGGCCCC<br>GTGCTTCCAGAAAGCGCTCAGCTGTGCCCAGCAGGCCCAGCGTCCCCAGCTGCA<br>GAGGCAGGTCTTGCAGCATCTCCATACCGTGCAGCTGAGGCTGCAGCCCCAGGA<br>GGCCCCTGAGACCGAAACCAGACTGCGGGAGCTCAGTGTAGCTGAAGATGAAG<br>ATGAGGAGGAGGAGGCGGAGGAGGCGGCAGCCACAGCGGAGAGCGAAGCCCT<br>GGAGGCCGGCGAGGTGGAGCTCTCAGAGGGCGAGGACGACACCGATGGCCTGA<br>CCCCGCAGCTGGAGGAGGACCTAGGAGCTTCAGGGCCACCTGGGCCGGCGGAAG<br>GGGAGCAAGTGGAACCGGCGAAACGACATGGGGGAGACCCTGCTGCACCGAGC<br>CTGCATCGAGGGCCAGCTGCGCCGCGTCCAGGACCTTGTGAGGCAGGGCCACCC<br>CCTTAACCCTCGG**GCC**TACTGTGGCTGGACACCTCTGCACGAGGCCTGCAACTA<br>CGGGCATCTAGAAATTGTCCGCTTCCTGCTGGACCACGGGGCCGCAGTGGACGA<br>CCCAGGTGGCCAGGGCTGCGAAGGCATCACCCCCCTCCACGATGCCCTCAACTG<br>TGGCCACTTCGAGGTGGCTGAGCTGCTGCTTGAACGGGGGGCGTCCGTCACCCT<br>CCGCACTCGAAAGGGCCTCAGCCCGCTGGAGACGCTGCAGCAGTGGGTGAAGC<br>TGTACCGCAGGGACCTGGACCTGGAGACGCGGCAGAAGGCCAGGGCCATGGAG<br>ATGCTGCTCCAGGCGGCTGCCTCGGGCCAAGATCCCCACAGCTCCCAGGCCTTC<br>CACACCCCAAGCAGCCTTCTGTTTGACCCCGAGACCTCTCCTCCTTTGAGCCCCT<br>GCCCAGAACCCCCCTCTAATAGCACTAGACTCCCAGAGGCCTCTCAGGTCCATG<br>TCAGGGTCTCCCCAGGGCAGGCGGCACCAGCCATGGCCAGGCCTCGGAGGAGC<br>AGGCATGGGCCAGCCAGCAGCAGCAGCAGCTCAGAAGGCGAGGACAGCGCAG<br>GCCCCGCACGGCCGTCCCAGAAGAGGCCTCGGTGCTCGGCCACAGCACAACGG<br>GTGGCAGCCTGGACGCCTGGCCCCGCCAGCAACAGGGAAGCAGCCACAGCCAG<br>CACCAGCCGGGCAGCCTACCAGGCAGCCATCCGGGGTGTGGGCAGTGCTCAGA<br>GCCGGCTGGGGCCTGGCCCACCGCGGGGCCACAGCAAAGCCCTTGCCCCCCAG<br>GCAGCGCTCATCCCGGAGGAGGAGTGCCTGGCTGGGGACTGGCTGGAGCTGGA<br>CATGCCCCTGACCCGCAGCCGCCGGCCCCGCCCCCGGGGCACTGGAGACAACCG<br>CAGGCCCAGTAGTACCTCTGGGTCGGACAGTGAGGAGAGCAGGCCCCGTGCCC<br>GAGCCAAGCAGGTCCGCCTGACCTGCATGCAGAGTTGCAGTGCGCCAGTTAACG<br>CAGGGCCCAGCAGCCTGGCTTCAGAACCTCCAGGGAGCCCCAGCACCCCCAGG<br>GTCTCAGAGCCCAGTGGGGACAGCTCTGCGGCAGGCCAGCCCTTGGGTCCGGCC<br>CCGCCCCCTCCCATCCCTGGTTCGAGTTCAAGTTCAGGATCATCTCTTCCTCATCC<br>CTGTCCCACACAGCAGTGACACCCACTCTGTGGCCTGGCTGGCCGAGCAGGCGG<br>CCCAGCGCTACTACCAGACCTGCGGGCTGCTGCCCAGGCTCACCCTACGGAAAG<br>AGGGGGCCCTGCTGGCCCCACAGGACCTCATCCCTGATCTTGCTGCAGACTCAATG<br>ACGAGGTGTTGGCTGAGGTGACTTCGTGGGACCTGCCCCCGTTGACTGACCGCT<br>ACCGCAGGGCCTGCCAGAGCCTGGGGCAAGGGGAGCACCAACAGGTGCTGCAG<br>GCCGTGGAGCTCCAGGGCTTGGGCCTCTCGTTCAGCGCCTGCTCCCTGGCCCTG<br>GACCAGGCCCAGCTTACACCCCTGCTGCGGGCCCTCAAGCTGCACACAGCACTC<br>CGGGAGCTGCGCCTGGCAGGGAACCGGCTGGGGGACAAGTGTGTGGCTGAGCT<br>GGTGGCTGCCCTGGGCACCATGCCCAGCCTGGCCCTCCTTGACCTCTCCTCCAAT<br>CACCTGGGTCCCGAAGGCCTGCGCCAGCTTGCCATGGGGCTCCCAGGCCAAGCC<br>ACCTTGCAGAGTTTGGAGgaattagatctatcgatgaACCCCCTGGGGGACGGCTGTGGCCA<br>GTCCCTGGCCTCCCTCCTGCACGCCTGCCCCTTACTCAGCACCCTGCGCCTGCAG<br>GCGTGTGGCTTCGGCCCCAGCTTCTTTCTGAGCCACCAGACAGCACTGGGTAGT<br>GCTTTCCAAGATGCTGAGCACCTGAAGACCCTGTCCCTGTCCTACAACGCCCTG<br>GGAGCCCCTGCCCTGGCCAGGACCCTGCAGAGCCTGCCCGCCGGCACCCTCCTG<br>CACTTAGAGCTCAGCTCCGTGGCAGCCGGCAAGGGTGATTCGGACCTCATGGAG<br>CCTGTATTCCGATACCTGGCCAAGGAAGGCTGTGCTCTAGCCCACCTGACCCTG<br>TCTGCAAACCACCTGGGGGACAAGGCTGTTAGAGACCTGTGCAGATGTCTCTCT<br>CTGTGCCCCTCACTCATCTCACTGGATCTGTCTGCCAACCCTGAGATCAGCTGTG<br>CCAGCTTGGAAGAGCTCCTGTCCACCCTCCAAAAGCGGCCCCAAGGCCTTAGCT<br>TCCTTGGCCTGTCAGGCTGCGCCGTCCAGGGTCCCCTGGGCCTGGGCCTGTGGG<br>ACAAGATAGCCGCGCAGCTCCGGGAACTGCAGCTGTGCAGCAGACGCCTCTGC<br>GCTGAGGACAGGGACGCCCTGCGCCAGCTGCAGCCCAGTCGGCCGGGCCCCGG<br>CGAGTGCACGCTGGACCACGGCTCCAAGCTCTTCTTTCGGCGCCTCTAG<br><br>SEQ ID NO: 6 - TONSL D559A / GFP<br>atggtgagcaagggcgaggagctgttcaccggggtggtgcccatcctggtcgagctggacggcgacgtaaacggccacaagttca<br>gcgtgtccggcgagggcgagggcgatgccacctacggcaagctgaccctgaagttcatctgcaccaccggcaagctgcccgtgc<br>cctggcccaccctcgtgaccaccctgacctacggcgtgcagtgcttcagccgctaccccgaccacatgaagcagcacgacttcttca |

-continued

| SEQUENCE DATA |
| --- |

agtccgccatgcccgaaggctacgtccaggagcgcaccatcttcttcaaggacgacggcaactacaagacccgcgccgaggtgaa
gttcgagggcgacaccctggtgaaccgcatcgagctgaagggcatcgacttcaaggaggacggcaacatcctggggcacaagct
ggagtacaactacaacagccacaacgtctatatcatggccgacaagcagaagaacggcatcaaggtgaacttcaagatccgccaca
acatcgaagacggcagcgtgcagctcgccgaccactaccagcagaacacccccatcggcgacggccccgtgctgctgcccgac
aaccactacctgagcacccagtccgccctgagcaaagaccccaacgagaagcgcgatcacatggtcctgctggagttcgtgaccg
ccgccgggatcactctcggcatggacgagctgtacaagggcgcgccaATGAGCCTGGAGCGCGAGCTTCG
CCAGCTGAGCAAGGCGAAAGCCAAGGCGCAGAGGGCCGGGCAGCGGCGCGAA
GAGGCCGCGCTGTGCCACCAGCTGGGGGAGCTCCTGGCCGGCCATGGCCGCTAC
GCCGAGGCTCTGGAGCAGCACTGGCAGGAGCTGCAGCTTCGGGAGCGCGCTGA
CGACCCTCTGGGCTGTGCCGTGGCCCACCGCAAGATCGGAGAGCGCCTGGCCGA
GATGGAGGACTACCCGGCTGCCTTGCAGCACCAGCACCAGTACCTGGAGCTGGC
ACATTCCCTGCGCAACCACACGGAGCTGCAGAGGGCCTGGGCCACCATCGGCCG
CACCCACCTGGACATCTATGACCACTGCCAGTCGAGGGATGCTTTGCTGCAGGC
ACAGGCTGCCTTTGAGAAGAGCTTGGCTATTGTGGATGAGGAGCTGGAGGGGA
CACTGGCCCAGGGAGAGCTGAATGAGATGAGGACCCGCCTCTATCTCAACCTGG
GCCTCACCTTTGAGCCTGCAGCAGACAGCCCTGTGCAACGATTACTTCAGGA
AGAGCATCTTCCTTGCGGAGCAGAACCACCTTTACGAGGACCTATTCCGCGCCC
GCTACAACCTGGGCACCATCCACTGGCGCGCGGGCCAGCACTCCCAGGCTATGC
GCTGCTTGGAGGGTGCCCGGGAGTGTGCGCACACCATGAGGAAAGCGGTTCATG
GAGAGCGAGTGCTGCGTGGTTATTGCACAGGTCCTCCAAGACCTGGGAGACTTT
TTGGCTGCCAAGCGAGCCCTGAAGAAGGCCTACAGGCTGGGCTCCCAGAAGCCT
GTGCAGAGGGCAGCCATCTGTCAGAACCTCCAGCATGTGCTGGCAGTGGTCCGG
CTGCAGCAACAGCTGGAAGAGGCTGAGGGCAGAGACCCTCAGGGTGCCATGGT
CATCTGTGAGCAGCTAGGGGACCTCTTCTCCAAGGCAGGAGACTTTCCCAGGGC
AGCTGAGGCTTACCAGAAGCAGCTGCGTTTTGCTGAGCTGCTGGACAGACCGGG
TGCTGAGCGGGCCATCATCCACGTGTCCCTGGCCACCACACTGGGAGACATGAA
GGACCACCATGGGGCCGTGCGCCACTATGAGGAGGAACTGAGGCTGCGCAGCG
GCAACGTGCTGGAGGAGGCCAAGACCTGGCTGAACATTGCACTGTCCCGCGAG
GAGGCCGGCGATGCCTACGAGCTGCTGGCCCCGTGCTTCCAGAAAGCGCTCAGC
TGTGCCCAGCAGGCCCAGCGTCCCCAGCTGCAGAGGCAGGTCTTGCAGCATCTC
CATACCGTGCAGCTGAGGCTGCAGCCCCAGGAGGCCCCTGAGACCGAAACCAG
ACTGCGGGAGCTCAGTGTAGCTGAAGATGAAGATGAGGAGGAGGAGGCGGAGG
AGGCGGCAGCCACAGCGGAGAGCGAAGCCCTGGAGGCCGGCGAGGTGGAGCTC
TCAGAGGGCGAGGACGACACCGATGGCCTGACCCCGCAGCTGGAGGAGGACGA
GGAGCTTCAGGGCCACCTGGGCCGGCGGAAGGGGAGCAAGTGGAACCGGCGAA
ACGACATGGGGGAGACCCTGCTGCACCGAGCCTGCATCGAGGGCCAGCTGCGC
CGCGTCCAGGACCTTGTGAGGCAGGGCCACCCCCTTAACCCTCGGGCCTACTGT
GGCTGGACACCTCTGCACGAGGCCTGCAACTACGGGCATCTAGAAATTGTCCGC
TTCCTGCTGGACCACGGGGCCGCAGTGGACGACCCAGGTGGCCAGGGCTGCGA
AGGCATCACCCCCCTCCACGATGCCCTCAACTGTGGCCACTTCGAGGTGGCTGA
GCTGCTGCTTGAACGGGGGGCGTCCGTCACCCTCCGCACTCGAAAGGGCCTCAG
CCCGCTGGAGACGCTGCAGCAGTGGGTGAAGCTGTACCGCAGGGACCTGGACC
TGGAGACGCGGCAGAAGGCCAGGGCCATGGAGATGCTGCTCCAGGCGGCTGCC
TCGGGCCAAGATCCCCACAGCTCCCAGGCCTTCCACACCCCAAGCAGCCTTCTG
TTTGACCCCGAGACCTCTCCTCCTTTGAGCCCCTGCCCAGAACCCCCCTCTAATA
GCACTAGACTCCCAGAGGCCTCTCAGGTCCATGTCAGGGTCTCCCCAGGGCAGG
CGGCACCAGCCATGGCCAGGCCTCGGAGGAGCAGGCATGGGCCAGCCAGCAGC
AGCAGCAGCTCAGAAGGCGAGGACAGCGCAGGCCCCGCACGGCCGTCCCAGAA
GAGGCCTCGGTGCTCGGCCACAGCACAACGGGTGGCAGCCTGGACGCCTGGCC
CCGCCAGCAACAGGGAAGCAGCCACAGCCAGCACCAGCCGGGCAGCCTACCAG
GCAGCCATCCGGGGTGTGGGCAGTGCTCAGAGCCGGCTGGGGCCTGGCCCACC
GCGGGGCCACAGCAAAGCCCTTGCCCCCCAGGCAGCGCTCATCCCGGAGGAGG
AGTGCCTGGCTGGGGACTGGCTGAGCTGGACATGCCCCTGACCCGCAGCCGCC
GGCCCCGCCCCCGGGGCACTGGAGACAACCGCAGGCCCAGTAGTACCTCTGGGT
CGGACAGTGAGGAGAGCAGGCCCCGTGCCCGAGCCAAGCAGGTCCGCCTGACC
TGCATGCAGAGTTGCAGTGCGCCAGTTAACGCAGGGCCCAGCAGCCTGGCTTCA
GAACCTCCAGGGAGCCCCAGCACCCCCAGGGTCTCAGAGCCCAGTGGGGACAG
CTCTGCGGCAGGCCAGCCCTTGGGTCCGGCCCCGCCCCCTCCCATCCGGGTTCG
AGTTCAAGTTCAGGATCATCTCTTCCTCATCCCTGTCCCACACAGCAGTGACACC
CACTCTGTGGCCTGGCTGGCCGAGCAGGCGGCCCAGCGCTACTACCAGACCTGC
GGGCTGCTGCCCAGGCTCACCCTACGGAAAGAGGGGGCCCTGCTGGCCCCACA
GGACCTCATCCCTGATGTGCTGCAGAGCAATGACGAGGTGTTGGCTGAGGTGAC
TTCGTGGGACCTGCCCCCGTTGACTGACCGCTACCGCAGGGCCTGCCAGAGCCT
GGGGCAAGGGGAGCACCAACAGGTGCTGCAGGCCGTGGAGCTCCAGGGCTTGG
GCCTCTCGTTCAGCGCCTGCTCCCTGGCCCTGGACCAGGCCCAGCTTACACCCCT
GCTGCGGGCCCTCAAGCTGCACACAGCACTCCGGGAGCTGCGCCTGGCAGGGA
ACCGGCTGGGGGACAAGTGTGTGGCTGAGCTGGTGGCTGCCCTGGGCACCATGC
CCAGCCTGGCCCTCCTTGACCTCTCCTCCAATCACCTGGGTCCCGAAGGCCTGCG
CCAGCTTGCCATGGGGCTCCCAGGCCAAGCCACCTTGCAGAGTTTGGAGgaattagat
ctatcgatgaACCCCCTGGGGGACGGCTGTGGCCAGTCCCTGGCCTCCCTCCTGCACG
CCTGCCCCTTACTCAGCACCCTGCGCCTGCAGGCGTGTGGCTTCGGCCCCAGCTT
CTTTCTGAGCCACCAGACAGCACTGGGTAGTGCTTTCCAAGATGCTGAGCACCT
GAAGACCCTGTCCCTGTCCTACAACGCCCTGGGAGCCCCTGCCCTGGCCAGGAC
CCTGCAGAGCCTGCCCGGCCGGCACCCTCCTGCACTTAGAGCTCAGCTCCGTGGC
AGCCGGCAAGGGTGATTCGGACCTCATGGAGCCTGTATTCCGATACCTGGCCAA
GGAAGGCTGTGCTCTAGCCCACCTGACCCTGTCTGCAAACCACCTGGGGGACAA
GGCTGTTAGAGACCTGTGCAGATGTCTCTCTCTGTGCCCCTCACTCATCTCACTG -continued

SEQUENCE DATA

GATCTGTCTGCCAACCCTGAGATCAGCTGTGCCAGCTTGGAAGAGCTCCTGTCC
ACCCTCCAAAAGCGGCCCCAAGGCCTTAGCTTCCTTGGCCTGTCAGGCTGCGCC
GTCCAGGGTCCCCTGGGCCTGGGCCTGTGGGACAAGATAGCCGCGCAGCTCCGG
GAACTGCAGCTGTGCAGCAGACGCCTCTGCGCTGAGGACAGGGACGCCCTGCG
CCAGCTGCAGCCCAGTCGGCCGGGCCCCGGCGAGTGCACCTCTGGACCACGGCTC
CAAGCTCTTCTTTCGGCGCCTCTAG

SEQ ID NO: 7 - TONSL W563A
ATGAGCCTGGAGCGCGAGCTTCGCCAGCTGAGCAAGGCGAAAGCCAAGGCGCA
GAGGGCCGGGCAGCGGCGCGAAGAGGCCGCGCTGTGCCACCAGCTGGGGGAGC
TCCTGGCCGGCCATGGCCGCTACGCCGAGGCTCTGGAGCAGCACTGGCAGGAGC
TGCAGCTTCGGGAGCGCGCTGACGACCCTCTGGGCTGTGCCGTGGCCCACCGCA
AGATCGGAGAGCGCCTGGCCGAGATGGAGGACTACCCGGCTGCCTTGCAGCAC
CAGCACCAGTACCTGGAGCTGGCACATTCCCTGCGCAACCACACGGAGCTGCAG
AGGGCCTGGGCCACCATCGGCCGCACCCACCTGGACATCTATGACCACTGCCAG
TCGAGGGATGCTTTGCTGCAGGCACAGGCTGCCTTTGAGAAGAGCTTGGCTATT
GTGGATGAGGAGCTGGAGGGGACACTGGCCCAGGGAGAGCTGAATGAGATGAG
GACCCGCCTCTATCTCAACCTGGGCCTCACCTTTGAGAGCCTGCAGCAGACAGC
CCTGTGCAACGATTACTTCAGGAAGAGCATCTTCCTTGCGGAGCAGAACCACCT
TTACGAGGACCTATTCCGCGCCCGCTACAACCTGGGCACCATCCACTGGCGCGC
GGGCCAGCACTCCCAGGCTATGCGCTGCTTGGAGGGTGCCCGGGAGTGTGCGCA
CACCATGAGGAAGCGGTTCATGGAGAGCGAGTGCTGCGTGGTTATTGCACAGGT
CCTCCAAGACCTGGGAGACTTTTTGGCTGCCAAGCGAGCCCTGAAGAAGGCCTA
CAGGCTGGGCTCCCAGAAGCCTGTGCAGAGGGCAGCCATCTGTCAGAACCTCCA
GCATGTGCTGGCAGTGGTCCGGCTGCAGCAACAGCTGGAAGAGGCTGAGGGCA
GAGACCCTCAGGGTGCCATGGTCATCTGTGAGCAGCTAGGGGACCTCTTCTCCA
AGGCAGGAGACTTTCCCAGGGCAGCTGAGGCTTACCAGAAGCAGCTGCGTTTTG
CTGAGCTGCTGGACAGACCGGGTGCTGAGCGGGCCATCATCCACGTGTCCCTGG
CCACCACACTGGGAGACATGAAGGACCACCATGGGGCCGTGCGCCACTATGAG
GAGGAACTGAGGCTGCGCAGCGGCAACGTGCTGGAGGAGGCCAAGACCTGGCT
GAACATTGCACTGTCCCGCGAGGAGGCCGGCGATGCCTACGAGCTGCTGGCCCC
GTGCTTCCAGAAAGCGCTCAGCTGTGCCCAGCAGGCCCAGCGTCCCCAGCTGCA
GAGGCAGGTCTTGCAGCATCTCCATACCGTGCAGCTGAGGCTGCAGCCCCAGGA
GGCCCCTGAGACCGAAACCAGACTGCGGGAGCTCAGTGTAGCTGAAGATGAAG
ATGAGGAGGAGGAGGCGGAGGAGGCGGCAGCCACAGCGGAGAGCGAAGCCCT
GGAGGCCGGCGAGGTGGAGCTCTCAGAGGGCGAGGACGACACCGATGGCCTGA
CCCCGCAGCTGGAGGAGGACGAGGAGCTTCAGGGCCACCTGGGCCGGCGGAAG
GGGAGCAAGTGGAACCGGCGAAACGACATGGGGGAGACCCTGCTGCACCGAGC
CTGCATCGAGGGCCAGCTGCGCCGCGTCCAGGACCTTGTGAGGCAGGGCCACCC
CCTTAACCCTCGGGACTACTGTGGCGCGACACCTCTGCACGAGGCCTGCAACTA
CGGGCATCTAGAAATTGTCCGCTTCCTGCTGGACCACGGGGCCGCAGTGGACGA
CCCAGGTGGCCAGGGCTGCGAAGGCATCACCCCCCTCCACGATGCCCTCAACTG
TGGCCACTTCGAGGTGGCTGAGCTGCTGCTTGAACGGGGGGCGTCCGTCACCCT
CCGCACTCGAAAGGGCCTCAGCCCGCTGGAGACGCTGCAGCAGTGGGTGAAGC
TGTACCGCAGGGACCTGGACCTGGAGACGCGGCAGAAGGCCAGGGCCATGGAG
ATGCTGCTCCAGGCGGCTGCCTCGGGCCAAGATCCCCACAGCTCCCAGGCCTTC
CACACCCCAAGCAGCCTTCTGTTTGACCCCGAGACCTCTCCTCCTTTGAGCCCCT
GCCCAGAACCCCCCTCTAATAGCACTAGACTCCCAGAGGCCTCTCAGGTCCATG
TCAGGGTCTCCCCAGGGCAGGCGGCACCAGCCATGGCCAGGCCTCGGAGGAGC
AGGCATGGGCCAGCCAGCAGCACTCAGCAGCTCAGAAGGCGAGGACAGCGCAG
GCCCCGCACGGCCGTCCCAGAAGAGGCCTCGGTGCTCGGCCACAGCACAACGG
GTGGCAGCCTGGACGCCTGGCCCCGCCAGCAACAGGGAAGCAGCCACAGCCAG
CACCAGCCGGGCAGCCTACCAGGCAGCCATCCGGGGTGTGGGCAGTGCTCAGA
GCCGGCTGGGGCCTGGCCCACCGCGGGGCCACAGCAAAGCCCTTGCCCCCCAG
GCAGCGCTCATCCCGGAGGAGGAGTGCCTGGCTGGGGACTGGCTGGAGCTGGA
CATGCCCCTGACCCGCAGCCGCCGGCCCCGCCCCCGGGGCACTGGAGACAACCG
CAGGCCCAGTAGTACCTCTGGGTCGGACAGTGAGGAGAGCAGGCCCCGTGCCC
GAGCCAAGCAGGTCCGCCTGACCTGCATGCAGAGTTGCACTTGCGCCAGTTAACG
CAGGGCCCAGCAGCCTGGCTTCAGAACCTCCAGGGAGCCCCAGCACCCCCAGG
GTCTCAGAGCCCAGTGGGGACAGCTCTGCGGCAGGCCAGCCCTTGGGTCCGGCC
CCGCCCCCTCCCATCCGCTGTTCGAGTTCAAGTTCAGGATCATCTCTTCCTCATCC
CTGTCCCACACAGCAGTGACACCCACTCTGTGGCCTGGCTGGCCGAGCAGGCGG
CCCAGCGCTACTACCAGACCTGCGGGCTGCTGCCCAGGCTCACCCTACGGAAAG
AGGGGGCCCTGCTGGCCCCACAGGACCTCATCCCTGATGTGCTGCAGAGCAATG
ACGAGGTGTTGGCTGAGGTGACTTCGTGGGACCTGCCCCCGTTGACTGACCGCT
ACCGCAGGGCCTGCCAGAGCCTGGGGCAAGGGGAGCACCAACAGGTGCTGCAG
GCCGTGGAGCTCCAGGGCTTGGGCCTCTCGTTCAGCGCCTGCTCCCTGGCCCTG
GACCAGGCCCAGCTTACACCCCTGCTGCGGGCCCTCAAGCTGCACACAGCACTC
CGGGAGCTGCGCCTGGCAGGGAACCGGCTGGGGGACAAGTGTCTTGGCTGAGCT
GGTGGCTGCCCTGGGCACCATGCCCAGCCTGGCCCTCCTTGACCTCTCCTCCAAT
CACCTGGGTCCCGAAGGCCTGCGCCAGCTTGCCATGGGGCTCCCAGGCCAAGCC
ACCTTGCAGAGTTTGGAGgaattagatctatcgatgaACCCCCTGGGGGACGGCTGTGGCCA
GTCCCTGGCCTCCCTCCTGCACGCCTGCCCCTTACTCAGCACCCTGCGCCTGCAG
GCCTTGTGGCTTCGGCCCCAGCTTCTTTCTGAGCCACCAGACAGCACTGGGTAGT
GCTTTCCAAGATGCTGAGCACCTGAAGACCCTGTCCCTGTCCTACAACGCCCTG
GGAGCCCCTGCCCTGGCCAGGACCCTGCAGAGCCTGCCCGCCGGCACCCTCCTG
CACTTAGAGCTCAGCTCCGTGGCAGCCGGCAAGGGTGATTCGGACCTCATGGAG -continued

SEQUENCE DATA

CCTGTATTCCGATACCTGGCCAAGGAAGGCTGTGCTCTAGCCCACCTGACCCTG
TCTGCAAACCACCTGGGGGACAAGGCTGTTAGAGACCTGTGCAGATGTCTCTCT
CTGTGCCCCTCACTCATCTCACTGGATCTGTCTGCCAACCCTGAGATCAGCTGTG
CCAGCTTGGAAGAGCTCCTGTCCACCCTCCAAAAGCGGCCCCAAGGCCTTAGCT
TCCTTGGCCTGTCAGGCTGCGCCGTCCAGGGTCCCCTGGGCCTGGGCCTGTGGG
ACAAGATAGCCGCGCAGCTCCGGGAACTGCAGCTGTGCAGCAGACGCCTCTGC
GCTGAGGACAGGGACGCCCTGCGCCAGCTGCAGCCCAGTCGGCCGGGCCCCGG
CGAGTGCACGCTGGACCACGGCTCCAAGCTCTTCTTTCGGCGCCTCTAG

SEQ ID NO: 8 - TONSL W563A / GFP
atggtgagcaagggcgaggagctgttcaccggggtggtgcccatcctggtcgagctggacggcgacgtaaacggccacaagttca
gcgtgtccggcgagggcgagggcgatgccacctacggcaagctgaccagaagttcatctgcaccaccggcaagctgcccgtgc
cctggcccaccctcgtgaccaccctgacctacggcgtgcagtgcttcagccgctaccccgaccacatgaagcagcacgacttcttca
agtccgccatgcccgaaggctacgtccaggagcgcaccatcttcttcaaggacgacggcaactacaagacccgcgccgaggtgaa
gttcgagggcgacaccaggtgaaccgcatcgagctgaagggcatcgacttcaaggaggacggcaacatcctggggcacaagct
ggagtacaactacaacagccacaacgtctatatcatggccgacaagcagaagaacggcatcaaggtgaacttcaagatccgccaca
acatcgaggacggcagcgtgcagctcgccgaccactaccagcagaacacccccatcggcgacggccccgtgctgctgcccgac
aaccactacctgagcacccagtccgccctgagcaaagaccccaacgagaagcgcgatcacatggtcctgctggagttcgtgaccg
ccgccgggatcactctcggcatggacgagctgtacaagggcgcgccaATGAGCCTGGAGCGCGAGCTTCG
CCAGCTGAGCAAGGCGAAAGCCAAGGCGCAGAGGGCCGGGCAGCGGCGCGAA
GAGGCCGCGCTGTGCCACCAGCTGGGGGAGCTCCTGGCCGGCCATGGCCGCTAC
GCCGAGGCTCTGGAGCAGCACTGGCAGGAGCTGCAGCTTCGGGAGCGCGCTGA
CGACCCTCTGGGCTGTGCCGTGGCCCACCGCAAGATCGGAGAGCGCCTGGCCGA
GATGGAGGACTACCCGGCTGCCTTGCAGCACCAGCACCAGTACCTGGAGCTGGC
ACATTCCCTGCGCAACCACACGGAGCTGCAGAGGGCCTGGGCCACCATCGGCCG
CACCCACCTGGACATCTATGACCACTGCCAGTCGAGGGATGCTTTGCTGCAGGC
ACAGGCTGCCTTTGAGAAGAGCTTGGCTATTGTGGATGAGGAGCTGGAGGGGA
CACTGGCCCAGGGAGAGCTGAATGAGATGAGGACCCGCCTCTATCTCAACCTGG
GCCTCACCTTTGAGAGCCTGCAGCAGACAGCCCTGTGCAACGATTACTTCAGGA
AGAGCATCTTCCTTGCGGAGCAGAACCACCTTTACGAGGACCTATTCCGCGCCC
GCTACAACCTGGGCACCATCCACTGGCGCGCGGGCCAGCACTCCCAGGCTATGC
GCTGCTTGGAGGGTGCCCGGGAGTGTGCGCACACCATGAGGAAGCGGTTCATG
GAGAGCGAGTGCTGCGTGGTTATTGCACAGGTCCTCCAAGACCTGGGAGACTTT
TTGGCTGCCAAGCGAGCCCTGAAGAAGGCCTACAGGCTGGGCTCCCAGAAGCCT
GTGCAGAGGGCAGCCATCTGTCAGAACCTCCAGCATGTGCTGGCAGTGGTCCGG
CTGCAGCAACAGCTGGAAGAGGCTGAGGGCAGAGACCCTCAGGGTGCCATGGT
CATCTGTGAGCAGCTAGGGGACCTCTTCTCCAAGGCAGGAGACTTTCCCAGGGC
AGCTGAGGCTTACCAGAAGCAGCTGCGTTTTGCTGAGCTGCTGGACAGACCGGG
TGCTGAGCGGGCCATCATCCACGTGTCCCTGGCCACCACACTGGGAGACATGAA
GGACCACCATGGGGCCGTGCGCCACTATGAGGAGGAACTGAGGCTGCGCAGCG
GCAACGTGCTGGAGGAGGCCAAGACCTGGCTGAACATTGCACTGTCCCGCGAG
GAGGCCGGCGATGCCTACGAGCTGCTGGCCCCGTGCTTCCAGAAAGCGCTCAGC
TGTGCCCAGCAGGCCCAGCGTCCCCAGCTGCAGAGGCAGGTCTTGCAGCATCTC
CATACCGTGCAGCTGAGGCTGCAGCCCCAGGAGGCCCCTGAGACCGAAACCAG
ACTGCGGGAGCTCAGTGTAGCTGAAGATGAAGATGAGGAGGAGGAGGCGGAGG
AGGCGGCAGCCACAGCGGAGAGCGAAGCCCTGGAGGCCGGCGAGGTGGAGCTC
TCAGAGGGCGAGGACGACACCGATGGCCTGACCCCGCAGCTGGAGGAGGACGA
GGAGCTTCAGGGCCACCTGGGCCGGCGGAAGGGGAGCAAGTGGAACCGGCGAA
ACGACATGGGGGAGACCCTGCTGCACCGAGCCTGCATCGAGGGCCAGCTGCGC
CGCGTCCAGGACCTTGTGAGGCAGGGCCACCCCCTTAACCCTCGGGACTACTGT
GGCGCGACACCTCTGCACGAGGCCTGCAACTACGGGCATCTAGAAATTGTCCGC
TTCCTGCTGGACCACGGGGCCGCAGTGGACGACCCAGGTGGCCAGGGCTGCGA
AGGCATCACCCCCCTCCACGATGCCCTCAACTGTGGCCACTTCGAGGTGGCTGA
GCTGCTGCTTGAACGGGGGGCGTCCGTCACCCTCCGCACTCGAAAGGGCCTCAG
CCCGCTGGAGACGCTGCAGCAGTGGGTGAAGCTGTACCGCAGGGACCTGGACC
TGGAGACGCGGCAGAAGGCCAGGGCCATGGAGATGCTGCTCCAGGCGGCTGCC
TCGGGCCAAGATCCCCACAGCTCCCAGGCCTTCCACACCCCAAGCAGCCTTCTG
TTTGACCCCGAGACCTCTCCTCCTTTGAGCCCCTGCCCAGAACCCCCCTCTAATA
GCACTAGACTCCCAGAGGCCTCTCAGGTCCATGTCAGGGTCTCCCCAGGGCAGG
CGGCACCAGCCATGGCCAGGCCTCGGAGGAGCAGGCATGGGCCAGCCAGCAGC
AGCAGCAGCTCAGAAGGCGAGGACAGCGCAGGCCCCGCACGGCCGTCCCAGAA
GAGGCCTCGGTGCTCGGCCACAGCACAACGGGTGGCAGCCTGGACGCCTGGCC
CCGCCAGCAACAGGGAAGCAGCCACAGCCAGCACCAGCCGGGCAGCCTACCAG
GCAGCCATCCGGGGTGTGGGCAGTGCTCAGAGCCGGCTGGGGCCTGGCCCACC
GCGGGGCCACAGCAAAGCCCTTGCCCCCCAGGCAGCGCTCATCCCGGAGGAGG
AGTGCCTGGCTGGGGACTGGCTGGAGCTGGACATGCCCCTGACCCGCAGCCGCC
GGCCCCGCCCCCGGGGCACTGGAGACAACCGCAGGCCCAGTAGTACCTCTGGGT
CGGACAGTGAGGAGAGCAGGCCCCGTGCCCGAGCCAAGCAGGTCCGCCTGACC
TGCATGCAGAGTTGCAGTGCGCCAGTTAACGCAGGGCCCAGCAGCCTGGCTTCA
GAACCTCCAGGGAGCCCCAGCACCCCCAGGGTCTCAGAGCCCAGTGGGGACAG
CTCTGCGGCAGGCCAGCCCTTGGGTCCGGCCCCGCCCCCTCCCATCCGGGTTCG
AGTTCAAGTTCAGGATCATCTCTTCCTCATCCCTGTCCCACACAGCAGTGACACC
CACTCTGTGGCCTGGCTGGCCGAGCAGGCGGCCCAGCGCTACTACCAGACCTGC
GGGCTGCTGCCCAGGCTCACCCTACGGAAAGAGGGGGCCCTGCTGGCCCCACA
GGACCTCATCCCTGATGTGCTGCAGAGCAATGACGAGGTGTTGGCTGAGGTGAC
TTCGTGGGACCTGCCCCCGTTGACTGACCGCTACCGCAGGGCCTGCCAGAGCCT
GGGGCAAGGGGAGCACCAACAGGTGCTGCAGGCCGTGGAGCTCCAGGGCTTGG -continued

| SEQUENCE DATA |
|---|
| GCCTCTCGTTCAGCGCCTGCTCCCTGGCCCTGGACCAGGCCCAGCTTACACCCCT<br>GCTGCGGGCCCTCAAGCTGCACACAGCACTCCGGGAGCTGCGCCTGGCAGGGA<br>ACCGGCTGGGGGACAAGTGTGTGGCTGAGCTGGTGGCTGCCCTGGGCACCATGC<br>CCAGCCTGGCCCTCCTTGACCTCTCCTCCAATCACCTGGGTCCCGAAGGCCTGCG<br>CCAGCTTGCCATGGGGCTCCCAGGCCAAGCCACCTTGCAGAGTTTGGAGgaattagat<br>ctatcgatgaACCCCCTGGGGGACGGCTGTGGCCAGTCCCTGGCCTCCCTCCTGCACG<br>CCTGCCCCTTACTCAGCACCCTGCGCCTGCAGGCGTGTGGCTTCGGCCCCAGCTT<br>CTTTCTGAGCCACCAGACAGCACTGGGTAGTGCTTTCCAAGATGCTGAGCACCT<br>GAAGACCCTGTCCCTGTCCTACAACGCCCTGGGAGCCCCTGCCCTGGCCAGGAC<br>CCTGCAGAGCCTGCCCGCCGGCACCCTCCTGCACTTAGAGCTCAGCTCCGTGGC<br>AGCCGGCAAGGGTGATTCGGACCTCATGGAGCCTGTATTCCGATACCTGGCCAA<br>GGAAGGCTGTGCTCTAGCCCACCTGACCCTGTCTGCAAACCACCTGGGGGACAA<br>GGCTGTTAGAGACCTGTGCAGATGTCTCTCTCTGTGCCCCTCACTCATCTCACTG<br>GATCTGTCTGCCAACCCTGAGATCAGCTGTGCCAGCTTGGAAGAGCTCCTGTCC<br>ACCCTCCAAAAGCGGCCCCAAGGCCTTACTCTTCCTTGGCCTGTCAGGCTGCGCC<br>GTCCAGGGTCCCCTGGGCCTGGGCCTGTGGGACAAGATAGCCGCGCAGCTCCGG<br>GAACTGCAGCTGTGCAGCAGACGCCTCTGCGCTGAGGACAGGGACGCCCTGCG<br>CCAGCTGCACTCCCAGTCCTGCCGGGCCCCGGCGAGTGCACGCTGGACCACGGCTC<br>CAAGCTCTTCTTTCGGCGCCTCTAG<br><br>SEQ ID NO: 9 - TONSL E568A<br>ATGAGCCTGGAGCGCGAGCTTCGCCAGCTGAGCAAGGCGAAAGCCAAGGCGCA<br>GAGGGCCGGGCAGCGGCGCCTAAGAGGCCGCGCTGTGCCACCAGCTGGGGGAGC<br>TCCTGGCCGGCCATGGCCGCTACGCCGAGGCTCTGGAGCAGCACTGGCAGGAGC<br>TGCAGCTTCGGGAGCGCGCTGACGACCCTCTGGGCTGTGCCGTGGCCCACCGCA<br>AGATCGGAGAGCGCCTGGCCGAGATGGAGGACTACCCGGCTGCCTTGCAGCAC<br>CAGCACCAGTACCTGGAGCTGGCACATTCCCTGCGCAACCACACGGAGCTGCAG<br>AGGGCCTGGGCCACCATCGGCCGCACCCACCTGGACATCTATGACCACTGCCAG<br>TCGAGGGATGCTTTGCTGCAGGCACAGGCTGCCTTTGAGAAGAGCTTGGCTATT<br>GTGGATGAGGAGCTGGAGGGGACACTGGCCCAGGGAGAGCTGAATGAGATGAG<br>GACCCGCCTCTATCTCAACCTGGGCCTCACCTTTGAGAGCCTGCAGCAGACAGC<br>CCTGTGCAACGATTACTTCAGGAAGAGCATCTTCCTTGCGGAGCAGAACCACCT<br>TTACGAGGACCTATTCCGCGCCCGCTACAACCTGGGCACCATCCACTGGCGCGC<br>GGGCCAGCACTCCCAGGCTATGCCTCTGCTTGGAGGGTGCCCGGGAGTCTTGCGCA<br>CACCATGAGGAAGCGGTTCATGGAGAGCGAGTGCTGCGTGGTTATTGCACAGGT<br>CCTCCAAGACCTGGGAGACTTTTTGGCTGCCAAGCGAGCCCTGAAGAAGGCCTA<br>CAGGCTGGGCTCCCAGAAGCCTGTGCAGAGGGCAGCCATCTGTCAGAACCTCCA<br>GCATGTGCTGGCAGTGGTCCGGCTGCAGCAACAGCTGGAAGAGGCTGAGGGCA<br>GAGACCCTCAGGGTGCCATCTGTCATCTGTGAGCAGCTAGGGGACCTCTTCTCCA<br>AGGCAGGAGACTTTCCCAGGGCAGCTGAGGCTTACCAGAAGCAGCTGCGTTTTG<br>CTGAGCTGCTGGACAGACCGGGTGCTGAGCGGGCCATCATCCACGTGTCCCTGG<br>CCACCACACTGGGAGACATGAAGGACCACCATGGGGCCGTGCGCCACTATGAG<br>GAGGAACTGAGGCTGCGCAGCGGCAACGTGCTGGAGGAGGCCAAGACCTGGCT<br>GAACATTGCACTGTCCCGCGAGGAGGCCGGCGATGCCTACGAGCTGCTGGCCCC<br>GTGCTTCCAGAAAGCGCTCAGCTGTGCCCAGCAGGCCCAGCGTCCCCAGCTGCA<br>GAGGCAGGTCTTGCAGCATCTCCATACCGTGCAGCTGAGGCTGCAGCCCCAGGA<br>GGCCCCTGAGACCGAAACCAGACTGCGGGAGCTCAGTGTAGCTGAAGATGAAG<br>ATGAGGAGGAGGAGGCGGAGGAGGCGGCAGCCACAGCGGAGAGCGAAGCCCT<br>GGAGGCCGGCGAGGTGGAGCTCTCAGAGGGCGAGGACGACACCGATGGCCTGA<br>CCCCGCAGCTGGAGGAGGACGAGGAGCTTCAGGGCCACCTGGGCCGGCGGAAG<br>GGGAGCAAGTGGAACCGGCGAAACGACATGGGGGAGACCCTGCTGCACCGAGC<br>CTGCATCGAGGGCCAGCTGCGCCGCGTCCAGGACCTTGTGAGGCAGGGCCACCC<br>CCTTAACCCTCGGGACTACTGTGGCTGGACACCTCTGCAC**GCG**GCCTGCAACTA<br>CGGGCATCTAGAAATTGTCCGCTTCCTGCTGGACCACGGGGCCGCAGTGGACGA<br>CCCAGGTGGCCAGGGCTGCGAAGGCATCACCCCCCTCCACGATGCCCTCAACTG<br>TGGCCACTTCGAGGTGGCTGAGCTGCTGCTTGAACGGGGGGCGTCCGTCACCCT<br>CCGCACTCGAAAGGGCCTCAGCCCGCTGGAGACGCTGCAGCAGTGGGTGAAGC<br>TGTACCGCAGGGACCTGGACCTGGAGACGCGGCAGAAGGCCAGGGCCATGGAG<br>ATGCTGCTCCAGGCGGCTGCCTCGGGCCAAGATCCCCACAGCTCCCAGGCCTTC<br>CACACCCCAAGCAGCCTTCTGTTTGACCCCGAGACCTCTCCTCCTTTGAGCCCCT<br>GCCCAGAACCCCCCTCTAATAGCACTAGACTCCCAGAGGCCTCTCAGGTCCATG<br>TCAGGGTCTCCCCAGGGCAGGCGGCACCAGCCATGGCCAGGCCTCGGAGGAGC<br>AGGCATGGGCCAGCCAGCAGCAGCAGCAGCTCAGAAGGCGAGGACAGCGCAG<br>GCCCCGCACGGCCGTCCCAGAAGAGGCCTCGGTGCTCGGCCACAGCACAACGG<br>GTGGCAGCCTGGACGCCTGGCCCCGCCAGCAACAGGGAAGCAGCCACAGCCAG<br>CACCAGCCGGGCAGCCTACCAGGCAGCCATCCGGGGTGTGGGCAGTGCTCAGA<br>GCCGGCTGGGGCCTGGCCCACCGCGGGGCCACAGCAAAGCCCTTGCCCCCCAG<br>GCAGCGCTCATCCCGGAGGAGGAGTGCCTGGCTGGGGACTGGCTGGAGCTGGA<br>CATGCCCCTGACCCGCAGCCGCCGGCCCCGCCCCCGGGGCACTGGAGACAACCG<br>CAGGCCCAGTAGTACCTCTGGGTCGGACAGTGAGGAGAGCAGGCCCCGTGCCC<br>GAGCCAAGCAGGTCCGCCTGACCTGCATGCAGAGTTGCAGTGCGCCAGTTAACG<br>CAGGGCCCAGCAGCCTGGCTTCAGAACCTCCAGGGAGCCCCAGCACCCCCAGG<br>GTCTCAGAGCCCAGTGGGGACAGCTCTGCGGCAGGCCAGCCCTTGGGTCCGGCC<br>CCGCCCCCTCCCATCCGGGTTCGAGTTCAAGTTCAGGATCATCTCTTCCTCATCC<br>CTGTCCCACACAGCAGTGACACCCACTCTGTGGCCTGGCTGGCCGAGCAGGCGG<br>CCCAGCGCTACTACCAGACCTGCGGGCTGCTGCCCAGGCTCACCCTACGGAAAG<br>AGGGGGCCCTGCTGGCCCCACAGGACCTCATCCCTGATGTGCTGCAGAGCAATG |

-continued

| SEQUENCE DATA |
|---|

ACGAGGTGTTGGCTGAGGTGACTTCGTGGGACCTGCCCCCGTTGACTGACCGCT
ACCGCAGGGCCTGCCAGAGCCTGGGGCAAGGGGAGCACCAACAGGTGCTGCAG
GCCGTGGAGCTCCAGGGCTTGGGCCTCTCGTTCAGCGCCTGCTCCCTGGCCCTG
GACCAGGCCCAGCTTACACCCCTGCTGCGGGCCCTCAAGCTGCACACAGCACTC
CGGGAGCTGCGCCTGGCAGGGAACCGGCTGGGGGACAAGTGTGTGGCTGAGCT
GGTGGCTGCCCTGGGCACCATGCCCAGCCTGGCCCTCCTTGACCTCTCCTCCAAT
CACCTGGGTCCCGAAGGCCTGCGCCAGCTTGCCATGGGGCTCCCAGGCCAAGCC
ACCTTGCAGAGTTTGGAGgaattagatctatcgatgaACCCCCTGGGGGACGGCTGTGGCCA
GTCCCTGGCCTCCCTCCTGCACGCCTGCCCCTTACTCAGCACCCTGCGCCTGCAG
GCGTGTGGCTTCGGCCCCAGCTTCTTTCTGAGCCACCAGACAGCACTGGGTAGT
GCTTTCCAAGATGCTGAGCACCTGAAGACCCTGTCCCTGTCCTACAACGCCCTG
GGAGCCCCTGCCCTGGCCAGGACCCTGCAGAGCCTGCCCGCCGGCACCCTCCTG
CACTTAGAGCTCAGCTCCGTGGCAGCCGGCAAGGGTGATTCGGACCTCATGGAG
CCTGTATTCCGATACCTGGCCAAGGAAGGCTGTGCTCTAGCCCACCTGACCCTG
TCTGCAAACCACCTGGGGGACAAGGCTGTTAGAGACCTGTGCAGATGTCTCTCT
CTGTGCCCCTCACTCATCTCACTGGATCTGTCTGCCAACCCTGAGATCAGCTGTG
CCAGCTTGGAAGAGCTCCTGTCCACCCTCCAAAAGCGGCCCCAAGGCCTTAGCT
TCCTTGGCCTGTCAGGCTGCGCCGTCCAGGGTCCCCTGGGCCTGGGCCTGTGGG
ACAAGATAGCCGCGCAGCTCCGGGAACTGCAGCTGTGCAGCAGACGCCTCTGC
GCTGAGGACAGGGACGCCCTGCGCCAGCTGCAGCCCAGTCGGCCGGGCCCCGG
CGAGTGCACGCTGGACCACGGCTCCAAGCTCTTCTTTCGGCGCCTCTAG SEQ ID NO: 10 - TONSL E568A / GFP
atggtgagcaagggcgaggagctgttcaccggggtggtgcccatcctggtcgagctggacggcgacgtaaacggccacaagttca
gcgtgtccggcgagggcgagggcgatgccacctacggcaagctgaccctgaagttcatctgcaccaccggcaagctgcccgtgc
cctggcccaccctcgtgaccaccctgacctacggcgtgcagtgcttcagccgctaccccgaccacatgaagcagcacgacttcttca
agtccgccatgcccgaaggctacgtccaggagcgcaccatcttcttcaaggacgacggcaactacaagacccgcgccgaggtgaa
gttcgagggcgacaccctggtgaaccgcatcgagctgaagggcatcgacttcaaggaggacggcaacatcctggggcacaagct
ggagtacaactacaacagccacaacgtctatatcatggccgacaagcagaagaacggcatcaaggtgaacttcaagatccgccaca
acatcgaggacggcagcgtgcagctcgccgaccactaccagcagaacacccccatcggcgacggccccgtgctgctgcccgac
aaccactacctgagcacccagtccgccctgagcaaagaccccaacgagaagcgcgatcacatggtcctgctggagttcgtgaccg
ccgccaggatcactctcggcatggacgagagtacaaaggcgcgccaATGAGCCTGGAGCGCGAGCTTCG
CCAGCTGAGCAAGGCGAAAGCCAAGGCGCAGAGGGCCGGGCAGCGGCGCGAA
GAGGCCGCGCTGTGCCACCAGCTGGGGGAGCTCCTGGCCGGCCATGGCCGCTAC
GCCGAGGCTCTGGAGCAGCACTGGCAGGAGCTGCAGCTTCGGGAGCGCGCTGA
CGACCCTCTGGGCTGTGCCGTGGCCCACCGCAAGATCGGAGAGCGCCTGGCCGA
GATGGAGGACTACCCGGCTGCCTTGCAGCACCAGCACCAGTACCTGGAGCTGGC
ACATTCCCTGCGCAACCACACGGAGCTGCAGAGGGCCTGGGCCACCATCGGCCG
CACCCACCTGGACATCTATGACCACTGCCAGTCGAGGGATGCTTTGCTGCAGGC
ACAGGCTGCCTTTGAGAAGAGCTTGGCTATTGTGGATGAGGAGCTGGAGGGGA
CACTGGCCCAGGGAGAGCTGAATGAGATGAGGACCCGCCTCTATCTCAACCTGG
GCCTCACCTTTGAGAGCCTGCAGCAGACAGCCCTGTGCAACGATTACTTCAGGA
AGAGCATCTTCCTTGCGGAGCAGAACCACCTTTACGAGGACCTATTCCGCGCCC
GCTACAACCTGGGCACCATCCACTGGCGCGCGGGCCAGCACTCCCAGGCTATGC
GCTGCTTGGAGGGTGCCCGGGAGTGTGCGCACACCATGAGGAAGCGGTTCATG
GAGAGCGAGTGCTGCGTGGTTATTGCACAGGTCCTCCAAGACCTGGGAGACTTT
TTGGCTGCCAAGCGAGCCCTGAAGAAGGCCTACAGGCTGGGCTCCCAGAAGCCT
GTGCAGAGGGCAGCCATCTGTCAGAACCTCCAGCATGTGCTGGCAGTGGTCCGG
CTGCAGCAACAGCTGGAAGAGGCTGAGGGCAGAGACCCTCAGGGTGCCATGGT
CATCTGTGAGCAGCTAGGGGACCTCTTCTCCAAGGCAGGAGACTTTCCCAGGGC
AGCTGAGGCTTACCAGAAGCAGCTGCGTTTTGCTGAGCTGCTGGACAGACCGGG
TGCTGAGCGGGCCATCATCCACGTGTCCCTGGCCACCACACTGGGAGACATGAA
GGACCACCATGGGGCCGTGCGCCACTATGAGGAGGAACTGAGGCTGCGCAGCG
GCAACGTGCTGGAGGAGGCCAAGACCTGGCTGAACATTGCACTGTCCCGCGAG
GAGGCCGGCGATGCCTACGAGCTGCTGGCCCCGTGCTTCCAGAAAGCGCTCAGC
TGTGCCCAGCAGGCCCAGCGTCCCCAGCTGCAGAGGCAGGTCTTGCAGCATCTC
CATACCGTGCAGCTGAGGCTGCAGCCCCAGGAGGCCCCTGAGACCGAAACCAG
ACTGCGGGAGCTCAGTGTAGCTGAAGATGAAGATGAGGAGGAGGAGGCGGAGG
AGGCGGCAGCCACAGCGGAGAGCGAAGCCCTGGAGGCCGGCGAGGTGGAGCTC
TCAGAGGGCGAGGACGACACCGATGGCCTGACCCCGCAGCTGGAGGAGGACGA
GGAGCTTCAGGGCCACCTGGGCCGGCGGAAGGGGAGCAAGTGGAACCGGCGAA
ACGACATGGGGGAGACCCTGCTGCACCGAGCCTGCATCGAGGGCCAGCTGCGC
CGCGTCCAGGACCTTGTGAGGCAGGGCCACCCCCTTAACCCTCGGGACTACTGT
GGCTGGACACCTCTGCACGCGGCCTGCAACTACGGGCATCTAGAAATTGTCCGC
TTCCTGCTGGACCACGGGGCCGCAGTGGACGACCCAGGTGGCCAGGGCTGCGA
AGGCATCACCCCCCTCCACGATGCCCTCAACTGTGGCCACTTCGAGGTGGCTGA
GCTGCTGCTTGAACGGGGGGCGTCCGTCACCCTCCGCACTCGAAAGGGCCTCAG
CCCGCTGGAGACGCTGCAGCAGTGGGTGAAGCTGTACCGCAGGGACCTGGACC
TGGAGACGCGGCAGAAGGCCAGGGCCATGGAGATGCTGCTCCAGGCGGCTGCC
TCGGGCCAAGATCCCCACAGCTCCCAGGCCTTCCACACCCCAAGCAGCCTTCTG
TTTGACCCCGAGACCTCTCCTCCTTTGAGCCCCTGCCCAGAACCCCCCTCTAATA
GCACTAGACTCCCAGAGGCCTCTCAGGTCCATGTCAGGGTCTCCCCAGGGCAGG
CGGCACCAGCCATGGCCAGGCCTCGAGGAGCAGGCATGGGCCAGCCAGCAGC
AGCAGCAGCTCAGAAGGCGAGGACAGCGCAGGCCCCGCACGGCCGTCCCAGAA
GAGGCCTCGGTGCTCGGCCACAGCACAACGGGTGGCAGCCTGGACGCCTGGCC
CCGCCAGCAACAGGGAAGCAGCCACAGCCAGCACCAGCCGGGCAGCCTACCAG
GCAGCCATCCGGGGTGTGGGCAGTGCTCAGAGCCGGCTGGGGCCTGGCCCACC -continued

SEQUENCE DATA

GCGGGGCCACAGCAAAGCCCTTGCCCCCCAGGCAGCGCTCATCCCGGAGGAGG
AGTGCCTGGCTGGGGACTGGCTGGAGCTGGACATGCCCCTGACCCGCAGCCGCC
GGCCCCGCCCCCGGGGCACTGGAGACAACCGCAGGCCCAGTAGTACCTCTGGGT
CGGACAGTGAGGAGAGCAGGCCCCGTGCCCGAGCCAAGCAGGTCCGCCTGACC
TGCATGCAGAGTTGCAGTGCGCCAGTTAACGCAGGGCCCAGCAGCCTGGCTTCA
GAACCTCCAGGGAGCCCCAGCACCCCCAGGGTCTCAGAGCCCAGTGGGGACAG
CTCTGCGGCAGGCCAGCCCTTGGGTCCGGCCCCGCCCCCTCCCATCCGGGTTCG
AGTTCAAGTTCAGGATCATCTCTTCCTCATCCCTGTCCCACACAGCAGTGACACC
CACTCTGTGGCCTGGCTGGCCGAGCAGGCGGCCCAGCGCTACTACCAGACCTGC
GGGCTGCTGCCCAGGCTCACCCTACGGAAAGAGGGGGCCCTGCTGGCCCCACA
GGACCTCATCCCTGATGTGCTGCAGAGCAATGACGAGGTGTTGGCTGAGGTGAC
TTCGTGGGACCTGCCCCCGTTGACTGACCGCTACCGCAGGGCCTGCCAGAGCCT
GGGGCAAGGGGAGCACCAACAGGTGCTGCAGGCCGTGGAGCTCCAGGGCTTGG
GCCTCTCGTTCAGCGCCTGCTCCCTGGCCCTGGACCAGGCCCAGCTTACACCCCT
GCTGCGGGCCCTCAAGCTGCACACAGCACTCCGGGAGCTGCGCCTGGCAGGGA
ACCGGCTGGGGGACAAGTGTGTGGCTGAGCTGGTGGCTGCCCTGGGCACCATGC
CCAGCCTGGCCCTCCTTGACCTCTCCTCCAATCACCTGGGTCCCGAAGGCCTGCG
CCAGCTTGCCATGGGGCTCCCAGGCCAAGCCACCTTGCAGAGTTTGGAGgaattagat
ctatcgatgaACCCCCTGGGGGACGGCTGTGGCCAGTCCCTGGCCTCCCTCCTGCACG
CCTGCCCCTTACTCAGCACCCTGCGCCTGCAGGCGTGTGGCTTCGGCCCCAGCTT
CTTTCTGAGCCACCAGACAGCACTGGGTAGTGCTTTCCAAGATGCTGAGCACCT
GAAGACCCTGTCCCTGTCCTACAACGCCCTGGGAGCCCCTGCCCTGGCCAGGAC
CCTGCAGAGCCTGCCCGCCGGCACCCTCCTGCACTTAGAGCTCAGCTCCGTGGC
AGCCGGCAAGGGTGATTCGGACCTCATGGAGCCTGTATTCCGATACCTGGCCAA
GGAAGGCTGTGCTCTAGCCCACCTGACCCTGTCTGCAAACCACCTGGGGGACAA
GGCTGTTAGAGACCTGTGCAGATGTCTCTCTCTGTGCCCCTCACTCATCTCACTG
GATCTGTCTGCCAACCCTGAGATCAGCTGTGCCAGCTTGGAAGAGCTCCTGTCC
ACCCTCCAAAAGCGGCCCCAAGGCCTTAGCTTCCTTGGCCTGTCAGGCTGCGCC
GTCCAGGGTCCCCTGGGCCTGGGCCTGTGGGACAAGATAGCCGCGCAGCTCCGG
GAACTGCAGCTGTGCAGCAGACGCCTCTGCGCTGAGGACAGGGACGCCCTGCG
CCAGCTGCAGCCCAGTCGGCCGGGCCCCGGCGAGTGCACGCTGGACCACGGCTC
CAAGCTCTTCTTTCGGCGCCTCTAG SEQ ID NO: 11 - TONSL N571A
ATGAGCCTGGAGCGCGAGCTTCGCCAGCTGAGCAAGGCGAAAGCCAAGGCGCA
GAGGGCCGGGCAGCGGCGCGAAGAGGCCGCGCTGTGCCACCAGCTGGGGGAGC
TCCTGGCCGGCCATGGCCGCTACGCCGAGGCTCTGGAGCAGCACTGGCAGGAGC
TGCAGCTTCGGGAGCGCGCTGACGACCCTCTGGGCTGTGCCGTGGCCCACCGCA
AGATCGGAGAGCGCCTGGCCGAGATGGAGGACTACCCGGCTGCCTTGCAGCAC
CAGCACCAGTACCTGGAGCTGGCACATTCCCTGCGCAACCACACGGAGCTGCAG
AGGGCCTGGGCCACCATCGGCCGCACCCACCTGGACATCTATGACCACTGCCAG
TCGAGGGATGCTTTGCTGCAGGCACAGGCTGCCTTTGAGAAGAGCTTGGCTATT
GTGGATGAGGAGCTGGAGGGGACACTGGCCCAGGGAGAGCTGAATGAGATGAG
GACCCGCCTCTATCTCAACCTGGGCCTCACCTTTGAGAGCCTGCAGCAGACAGC
CCTGTGCAACGATTACTTCAGGAAGAGCATCTTCCTTGCGGAGCAGAACCACCT
TTACGAGGACCTATTCCGCGCCCGCTACAACCTGGGCACCATCCACTGGCGCGC
GGGCCAGCACTCCCAGGCTATGCGCTGCTTGGAGGGTGCCCGGGAGTGTGCGCA
CACCATGAGGAAGCGCTTTCATGGAGAGCGAGTGCTGCGTGGTTATTGCACAGGT
CCTCCAAGACCTGGGAGACTTTTTGGCTGCCAAGCGAGCCCTGAAGAAGGCCTA
CAGGCTGGGCTCCCAGAAGCCTGTGCAGAGGGCAGCCATCTGTCAGAACCTCCA
GCATGTGCTGGCAGTGGTCCGGCTGCAGCAACAGCTGGAAGAGGCTGAGGGCA
GAGACCCTCAGGGTGCCATGGTCATCTGTGAGCAGCTAGGGGACCTCTTCTCCA
AGGCAGGAGACTTTCCCAGGGCAGCTGAGGCTTACCAGAAGCAGCTGCGTTTTG
CTGAGCTGCTGGACAGACCGGGTGCTGAGCGGGCCATCATCCACGTGTCCCTGG
CCACCACACTGGGAGACATGAAGGACCACCATGGGGCCGTGCGCCACTATGAG
GAGGAACTGAGGCTGCGCAGCGGCAACGTGCTGGAGGAGGCCAAGACCTGGCT
GAACATTGCACTGTCCCGCGAGGAGGCCGGCGATGCCTACGAGCTGCTGGCCCC
GTGCTTCCAGAAAGCGCTCAGCTGTGCCCAGCAGGCCCAGCGTCCCCAGCTGCA
GAGGCAGGTCTTGCAGCATCTCCATACCGTGCACTCTGAGGCTGCAGCCCCAGGA
GGCCCCTGAGACCGAAACCAGACTGCGGGAGCTCAGTGTAGCTGAAGATGAAG
ATGAGGAGGAGGAGGCGGAGGAGGCGGCAGCCACAGCGGAGAGCGAAGCCCT
GGAGGCCGGCGAGGTGGAGCTCTCAGAGGGCGAGGACGACACCGATGGCCTGA
CCCCGCAGCTGGAGGAGGACGAGGAGCTTCAGGGCCACCTGGGCCGGCGGAAG
GGGAGCAAGTGGAACCGGCCTAAACGACATGGGGGAGACCCTGCTGCACCGAGC
CTGCATCGAGGGCCAGCTGCGCCGCGTCCAGGACCTTGTGAGGCAGGGCCACCC
CCTTAACCCTCGGGACTACTGTGGCTGGACACCTCTGCACGAGGCCTGCGCCTA
CGGGCATCTAGAAATTGTCCGCTTCCTGCTGGACCACGCTGGCCGCACTTGGACGA
CCCAGGTGGCCAGGGCTGCGAAGGCATCACCCCCCTCCACGATGCCCTCAACTG
TGGCCACTTCGAGGTGGCTGAGCTGCTGCTTGAACGGGGGGCGTCCGTCACCCT
CCGCACTCGAAAGGGCCTCAGCCCGCTGGAGACGCTGCAGCAGTGGGTGAAGC
TGTACCGCAGGGACCTGGACCTGGAGACGCGGCAGAAGGCCAGGGCCATGGAG
ATGCTGCTCCAGGCGGCTGCCTCGGGCCAAGATCCCCACAGCTCCCAGGCCTTC
CACACCCCAAGCAGCCTTCTGTTTGACCCCGAGACCTCTCCTCCTTTGAGCCCCT
GCCCAGAACCCCCCTCTAATAGCACTAGACTCCCAGAGGCCTCTCAGGTCCATG
TCAGGGTCTCCCCAGGGCAGGCGGCACCAGCCATGGCCAGGCCTCGGAGGAGC
AGGCATGGGCCAGCCAGCAGCAGCAGCAGCTCAGAAGGCGAGGACAGCGCAG
GCCCCGCACGGCCGTCCCAGAAGAGGCCTCGGTGCTCGGCCACAGCACAACGG -continued

| SEQUENCE DATA |
|---|
| GTGGCAGCCTGGACGCCTGGCCCCGCCAGCAACAGGGAAGCAGCCACAGCCAG<br>CACCAGCCGGGCAGCCTACCAGGCAGCCATCCGGGGTGTGGGCAGTGCTCAGA<br>GCCGGCTGGGGCCTGGCCCACCGCGCTGGCCACAGCAAAGCCCTTGCCCCCCAG<br>GCAGCGCTCATCCCGGAGGAGGAGTGCCTGGCTGGGGACTGGCTGGAGCTGGA<br>CATGCCCCTGACCCGCAGCCGCCGGCCCCGCCCCCGGGGCACTGGAGACAACCG<br>CAGGCCCAGTAGTACCTCTGGGTCGGACAGTGAGGAGACTCAGGCCCCCTTGCCC<br>GAGCCAAGCAGGTCCGCCTGACCTGCATGCAGAGTTGCAGTGCGCCAGTTAACG<br>CAGGGCCCAGCAGCCTGGCTTCAGAACCTCCAGGGAGCCCCAGCACCCCCAGG<br>GTCTCAGAGCCCAGTGGGGACAGCTCTGCGGCAGGCCAGCCCTTGGGTCCGGCC<br>CCGCCCCCTCCCATCCGGGTTCGAGTTCAAGTTCAGGATCATCTCTTCCTCATCC<br>CTGTCCCACACAGCAGTGACACCCACTCTGTGGCCTGGCTGGCCGAGCAGGCGG<br>CCCAGCGCTACTACCAGACCTGCGGGCTGCTGCCCAGGCTCACCCTACGGAAAG<br>AGGGGGCCCTGCTGGCCCCACAGGACCTCATCCCTGATGTGCTGCAGAGCAATG<br>ACGAGGTGTTGGCTGAGGTGACTTCGTGGGACCTGCCCCCGTTGACTGACCGCT<br>ACCGCAGGGCCTGCCAGAGCCTGGGGCAAGGGGAGCACCAACAGGTGCTGCAG<br>GCCGTGGAGCTCCAGGGCTTGGGCCTCTCGTTCAGCGCCTGCTCCCTGGCCCTG<br>GACCAGGCCCAGCTTACACCCCTGCTGCGGGCCCTCAAGCTGCACACAGCACTC<br>CGGGAGCTGCGCCTGGCAGGGAACCGGCTGGGGGACAAGTGTGTGGCTGAGCT<br>GGTGGCTGCCCTGGGCACCATGCCCAGCCTGGCCCTCCTTGACCTCTCCTCCAAT<br>CACCTGGGTCCCGAAGGCCTGCGCCAGCTTGCCATGGGGCTCCCAGGCCAAGCC<br>ACCTTGCAGAGTTTGGAGgaattagatctatcgatgaACCCCCTGGGGGACGGCTGTGGCCA<br>GTCCCTGGCCTCCCTCCTGCACGCCTGCCCCTTACTCAGCACCCTGCGCCTGCAG<br>GCGTGTGGCTTCGGCCCCAGCTTCTTTCTGAGCCACCAGACAGGACTGGGTAGT<br>GCTTTCCAAGATGCTGAGCACCTGAAGACCCTGTCCCTGTCCTACAACGCCCTG<br>GGAGCCCCTGCCCTGGCCAGGACCCTGCAGAGCCTGCCCGCCGGCACCCTCCTG<br>CACTTAGAGCTCAGCTCCGTGGCAGCCGGCAAGGGTGATTCGGACCTCATGGAG<br>CCTGTATTCCGATACCTGGCCAAGGAAGGCTGTGCTCTAGCCCACCTGACCCTG<br>TCTGCAAACCACCTGGGGGACAAGGCTGTTAGAGACCTGTGGAGATGTCTCTCT<br>CTGTGCCCCTCACTCATCTCACTGGATCTGTCTGCCAACCCTGAGATCAGCTGTG<br>CCAGCTTGGAAGAGCTCCTGTCCACCCTCCAAAAGCGGCCCCAAGGCCTTAGCT<br>TCCTTGGCCTGTCAGGCTGCGCCGTCCAGGGTCCCCTGGGCCTGGGCCTGTGGG<br>ACAAGATAGCCGCGCAGCTCCGGGAACTGCAGCTGTGCAGCAGACGCCTCTGC<br>GCTGAGGACAGGGACGCCCTGCGCCAGCTGCAGCCCAGTCGGCCGGGCCCCGG<br>CGAGTGCACGCTGGACCACGGCTCCAAGCTCTTCTTTCGGCGCCTCTAG |
| SEQ ID NO: 12 - TONSL N571A / GFP<br>atggtgagcaagggcgaggagctgttcaccggggtggtgcccatcctggtcgagctggacggcgacgtaaacggccacaagttca<br>gcgtgtccggcgagggcgagggcgatgccacctacggcaagctgaccctgaagttcatctgcaccaccggcaagctgcccgtgc<br>cctagcccaccctcgtgaccaccctgacctacggcgtacagtgcttcagccgctaccccgaccacatgaagcagcacaacttcttca<br>agtccgccatgcccgaaggctacgtccaggagcgcaccatcttcttcaaggacgacggcaactacaagacccgcgccgaggtgaa<br>gttcgagggcgacaccctggtgaaccgcatcgagctgaagggcatcgacttcaaggaggacggcaacatcctggggcacaagct<br>ggagtacaactacaacagccacaacgtctatatcatggccgacaagcagaagaacggcatcaaggtgaacttcaagatccgccaca<br>acatcgaggacggcagcgtgcagctcgccgaccactaccagcagaacacccccatcggcgacggccccgtgctgctgcccgac<br>aaccactacctgagcacccagtccgccctgagcaaagaccccaacgagaagcgcgatcacatggtcctgctggagttcgtgaccg<br>ccgccgggatcactctcggcatggacgagctgtacaagggcgcgccaATGAGCCTGGAGCGCGAGCTTCG<br>CCAGCTGAGCAAGGCGAAAGCCAAGGCGCAGAGGGCCGGGCAGCGGCGCGAA<br>GAGGCCGCGCTGTGCCACCAGCTGGGGGAGCTCCTGGCCGGCCATGGCCGCTAC<br>GCCGAGGCTCTGGAGCAGCACTGGCAGGAGCTGCAGCTTCGGGAGCGCGCTGA<br>CGACCCTCTGGGCTGTGCCGTGGCCCACCGCAAGATCGGAGAGCGCCTGGCCGA<br>GATGGAGGACTACCCGGCTGCCTTGCAGCACCAGCACCAGTACCTGGAGCTGGC<br>ACATTCCCTGCGCAACCACACGGAGCTGCAGAGGGCCTGGGCCACCATCGGCCG<br>CACCCACCTGGACATCTATGACCACTGCCAGTCGAGGGATGCTTTGCTGCAGGC<br>ACAGGCTGCCTTTGAGAAGAGCTTGGCTATTGTGGATGAGGAGCTGGAGGGGA<br>CACTGGCCCAGGGAGAGCTGAATGAGATGAGGACCCGCCTCTATCTCAACCTGG<br>GCCTCACCTTTGAGAGCCTGCAGCAGACAGCCCTGTGCAACGATTACTTCAGGA<br>AGAGCATCTTCCTTGCGGAGCAGAACCACCTTTACGAGGACCTATTCCGCGCCC<br>GCTACAACCTGGGCACCATCCACTGGCGCGCGGGCCAGCACTCCCAGGCTATGC<br>GCTGCTTGGAGGGTGCCCGGGAGTGTGCGCACACCATGAGGAAGCGGTTCATG<br>GAGAGCGAGTGCTGCGTGGTTATTGCACAGGTCCTCCAAGACCTGGGAGACTTT<br>TTGGCTGCCAAGCGAGCCCTGAAGAAGGCCTACAGGCTGGGCTCCCAGAAGCCT<br>GTGCAGAGGGCAGCCATCTGTCAGAACCTCCAGCATGTGCTGGCAGTGGTCCGG<br>CTGCAGCAACAGCTGGAAGAGGCTGAGGGCAGAGACCCTCAGGGTGCCATGGT<br>CATCTGTGAGCAGCTAGGGGACCTCTTCTCCAAGGCAGGAGACTTTCCCAGGGC<br>AGCTGAGGCTTACCAGAAGCAGCTGCGTTTTGCTGAGCTGCTGGACAGACCGGG<br>TGCTGAGCGGGCCATCATCCACGTGTCCCTGGCCACCACACTGGGAGACATGAA<br>GGACCACCATGGGGCCGTGCGCCACTATGAGGAGGAACTGAGGCTGCGCAGCG<br>GCAACGTGCTGGAGGAGGCCAAGACCTGGCTGAACATTGCACTGTCCCGCGAG<br>GAGGCCGGCGATGCCTACGAGCTGCTGGCCCCGTGCTTCCAGAAAGCGCTCAGC<br>TGTGCCCAGCAGGCCCAGCGTCCCCAGCTGCAGAGGCAGGTCTTGCAGCATCTC<br>CATACCGTGCAGCTGAGGCTGCAGCCCCAGGAGGCCCCTGAGACCGAAACCAG<br>ACTGCGGGAGCTCAGTGTAGCTGAAGATGAAGATGAGGAGGAGGAGGCGGAGG<br>AGGCGGCAGCCACAGCGGAGAGCGAAGCCCTGGAGGCCGGCGAGGTGGAGCTC<br>TCAGAGGGCGAGGACGACACCGATGGCCTGACCCCGCAGCTGGAGGAGGACGA<br>GGAGCTTCAGGGCCACCTGGGCCGGCGGAAGGGGAGCAAGTGGAACCGGCGAA<br>ACGACATGGGGGAGACCCTGCTGCACCGAGCCTGCATCGAGGGCCAGCTGCGC<br>CGCGTCCAGGACCTTGTGAGGCAGGGCCACCCCCTTAACCCTCGGGACTACTGT<br>GGCTGGACACCTCTGCACGAGGCCTGC**GCC**TACGGGCATCTAGAAATTGTCCGC |

-continued

SEQUENCE DATA

TTCCTGCTGGACCACGGGGCCGCAGTGGACGACCCAGGTGGCCAGGGCTGCGA
AGGCATCACCCCCCTCCACGATGCCCTCAACTGTGGCCACTTCGAGGTGGCTGA
GCTGCTGCTTGAACGGGGGGCGTCCGTCACCCTCCGCACTCGAAAGGGCCTCAG
CCCGCTGGAGACGCTGCAGCAGTGGGTGAAGCTGTACCGCAGGGACCTGGACC
TGGAGACGCGGCAGAAGGCCAGGGCCATGGAGATGCTGCTCCAGGCGGCTGCC
TCGGGCCAAGATCCCCACAGCTCCCAGGCCTTCCACACCCCAAGCAGCCTTCTG
TTTGACCCCGAGACCTCTCCTCCTTTGAGCCCCTGCCCAGAACCCCCCTCTAATA
GCACTAGACTCCCAGAGGCCTCTCAGGTCCATGTCAGGGTCTCCCCAGGGCAGG
CGGCACCAGCCATGGCCAGGCCTCGGAGGAGCAGGCATGGGCCAGCCAGCAGC
AGCAGCAGCTCAGAAGGCGAGGACAGCGCAGGCCCCGCACGGCCGTCCCAGAA
GAGGCCTCGGTGCTCGGCCACAGCACAACGGGTGGCAGCCTGGACGCCTGGCC
CCGCCAGCAACAGGGAAGCAGCCACAGCCAGCACCAGCCGGGCAGCCTACCAG
GCAGCCATCCGGGGTGTGGGCAGTGCTCAGAGCCGGCTGGGGCCTGGCCCACC
GCGGGGCCACAGCAAAGCCCTTGCCCCCCAGGCAGCGCTCATCCCGGAGGAGG
AGTGCCTGGCTGGGGACTGGCTGGAGCTGGACATGCCCCTGACCCGCAGCCGCC
GGCCCCGCCCCCGGGGCACTGGAGACAACCGCAGGCCCAGTAGTACCTCTGGGT
CGGACAGTGAGGAGAGCAGGCCCCGTGCCCGAGCCAAGCAGGTCCGCCTGACC
TGCATGCAGAGTTGCAGTGCGCCAGTTAACGCAGGGCCCAGCAGCCTGGCTTCA
GAACCTCCAGGGAGCCCCAGCACCCCCAGGGTCTCAGAGCCCAGTGGGGACAG
CTCTGCGGCAGGCCAGCCCTTGGGTCCGGCCCCGCCCCCTCCCATCCGGGTTCG
AGTTCAAGTTCAGGATCATCTCTTCCTCATCCCTGTCCCACACAGCACTTGACACC
CACTCTGTGGCCTGGCTGGCCGAGCAGGCGGCCCAGCGCTACTACCAGACCTGC
GGGCTGCTGCCCAGGCTCACCCTACGGAAAGAGGGGGCCCTGCTGGCCCCACA
GGACCTCATCCCTGATGTGCTGCAGAGCAATGACGAGGTGTTGGCTGAGGTGAC
TTCGTGGGACCTGCCCCCGTTGACTGACCGCTACCGCAGGGCCTGCCAGAGCCT
GGGGCAAGGGGAGCACCAACAGGTGCTGCAGGCCGTGGAGCTCCAGGGCTTGG
GCCTCTCGTTCAGCGCCTGCTCCCTGGCCCTGGACCAGGCCCAGCTTACACCCCT
GCTGCGGGCCCTCAAGCTGCACACAGCACTCCGGGAGCTGCGCCTGGCAGGGA
ACCGGCTGGGGGACAAGTGTGTGGCTGAGCTGGTGGCTGCCCTGGGCACCATGC
CCAGCCTGGCCCTCCTTGACCTCTCCTCCAATCACCTGGGTCCCGAAGGCCTGCG
CCAGCTTGCCATGGGGCTCCCAGGCCAAGCCACCTTGCAGAGTTTGGAGgaattagat
ctatcgatgaACCCCCTGGGGGACGGCTGTGGCCAGTCCCTGGCCTCCCTCCTGCACG
CCTGCCCCTTACTCAGCACCCTGCGCCTGCAGGCGTGTGGCTTCGGCCCCAGCTT
CTTTCTGAGCCACCAGACAGCACTGGGTAGTGCTTTCCAAGATGCTGAGCACCT
GAAGACCCTGTCCCTGTCCTACAACGCCCTGGGAGCCCCTGCCCTGGCCAGGAC
CCTGCAGAGCCTGCCCGCCGGCACCCTCCTGCACTTAGAGCTCAGCTCCGTGGC
AGCCGGCAAGGGTGATTCGGACCTCATGGAGCCTGTATTCCGATACCTGGCCAA
GGAAGGCTGTGCTCTAGCCCACCTGACCCTGTCTGCAAACCACCTGGGGGACAA
GGCTGTTAGAGACCTGTGCAGATGTCTCTCTCTGTGCCCCTCACTCATCTCACTG
GATCTGTCTGCCAACCCTGAGATCAGCTGTGCCAGCTTGGAAGAGCTCCTGTCC
ACCCTCCAAAAGCGGCCCCAAGGCCTTAGCTTCCTTGGCCTGTCAGGCTGCGCC
GTCCAGGGTCCCCTGGGCCTGGGCCTGTGGGACAAGATAGCCGCGCAGCTCCGG
GAACTGCAGCTGTGCAGCAGACGCCTCTGCGCTGAGGACAGGGACGCCCTGCG
CCAGCTGCAGCCCAGTCGGCCGGGCCCCGGCGAGTGCACGCTGGACCACGGCTC
CAAGCTCTTCTTTCGGCGCCTCTAG SEQ ID NO: 13 - TONSL D604/T
ATGAGCCTGGAGCGCGAGCTTCGCCAGCTGAGCAAGGCGAAAGCCAAGGCGCA
GAGGGCCGGGCAGCGGCGCGAAGAGGCCGCGCTGTGCCACCAGCTGGGGGAGC
TCCTGGCCGGCCATGGCCGCTACGCCGAGGCTCTGGAGCAGCACTGGCAGGAGC
TGCAGCTTCGGGAGCGCGCTGACGACCCTCTGGGCTGTGCCGTGGCCCACCGCA
AGATCGGAGAGCGCCTGGCCGAGATGGAGGACTACCCGGCTGCCTTGCAGCAC
CAGCACCAGTACCTGGAGCTGGCACATTCCCTGCGCAACCACACGGAGCTGCAG
AGGGCCTGGGCCACCATCGGCCGCACCCACCTGGACATCTATGACCACTGCCAG
TCGAGGGATGCTTTGCTGCAGGCACAGGCTGCCTTTGAGAAGAGCTTGGCTATT
GTGGATGAGGAGCTGGAGGGGACACTGGCCCAGGGAGAGCTGAATGAGATGAG
GACCCGCCTCTATCTCAACCTGGGCCTCACCTTTGAGAGCCTGCAGCAGACAGC
CCTGTGCAACGATTACTTCAGGAAGAGCATCTTCCTTGCGGAGCAGAACCACCT
TTACGAGGACCTATTCCGCGCCCGCTACAACCTGGGCACCATCCACTGGCGCGC
GGGCCAGCACTCCCAGGCTATGCGCTGCTTGGAGGGTGCCCGGGAGTGTGCGCA
CACCATGAGGAAGCGCTTTCATGGAGAGCGAGTGCTGCGTGGTTATTGCACAGGT
CCTCCAAGACCTGGGAGACTTTTTGGCTGCCAAGCGAGCCCTGAAGAAGGCCTA
CAGGCTGGGCTCCCAGAAGCCTGTGCAGAGGGCAGCCATCTGTCAGAACCTCCA
GCATGTGCTGGCAGTGGTCCGGCTGCAGCAACAGCTGGAAGAGGCTGAGGGCA
GAGACCCTCAGGGTGCCATGGTCATCTGTGAGCAGCTAGGGGACCTCTTCTCCA
AGGCAGGAGACTTTCCCAGGGCAGCTGAGGCTTACCAGAAGCAGCTGCGTTTTG
CTGAGCTGCTGGACAGACCGGGTGCTGAGCGGGCCATCATCCACGTGTCCCTGG
CCACCACACTGGGAGACATGAAGGACCACCATGGGGCCGTGCGCCACTATGAG
GAGGAACTGAGGCTGCGCAGCGGCAACGTGCTGGAGGAGGCCAAGACCTGGCT
GAACATTGCACTGTCCCGCGAGGAGGCCGGCGATGCCTACGAGCTGCTGGCCCC
GTGCTTCCAGAAAGCGCTCAGCTGTGCCCAGCAGGCCCAGCGTCCCCAGCTGCA
GAGGCAGGTCTTGCAGCATCTCCATACCGTGCAGCTGAGGCTGCAGCCCCAGGA
GGCCCCTGAGACCGAAACCAGACTGCGGGAGCTCAGTGTAGCTGAAGATGAAG
ATGAGGAGGAGGAGGCGGAGGAGGCGGCAGCCACAGCGGAGAGCGAAGCCCT
GGAGGCCGGCGAGGTGGAGCTCTCAGAGGGCGAGGACGACACCGATGGCCTGA
CCCCGCAGCTGGAGGAGGACGAGGAGCTTCAGGGCCACCTGGGCCGGCGGAAG
GGGAGCAAGTGGAACCGGCGAAACGACATGGGGGAGACCCTGCTGCACCGAGC -continued

| SEQUENCE DATA |
| --- |
| CTGCATCGAGGGCCAGCTGCGCCGCGTCCAGGACCTTGTGAGGCAGGGCCACCC<br>CCTTAACCCTCGGGACTACTGTGGCTGGACACCTCTGCACGAGGCCTGCAACTA<br>CGGGCATCTAGAAATTGTCCGCTTCCTGCTGGACCACGGGGCCGCAGTGGACGA<br>CCCAGGTGGCCAGGGCTGCGAAGGCATCACCCCCCTCCAC**GCT**GCCCTCAACTG<br>TGGCCACTTCGAGGTGGCTGAGCTGCTGCTTGAACGGGGGGCGTCCGTCACCCT<br>CCGCACTCGAAAGGGCCTCAGCCCGCTGGAGACGCTGCAGCAGTGGGTGAAGC<br>TGTACCGCAGGGACCTGGACCTGGAGACGCGGCAGAAGGCCAGGGCCATGGAG<br>ATGCTGCTCCAGGCGGCTGCCTCGGGCCAAGATCCCCACAGCTCCCAGGCCTTC<br>CACACCCCAAGCAGCCTTCTGTTTGACCCCGAGACCTCTCCTCCTTTGAGCCCCT<br>GCCCAGAACCCCCCTCTAATAGCACTAGACTCCCAGAGGCCTCTCAGGTCCATG<br>TCAGGGTCTCCCCAGGGCAGGCGGCACCAGCCATGGCCAGGCCTCGGAGGAGC<br>AGGCATGGGCCAGCCAGCAGCAGCAGCAGCTCAGAAGGCGAGGACAGCGCAG<br>GCCCCGCACGGCCGTCCCAGAAGAGGCCTCGGTGCTCGGCCACAGCACAACGG<br>GTGGCAGCCTGGACGCCTGGCCCCGCCAGCAACAGGGAAGCAGCCACAGCCAG<br>CACCAGCCGGGCAGCCTACCAGGCAGCCATCCGGGGTGTGGGCAGTGCTCAGA<br>GCCGGCTGGGGCCTGGCCCACCGCGGGGCCACAGCAAAGCCCTTGCCCCCCAG<br>GCAGCGCTCATCCCGGAGGAGGAGTGCCTGGCTGGGGACTGGCTGGAGCTGGA<br>CATGCCCCTGACCCGCAGCCGCCGGCCCCGCCCCCGGGGCACTGGAGACAACCG<br>CAGGCCCAGTAGTACCTCTGGGTCGGACAGTGAGGAGAGCAGGCCCCGTGCCC<br>GAGCCAAGCAGGTCCGCCTGACCTGCATGCAGAGTTGCAGTGCGCCAGTTAACG<br>CAGGGCCCAGCAGCCTGGCTTCAGAACCTCCAGGGAGCCCCAGCACCCCCAGG<br>GTCTCAGAGCCCAGTGGGGACAGCTCTGCGGCAGGCCAGCCCTTGGGTCCGGCC<br>CCGCCCCCTCCCATCCGGGTTCGAGTTCAAGTTCAGGATCATCTCTTCCTCATCC<br>CTGTCCCACACAGCAGTGACACCCACTCTGTGGCCTGGCTGGCCGAGCAGGCGG<br>CCCAGCGCTACTACCAGACCTGCGGGCTGCTGCCCAGGCTCACCCTACGGAAAG<br>AGGGGGCCCTGCTGGCCCCACAGGACCTCATCCCTGATGTGCTGCAGAGCAATG<br>ACGAGGTGTTGGCTGAGGTGACTTCGTGGGACCTGCCCCCGTTGACTGACCGCT<br>ACCGCAGGGCCTGCCAGAGCCTGGGGCAAGGGGAGCACCAACAGGTGCTGCAG<br>GCCGTGGAGCTCCAGGGCTTGGGCCTCTCGTTCAGCGCCTGCTCCCTGGCCCTG<br>GACCAGGCCCAGCTTACACCCCTGCTGCGGGCCCTCAAGCTGCACACAGCACTC<br>CGGGAGCTGCGCCTGGCAGGGAACCGGCTGGGGGACAAGTGTGTGGCTGAGCT<br>GGTGGCTGCCCTGGGCACCATGCCCAGCCTGGCCCTCCTTGACCTCTCCTCCAAT<br>CACCTGGGTCCCGAAGGCCTGCGCCAGCTTGCCATGGGGCTCCCAGGCCAAGCC<br>ACCTTGCAGAGTTTGGAGgaattagatctatcgatgaACCCCCTGGGGGACGGCTGTGGCCA<br>GTCCCTGGCCTCCCTCCTGCACGCCTGCCCCTTACTCAGCACCCTGCGCCTGCAG<br>GCGTGTGGCTTCGGCCCCAGCTTCTTTCTGAGCCACCAGACAGCACTGGGTAGT<br>GCTTTCCAAGATGCTGAGCACCTGAAGACCCTGTCCCTGTCCTACAACGCCCTG<br>GGAGCCCCTGCCCTGGCCAGGACCCTGCAGAGCCTGCCCGCCGGCACCCTCCTG<br>CACTTAGAGCTCAGCTCCGTGGCAGCCGGCAAGGGTGATTCGGACCTCATGGAG<br>CCTGTATTCCGATACCTGGCCAAGGAAGGCTGTGCTCTAGCCCACCTGACCCTG<br>TCTGCAAACCACCTGGGGGACAAGGCTGTTAGAGACCTGTGCAGATGTCTCTCT<br>CTGTGCCCCTCACTCATCTCACTGGATCTGTCTGCCAACCCTGAGATCAGCTGTG<br>CCAGCTTGGAAGAGCTCCTGTCCACCCTCCAAAAGCGGCCCCAAGGCCTTAGCT<br>TCCTTGGCCTGTCAGGCTGCGCCGTCCAGGGTCCCCTGGGCCTGGGCCTGTGGG<br>ACAAGATAGCCGCGCAGCTCCGGGAACTGCAGCTGTGCAGCAGACGCCTCTGC<br>GCTGAGGACAGGGACGCCCTGCGCCAGCTGCAGCCCAGTCGGCCGGGCCCCGG<br>CGAGTGCACGCTGGACCACGGCTCCAAGCTCTTCTTTCGGCGCCTCTAG |
| SEQ ID NO: 14 - TONSL D604A / GFP<br>atggtgagcaagggcgaggagctgttcaccggggtggtgcccatcctggtcgagctggacggcgacgtaaacggccacaagttca<br>gcgtgtccggcgagggcgagggcgatgccacctacggcaagctgaccctgaagttcatctgcaccaccggcaagctgcccgtgc<br>cctggcccaccctcgtgaccaccctgacctacggcgtgcagtgcttcagccgctaccccgaccacatgaagcagcacgacttcttca<br>agtccgccatgcccgaaggctacgtccaggagcgcaccatcttcttcaaggacgacggcaactacaagacccgcgccgaggtgaa<br>gttcgagggcgacaccctggtgaaccgcatcgagctgaagggcatcgacttcaaggaggacggcaacatcctggggcacaagct<br>ggagtacaactacaacagccacaacgtctatatcatggccgacaagcagaagaacggcatcaaggtgaacttcaagatccgccaca<br>acatcgaggacggcagcgtgcagctcgccgaccactaccagcagaacacccccatcggcgacggccccgtgctgctgcccgac<br>aaccactacctgagcacccagtccgccctgagcaaagaccccaacgagaagcgcgatcacatggtcctgctggagttcgtgaccg<br>ccgccgggatcactctcggcatggacgagagtacaagggcgcgccaATGAGCCTGGAGCGCGAGCTTCG<br>CCAGCTGAGCAAGGCGAAAGCCAAGGCGCAGAGGGCCGGGCAGCGGCGCGAA<br>GAGGCCGCGCTGTGCCACCAGCTGGGGGAGCTCCTGGCCGGCCATGGCCGCTAC<br>GCCGAGGCTCTGGAGCAGCACTGGCAGGAGCTGCAGCTTCGGGAGCGCGCTGA<br>CGACCCTCTGGGCTGTGCCGTGGCCCACCGCAAGATCGGAGAGCGCCTGGCCGA<br>GATGGAGGACTACCCGGCTGCCTTGCAGCACCAGCACCAGTACCTGGAGCTGGC<br>ACATTCCCTGCGCAACCACACGGAGCTGCAGAGGGCCTGGGCCACCATCGGCCG<br>CACCCACCTGGACATCTATGACCACTGCCAGTCGAGGGATGCTTTGCTGCAGGC<br>ACAGGCTGCCTTTGAGAAGAGCTTGGCTATTGTGGATGAGGAGCTGGAGGGGA<br>CACTGGCCCAGGGAGAGCTGAATGAGATGAGGACCCGCCTCTATCTCAACCTGG<br>GCCTCACCTTTGAGAGCCTGCAGCAGACAGCCCTGTGCAACGATTACTTCAGGA<br>AGAGCATCTTCCTTGCGGAGCAGAACCACCTTTACGAGGACCTATTCCGCGCCC<br>GCTACAACCTGGGCACCATCCACTGGCGCGCGGGCCAGCACTCCCAGGCTATGC<br>GCTGCTTGGAGGGTGCCCGGGAGTGTGCGCACACCATGAGGAAGCGGTTCATG<br>GAGAGCGAGTGCTGCGTGGTTATTGCACAGGTCCTCCAAGACCTGGGAGACTTT<br>TTGGCTGCCAAGCGAGCCCTGAAGAAGGCCTACAGGCTGGGCTCCCAGAAGCCT<br>GTGCAGAGGGCAGCCATCTGTCAGAACCTCCAGCATGTGCTGGCAGTGGTCCGG<br>CTGCAGCAACAGCTGGAAGAGGCTGAGGGCAGAGACCCTCAGGGTGCCATGGT<br>CATCTGTGAGCAGCTAGGGGACCTCTTCTCCAAGGCAGGAGACTTTCCCAGGGC<br>AGCTGAGGCTTACCAGAAGCAGCTGCGTTTTGCTGAGCTGCTGGACAGACCGGG |

-continued

SEQUENCE DATA

TGCTGAGCGGGCCATCATCCACGTGTCCCTGGCCACCACACTGGGAGACATGAA
GGACCACCATGGGGCCGTGCGCCACTATGAGGAGGAACTGAGGCTGCGCAGCG
GCAACGTGCTGGAGGAGGCCAAGACCTGGCTGAACATTGCACTGTCCCGCGAG
GAGGCCGGCGATGCCTACGAGCTGCTGGCCCCGTGCTTCCAGAAAGCGCTCAGC
TGTGCCCAGCAGGCCCAGCGTCCCCAGCTGCAGAGGCAGGTCTTGCAGCATCTC
CATACCGTGCAGCTGAGGCTGCAGCCCCAGGAGGCCCCTGAGACCGAAACCAG
ACTGCGGGAGCTCAGTGTAGCTGAAGATGAAGATGAGGAGGAGGAGGCGGAGG
AGGCGGCAGCCACAGCGGAGAGCGAAGCCCTGGAGGCCGGCGAGGTGGAGCTC
TCAGAGGGCGAGGACGACACCGATGGCCTGACCCCGCAGCTGGAGGAGGACGA
GGAGCTTCAGGGCCACCTGGGCCGGCGGAAGGGGAGCAAGTGGAACCGGCGAA
ACGACATGGGGGAGACCCTGCTGCACCGAGCCTGCATCGAGGGCCAGCTGCGC
CGCGTCCAGGACCTTGTGAGGCAGGGCCACCCCCTTAACCCTCGGGACTACTGT
GGCTGGACACCTCTGCACGAGGCCTGCAACTACGGGCATCTAGAAATTGTCCGC
TTCCTGCTGGACCACGGGGCCGCAGTGGACGACCCAGGTGGCCAGGGCTGCGA
AGGCATCACCCCCCTCCACGCTGCCCTCAACTGTGGCCACTTCGAGGTGGCTGA
GCTGCTGCTTGAACGGGGGGCGTCCGTCACCCTCCGCACTCGAAAGGGCCTCAG
CCCGCTGGAGACGCTGCAGCAGTGGGTGAAGCTGTACCGCAGGGACCTGGACC
TGGAGACGCGGCAGAAGGCCAGGGCCATGGAGATGCTGCTCCAGGCGGCTGCC
TCGGGCCAAGATCCCCACAGCTCCCAGGCCTTCCACACCCCAAGCAGCCTTCTG
TTTGACCCCGAGACCTCTCCTCCTTTGAGCCCCTGCCCAGAACCCCCCTCTAATA
GCACTAGACTCCCAGAGGCCTCTCAGGTCCATGTCAGGGTCTCCCCAGGGCAGG
CGGCACCAGCCATGGCCAGGCCTCGGAGGAGCAGGCATGGGCCAGCCAGCAGC
AGCAGCAGCTCAGAAGGCGAGGACAGCGCAGGCCCCGCACGGCCGTCCCAGAA
GAGGCCTCGGTGCTCGGCCACAGCACAACGGGTGGCAGCCTGGACGCCTGGCC
CCGCCAGCAACAGGGAAGCAGCCACAGCCAGCACCAGCCGGGCAGCCTACCAG
GCAGCCATCCGGGGTGTGGGCAGTGCTCAGAGCCGGCTGGGGCCTGGCCCACC
GCGGGGCCACAGCAAAGCCCTTGCCCCCCAGGCAGCGCTCATCCCGGAGGAGG
AGTGCCTGGCTGGGGACTGGCTGGAGCTGGACATGCCCCTGACCCGCAGCCGCC
GGCCCCGCCCCCGGGGCACTGGAGACAACCGCAGGCCCAGTAGTACCTCTGGGT
CGGACAGTGAGGAGAGCAGGCCCCGTGCCCGAGCCAAGCAGGTCCGCCTGACC
TGCATGCAGAGTTGCAGTGCGCCAGTTAACGCAGGGCCCAGCAGCCTGGCTTCA
GAACCTCCAGGGAGCCCCAGCACCCCCAGGGTCTCAGAGCCCAGTGGGGACAG
CTCTGCGGCAGGCCAGCCCTTGGGTCCGGCCCCGCCCCCTCCCATCCGGGTTCG
AGTTCAAGTTCAGGATCATCTCTTCCTCATCCCTGTCCCACACAGCAGTGACACC
CACTCTGTGGCCTGGCTGGCCGAGCAGGCGGCCCAGCGCTACTACCAGACCTGC
GGGCTGCTGCCCAGGCTCACCCTACGGAAAGAGGGGGCCCTGCTGGCCCCACA
GGACCTCATCCCTGATGTGCTGCAGAGCAATGACGAGGTGTTGGCTGAGGTGAC
TTCGTGGGACCTGCCCCCGTTGACTGACCGCTACCGCAGGGCCTGCCAGAGCCT
GGGGCAAGGGGAGCACCAACAGGTGCTGCAGGCCGTGGAGCTCCAGGGCTTGG
GCCTCTCGTTCAGCGCCTGCTCCCTGGCCCTGGACCAGGCCCAGCTTACACCCCT
GCTGCGGGCCCTCAAGCTGCACACAGCACTCCGGGAGCTGCGCCTGGCAGGGA
ACCGGCTGGGGGACAAGTGTGTGGCTGAGCTGGTGGCTGCCCTGGGCACCATGC
CCAGCCTGGCCCTCCTTGACCTCTCCTCCAATCACCTGGGTCCCGAAGGCCTGCG
CCAGCTTGCCATGGGGCTCCCAGGCCAAGCCACCTTGCAGAGTTTGGAGgaattagat
ctatcgatgaACCCCCTGGGGGACGGCTGTGGCCAGTCCCTGGCCTCCCTCCTGCACG
CCTGCCCCTTACTCAGCACCCTGCGCCTGCAGGCGTGTGGCTTCGGCCCCAGCTT
CTTTCTGAGCCACCAGACAGCACTGGGTAGTGCTTTCCAAGATGCTGAGCACCT
GAAGACCCTGTCCCTGTCCTACAACGCCCTGGGAGCCCCTGCCCTGGCCAGGAC
CCTGCAGAGCCTGCCCGCCGGCACCCTCCTGCACTTAGAGCTCAGCTCCGTGGC
AGCCGGCAAGGGTGATTCGGACCTCATGGAGCCTGTATTCCGATACCTGGCCAA
GGAAGGCTGTGCTCTAGCCCACCTGACCCTGTCTGCAAACCACCTGGGGGACAA
GGCTGTTAGAGACCTGTGCAGATGTCTCTCTCTGTGCCCCTCACTCATCTCACTG
GATCTGTCTGCCAACCCTGAGATCAGCTGTGCCAGCTTGGAAGAGCTCCTGTCC
ACCCTCCAAAAGCGGCCCCAAGGCCTTAGCTTCCTTGGCCTGTCAGGCTGCGCC
GTCCAGGGTCCCCTGGGCCTGGGCCTGTGGGACAAGATAGCCGCGCAGCTCCGG
GAACTGCAGCTGTGCAGCAGACGCCTCTGCGCTGAGGACAGGGACGCCCTGCG
CCAGCTGCAGCCCAGTCGGCCGGGCCCCGGCGAGTGCACGCTGGACCACGGCTC
CAAGCTCTTCTTTCGGCGCCTCTAG SEQ ID NO: 15 - TONSL FUSION (MCM2 HBD - TONSL ARD)
GGATCCGGGCCCCTGGAGGAAGAAGAGGATGGAGAGGAGCTCATTGGAGATGG
CATGGAAAGGGACTACCGCGCCATCCCAGAGCTGGACGCCTATGAGGCCGAGG
GACTGGCTCTGGATGATGAGGACGTAGAGGAGCTGACGGCCAGTCAGAGGGAG
GCAGCAGAGCGGGCCATGCGGCAGCGTGACCGGGAGGCTGGCCGGGGCCTGGG
CCGAGGAGGTGGAGGTGGCCACCTGGGCCGGCGGAAGGGGAGCAAGTGGAACC
GGCGAAACGACATGGGGGAGACCCTGCTGCACCGAGCCTGCATCGAGGGCCAG
CTGCGCCGCGTCCAGGACCTTGTGAGGCAGGGCCACCCCCTTAACCCTCGGGAC
TACTGTGGCTGGACACCTCTGCACGAGGCCTGCAACTACGGGCATCTAGAAATT
GTCCGCTTCCTGCTGGACCACGGGGCCGCAGTGGACGACCCAGGTGGCCAGGGC
TGCGAAGGCATCACCCCCCTCCACGATGCCCTCAACTGTGGCCACTTCGAGGTG
GCTGAGCTGCTGCTTGAACGGGGGGCGTCCGTCACCCTCCGCACTCGAAAGGGC
CTCAGCCCGCTGGAGACGCTGCAGCAGTGGGTGAAGCTGTACCGCAGGGACCT
GGACCTGGAGACGCGGCAGAAGGCCAGGGCCATGGAGATGCTGCTCCAGGCGG
CTGCCTCGGGCCAAGATCCCCACAGCTCCX:AGGCCTTCCACACCCCAAGCAGCC
TTCTGTTTGACCCCGAGACCTCTTAACTCGAG SEQ ID NO: 16 - TONSL wild-type (amino acids mutated in single-mutants are highlighted)

| SEQUENCE DATA |
| --- |

>gi|187608777|ref|NP_038460.4| tonsoku-like protein [Homo sapiens]
MSLERELRQLSKAKAKAQRAGQRREEAALCHQLGELLAGHGRYAEALEQHWQEL
QLRERADDPLGCAVAHRKIGERLAEMEDYPAALQHQHQYLELAHSLRNHTELQRA
WATIGRTHLDIYDHCQSRDALLQAQAAFEKSLAWDEELEGTLAQGELNEMRTRLY
LNLGLTFESLQQTALCNDYFRKSIFLAEQNHLYEDLFRARYNLGTIHWRAGQHSQA
MRCLEGARECAHTMRKRFMESECCVVIAQVLQDLGDFLAAKRALKKAYRLGSQK
PVQRAAICQNLQHVLAVVRLQQQLEEAEGRDPQGAMVICEQLGDLFSKAGDFPRA
AEAYQKQLRFAELLDRPGAERAIIHVSLATTLGDMKDHHGAVRHYEEELRLRSGNV
LEEAKTWLNIALSREEAGDAYELLAPCFQKALSCAQQAQRPQLQRQVLQHLHTVQ
LRLQPQEAPETETRLRELSVAEDEDEEEEAEEAAATAESEALEAGEVELSEGEDDTD
GLTPQLEEDEELQGHLGRRKGSKWNRRNDMGETLLHRACIEGQLRRVQDLVRQGH
PLNPRDYCGWTPLHEACNYGHLEIVRFLLDHGAAVDDPGGQGCEGITPLHD**ALNC
GHFEVAELLLERGASVTLRTRKGLSPLETLQQWVKLYRRDLDLETRQKARAMEML
LQAAASGQDPHSSQAFHTPSSLLFDPETSPPLSPCPEPPSNSTRLPEASQAHVRVSPG
QAAPAMARPRRSRHGPASSSSSSEGEDSAGPARPSQKRPRCSATAQRVAAWTPGPA
SNREAATASTSRAAYQAAIRGVGSAQSRLGPGPPRGHSKALAPQAALIPEEECLAGD
WLELDMPLTRSRRPRPRGTGDNRRPSSTSGSDSEESRPRARAKQVRLTCMQSCSAP
VNAGPSSLASEPPGSPSTPRVSEPSGDSSAAGQPLGPAPPPPIRVRVQVQDHLFLIPVP
HSSDTHSVAWLAEQAAQRYYQTCGLLPRLTLRKEGALLAPQDLIPDVLQSNDEVLA
EVTSWDLPPLTDRYRRACQSLGQGEHQQVLQAVELQGLGLSFSACSLALDQAQLTP
LLRALKLHTALRELRLAGNRLGDKCVAELVAALGTMPSLALLDLSSNHLGPEGLRQ
LAMGLPGQATLQSLEELDLSMNPLGDGCGQSLASLLHACPLLSTLRLQACGFGPSFF
LSHQTALGSAFQDAEHLKTLSLSYNALGAPALARTLQSLPAGTLLHLELSSVAAGK
GDSDLMEPVFRYLAKEGCALAHLTLSANHLGDKAVRDLCRCLSLCPSLISLDLSAN
PEISCASLEELLSTLQKRPQGLSFLGLSGCAVQGPLGLGLWDKIAAQLRELQLCSRRL
CAEDRDALRQLQPSRPGPGECTLDHGSKLFFRRL SEQ ID NO: 17 - Protein sequences of TONSL E530A single mutants (mutated alanins are highlighted)
MSLERELRQLSKAKAKAQRAGQRREEAALCHQLGELLAGHGRYAEALEQHWQEL
QLRERADDPLGCAVAHRKIGERLAEMEDYPAALQHQHQYLELAHSLRNHTELQRA
WATIGRTHLDIYDHCQSRDALLQAQAAFEKSLAIVDEELEGTLAQGELNEMRTRLY
LNLGLTFESLQQTALCNDYFRKSIFLAEQNHLYEDLFRARYNLGTIHWRAGQHSQA
MRCLEGARECAHTMRKRFMESECCVVIAQVLQDLGDFLAAKRALKKAYRLGSQK
PVQRAAICQNLQHVLAVVRLQQQLEEAEGRDPQGAMVICEQLGDLFSKAGDFPRA
AEAYQKQLRFAELLDRPGAERAIIHVSLATTLGDMKDHHGAVRHYEEELRLRSGNV
LEEAKTWLNIALSREEAGDAYELLAPCFQKALSCAQQAQRPQLQRQVLQHLHTVQ
LRLQPQEAPETETRLRELSVAEDEDEEEEAEEAAATAESEALEAGEVELSEGEDDTD
GLTPQLEEDEELQGHLGRRKGSKWNRRNDMGATLLHRACIEGQLRRVQDLVRQG
HPLNPRDYCGWTPLHEACNYGHLEIVRFLLDHGAAVDDPGGQGCEGITPLHDALN
CGHFEVAELLLERGASVTLRTRKGLSPLETLQQWVKLYRRDLDLETRQKARAMEM
LLQAAASGQDPHSSQAFHTPSSLLFDPETSPPLSPCPEPPSNSTRLPEASQAHVRVSPG
QAAPAMARPRRSRHGPASSSSSSEGEDSAGPARPSQKRPRCSATAQRVAAWTPGPA
SNREAATASTSRAAYQAAIRGVGSAQSRLGPGPPRGHSKALAPQAALIPEEECLAGD
WLELDMPLTRSRRPRPRGTGDNRRPSSTSGSDSEESRPRARAKQVRLTCMQSCSAP
VNAGPSSLASEPPGSPSTPRVSEPSGDSSAAGQPLGPAPPPPIRVRVQVQDHLFLIPVP
HSSDTHSVAWLAEQAAQRYYQTCGLLPRLTLRKEGALLAPQDLIPDVLQSNDEVLA
EVTSWDLPPLTDRYRRACQSLGQGEHQQVLQAVELQGLGLSFSACSLALDQAQLTP
LLRALKLHTALRELRLAGNRLGDKCVAELVAALGTMPSLALLDLSSNHLGPEGLRQ
LAMGLPGQATLQSLEELDLSMNPLGDGCGQSLASLLHACPLLSTLRLQACGFGPSFF
LSHQTALGSAMDAEHLKILSLSYNALGAPALARTLQSLPAGTLLHLELSSVAAGK
GDSDLMEPVFRYLAKEGCALAHLTLSANHLGDKAVRDLCRCLSLCPSLISLDLSAN
PEISCASLEELLSTLQKRPQGLSFLGLSGCAVQGPLGLGLWDKIAAQLRELQLCSRRL
CAEDRDALRQLQPSRPGPGECTLDHGSKLFFRRL SEQ ID NO: 18 - Protein sequences of TONSL D559A
MSLERELRQLSKAKAKAQRAGQRREEAALCHQLGELLAGHGRYAEALEQHWQEL
QLRERADDPLGCAVAHRKIGERLAEMEDYPAALQHQHQYLELAHSLRNHTELQRA
WATIGRTHLDIYDHCQSRDALLQAQAAFEKSLAIVDEELEGTLAQGELNEMRTRLY
LNLGLTFESLQQTALCNDYFRKSIFLAEQNHLYEDLFRARYNLGTIHWRAGQHSQA
MRCLEGARECAHTMRKRFMESECCVVIAQVLQDLGDFLAAKRALKKAYRLGSQK
PVQRAAICQNLQHVLAVVRLQQQLEEAEGRDPQGAMVICEQLGDLFSKAGDFPRA
AEAYQKQLRFAELLDRPGAERAIIHVSLATTLGDMKDHHGAVRHYEEELRLRSGNV
LEEAKTWLNIALSREEAGDAYELLAPCFQKALSCAQQAQRPQLQRQVLQHLHTVQ
LRLQPQEAPETETRLRELSVAEDEDEEEEAEEAAATAESEALEAGEVELSEGEDDTD
GLTPQLEEDEELQGHLGRRKGSKWNRRNDMGETLLHRACIEGQLRRVQDLVRQGH
PLNPRAYCGWTPLHEACNYGHLEIVRFLLDHGAAVDDPGGQGCEGITPLHDALNC
GHFEVAELLLERGASVTLRTRKGLSPLETLQQWVKLYRRDLDLETRQKARAMEML
LQAAASGQDPHSSQAFHTPSSLLFDPETSPPLSPCPEPPSNSTRLPEASQAHVRVSPG
QAAPAMARPRRSRHGPASSSSSSEGEDSAGPARPSQKRPRCSATAQRVAAWTPGPA
SNREAATASTSRAAYQAAIRGVGSAQSRLGPGPPRGHSKALAPQAALIPEEECLAGD
WLELDMPLTRSRRPRPRGTGDNRRPSSTSGSDSEESRPRARAKQVRLTCMQSCSAP
VNAGPSSLASEPPGSPSTPRVSEPSGDSSAAGQPLGPAPPPPIRVRVQVQDHLFLIPVP
HSSDTHSVAWLAEQAAQRYYQTCGLLPRLTLRKEGALLAPQDLIPDVLQSNDEVLA
EVTSWDLPPLTDRYRRACQSLGQGEHQQVLQAVELQGLGLSFSACSLALDQAQLTP
LLRALKLHTALRELRLAGNRLGDKCVAELVAALGTMPSLALLDLSSNHLGPEGLRQ
LAMGLPGQATLQSLEELDLSMNPLGDGCGQSLASLLHACPLLSTLRLQACGFGPSFF -continued

| SEQUENCE DATA |
|---|
| LSHQTALGSAFQDAEHLKTLSLSYNALGAPALARTLQSLPAGTLLHLELSSVAAGK<br>GDSDLMEPVFRYLAKEGCALAHLTLSANHLGDKAVRDLCRCLSLCPSLISLDLSAN<br>PEISCASLEELLSTLQKRPQGLSFLGLSGCAVQGPLGLGLWDKIAAQLRELQLCSRRL<br>CAEDRDALRQLQPSRPGPGECTLDHGSKLFFRRL |
| SEQ ID NO: 19 - Protein sequences of TONSL W563A<br>MSLERELRQLSKAKAKAQRAGQRREEAALCHQLGELLAGHGRYAEALEQHWQEL<br>QLRERADDPLGCAVAHRKIGERLAEMEDYPAALQHQHQYLELAHSLRNHTELQRA<br>WATIGRTHLDIYDHCQSRDALLQAQAAFEKSLAIVDEELEGTLAQGELNEMRTRLY<br>LNLGLTFESLQQTALCNDYFRKSIFLAEQNHLYEDLFRARYNLGTIHWRAGQHSQA<br>MRCLEGARECAHTMRKRFMESECCVVIAQVLQDLGDFLAAKRALKKAYRLGSQK<br>PVQRAAICQNLQHVLAVVRLQQQLEEAEGRDPQGAMVICEQLGDLFSKAGDFPRA<br>AEAYQKQLRFAELLDRPGALERAIIHVSLATTLGDMKDHHGAVRHYEEELRLRSGNV<br>LEEAKTWLNIALSREEAGDAYELLAPCFQKALSCAQQAQRPQLQRQVLQHLHTVQ<br>LRLQPQEAPETETRLRELSVAEDEDEEEEAEEAAATAESEALEAGEVELSEGEDDTD<br>GLTPQLEEDEELQGHLGRRKGSKWNRRNDMGETLLHRACIEGQLRRVQDLVRQGH<br>PLNPRDYCGATPLHEACNYGHLEIVRFLLDHGAAVDDPGGQGCEGITPLHDALNCG<br>HFEVAELLLERGASVTLRTRKGLSPLETLQQWVKLYRRDLDLETRQKARAMEMLL<br>QAAASGQDPHSSQAFHTPSSLLFDPETSPPLSPCPEPPSNSTRLPEASQAHVRVSPGQ<br>AAPAMARPRRSRHGPASSSSSSEGEDSAGPARPSQKRPRCSATAQRVAAWTPGPAS<br>NREAATASTSRAAYQAAIRGVGSAQSRLGPPGPPRGHSKALAPQAALIPEEECLAGD<br>WLELDMPLTRSRRPRPRGTGDNRRPSSTSGSDSEESRPRARAKQVRLTCMQSCSAP<br>VNAGPSSLASEPPGSPSTPRVSEPSGDSSAAGQPLGPAPPPPIRVRVQVQDHLFLIPVP<br>HSSDTHSVAWLAEQAAQRYYQTCGLLPRLTLRKEGALLAPQDLIPDVLQSNDEVLA<br>EVTSWDLPPLTDRYRRACQSLGQGEHQQVLQAVELQGLGLSFSACSLALDQAQLTP<br>LLRALKLHTALRELRLAGNRLGDKCVAELVAALGTMPSLALLDLSSNHLGPEGLRQ<br>LAMGLPGQATLQSLEELDLSMNPLGDGCGQSLASLLHACPLLSTLRLQACGFGPSFF<br>LSHQTALGSAFQDAEHLKTLSLSYNALGAPALARTLQSLPAGTLLHLELSSVAAGK<br>GDSDLMEPVFRYLAKEGCALAHLTLSANHLGDKAVRDLCRCLSLCPSLISLDLSAN<br>PEISCASLEELLSTLQKRPQGLSFLGLSGCAVQGPLGLGLWDKIAAQLRELQLCSRRL<br>CAEDRDALRQLQPSRPGPGECTLDHGSKLFFRRL |
| SEQ ID NO: 20 - Protein sequences of TONSL E568A<br>MSLERELRQLSKAKAKAQRAGQRREEAALCHQLGELLAGHGRYAEALEQHWQEL<br>QLRERADDPLGCAVAHRKIGERLAEMEDYPAALQHQHQYLELAHSLRNHTELQRA<br>WATIGRTHLDIYDHCQSRDALLQAQAAFEKSLAIVDEELEGTLAQGELNEMRTRLY<br>LNLGLTFESLQQTALCNDYFRKSIFLAEQNHLYEDLFRARYNLGTIHWRAGQHSQA<br>MRCLEGARECAHTMRKRFMESECCVVIAQVLQDLGDFLAAKRALKKAYRLGSQK<br>PVQRAAICQNLQHVLAVVRLQQQLEEAEGRDPQGAMVICEQLGDLFSKAGDFPRA<br>AEAYQKQLRFAELLDRPGAERAIIHVSLATTLGDMKDHHGAVRHYEEELRLRSGNV<br>LEEAKTWLNIIALSREEAGDAYELLAPCFQKALSCAQQAQRPQLQRQVLQHLHTVQ<br>LRLQPQEAPETETRLRELSVAEDEDEEEEAEEAAATAESEALEAGEVELSEGEDDTD<br>GLTPQLEEDEELQGHLGRRKGSKWNRRNDMGETLLHRACIEGQLRRVQDLVRQGH<br>PLNPRDYCGWTPLHAACNYGHLEIVRFLLDHGAAVDDPGGQGCEGITPLHDALNC<br>GHFEVAELLLERGASVTLRTRKGLSPLETLQQWVKLYRRDLDLETRQKARAMEML<br>LQAAASGQDPHSSQAFHTPSSLLFDPETSPPLSPCPEPPSNSTRLPEASQAHVRVSPG<br>QAAPAMARPRRSRHGPASSSSSSEGEDSAGPARPSQKRPRCSATAQRVAAWTPGPA<br>SNREAATASTSRAAYQAAIRGVGSAQSRLGPGPPRGHSKALAPQAALIPEEECLAGD<br>WLELDMPLTRSRRPRPRGTGDNRRPSSTSGSDSEESRPRARAKQVRLTCMQSCSAP<br>VNAGPSSLASEPPGSPSTPRVSEPSGDSSAAGQPLGPAPPPPIRVRVQVQDHLFLIPVP<br>HSSDTHSVAWLAEQAAQRYYQTCGLLPRLTLRKEGALLAPQDLIPDVLQSNDEVLA<br>EVTSWDLPPLTDRYRRACQSLGQGEHQQVLQAVELQGLGLSFSACSLALDQAQLTP<br>LLRALKLHTALRELRLAGNRLGDKCVAELVAALGTMPSLALLDLSSNHLGPEGLRQ<br>LAMGLPGQATLQSLEELDLSMNPLGDGCGQSLASLLHACPLLSTLRLQACGFGPSFF<br>LSHQTALGSAFQDAEHLKTLSLSYNALGAPALARTLQSLPAGTLLHLELSSVAAGK<br>GDSDLMEPVFRYLAKEGCALAHLTLSANHLGDKAVRDLCRCLSLCPSLISLDLSAN<br>PEISCASLEELLSTLQKRPQGLSFLGLSGCAVQGPLGLGLWDKIAAQLRELQLCSRRL<br>CAEDRDALRQLQPSRPGPGECTLDHGSKLFFRRL |
| SEQ ID NO: 21 - Protein sequences of TONSL N571A<br>MSLERELRQLSKAKAKAQRAGQRREEAALCHQLGELLAGHGRYAEALEQHWQEL<br>QLRERADDPLGCAVAHRKIGERLAEMEDYPAALQHQHQYLELAHSLRNHTELQRA<br>WATIGRTHLDIYDHCQSRDALLQAQAAFEKSLAIVDEELEGTLAQGELNEMRTRLY<br>LNLGLTFESLQQTALCNDYFRKSIFLAEQNHLYEDLFRARYNLGTIHWRAGQHSQA<br>MRCLEGARECAHTMRKRFMESECCVVIAQVLQDLGDFLAAKRALKKAYRLGSQK<br>PVQRAAICQNLQHVLAVVRLQQQLEEAEGRDPQGAMVICEQLGDLFSKAGDFPRA<br>AEAYQKQLRFAELLDRPGAERAIIHVSLATTLGDMKDHHGAVRHYEEELRLRSGNV<br>LEEAKTWLNIALSREEAGDAYELLAPCFQKALSCAQQAQRPQLQRQVLQHLHTVQ<br>LRLQPQEAPETETRLRELSVAEDEDEEEEAEEAAATAESEALEAGEVELSEGEDDTD<br>GLTPQLEEDEELQGHLGRRKGSKWNRRNDMGETLLHRACIEGQLRRVQDLVRQGH<br>PLNPRDYCGWTPLHEACAYGHLEIVRFLLDHGAAVDDPGGQGCEGITPLHDALNC<br>GHFEVAELLLERGASVTLRTRKGLSPLETLQQWVKLYRRDLDLETRQKARAMEML<br>LQAAASGQDPHSSQAFHTPSSLLFDPETSPPLSPCPEPPSNSTRLPEASQAHVRVSPG<br>QAAPAMARPRRSRHGPASSSSSSEGEDSAGPARPSQKRPRCSATAQRVAAWTPGPA<br>SNREAATASTSRAAYQAAIRGVGSAQSRLGPGPPRGHSKALAPQAALIPEEECLAGD<br>WLELDMPLTRSRRPRPRGTGDNRRPSSTSGSDSEESRPRARAKQVRLTCMQSCSAP<br>VNAGPSSLASEPPGSPSTPRVSEPSGDSSAAGQPLGPAPPPPIRVRVQVQDHLFLIPVP |

-continued

| SEQUENCE DATA |
|---|

HSSDTHSVAWLNEQAAQRYYQTCGLLPRLTLRKEGALLAPQDLIPDVLQSNDEVLA
EVTSWDLPPLTDRYRRACQSLGQGEHQQVLQAVELQGLGLSFSACSLALDQAQLTP
LLRALKLHTALRELRLAGNRLGDKCVAELVAALGTMPSLALLDLSSNHLGPEGLRQ
LAMGLPGQATLQSLEELDLSMNPLGDGCGQSLASLLHACPLLSTLRLQACGFGPSFF
LSHQTALGSAFQDAEHLKTLSLSYNALGAPALARTLQSLPAGTLLHLELSSVAAGK
GDSDLMEPVFRYLAKEGCALAHLTLSANHLGDKAVRDLCRCLSLCPSLISLDLSAN
PEISCASLEELLSTLQKRPQGLSFLGLSGCAVQGPLGLGLWDKIAAQLRELQLCSRRL
CAEDRDALRQLQPSRPGPGECTLDHGSKLFFRRL

SEQ ID NO: 22 - Protein sequences of TONSL D604A
MSLERELRQLSKAKAKAQRAGQRREEAALCHQLGELLAGHGRYAEALEQHWQEL
QLRERADDPLGCAVAHRKIGERLAEMEDYPAALQHQHQYLELAHSLRNHTELQRA
WATIGRTHLDIYDHCQSRDALLQAQAAFEKSLAIVDEELEGTLAQGELNEMRTRLY
LNLGLTFESLQQTALCNDYFRKSIFLAEQNHLYEDLFRARYNLGTIHWRAGQHSQA
MRCLEGARECAHTMRKRFMESECCVVIAQVLQDLGDFLAAKRALKKAYRLGSQK
PVQRAAICQNLQHVLAVVRLQQQLEEAEGRDPQGAMVICEQLGDLFSKAGDFPRA
AEAYQKQLRFAELLDRPGAERAIIHVSLATTLGDMKDHHGAVRHYEEELRLRSGNV
LEEAKTWLNIALSREEAGDAYELLAPCFQKALSCAQQAQRPQLQRQVLQHLHTVQ
LRLQPQEAPETETRLRELSVAEDEDEEEEAEEAAATAESEALEAGEVELSEGEDDTD
GLTPQLEEDEELQGHLGRRKGSKWNRRNDMGETLLHRACIEGQLRRVQDLVRQGH
PLNPRDYCGWTPLHEACNYGHLEIVRFLLDHGAAVDDPGGQGCEGITPLHAALNC
GHFEVAELLLERGASVTLRTRKGLSPLETLQQWVKLYRRDLDLETRQKARAMEML
LQAAASGQDPHSSQAFHTPSSLLFDPETSPPLSPCPEPPSNSTRLPEASQAHVRVSPG
QAAPAMARPRRSRHGPASSSSSSEGEDSAGPARPSQKRPRCSATAQRVAAWTPGPA
SNREAATASTSRAAYQAAIRGVGSAQSRLGPGPPRGHSKALAPQAALIPEEECLAGD
WLELDMPLTRSRRPRPRGTGDNRRPSSTSGSDSEESRPRARAKQVRLTCMQSCSAP
VNAGPSSLASEPPGSPSTPRVSEPSGDSSAAGQPLGPAPPPPIRVRVQVQDHLFLIPVP
HSSDTHSVAWLAEQAAQRYYQTCGLLPRLTLRKEGALLAPQDLIPDVLQSNDEVLA
EVTSWDLPPLTDRYRRACQSLGQGEHQQVLQAVELQGLGLSFSACSLALDQAQLTP
LLRALKLHTALRELRLAGNRLGDKCVAELVAALGTMPSLALLDLSSNHLGPEGLRQ
LAMGLPGQATLQSLEELDLSMNPLGDGCGQSLASLLHACPLLSTLRLQACGFGPSFF
LSHQTALGSAFQDAEHLKTLSLSYNALGAPALARTLQSLPAGTLLHLELSSVAAGK
GDSDLMEPVFRYLAKEGCALAHLTLSANHLGDKAVRDLCRCLSLCPSLISLDLSAN
PEISCASLEELLSTLQKRPQGLSFLGLSGCAVQGPLGLGLWDKIAAQLRELQLCSRRL
CAEDRDALRQLQPSRPGPGECTLDHGSKLFFRRL SEQ ID NO: 23 - protein sequence of Histone H4
>sp|1362805|H4_HUMAN Histone H4 OS = *Homo sapiens*
IMSGRGKGGKGLGKGGAKRHRKVLRDNIQGITKPAIRRLARRGGVKRISGLIYEETR
GVLK
VFLENVIRDAVTYTEHAKRKTVTAMDVVYALKRQGRTLYGFGG SEQ ID NO: 24 - protein sequence of MCM2
>sp|P49736|MCM2_HUMAN DNA replication licensing factor MCM2 OS = *Homo sapiens*
MAESSESFTMASSPAQRRRGNDPLTSSPGRSSRRTDALTSSPGRDLPPFEDESEGLLG
TE
GPLEEEEDGEELIGDGMERDYRAIPELDAYEAEGLALDDEDVEELTASQREAAERA
MRQR
DREAGRGLGRMRRGLLYDSDEEDEERPARKRRQVERATEDGEEDEEMIESIENLED
LKGH
SVREWVSMAGPRLEIHHRFKNFLRTHVDSHGHNVFKERISDMCKENRESLVVNYE
DLAAR
EHVLAYFLPEAPAELLQIFDEAALEVVLAMYPKYDRITNHIHVRISHLPLVEELRSLR
QL
HLNQLIRTSGVVTSCTGVLPQLSMVKYNCNKCNFVLGPFCQSQNQEVKPGSCPECQ
SAGP
FEVNMEETIYQNYQRIRIQESPGKVAAGRLPRSKDAILLADLVDSCKPGDEIELTGIY
HN
NYDGSLNTANGFPVFATVILANHVAKKDNKVAVGELTDEDVKMITSLSKDQQIGE
KIFAS
IAPSIYGHEDIKRGLALALFGGEPKNPGGKHKVRGDINVLLCGDPGTAKSQFLKYIE
KVS
SRAIFTTGQGASAVGLTAYVQRHPVSREWTLEAGALVLADRGVCLIDEFDKMNDQ
DRTSI
HEAMEQQSISISKAGIVTSLQARCTVIAAANPIGGRYDPSLTFSENVDLTEPIISRFDIL
CVVRDTVDPVQDEMLARFVVGSHVRHHPSNKEEEGLANGSAAEPAMPNTYGVEPL
PQEVL
KKYIIYAKERVHPKLNQMDQDKVAKMYSDLRKESMATGSIPITVRHIESMIRMAEA
HARI
HLRDYVIEDDVNMAIRVMLESFIDTQKFSVMRSMRKTFARYLSFRRDNNELLLFILK
QLV
AEQVTYQRNRFGAQQDTIEVPEKDLVDKARQINIHNLSAFYDSELFRMNKFSHDLK
RKMI
LQQF -continued

| SEQUENCE DATA |
|---|

SEQ ID NO: 25 - protein sequence of Histone H3.3
>sp|P84243|H33_HUMAN Histone H3.3 OS = *Homo sapiens*
MARTKQTARKSTGGKAPRKQLATKAARKSAPSTGGVKKPHRYRPGTVALREIRRY
QKSTE
LLIRKLPFQRLVREIAQDFKTDLRFQSAAIGALQEASEAYLVGLFEDTNLCAIHAKRV
TI
MPKDIQLARRIRGERA

SEQ ID NO: 26
RHXK

SEQ ID NO: 27
RHXKVL

SEQ ID NO: 28
RHXKVLR

SEQ ID NO: 29
Ala-Lys-Arg-His-Arg-Lys-Val-Leu-Arg

SEQ ID NO: 30
Lys-Gly-Gly-Ala-Lys-Arg-His-Arg-Lys-Val-Leu-Arg

SEQ ID NO: 31
Lys-Gly-Gly-Ala-Lys-Arg-His-Ala-Lys-Val-Leu-Arg

SEQ ID NO: 32
Lys-Gly-Gly-Ala-Ala-Arg-His-Arg-Lys-Val-Leu-Arg

SEQ ID NO: 33
*Leu-Gly*-Lys-Gly-Gly-Ala-Lys-Arg-His-Arg-Lys-Val-Leu-Arg-Asp-Asn-1le

SEQ ID NO: 34 - protein sequence of Histone H4
SGRGKGGKGLGKGGAKRHRKVLRDNIQGITKPAIRRLARRGGVKRISGLIYEETRG
VLK
VFLENVIRDAVTYTEHAKRKTVTAMDVVYALKRQGRTLYGFGG

ITEMS OF THE INVENTION

Some aspects of the invention may further be identified by the following items:

1. A small molecule, which targets the conformational space of the TONSL ARD occupied by the histone H4 tail encompassing residues K12-R23 and acting to prevent or disrupt the binding of the H4 tail K12-R23 with the TONSL ARD via direct competition or via allosteric disruption of the binding pocket.
2. A small molecule according to item 1, that targets the H4 tail spanning residues Lys12 to Arg23 through intermolecular hydrogen-bonding, electrostatic and/or van der Waals interactions.
3. A small molecule according to any of items 1-2, wherein the molecule targets the intermolecular contacts spanning the Lys12-Gly13-Gly14-Ala15 segment of H4.
4. A small molecule according to any of items 1-3, wherein the molecule targets the hydrophobic interactions between residues Gly13, Gly14 and Ala15 of H4 and residues Asn507, Cys508, Trp641, Tyr645 and Leu649 of ARD.
5. A small molecule according to any of items 1-4, wherein the molecule targets the hydrogen bonds between the main-chain O of H4 Gly14 and Nε1 of ARD Trp641, and between the main-chain N of H4 Ala15 and Oδ1 of ARD Tyr645.
6. A small molecule according to any of items 1-5, wherein the molecule targets the main-chain O of H4 Lys16 hydrogen bonds with the Nδ2 of ARD Asn571.
7. A small molecule according to any of items 1-6, wherein the molecule targets the side-chain of H4 Arg17, which stacks over the side-chains of ARD Tyr572 and Cys608, while its Nη1 atom forms two hydrogen bonds with main-chain O and Oδ1 of ARD Asn571.
8. A small molecule according to any of items 1-7, wherein the molecule targets the side-chain of H4 H18, which penetrates into a pocket lined by four strictly conserved residues (Trp563, Glu568, Asn571 and Asp604) and is positioned over His567 of ARD.
9. A small molecule according to any of items 1-8, wherein the molecule targets the side chain of H4 His18, which is stacked between Trp563 and Asn571 and forms hydrogen bonds to Glu568 and Asp604 of ARD.
10. A small molecule according to any of items 1-9, wherein the molecule targets the main-chain O of H4 Arg19, which forms a hydrogen bond with Nε1 of Trp563 and its side-chain forms contacts with Cys561 and Gly595 of ARD.
11. A small molecule according to any of items 1-10, wherein the molecule targets the H4 Lys20 residue that is bound within an acidic surface pocket on ARD adjacent to the H4 His18 binding pocket.
12. A small molecule according to any of items 1-11, wherein the molecule targets side-chain of H4 Lys20 which interacts with the side-chain of Met528 and contacts the edge of Trp563 of ARD, while the main-chain atoms of H4 Lys20 packs against Cys561 of ARD.
13. A small molecule according to any of items 1-12, wherein the molecule targets the Nζ atom of H4 Lys20 that forms three strong hydrogen bonds (distance <3 Å) with the side-chains of strictly conserved residues Glu530, Asp559 and Glu568 of ARD, which surround H4 Lys20 within a regular triangle-like alignment.

14. A small molecule according to any of items 1-13, wherein the molecule targets intermolecular contacts spanning the Val2-Leu22-Arg23 segment of H4, which includes contacts between side-chains of H4 Val21 with Tyr560 and Cys561 of ARD, while H4 Leu22 interacts with Asp527 and Met528 of ARD.

15. A small molecule according to any of items 1-14, wherein the molecule targets the main-chain N of H4 Arg23 which forms a hydrogen bond with the main-chain O of Asp527 of ARD, while the side-chain packs against the side-chain of Tyr560 of ARD.

16. A small molecule according to any of items 1-15, capable of blocking histone reader domains in a protein selected from the group consisting of TONSL, BARD1 and ANKRD11.

17. A small molecule according to any of items 1-16 for use as a medicament.

18. A small molecule according to any of items 1-17 for use in treatment of cancer.

19. A method of selecting or designing a small molecule capable of interfering with the histone H4H18 and H4K20 binding pocket on the surface of the Ankyrin repeats of TONSL, said method comprises use of at least part of the atomic co-ordinates data contained in PDB ID 5JA4 or data derivable therefrom, wherein said method involves use of a computer modelling package or a computer program to model all or part of the structure of MCM2 HBD-G4-TONSL ARD in complex with H3 (57-135) and H4, thereby identifying said molecule by designing or selecting the molecule based on its likely ability to interact with a modelled structure.

20. An isolated polynucleotide or amino acid sequence having at least 90% sequence identity to any of SEQ ID NO 1-22.

21. A crystal comprising covalently linked MCM2 HBD-G4-TONSL ARD in complex with H3 (57-135) and H4 (that diffracted to 2.43 Å resolution).

22. A crystal structure having the atomic coordinates or a subset hereof set out in PDB ID 5JA4 or having a structure in which the atomic coordinates vary by less than 3 Å in any direction from those set out therein.

The invention claimed is:

1. A method for treating cancer comprising administering an inhibitor of Tonsuku-like protein (TONSL) to a subject in need thereof, wherein the inhibitor is capable of inhibiting binding of TONSL Ankyrin Repeat Domain (ARD) to histone H4.

2. The method according to claim 1, wherein the inhibitor is capable of binding a conformational space of the TONSL ARD occupied by historic H4 tail encompassing residues K12-R23 and acting to prevent or disrupt the binding of the histone H4 tail with the TONSL ARD via direct competition or via allosteric disruption of a binding pocket.

3. The method according to claim 1, wherein the inhibitor is capable of binding to a His18-binding pocket of TONSL ARD, wherein the His18-binding pocket comprises amino acids Trp563, Glu568, Asn571 and Asp604 of SEQ ID NO:16.

4. The method according to claim 1, wherein the inhibitor is capable of binding to a Lys20-binding pocket of TONSL ARD, wherein the Lys20-binding pocket comprises Met528, Trp563, Glu530, Asp559 and Glu568 of SEQ ID NO:16.

5. The method according to claim 1, wherein the inhibitor is capable of binding a histone H4 tail of TONSL ARD, wherein the H4 tail binding surface of TONSL ARD comprises amino acids Asp527, Met528, Glu530, Asp559, Tyr560, Cys561, Trp563, Glu568, Asn571, Tyr572, Gy595, Glu597, Asp604, Asn607, Cys608, Trp641, Tyr645 and Leu649 of SEQ ID NO:16.

6. The method according to claim 1, wherein the inhibitor is a peptide or polypeptide optionally linked to a conjugated moiety.

7. The method according to claim 4, wherein peptide or polypeptide comprises Arg-His-Xaa-Lys (SEQ ID NO:26), wherein Xaa may be any amino acid.

8. The method according to claim 6, wherein the peptide or polypeptide comprises Val-Leu-Arg.

9. The method according to claim 6, wherein the peptide or polypeptide comprises Arg-His-Xaa-Lys-Val-Leu-Arg (SEQ ID NO: 28), wherein Xaa may be any amino acid.

10. The method according to claim 6, wherein the peptide or polypeptide consists of at most 40 amino acids.

11. The method according to claim 6, wherein the peptide or polypeptide is a peptide or polypeptide linked to a conjugated moiety, wherein the peptide or polypeptide comprises Arg-His-Xaa-Lys-Val-Leu-Arg (SEQ ID NO: 28), wherein Xaa may be any amino acid and consists of at most 20 amino acids.

12. The method according to claim 6, wherein peptide or polypeptide comprises an amino acid sequence selected from the group consisting of SEQ ID NO:29, SEQ ID NO:30, SEQ ID NO:31, SEQ ID NO:32 and SEQ ID NO:33, wherein said peptide is optionally linked to a conjugated moiety.

13. The method according to claim 6, wherein the peptide or polypeptide comprises a sequence of amino acids 9 to 25 of SEQ ID NO: 23, with the proviso that the inhibitor is different from histone H4 of SEQ ID NO: 23.

14. The method according to claim 13, wherein the amino acid corresponding to Lys20 of SEQ ID NO: 23 is unmethylated.

15. The method according to claim 6, wherein the N-terminal of the peptide or polypeptide is acetylated or formylated and/or the C-terminal of the peptide or polypeptide is amidated or alkylated.

16. The method according to claim 4, wherein the inhibitor is a small molecule.

17. The method according to claim 16, wherein the small molecule is capable of targeting the conformational space of the TONSL ARD occupied by the histone H4 tail encompassing residues K12-R23 and acting to prevent or disrupt binding of the histone H4 tail K12-R23 with the TONSL ARD via direct competition or via allosteric disruption of a binding pocket.

18. The method according to claim 16, wherein the small molecule has a 3-[(3-Aminocyclopentyl)carbonyl]-H-quinolin-4-one core.

* * * * *